(12) United States Patent
Corper et al.

(10) Patent No.: US 11,286,293 B2
(45) Date of Patent: *Mar. 29, 2022

(54) ENGINEERED IMMUNOGLOBULIN HEAVY CHAIN-LIGHT CHAIN PAIRS AND USES THEREOF

(71) Applicant: ZYMEWORKS INC., Vancouver (CA)

(72) Inventors: Adam Louis Corper, Vancouver (CA); Dunja Urosev, Vancouver (CA); Stacey A. L. Tom-Yew, Coquitlam (CA); Dustin Weyland Blue Bleile, Vancouver (CA); Thomas Spreter Von Kreudenstein, Vancouver (CA); Surjit Dixit, Richmond (CA); Paula Irene Lario, South Vancouver (CA); Mario Sanches, Vancouver (CA)

(73) Assignee: ZYMEWORKS, INC., Vancouver (CA)

(*) Notice: Subject to any disclaimer, the term of this patent is extended or adjusted under 35 U.S.C. 154(b) by 70 days.

This patent is subject to a terminal disclaimer.

(21) Appl. No.: 16/122,417

(22) Filed: Sep. 5, 2018

(65) Prior Publication Data

US 2019/0085055 A1 Mar. 21, 2019

Related U.S. Application Data

(62) Division of application No. 14/648,222, filed as application No. PCT/CA2013/050914 on Nov. 28, 2013, now Pat. No. 10,077,298.

(60) Provisional application No. 61/730,906, filed on Nov. 28, 2012, provisional application No. 61/761,641, filed on Feb. 6, 2013, provisional application No. 61/818,874, filed on May 2, 2013, provisional application No. 61/869,200, filed on Aug. 23, 2013.

(51) Int. Cl.
| | |
|---|---|
| *C07K 16/00* | (2006.01) |
| *G16B 40/00* | (2019.01) |
| *C07K 16/28* | (2006.01) |
| *C07K 16/32* | (2006.01) |
| *C07K 16/36* | (2006.01) |
| *G16B 40/10* | (2019.01) |

(52) U.S. Cl.
CPC .......... *C07K 16/00* (2013.01); *C07K 16/2863* (2013.01); *C07K 16/32* (2013.01); *C07K 16/36* (2013.01); *G16B 40/00* (2019.02); *G16B 40/10* (2019.02); *C07K 2317/10* (2013.01); *C07K 2317/31* (2013.01); *C07K 2317/35* (2013.01); *C07K 2317/51* (2013.01); *C07K 2317/515* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/72* (2013.01); *C07K 2317/92* (2013.01); *C07K 2317/94* (2013.01)

(58) Field of Classification Search
CPC .................. C07K 2317/51; C07K 2317/515
USPC .......................................... 424/133.1, 136.1
See application file for complete search history.

(56) References Cited

U.S. PATENT DOCUMENTS

| | | | |
|---|---|---|---|
| 5,731,168 A | 3/1998 | Carter et al. | |
| 5,807,706 A | 9/1998 | Carter et al. | |
| 5,821,333 A | 10/1998 | Carter et al. | |
| 6,809,185 B1 | 10/2004 | Schoonjans et al. | |
| 7,183,076 B2 | 2/2007 | Arathoon et al. | |
| 7,642,228 B2 | 1/2010 | Carter et al. | |
| 7,695,936 B2 | 4/2010 | Carter et al. | |
| 7,951,917 B1 | 5/2011 | Arathoon et al. | |
| 8,501,185 B2 | 8/2013 | Heitner Hansen et al. | |

(Continued)

FOREIGN PATENT DOCUMENTS

| | | |
|---|---|---|
| EP | 1870459 | 12/2007 |
| EP | 2543680 A1 | 1/2013 |

(Continued)

OTHER PUBLICATIONS

Wiens et al (J Immunology 167: 2179-2186, 2001).*

(Continued)

*Primary Examiner* — Lynn A Bristol

(74) *Attorney, Agent, or Firm* — Kilpatrick Townsend & Stockton LLP

(57) ABSTRACT

The present invention provides heterodimer pairs that can comprise a first heterodimer and a second heterodimer wherein each heterodimer comprises an immunoglobulin heavy chain or fragment thereof and an immunoglobulin light chain or fragment thereof. At least one of the heterodimers can comprise one or more amino acid modifications in the $C_{H1}$ and/or $C_L$ domains, one or more amino acid modifications in the $V_H$ and/or $V_L$ domains, or a combination thereof. The modified amino acid(s) can be part of the interface between the light chain and heavy chain and are typically modified to create preferential pairing between each heavy chain and a desired light chain such that when the two heavy chains and two light chains of the heterodimer pair are co-expressed in a cell, the heavy chain of the first heterodimer preferentially pairs with one of the light chains rather than the other. Likewise, the heavy chain of the second heterodimer typically preferentially pairs with the second light chain rather than first.

25 Claims, 23 Drawing Sheets

Specification includes a Sequence Listing.

(56) References Cited

U.S. PATENT DOCUMENTS

| | | |
|---|---|---|
| 8,592,562 B2 | 11/2013 | Kannan et al. |
| 9,499,634 B2 | 11/2016 | Dixit et al. |
| 9,527,927 B2 | 12/2016 | Chowdhury et al. |
| 9,562,109 B2 | 2/2017 | Von Keudenstein et al. |
| 9,574,010 B2 | 2/2017 | Spreter Von Keudenstein et al. |
| 9,708,388 B2 | 7/2017 | Dutalys |
| 9,771,573 B2 | 9/2017 | Corper et al. |
| 9,914,785 B2* | 3/2018 | Corper ............... C07K 16/36 |
| 10,077,298 B2* | 9/2018 | Corper ............. C07K 16/2863 |
| 10,392,438 B2* | 8/2019 | Bennett ............... C07K 16/24 |
| 2003/0129659 A1 | 7/2003 | Whelihan et al. |
| 2005/0069549 A1 | 3/2005 | Herman |
| 2006/0160184 A1 | 7/2006 | Hoogenboom et al. |
| 2007/0196363 A1 | 8/2007 | Arathoon et al. |
| 2008/0050370 A1 | 2/2008 | Glaser et al. |
| 2009/0162360 A1 | 6/2009 | Klein et al. |
| 2009/0182127 A1 | 7/2009 | Kjaergaard et al. |
| 2009/0232811 A1 | 9/2009 | Klein et al. |
| 2009/0263392 A1 | 10/2009 | Igawa et al. |
| 2010/0015133 A1 | 1/2010 | Igawa et al. |
| 2010/0105874 A1 | 4/2010 | Schuurman et al. |
| 2010/0256338 A1 | 10/2010 | Brinkmann et al. |
| 2010/0286374 A1 | 11/2010 | Kannan et al. |
| 2010/0322934 A1 | 12/2010 | Imhof-Jung et al. |
| 2010/0322935 A1 | 12/2010 | Croasdale et al. |
| 2010/0331527 A1 | 12/2010 | Davis et al. |
| 2011/0008345 A1 | 1/2011 | Ashman et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0143580 A1 | 6/2012 | Constantine et al. |
| 2012/0149876 A1 | 6/2012 | Von Kreudenstein et al. |
| 2012/0244578 A1 | 9/2012 | Kannan et al. |
| 2013/0078249 A1 | 3/2013 | Ast et al. |
| 2013/0195849 A1 | 8/2013 | Spreter Von Kreudenstein et al. |
| 2013/0336973 A1 | 12/2013 | Spreter Von Kreudenstein et al. |
| 2014/0051835 A1 | 2/2014 | Dixit et al. |
| 2014/0066599 A2 | 3/2014 | Blein et al. |
| 2014/0154254 A1 | 6/2014 | Kannan et al. |
| 2014/0179547 A1 | 6/2014 | Fischer et al. |
| 2014/0200331 A1 | 7/2014 | Corper et al. |
| 2014/0370020 A1 | 12/2014 | Kuramochi et al. |
| 2015/0211001 A1 | 7/2015 | Ohrn et al. |
| 2015/0307594 A1 | 10/2015 | Corper et al. |
| 2017/0204199 A1* | 7/2017 | Sanches ............... C07K 16/32 |
| 2018/0179296 A1* | 6/2018 | Corper ............... C07K 16/36 |
| 2019/0338048 A1* | 11/2019 | Urosev ................ A61P 43/00 |
| 2020/0087414 A1 | 3/2020 | Spreter Von Kreudenstein et al. |

FOREIGN PATENT DOCUMENTS

| | | |
|---|---|---|
| EP | 2647707 | 10/2013 |
| WO | 199404690 | 3/1994 |
| WO | 199627011 | 9/1996 |
| WO | 2006106905 | 10/2006 |
| WO | 2007110205 | 10/2007 |
| WO | 2009089004 | 7/2009 |
| WO | 2010085682 | 7/2010 |
| WO | 2010115553 | 10/2010 |
| WO | 2011028952 | 3/2011 |
| WO | 2011063348 | 5/2011 |
| WO | 2011120134 | 10/2011 |
| WO | 2011131746 | 10/2011 |
| WO | 2011143545 | 11/2011 |
| WO | 2011133886 | 12/2011 |
| WO | 2011147982 | 12/2011 |
| WO | 2012020096 | 2/2012 |
| WO | 2012023053 | 2/2012 |
| WO | 2012058768 | 5/2012 |
| WO | 2012073985 | 6/2012 |
| WO | 2012131555 | 10/2012 |
| WO | 2012143523 | 10/2012 |
| WO | 2013002362 A1 | 1/2013 |
| WO | 2013005194 | 1/2013 |
| WO | 2013060867 | 5/2013 |
| WO | 2013063702 | 5/2013 |
| WO | 2013065708 A1 | 5/2013 |
| WO | 2013096291 | 6/2013 |
| WO | 2014005784 | 4/2014 |
| WO | 2014081955 A1 | 5/2014 |
| WO | 2014082179 | 6/2014 |
| WO | 2014150973 | 9/2014 |
| WO | 2015181805 | 12/2015 |
| WO | 2017059551 | 4/2017 |

OTHER PUBLICATIONS

Rudikoff et al. (Proceedings of the National Academy of Sciences vol. 79: 1979-1983, 1982).*

Colman (Research in Immunology vol. 145, pp. 33-36, 1994).*

Wu et al (J. Mol. Biol. 294: 151-162, 1999).*

MacCallum, et al. (Journal of Molecular Biology 262: 732-745, 1996).*

Braden et al. (FASEB J Jan. 1995;9(1):9-16).*

Edwards, B.M., et al., The remarkable flexibility of the human antibody repertoire; isolation of over one thousand different antibodies to a single protein, BLyS. J. Mol. Biol. 2003; 334(1):103-118.

Labrijin, A. F., et al., Efficient generation of stable bispecific IgG1 by controlled Fab-arm exchange. PNAS, Mar. 26, 2013; 110(13):5145-5150.

U.S. Appl. No. 15/765,574, Notice of Allowance dated Sep. 2, 2020.

U.S. Appl. No. 13/289,934, Advisory Action dated Feb. 5, 2016, 5 pages.

U.S. Appl. No. 13/289,934, Non-Final Office Action dated Feb. 27, 2015, 15 pages.

U.S. Appl. No. 13/289,934, Non-Final Office Action dated May 13, 2015, 17 pages.

U.S. Appl. No. 13/289,934, Notice of Allowance dated Apr. 25, 2016, 9 pages.

U.S. Appl. No. 13/289,934, Restriction Requirement dated Sep. 16, 2014, 6 pages.

U.S. Appl. No. 13/289,934, Final Office Action dated Nov. 16, 2015.

U.S. Appl. No. 13/289,934, Notice of Allowance dated Sep. 29, 2017.

U.S. Appl. No. 13/668,098, Final Office Action dated Nov. 17, 2015, 16 pages.

U.S. Appl. No. 13/668,098, Non-Final Office Action dated Apr. 3, 2015, 18 pages.

U.S. Appl. No. 13/668,098, Restriction Requirement dated Dec. 5, 2014, 10 pages.

U.S. Appl. No. 13/668,098, Notice of Allowance dated Sep. 23, 2016.

U.S. Appl. No. 13/927,065, Non-Final Office Action dated Oct. 7, 2015, 10 pages.

U.S. Appl. No. 13/927,065, Final Office Action, dated Feb. 22, 2016.

U.S. Appl. No. 13/927,065, Notice of Allowance dated Aug. 26, 2016, 7 pages.

U.S. Appl. No. 13/927,065, Restriction Requirement dated Apr. 15, 2015, 9 pages.

U.S. Appl. No. 14/092,804, Restriction Requirement dated Jun. 18, 2015.

U.S. Appl. No. 14/092,804, Final Office Action dated Dec. 29, 2016, 46 pages.

U.S. Appl. No. 14/092,804, Non-Final Office Action dated Sep. 10, 2015, 33 pages.

U.S. Appl. No. 14/092,804, Restriction Requirement dated May 12, 2016, 5 pages.

U.S. Appl. No. 14/092,804, Notice of Allowance dated Nov. 1, 2017.

U.S. Appl. No. 14/432,153, Restriction Requirement dated Jun. 30, 2016, 7 pages.

U.S. Appl. No. 14/432,153, Non-Final Office Action dated Oct. 27, 2016.

U.S. Appl. No. 14/432,153, Notice of Allowance dated May 15, 2017.

(56) References Cited

OTHER PUBLICATIONS

U.S. Appl. No. 14/432,153, Corrected Notice of Allowance dated Aug. 18, 2017.
U.S. Appl. No. 14/648,222, Final Office Action dated Dec. 29, 2017, 12 pages.
U.S. Appl. No. 14/648,222, Non-Final Office Action dated May 16, 2017, 43 pages.
U.S. Appl. No. 14/648,222, Notice of Allowance dated May 8, 2018, 7 pages.
U.S. Appl. No. 14/648,222, Restriction Requirement dated Dec. 2, 2016, 33 pages.
U.S. Appl. No. 14/648,222, Restriction Requirement dated May 9, 2016, 14 pages.
U.S. Appl. No. 15/355,019, Non-Final Office Action, dated Jul. 21, 2017.
U.S. Appl. No. 15/355,019, Notice of Allowance, dated Nov. 17, 2017.
U.S. Appl. No. 15/355,019, Notice of Allowance, dated May 22, 2018.
U.S. Appl. No. 15/355,019, Notice of Allowance, dated Jul. 29, 2019.
U.S. Appl. No. 15/355,019: Non-Final Office Action dated Jan. 8, 2019, 5 pages.
U.S. Appl. No. 15/409,456, Restriction Requirement dated Jan. 10, 2019.
U.S. Appl. No. 15/409,456, Non-Final Office Action dated May 23, 2019.
U.S. Appl. No. 15/411,799, Restriction Requirement dated Jan. 25, 2019.
U.S. Appl. No. 15/411,799, Notice of Allowance dated Jun. 10, 2019.
U.S. Appl. No. 15/896,170, Restriction Requirement dated Jun. 26, 2019.
U.S. Appl. No. 15/896,170, Office Action dated Sep. 18, 2019.
U.S. Appl. No. 15/896,170, Final Office Action dated May 18, 2020.
U.S. Appl. No. 15/314,496, Restriction Requirement dated May 8, 2018.
U.S. Appl. No. 15/314,496, Non-Final Office Action dated Oct. 17, 2018.
U.S. Appl. No. 15/314,496, Final Office Action dated Apr. 24, 2019.
U.S. Appl. No. 15/314,496, Office Action dated Jan. 6, 2020.
U.S. Appl. No. 15/314,496, Final Office Action dated Jul. 28, 2020.
U.S. Appl. No. 15/765,574, Restriction Requirement dated Sep. 10, 2019.
U.S. Appl. No. 15/765,574, Office Action dated Dec. 27, 2019.
U.S. Appl. No. 14/989,648, Heteromultimer Constructs of Immunoglobulin Heavy Chains With Mutations in the Fc Domain, filed Jan. 6, 2016, 247 pages.
Altintas et al., Targeting Epidermal Growth Factor Receptor in Tumors: From Conventional Monoclonal Antibodies via Heavy Chain-only Antibodies to Nanobodies, Eur J Pharm Sci., vol. 45, No. 4, Mar. 12, 2012, pp. 399-407.
Atwell et al., Stable Heterodimers From Remodeling the Domain Interface of a Homodimer Using a Phage Display Library, Journal of Molecular Biology, vol. 270, Issue 1, Jul. 4, 1997, pp. 26-35.
Beck et al., Strategies and Challenges for the Next Generation of Therapeutic Antibodies, Nature Reviews Immunology, vol. 10, No. 5, May 2010, pp. 345-352.
Carter et al., Humanization of An Anti-p185HER2 Antibody for Human Cancer Therapy, Proc. Natl. Acad. Sci. USA, vol. 89, No. 10, 1992, pp. 4285-4289.
Carter, Introduction to Current and Future Protein Therapeutics: a Protein Engineering Perspective, Experimental Cell Research, vol. 317, No. 9, May 15, 2011, pp. 1261-1269.
Chames et al., Therapeutic Antibodies: Successes, Limitations and Hopes for the Future, British Journal of Pharmacology, vol. 157, No. 2, 2009, pp. 220-223.

Chen, Lei, et al., "Preferential Germline Usage and VH/VL Pairing Observed in Human Antibodies selected by mRNA display ", Protein Engineering, Design & Selection: Peds, Oct. 2015, vol. 28, No. 10, pp. 427-435.
Colman, Effects of Amino Acid Sequence Changes on Antibody-antigen Interactions, Research in Immunology, vol. 145, No. 1, Jan. 1994, pp. 33-36.
Coloma et al., Design and Production of Novel Tetravalent Bispecific Antibodies, Nature Biotechnology, vol. 15, No. 2, Feb. 1997, pp. 159-163.
Dall'Acqua et al., Contribution of Domain Interface Residues to the Stability of Antibody CH3 Domain Homodimers, Biochemistry, American Chemical Society, US, vol. 37, No. 26, Jun. 30, 1998, pp. 9266-9273.
Davis et al., SEEDbodies: Fusion Proteins Based on Strand-exchange Engineered Domain (SEED) CH3 Heterodimers in an Fc Analogue Platform for Asymmetric Binders or Immunofusions and Bispecific Antibodies, Protein Engineering, Design & Selection, vol. 23, No. 4, Feb. 4, 2010, pp. 195-202.
Demarest et al., Antibody Therapeutics, Antibody Engineering, and the Merits of Protein Stability, Current Opinion in Drug Discovery and Development. vol. 11, No. 5, Sep. 2008, pp. 675-687.
Demarest et al., Optimization of the Antibody CH3 Domain by Residue Frequency Analysis of IgG Sequences, Journal of Molecular Biology, vol. 335, Issue 1, Jan. 2, 2004, pp. 41-48.
Fischer, N., et al., Exploiting light chains for the scalable generation and platform purification or native human bispecific IgG. Nature Communications, Feb. 12, 2015; 6(6113):1-12.
Gramer, M. J., et al., Production of stable bispecific IgG1 by controlled Fab-arm exchange Scalability from bench to Targe-scale manufacturing by application of standard approaches. mAbs. Nov. 1, 2013;5(6):962-973.
Gunasekaran et al., Enhancing Antibody Fc Heterodimer Formation Through Electrostatic Steering Effects Applications to Bispecific Molecules and Monovalent IgG, J. Biol. Chem., vol. 285, Issue 25, Jun. 18, 2010, pp. 19637-19646.
Heads, J.T., Relative stabilities of IgG1 and IgG4 Fab Domains: Influence of the Light-Heavy interchain disulfide bond architecture. Protein Science. Jul. 2012; 21(9):1315-1322.
Huang et al., A De Novo Designed Protein Interface, Protein Science, vol. 16, No. 12, 2007, pp. 2770-2774.
Igawa et al., VH/VL Interface Engineering to Promote Selective Expression and Inhibit Conformational Isomerization of Thrombopoietin Receptor Against Single-chain Diabody, Protein Engineering, Design & Selection, vol. 23, No. 8, Aug. 2010, pp. 667-677.
Jackman et al., Development of a Two-part Strategy to Identify a Therapeutic Human Bispecific Antibody That Inhibits IgE Receptor Signaling, J Biol Chem., vol. 285, No. 27, Jul. 2, 2010, pp. 20850-20859.
Janeway et al., Structure of the Antibody Molecule and Immunoglobulin Genes, Immunology Third Edition, Garland Publishing Inc. Chapters, 1997, pp. 3:1-3:11.
Jordan et al., Structural Understanding of Stabilization Patterns in Engineered Bispecific Ig-like Antibody Molecules, Proteins: Structure, Function and Bioinformatics, vol. 77, No. 4, Dec. 1, 2009, pp. 832-841.
Kabat, E.A., et al.. Sequences of proteins of Immunological Interest. Diae publishing, 5th Ed., vol. 1, 1991, NIH Publication 91-3242 (pp. 647-657, 661-669).
Klein et al., Progress in Overcoming the Chain Association Issue in Bispecific Heterodimeric LgG Antibodies, Mabs, vol. 4, No. 6, Nov. 2012, pp. 653-663.
Lewis et al., Generation of Bispecific IgG Antibodies by Structure-Based Design of an Orthogonal Fab Interface, Nature Biotechnology, vol. 32, No. 2, Jan. 26, 2014, pp. 191-198.
Liu, Z., et al., A Novel Antibody Engineering Strategy for Making Monovalent Bispecific Heterodimeric IgG Antibodies by Electrostatic Steering Mechanism. Journal of Biological Chemistry. Mar. 2015; 290(12):7535-7562.
Lloyd, C., et al., Modelling the human immune response: performance of a 1011 human antibody repertoire against a broad panel of therapeutically relevant antigens. Peds. 2009; 22(3):159-168.

(56) References Cited

OTHER PUBLICATIONS

Lu, D et al., Fab-scFv Fusion Protein: an Efficient Approach to Production of Bispecific Antibody Fragments mailed on Journal of Immunological Methods, vol. 267, No. 2, 2002, pp. 213-226.

Merchant et al., An Efficient Route to Human Bispecific IgG, Nature Biotechnology, vol. 16, No. 7, Jul. 16, 1998, pp. 677-681.

Merk et al., Cell-Free Expression of Two single-Chain Monoclonal Antibodies against Lysozyme: Effect of Domain Arrangement on the Expression, J. Biochem., vol. 125, Dec. 31, 1999, pp. 328-333.

Miller et al.. Stability Engineering of scFvs for the Development of Bispecific and Multivalent Antibodies, Protein Engineering. Design and Selection, Oxford Journal, vol. 23, No. 7, Jul. 1, 2010, pp. 549-557.

Milstein et al., Hybrid Hybridomas and Their Use in Immunohistochemistry, Nature, vol. 305, No. 6, Oct. 6, 1983, pp. 537-540.

Moore et al., A Novel Bispecific Antibody Format Enables Simultaneous Bivalent and Monovalent Co-engagement of Distinct Target Antigens, mAbs, vol. 3, No. 6, 2011, pp. 546-557.

Osborn et al.. Pharmacokinetic and Pharmacodynamics Studies of a Human Serum Albumin-interferon-a Fusion Protein in Cynomolgus Monkeys, J. Pharamcology and Experiemental Therapeutics, vol. 330, Nov. 2002, pp. 540-548.

Padlan, E. A., et al.. Antibody Fab assembly: The interface residues between CH1 and CL. Molecular Immunology, Sep. 1986; 23(9):951-960.

Paul, Protein and Polypeptide Antigenic Determinants, Fundamental Immunology, 3d ed., 1993, 1 page.

International Application No. PCT/IB2015/054107, International Search Report and Written Opinion dated Sep. 1, 2015, 19 pages.

International Application No. PCT/CA2013/050914, International Search Report and Written Opinion dated Feb. 7, 2014, 11 pages.

Presta, et al., Engineering Therapeutic Antibodies for Improved Function, Biochem. Soc. Trans., vol. 30, No. 4, Aug. 2002, pp. 487-490.

Ridgway et al., Knobs-into-Holes' Engineering of Antibody CH3 Domains for Heavy Chain Heterodimerization, Protein Engineering, vol. 9, No. 7, Jul. 1996, pp. 617-621.

Rudikoff et al., Single Amino Acid Substitution Altering Antigen-Binding Specificity, Proc. Natl Acad Sci., vol. 79, No. 6, 1982, pp. 1979-1983.

Schaefer, W., et a., Immunoglobulin domain crossover as a generic approach for the production of bispecific IgG antibodies. PNAS, Jul. 5, 2011; 108(27):11187-11192.

Schlatter et al.. On the Optimal Ratio of Heavy to Light Chain Genes for Efficient Recombinant Antibody Production by CHO Cells, Biotechnology Progress, vol. 21, No. 1, Jan.-Feb. 2005, pp. 122-133.

Segal et al.. Introduction: Bispecific Antibodies, Journal of Immunological Methods, vol. 248, No. 1-2, Feb. 1, 2001, pp. 1-6.

Shields et al.. High Resolution Mapping of the Binding Site on Human IgG1 for Fc Gamma RI, Fc Gamma RII, Fc Gamma RIII, and FcRn and Design of IgG1 Variants With Improved Binding to the Fc Gamma R, Journal of Biological Chemistry, vol. 276, No. 9, Mar. 2, 2001, pp. 6591-6604.

Spreter Von Kreudenstein, T., et al., Improving biophysical properties of a bispecific antibody scaffold to aid developability. Sep./Oct. 2013, mAbs, vol. 5, No. 5, pp. 646-654.

Spreter Von Kreudenstein, T., et al., Protein engineering and the use of molecular modeling and simulation the case of heterodimeric Fc engineering. Methods. Jan. 1, 2014; 65(1):77-94.

Stanglmaier et al., Bi20 (fBTA05), a Novel Trifunctional Bispecific Antibody (Anti-CD20 X Anti-CD3), Mediates Efficient Killing of B-cell Lymphoma Cells Even with Very Low CD20 Expression Levels, International Journal of Cancer, vol. 123, 2008, pp. 1181-1189.

Strop, P., et al.. Generating bispecific human IgG1 and IgG2 antibodies from any antibody pair. J Mol Biol. Jul. 13, 2012; 420(3):204-219.

Suresh et al., Bispecific Monoclonal Antibodies From Hybrid Hybridomas, Methods in Enzymology, vol. 121, 1986, pp. 210-228.

Tamaskovic et al.. Designed Ankyrin Repeat Proteins (DARPins): From Reserach to Therapy, Methods in Enzymology, vol. 503, 2012, pp. 101-134.

Traunecker et al., Bispecific Single Chain Molecules (Janusins) Target Cytotoxic Lymphocytes on HIV Infected Cells, EMBO Journal, vol. 10, No. 12, Dec. 1991, pp. 3655-3699.

Zhu et al.. Remodeling Domain Interfaces to Enhance Heterodimer Formation, Protein Science, vol. 6, No. 4, Apr. 1997, pp. 781-788.

U.S. Appl. No. 15/409,456, Final Office Action dated Oct. 24, 2019.

U.S. Appl. No. 15/409,456, Final Office Action dated May 13, 2020.

U.S. Appl. No. 15/409,456, Notice of Allowance dated Aug. 27, 2020.

U.S. Appl. No. 15/896,170, Final Office Action dated Feb. 1, 2021.

U.S. Appl. No. 15/896,170, Notice of Allowance dated Mar. 30, 2021.

U.S. Appl. No. 15/314,496, Non-Final Office Action dated Mar. 30, 2021.

U.S. Appl. No. 15/765,574, Notice of Allowance dated Jan. 27, 2021.

U.S. Appl. No. 15/765,574 Supplemental Notice of Allowability dated Apr. 26, 2021.

U.S. Appl. No. 16/568,611 Application dated Sep. 12, 2019.

U.S. Appl. No. 17/107,217 Application dated Nov. 30, 2020.

Feng, et al., "Dual function antibody drug substance research study progress", Chin Med Biotechnol, Aug. 2014, vol. 9, No. 4., pp. 1-6.

* cited by examiner

Figure 1

| Co-expression set | | Mutations from wild-type | | Mutations from wild-type | | Competition assay screen results | | | Competition assay verification results | |
|---|---|---|---|---|---|---|---|---|---|---|
| | | Variable domain (VH:VL) | | | | | | | | |
| Set # | Set # | H1 mutation | L1 mutation | H2 mutation | L2 mutation | H1_L1:H1_L2 | H2_L2:H2_L1 | | | |
| V001 | V002 | V37W_W103H* | F98L | V37I | F98W | 57.22:30.0 | 65.71:21.67 | | 62.29:30.52 | |
| V001 | V003 | V37W_W103H | F98L | WT | F98W | 57.22:30.0 | 74.2:27.76 | | 62.29:30.52 | 50.8:23.6 |
| V004 | V005 | V37W_W103H | F98L | V37A_W103H | P44W | 48.27:29.21 | 66.54:6.378 | | 56.02:21.18 | |
| V006 | V002 | V37W_W103H | F98L | V37I | F98W | 64.17:14.8 | 65.71:21.67 | | 38.2:27.7 | |
| V006 | V003 | V37W_W103F | F98L | WT | F98W | 64.17:14.8 | 74.2:27.76 | | 38.2:27.7 | 50.8:23.6 |
| V007 | V008 | V37W | F98A | V37I | F98W | 62.4:23.5 | 66.51:30.86 | | 61.5:23.4 | |
| V009 | V010 | V37W | F98A | V37I | WT | 64.1:28.8 | 72.56:28.69 | | | |
| V011 | V012 | V37I | WT | F100W | F98L | 78.51:7.343 | 56.83:29.68 | | | 38.9:44.9 |
| V013 | V014 | V37A_W103V | P44W | V37W | F98A | 58.9:25.3 | 83.08:29.68 | | | |
| V015 | V014 | V37A_W103H | P44W | V37W | F98A | 67.47:8.787 | 83.08:9.413 | | 47.07:12.28 | |
| V016 | V017 | V37A_W103H | P44W | V37A_W103V | F98W | 53.6:19.59 | 52.96:18.56 | | | 23.3:44.7 |
| V018 | V005 | V37A_W103H | P44W | V37A_W103V | F98L | 66.54:6.378 | 54.8:22.76 | | | 52.0:23.0 |
| V019 | V005 | V37A_W103H | P44W | V37I_F100W | F98L | 66.54:6.378 | 67.33:26.86 | | | 30.5:47.9 |
| V020 | V021 | L45W | Y87G | V37A_W103H | P44W | 54.53:23.86 | 53.1:18.9 | | 58.1:31.0 | |
| V022 | V007 | WT | F98W | V37W | F98A | 67.1:28.7 | 62.4:23.5 | | 67.1:28.7 | 61.5:23.4 |
| V023 | V009 | WT | WT | V37W | F98A | 84.5:7.5 | 64.1:28.8 | | | |
| V024 | V026 | Q39R | Q38E | V37W | F98A | 82.55:4.303 | 65.9:8.054 | | 76.6:4.0 | 70.5:10.3 |
| V025 | V027 | Q39R | Q38E | WT | WT | 66.36:19.12 | 58.83:32.93 | | 68.7:21.8 | 57.9:36.9 |
| V028 | V029 | Q39R | Q38E | Q39E | Q38E | 71.07:22.74 | 65.35:29.89 | | 85.1:8.4 | 62.7:30.2 |
| V030 | V031 | Q39R | Q38D | Q39E | Q38R | 73.3:10.75 | 60.01:18.02 | | | |
| V032 | V033 | Q39M | Q38M | Q39R | Q38E | 69.64:33.29 | 68.33:23.52 | | 60.2:31.3, 58.8:40.6 | 82.9:17.3, 70.6:27.4 |
| V034 | V035 | Q39K | Q38N_T85E | Q39D | Q38N_T85K | 54.77:30.08 | 71.7:27.38 | | | |
| V034 | V036 | Q39K | Q38N_T85E | Q39E | Q38N_T85K | 54.77:30.08 | 71.93:30.37 | | 66.45:21.72 | 59.09:33.49 |
| V037 | V038 | Q39E | Q38R | V37W | F98A | 47.62:29.67 | 48.92:26.84 | | 75.17.2 | 47.8:26.7 |
| V039 | V030 | Q39D | Q38R | Q39R | Q38D | 66.92:34.51 | 73.3:10.75 | | 61.8:31.1 | 85.2:11.1 |
| V040 | V041 | V37E | L89R_F98T | WT | WT | 54.1:25.0 | 78.0:2.2 | | 90.9:16.5 | 89.8:4.6 |
| V042 | V043 | V37E_F100D | L89R_F98W | WT | WT | 98.7:4.2 | 85.2:6.2 | | 118.6:4.5 | 83.1:14.1 |
| V044 | V045 | V37E_F100D | L89R_F98W | V37S_A97K | F98Y | 67.8:24.4 | 71.6:0.5 | | 76.3:18.1 | 65.6:11.7 |

*Kabat numbering. #WT: Wild-type D3H44 HC (with C-terminus ABD2-His₆ tag) or wild-type D3H44 LC (with a N-terminus HA or FLAG tag).

Figure 2

| Co-expression set | | Mutations from wild-type Constant domain (CH1:CL) | | | | | Competition assay screen results | | Competition assay verification results | |
|---|---|---|---|---|---|---|---|---|---|---|
| Set # | Set # | H1_mutation* | L1_mutation | H2_mutation | L2_mutation | | H1_L1:H1_L2 | H2_L2:H2_L1 | | |
| C500 | C501 | WT | WT | A139W_V190S | F116A | | 67.8:26.3 | 66.92:21.06 | | 43.0:22.3 |
| C500 | C502 | WT | WT | A139W_V190A | F116A | | 67.8:26.3 | 74.52:17.84 | | 51.4:19.7 |
| C503 | C504 | WT | WT | F100W | F98L | | 71.22:13.34 | 56.83:29.68 | | 38.9:44.9 |
| C505 | C506 | A139W_V190S | F116S | A139W | F118W_V133S | | 84.85:15.74 | 76.51:4.6 | 55.4:20.2 | 38.1:40.9 |
| C507 | C508 | A139W_V190S | F116A | A139V | F118W_V133S | | 68.74:33.42 | 63.92:35.74 | 83.78:0.722 | 24.5:56.1 |
| C509 | C501 | A139W | WT | A139W_V190S | F116A | | 58.7:30.5 | 66.92:21.06 | | 43.0:22.3 |
| C509 | C502 | A139W | WT | A139W_V190A | F116A | | 58.7:30.5 | 74.52:17.84 | | 51.4:19.7 |
| C510 | C508 | A139V_V190S | F116A | A139V | F118W_V133S | | 68.66:35.07 | 63.92:35.74 | 42.12:10.05 | 24.5:56.1 |
| C511 | C512 | A139V_V190S | WT | A139I | F118W_V133S | | 58.8:35.25 | 51.87:28.86 | 52.18:8.664 | |
| C513 | C508 | A139I_V190S | F116A | A139V | F118W_V133S | | 64.68:25.15 | 63.92:35.74 | 59.82:0.7587 | 24.5:56.1 |
| C514 | C512 | A139I_V190S | WT | A139I | F118W_V133S | | 67.09:28.03 | 51.87:28.86 | 77.0:8.2 | |
| C515 | C516 | A139G_V190A | L135W_N137A | A139W | F116A_L135A | | 70.46:5.156 | 73.59:19.83 | | |
| C517 | C518 | A139G_V190A | L135W | A139W | F116A_L135A | | 65.02:10.13 | 77.41:17.4 | 69.49:10.64 | 78.7:10.16 |
| C519 | C520 | A139G_V190A | L135W | A139W | F116A_L135V | | 68.43:13.76 | 62.66:34.63 | 49.05:48.32 | 76.67:19.07 |
| C521 | C522 | S188I | WT | WT | S176V_T178L | | 61.87:41.89 | 99.36:0.0 | | |
| C523 | C508 | V190G | F116A | A139V | F118W_V133S | | 55.06:35.32 | 63.92:35.74 | | 56.1:24.5 |
| C524 | C506 | V190G | F116S | A139W | F118W_V133S | | 78.25:24.05 | 76.51:4.6 | 25.9:50.8 | 40.9:38.1 |
| C525 | C526 | S188L_V190Y | V133S | F174V_P175S_S188G | S176L | | 90.03:7.72 | 81.12:1.44 | 81.2:12.4 | 68.1:2.9 |
| C527 | C528 | F174V_P175S_S188G | S176L | F174V_S188L | S176L | | 53.39:9.68 | 102.9:5.94 | | |
| C527 | C529 | F174V_P175S_S188G | S176L | S188L | WT | | 53.39:9.68 | 92.45:9.32 | | |
| C530 | C531 | D146G_Q179R | Q124E_Q160E_T178D | K145T_Q179D_S188L | Q160K_T178R | | 86.7:1.4 | 71.0:7.2 | 97.0:0.9 | 74.3:20.0 |
| C532 | C533 | L143A_D144G_Q179R | Q124E_V133W_Q160E_T180E | K145T_Q179D_S188F | V133A_Q160K_T178R | | 97.4:0.4 | 87.3:1.5 | 93.6:0.6 | 83.2:11.5 |

*Kabat numbering. *WT: Wild-type D3H44 HC (with C-terminus ABD2-His6 tag) or wild-type D3H44 LC (with a N-terminus HA or FLAG tag).

Figure 3

| Heterodimer | Mutations from wild-type | | | Corresponding Co-expression Set # | | Tm (°C) | Antigen affinity (M)^ |
|---|---|---|---|---|---|---|---|
| | H1_mutation | L1_mutation | | Paired | Mispaired | | |
| WT#(940) | - | - | | - | - | 76.0 | $3.30 \times 10^{-11}$ |
| HD100 | Q39E | Q38R | | V029, V031, V037 | | 72.9 | $1.26 \times 10^{-10}$ |
| HD101 | Q39E | Q38E | | | V029 | 67.4 | $2.32 \times 10^{-11}$ |
| HD102 | Q39R | Q38E | | V028, V033, V026, V024 | | 72.8 | $5.53 \times 10^{-11}$ |
| HD103 | Q39R | Q38R | | | V028, V030 | 66.5 | $6.53 \times 10^{-11}$ |
| HD104 | V37A_W103H | P44W | | V015, V005, V016 | | 56.2 | $7.70 \times 10^{-10}$ |
| HD105 | V37W | F98A | | V009, V007, V014, V038, V025 | | 76.9 | $9.77 \times 10^{-10}$ |
| HD106 | V37W | P44W | | | V014 | 64.5 | $8.31 \times 10^{-09}$ |
| HD107 | A139G_V190A | L135W_N137A | | C515 | | 70.7 | $3.91 \times 10^{-11}$ |
| HD108 | A139G_V190A | F116A_L135A | | | C517, C515 | 60.1 | $6.45 \times 10^{-11}$ |
| HD109 | A139W | F116A_L135A | | C516, C518 | | 72.5 | $5.06 \times 10^{-11}$ |
| HD110 | S188H | S176G_T178V | | | | 74.3 | $4.03 \times 10^{-11}$ |
| HD111 | S188H | S176L_T178S | | | | 75.2 | $7.68 \times 10^{-11}$ |
| HD112 | V37W_W103H | F98L | | V001, V004 | | 60.9 | $5.17 \times 10^{-09}$ |
| HD113 | V37W_W103H | F98W | | | V001 | 61.5 | $3.24 \times 10^{-09}$ |
| HD114 | V37I | F98W | | V002, V008 | | 75.8 | $3.93 \times 10^{-11}$ |
| HD115 | V37I | F98L | | | V002, V011 | 70.0 | $2.42 \times 10^{-10}$ |

WT: Wild-type tagged D3H44 Fab. HC tag is a C-terminus ABD2-His$_6$ tag. LC tag is a N-terminus HA or FLAG tag.
^Antigen used: Tissue Factor extracellular domains

```
           FR1                                      CDR1        FR2              CDR2                    FR3
                                                                 # #             
                                                                 + +             
D3H44   EVQLVESGGGLVQPGGSLRLSCAASGFNI              KE---YMH   WVRQAPGKGLEWVG   LIDP---EQGNTIYDPKFQD   RATISADNSKNTAYLQMNSLRAEDTAVYYCAR
        ************************                    *  *    ************                *            ****  * **  ***********************+

VH1     QVQLVQSGAEVKKPGASVKVSCKASGYTF              TG---YMH   WVRQAPGQGLEWMG   WINP--NSGGTNYAQKFQG    RVTMTRDTSISTAYMELSRLRSDDTAVYYCAR
VH2     QITLKESGPTLVKPTQTLTLTCTFSGFSL              STSGVGVG   WIRQPPGKALEWLA   LIY----WNDDKRYSPSLKS   RLTITKDTSKNQVVLTMTNMDPVDTATYYCAHR
VH3     EVQLVESGGGLVQPGGSLRLSCAASGFTF              SS---YWMS   WVRQAPGKGLEWVA   NIKQ--DGSEKYYVDSVKG    RFTISRDNAKNSLYLQMNSLRAEDTAVYYCAR
VH4     QVQLQESGPGLVKPSGTLSLTCAVSGGSI              SSS-NWWS    WVRQPPGKGLEWIG   EIY----HSGSTNYNPSLKS   RVTISVDKSKNQFSLKLSSVTAADTAVYYCAR
VH5     EVQLVQSGAEVKKPGESLKISCKGSGYSF              TS---YWIG   WVRQMPGKGLEWMG   IIYP--GDSDTRYSPSFQG    QVTISADKSISTAYLQWSSLKASDTAMYYCAR
VH6     QVQLQQSGPGLVKPSQTLSLTCAISGDSV              SSNSAAWN    WIRQSPSRGLEWLG   RTYYR-SKWYNDYAVSVKS    RITINPDTSKNQFSLQLNSVTPEDTAVYYCAR
VH7     QVQLVQSGSELKKPGASVKVSCKASGYTF              TS---YAMN   WVRQAPGQGLEWMG   WINT--NTGNPTYAQGFTG    RFVFSLDTSVSTAYLQICSLKAEDTAVYYCAR
```

```
             CDR3
                 # #
                 + +
D3H44   -DTAAYFDYWGQGTLVTVSS
         ** ****** *****

IGHJ1*01  ----AEYFQHWGQGTLVTVSS
IGHJ2*01  ----YWYFDLWGRGTLVTVSS
IGHJ3*02  -----DAFDIWGQGTMVTVSS
IGHJ4*01  -------YFDYWGQGTLVTVSS
IGHJ5*02  ----NWFDPWGQGTLVTVSS
IGHJ6*01  YYYYYGMDVWGQGTTVTVSS
```

Figure 6B

VL (kappa)

```
              FR1                            CDR1              FR2           CDR2              FR3                    CDR3
              ----------------------------   ------------      ---------     -------           ----------------------------------------   -------
                                                               # #           # #                                                          #
                                                                 +             +                                                  +       +
D3H44         DIQMTQSPSSLSASVGDRVTITC        RASRDIKS------YLN  WYQQKPGKAPKVLIY  YATSLAE        GVPSRFSGSGSGTDYTLTISSLQPEDFATYYC          LQHGESP
              **********************         ***      ***      ************* *  *  **          *******************************          *

VKI           DIQMTQSPSSLSASVGDRVTITC        RASQSISS------YLN  WYQQKPGKAPKLLIY  AASSLQS        GVPDRFSGSGSGTDFTLTISSLQPEDFATYYC          QQSYSTP
VKII          DIVMTQTPLSLPVTPGEPASISC        RSSQSLLDSDDGNTYLD  WYLQKPGQSPQLLIY  TLSYRAS        GVPDRFSGSGSGTDFTLKISRVEAEDVGVYYC          MQRIEFP
VKIII         EIVLTQSPGTLSLSPGERATLSC        RASQSVSSS-----YLA  WYQQKPGQAPRLLIY  GASSRAT        GIPDRFSGSGSGTDFTLTISRLEPEDFAVYYC          QQYGSSP
VKIV          DIVMTQSPDSLAVSLGERATINC        KSSQSVLYSSNNKNYLA  WYQQKPGQPPKLLIY  WASTRES        GVPDRFSGSGSGTDFTLTISSLQAEDVAVYYC          QQYYSTP
VKV           ETTLTQSPAFMSATPGDKVNISC        KASQDIDD-------DMN WYQQKPGEAAIFIIQ  EATTLVP        GIPPRFSGSGYGTDFTLTINNIESEDAAYYFC          LQHDNFP
VKVI          EIVLTQSPDFQSVTPKEKVTITC        RASQSIGS-------SLH WYQQKPDQSPKLLIK  YASQSFS        GVPSRFSGSGSGTDFTLTINSLEAEDAATYYC          HQSSSLP
```

```
          CDR3
          -----------
            #
            +
D3H44     WTFGQGTKVEIK
          ***********

IGKJ1*01  WTFGQGTKVEIK
IGKJ2*01  YTFGQGTKLEIK
IGKJ3*01  FTFGPGTKVDIK
IGKJ4*01  LTFGGGTKVEIK
IGKJ5*01  ITFGQGTRLEIK
```

Figure 6C

VL (lambda)

|  | FR1 | CDR1 | FR2 | CDR2 | FR3 | CDR3 |
|---|---|---|---|---|---|---|
|  |  |  | # # | | + + | # |
|  |  |  | + + | | + + | + |
| D3H44 | DIQMTQSPSSLSASVGDRVTITC | R--AS--RDIKS--YLN | WYQQKPGKAPKVLIY | YATS------LAE | GVPSRFSGSG---SGTDYTLTISSLQPEDFATYYC | LQHGESP------ |
|  | ** *** * | * | ***** ******* | * | ** ****** ** ** *** | * |
| VLI | QSVLTQPPS-VSEAPRQRVTISC | SGSS-SNIGNNAVN | WYQQLPGKAPKLLIY | YDDL------LPS | GVSDRFSGSK---SGTSASLAISGLQSEDEADYYC | AAWDDSLNG-- |
| VLII | QSALTQPPS-ASGSPGQSVTISC | TGTSSDVGGYNYVS | WYQQHPGKAPKLMIY | EVSK------RPS | GVPDRFSGSK---SGNTASLTVSGLQAEDEADYYC | SSYAGSNNF-- |
| VLIII | SYELTQPPS-VSVSPGQTASITC | SGDK----LGDKYAC | WYQQKPGQSPVLVIY | QDSK------RPS | GIPERFSGSN---SGNTATLTISGTQAMDEADYYC | QAWDSSTA--- |
| VLIV | LPVLTQPPS-ASALLGASIKLTC | TLSS--EHSTYTIE | WYQQRPGRSPQYIMK | VKSDGSH-SKGD | GIPDRFMGSS---SGADRYLTFSNLQSDEAEYHC | GESHTIDGQVG |
| VLV | QPVLTQPPS-SSASPGESARLTC | TLPSDINVGSYNIY | WYQQKPGSPPRYLLY | YYSDSDK-GQGS | GVPSRFSGSKDASANTGILLISGLQSEDEADYYC | MIWPSNAS--- |
| VLVI | NFMLTQPHS-VSESPGKTVTISC | TRSS-GSIASNYVQ | WYQQRPGSSPTTVIY | EDNQ------RPS | GVPDRFSGSIDSSSNSASLTISGLKTEDEADYYC | QSYDSSN---- |
| VLVII | QTVVTQEPS-LTVSPGGTVTLTC | ASSTGAVTSGYYEN | WFQQKPGQAPRALIY | STSN------KHS | WTPARFSGSLLG---GKAALTLSGVQPEDEAEYYC | LLYYGGAQ--- |
| VLVIII | QTVVTQEPS-FSVSPGGTVTLTC | GLSSGVSTSYYPS | WYQQTPGQAPRTLIY | STNT------RSS | GVPDRFSGSILG---NKAALTITGAQADDESDYYC | VLYMGSGI--- |
| VLIX | QPVLTQPPS-ASASLGASVTLTC | TLSS--GYSNYKVD | WYQQRPGKGPRFVMR | VGTGGIVGSKGD | GIPDRFSVLG---SGLNRYLTIKNIQEEDESDYHC | GADHGSGSNFV |
| VLX | QAGLTQPPS-VSKGLRQTATITC | TGNS-NNVGNQGAA | WLQQHQGHPPKLLSY | RNNN------RPS | GISERLSASR---SGNTASLITTGLQPEDEADYYC | SAWDSSLSA-- |

|  | CDR3 |
|---|---|
|  | # |
|  | + |
| D3H44 | WTFGQGTKVEIK |
|  | ** ***** |
| IGLJ1*01 | YVFGTGTKVTVL |
| IGLJ2*01 | VVFGGGTKLTVL |
| IGLJ3*01 | VVFGGGTKLTVL |
| IGLJ4*01 | FVFGGGTQLIIL |
| IGLJ5*01 | WVFGEGTELTVL |
| IGLJ6*01 | NVFGSGTKVTVL |
| IGLJ7*01 | AVFGGGTQLTVL |

```
D3H44      ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV(EPKSCDKTHT)
           ***************************************************************************************************+
                     #        #    + + +  ++                                    #                                   +
                     ++                                                         ++     +++
IGHG1*01   ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV
IGHG1*03   ..................................................................................................R.
IGHG3*06   ...........C.R....................................................T..............................R.
IGHG3*18   ...........C.R....................................................T..............................R.
IGHG3*17   ...........C.R..........................................Y.........T..............................R.
IGHG2*04   ...........C.R:.ES................................................NF.........K.T:.....D.........R.
IGHG4*01   ...........C.R:.ES.................................................................T:.....D.........T.
IGHG2*03   ...........C.R:.ES.................................................NF..............T:.....D.........T.
IGHG2*02   ...........C.R:.ES...............................................T.NF..............T:.....D.........T.
```

: identical residues to that of IGHG1*01

Figure 6E

CL (kappa)

```
                                   ##              #  #                                  +   +++
                          +  + +   ++              +  +                                  +   +++
D3H44     RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC
          **************************************************************************************************
IGKC*01   RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC
IGKC*04   ................................................................L.................................
IGKC*05   ..............................................................N...................................
IGKC*02   ..............................................E.....................................G.............
IGKC*03   .............................R...................E................................................
```

: identical residues to that of IGKC*01

CL (lambda)

```
                                   ##              #  #                                  +   +++
                          +  + +   ++              +  +                                  +   +++
D3H44     RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC-
          *  ****   ***    ***       ***                 *      *               *  *                          **
IGλC1     -PKANPTVTLFPPSSEELQANKATLVCLISDFYPGAVTVAWKADGSPVKAGVETTKPSKQS-NNKYAASSYLSLTPEQWKSHRSYSCQVTHEG--STVEKTVAPTECS
IGλC7     Q:::...A:S:::::::::::::::::::::::::::::::::::::::::::S::::::::::::::::::::::::::::::::::::::::::::::::::::
IGλC2     Q:::...A:S:::::::::::::::::::::::::::::::::::::::::::S::::::T::::::::::::::::::::::::::::::::::::::A::::::
IGλC3     :::::::A:S::::::::::::::::::::::::::::::::::::::::::NT::::::T:::::::::::::::::::::::K:::::::::::::::::::::
IGλC6     Q:::...A:S:::::::::::::::::::::::::::::::::::::K::::NT::::::T::::::::::::::::::::::::::::::::::::::A::::::
```

: identical residues to that of IGλC1

Assay Requirements:

Engineering Goal: H1-L1 + H2-L2 + H1-L2 + H2-L1

→ Quantification of H1-L1 : H1-L2 and H2-L2 : H2-L1 ratios →

Assay Requirement:

Simplified Assay:
1. H1 + L1 + L2 ⇒ H1-L1 + H1-L2
2. H2 + L2 + L1 ⇒ H2-L2 + H2-L1

Separate Quantification of

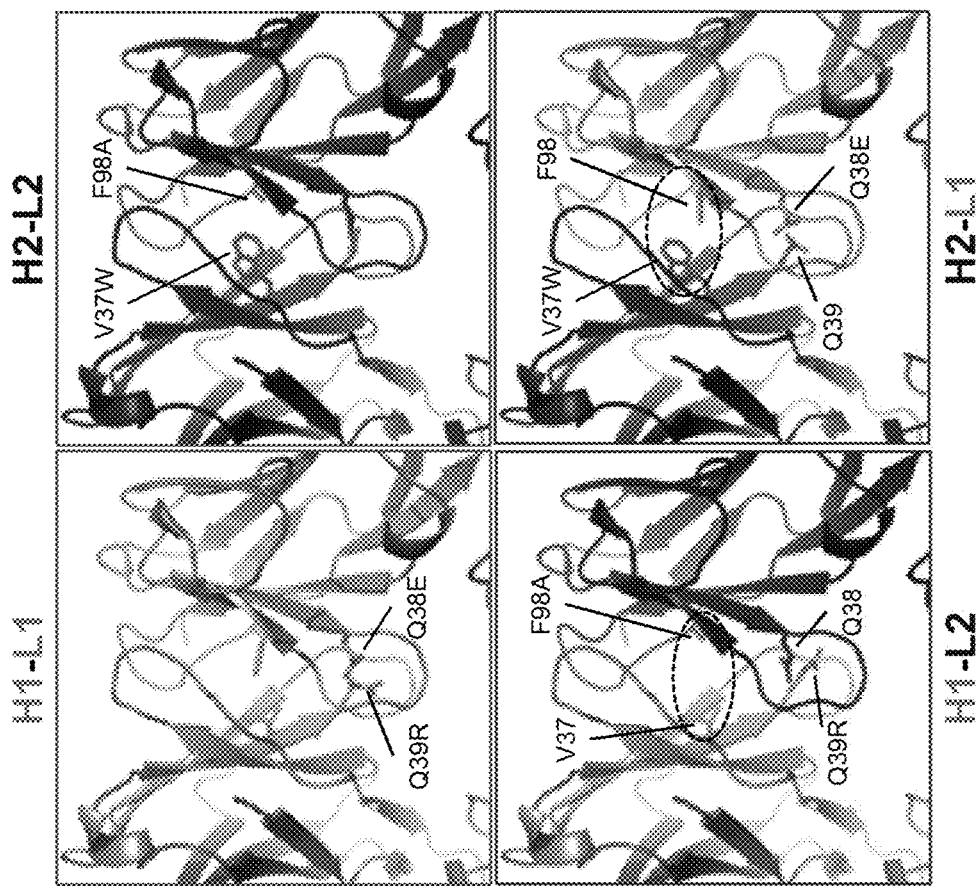
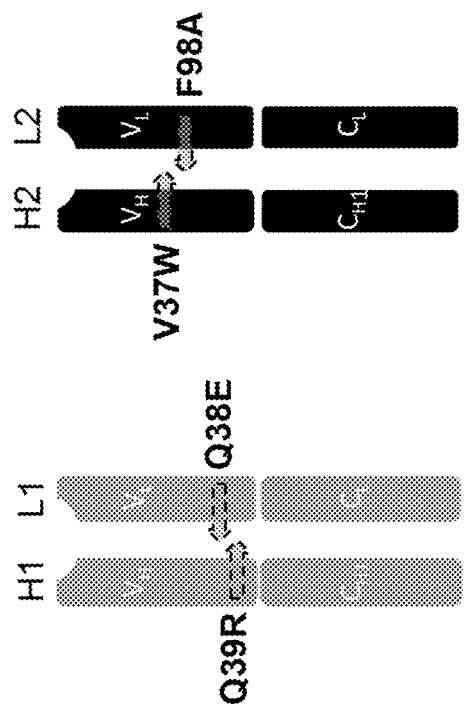
Figure 11

17A

17B

SEQUENCE LISTING

```
<160> NUMBER OF SEQ ID NOS: 85

<210> SEQ ID NO 1
<211> LENGTH: 217
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
```

```
                145                 150                 155                 160
Tyr Lys Thr Thr Pro Pro Val Leu Asp Ser Asp Gly Ser Phe Phe Leu
                    165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      Penta His tag

<400> SEQUENCE: 3

His His His His His
1               5

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Lys Ser Tyr
                20                  25                  30

Leu Asn Trp Tyr Gln Gln Lys Pro Gly Lys Ala Pro Lys Val Leu Ile
            35                  40                  45

Tyr Tyr Ala Thr Ser Leu Ala Glu Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 7
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 8
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ala Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 9
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
          195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 10
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln

```
                100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 11
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Gln Ser Gly Gly Gly Leu Val Lys Pro Gly Gly
```

```
1               5                   10                  15
Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly
        435                 440                 445

<210> SEQ ID NO 12
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gccaccatgg ccgtgatggc tcctagaacc ctggtgctgc tgctgtctgg agctctggct      60
ctgactcaga cctgggctgg agaggtgcag ctggtggaaa gcggaggagg actggtgcag    120
ccaggaggat ctctgcgact gagttgcgcc gcttcaggat caacatcaa ggacacctac     180 attcactggg tgcgacaggc tccaggaaaa ggactggagt gggtggctcg aatctatccc    240
actaatggat acacccggta tgccgactcc gtgaagggga ggtttactat tagcgccgat    300
acatccaaaa acactgctta cctgcagatg aacagcctgc gagccgaaga taccgctgtg    360
tactattgca gtcgatgggg aggagacgga ttctacgcta tggattattg gggacagggg    420
accctggtga cagtgagctc cgcctctacc aagggcccca gtgtgtttcc cctggctcct    480
tctagtaaat ccacctctgg agggacagcc gctctgggat gtctggtgaa ggactatttc    540
cccgagcctg tgaccgtgag ttggaactca ggcgccctga agcggagt gcacactttt     600 cctgctgtgc tgcagtcaag cgggctgtac tccctgtcct ctgtggtgac agtgccaagt    660
tcaagcctgg gcacacagac ttatatctgc aacgtgaatc ataagccctc aaatacaaaa    720
gtggacaaga agtggagcc caagagctgt gataagaccc acacctgccc tcccgtccca    780
gctccagaac tgctgggagg acctagcgtg ttcctgtttc cccctaagcc aaaagacact    840
ctgatgattt ccaggactcc cgaggtgacc tgcgtggtgg tggacgtgtc tcacgaggac    900
cccgaagtga agttcaactg gtacgtggat ggcgtggaag tgcataatgc taagacaaaa    960
ccaagagagg aacagtacaa ctccacttat cgcgtcgtga gcgtgctgac cgtgctgcac   1020
caggactggc tgaacgggaa ggagtataag tgcaaagtca gtaataaggc cctgcctgct   1080
ccaatcgaaa aaaccatctc taaggccaaa ggccagccaa gggagcccca ggtgtacaca   1140
ctgccaccca gcagagacga actgaccaag aaccaggtgt ccctgacatg tctggtgaaa   1200
ggcttctatc ctagtgatat tgctgtggag tgggaatcaa atggacagcc agagaacaat   1260
tacaagacca cacctccagt gctggacagc gatggcagct tcttcctgta ttccaagctg   1320
acagtggata atctcgatg gcagcagggg aacgtgttta ttgttcagt gatgcatgaa    1380 gccctgcaca atcattacac tcagaagagc ctgtccctgt ctcccggctg a           1431

<210> SEQ ID NO 13
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gccactatgg ctgtgatggc ccctaggacc ctggtgctgc tgctgtccgg agctctggct      60
ctgactcaga cctgggctgg agacatccag atgacccagt ctccatcctc cctgtctgca    120
tctgtaggag acagagtcac catcacttgc cgggcaagtc aggacgttaa caccgctgta    180
```

| | |
|---|---|
| gcttggtatc agcagaaacc agggaaagcc cctaagctcc tgatctattc tgcatccttt | 240 |
| ttgtacagtg gggtcccatc aaggttcagt ggcagtcgat ctgggacaga tttcactctc | 300 |
| accatcagca gtctgcaacc tgaagatttt gcaacttact actgtcaaca gcattacact | 360 |
| accccaccca ctttcggcca agggaccaaa gtggagatca aacgaactgt ggctgcacca | 420 |
| tctgtcttca tcttcccgcc atctgatgag cagttgaaat ctggaactgc ctctgttgtg | 480 |
| tgcctgctga taacttcta tcccagagag gccaaagtac agtggaaggt ggataacgcc | 540 |
| ctccaatcgg gtaactccca agagagtgtc acagagcagg acagcaagga cagcacctac | 600 |
| agcctcagca gcaccctgac gctgagcaaa gcagactacg agaaacacaa agtctacgcc | 660 |
| tgcgaagtca cccatcaggg cctgagctcg cccgtcacaa agagcttcaa caggggagag | 720 |
| tgttga | 726 |

<210> SEQ ID NO 14
<211> LENGTH: 1419
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

| | |
|---|---|
| gccaccatgg ccgtgatggc tcctagaaca ctggtcctgc tgctgtcagg ggcactggca | 60 |
| ctgactcaga cttgggctgg ggaggtccag ctggtccagt ccggaggagg actggtgaag | 120 |
| cctggaggga gtctgcgact gtcatgcgcc gctagcgggt tcacctttag ctcctacagc | 180 |
| atgaactggg tgcgacaggc accaggcaaa ggactggaat gggtgtctag tatctcaagc | 240 |
| tcctctagtt acatctacta tgcagacagc gtgaagggcc ggttcaccat cagcagagat | 300 |
| aacgccaaaa attccctgta tctgcagatg aacagcctgc gagccgagga caccgctgtc | 360 |
| tactattgcg cacgggtgac agacgccttc gatatttggg gacagggcac catggtcaca | 420 |
| gtgtcaagcg cctccaccaa gggaccaagc gtgttcccac tggctccatc ctctaaaagc | 480 |
| acttccggag gaaccgcagc cctgggatgt ctggtgaagg attactccc agagcccgtc | 540 |
| acagtgtcat ggaacagcgg ggctctgacc tctggagtcc acacatttcc agcagtgctg | 600 |
| cagagttcag gactgtacag cctgagctcc gtggtcacag tgccctctag ttcactgggc | 660 |
| actcagacct atatctgcaa cgtgaatcac aagccaagca atactaaagt cgacaagaaa | 720 |
| gtggaaccca gtcctgtga taaaacacat acttgcccac cttgtcctgc accagagctg | 780 |
| ctgggaggac catccgtgtt cctgtttcca cccaagccta agacactct gatgatttct | 840 |
| aggcacaccc g aagtcacttg cgtggtcgtg gacgtgagcc acgaggaccc cgaagtcaag | 900 |
| tttaactggt acgtggatgg cgtcgaggtg cataatgcta agacaaaacc tagggaggaa | 960 |
| cagtacaaca gtacatatag agtcgtgtca gtcctgactg tgctgcatca ggactggctg | 1020 |
| aacggaaagg aatataagtg caaagtgagc ataaggctc tgcccgcacc tatcgagaaa | 1080 |
| actatttcca aggctaaagg ccagcctaga gaaccacagg tgtacaccct gcctccatct | 1140 |
| agggacgagc tgactaagaa ccaggtcagt ctgacctgtc tggtgaaagg cttctatcct | 1200 |
| agcgatatcg cagtggagtg ggaatccaat gggcagccag agaacaatta caagaccaca | 1260 |
| cccctgtgc tggactccga tgggtcttt tttctgtata gtaagctgac cgtcgataaa | 1320 |
| tcacggtggc agcagggaaa cgtgttcagc tgtagtgtca tgcacgaagc actgcacaat | 1380 |
| cattacaccc agaagagcct gtcactgtca cccggatga | 1419 |

<210> SEQ ID NO 15
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | | | | | |
|---|---|---|---|---|---|
| gccaccatgg | ctgtgatggc | acctagaaca | ctggtcctgc | tgctgtccgg | ggcactggca | 60 |
| ctgactcaga | cttgggctgg | cgatattcag | atgacccaga | gtccaagctc | cgtgtccgcc | 120 |
| tctatcggcg | accgagtcac | cattacatgc | agagctagcc | agggcatcga | taactggctg | 180 |
| gggtggtacc | agcagaagcc | tggaaaagcc | ccaaagctgc | tgatctacga | cgcttccaat | 240 |
| ctggatacag | gcgtgccctc | taggttcagt | ggctcaggga | gcggaactta | ctttactctg | 300 |
| accatctcta | gtctgcaggc | tgaggacttc | gcagtgtatt | tttgccagca | ggcaaaagcc | 360 |
| ttcccccta | cctttggcgg | gggaacaaaa | gtcgacatca | gggggaccgt | ggccgctccc | 420 |
| tcagtcttca | tttttccacc | cagcgatgag | cagctgaagt | ctggaacagc | cagtgtggtc | 480 |
| tgtctgctga | acaatttcta | ccctcgggaa | gcaaagtgc | agtggaaggt | cgacaacgcc | 540 |
| ctgcagtccg | gcaacagcca | ggagagtgtg | actgaacagg | actcaaaaga | tagcacctat | 600 |
| tccctgtcaa | gcacactgac | tctgtccaag | gctgattacg | aaaagcacaa | agtgtatgca | 660 |
| tgtgaggtca | cccatcaggg | gctgtcaagt | ccagtcacaa | aaagtttcaa | ccgaggagag | 720 |
| tgctga | | | | | | 726 |

<210> SEQ ID NO 16
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

| | | | | | |
|---|---|---|---|---|---|
| gccacaatgg | ccgtgatggc | tcctagaaca | ctggtcctgc | tgctgtccgg | ggctctggct | 60 |
| ctgactcaga | cttgggctgg | ggaggtgcag | ctggtcgaat | ctggaggagg | actggtgcag | 120 |
| ccaggagggt | cactgagact | gagctgcgcc | gcttccggct | tcaacatcaa | ggagtactat | 180 |
| atgcactggg | tgaggcaggc | acctggcaaa | ggactggagt | gggtgggact | gatcgaccca | 240 |
| gaacagggga | acaccatcta | cgaccctaag | tttcaggata | gggcaaccat | ttctgccgac | 300 |
| aacagtaaaa | atacagctta | tctgcagatg | aacagcctga | gggctgaaga | tactgcagtg | 360 |
| tactattgcg | cacgcgacac | cgcagcctac | ttcgattatt | ggggacaggg | caccctggtc | 420 |
| acagtgagct | ccgcatcaac | taagggaccc | agcgtgtttc | cactggcccc | ctctagtaaa | 480 |
| tccacttctg | gaggcaccgc | tgcactgggc | tgtctggtga | aggattactt | cccagagccc | 540 |
| gtcacagtga | gctggaactc | cggggccctg | accagcggag | tccatacatt | tcctgctgtg | 600 |
| ctgcagtcaa | gcgggctgta | ctccctgtcc | tctgtggtca | ccgtgccaag | ttcaagcctg | 660 |
| ggaactcaga | cctatatctg | caacgtgaat | cacaagcctt | caaatacaaa | agtcgacaag | 720 |
| aaagtggaac | caaagagctg | tgataaaaca | catacttgcc | caccttgtcc | tgcaccagag | 780 |
| ctgctgggag | gaccaagcgt | gttcctgttt | ccacccaagc | ccaaagacac | cctgatgatt | 840 |
| tcccgcacac | cagaagtcac | ttgcgtggtc | gtggacgtgt | ctcacgagga | ccccgaagtc | 900 |

| | |
|---|---|
| aagttcaact ggtacgtgga tggcgtcgag gtgcataatg ccaagacaaa accccgggag | 960 |
| gaacagtaca actccacata tagagtcgtg tctgtcctga ctgtgctgca ccaggactgg | 1020 |
| ctgaacggga aggagtataa gtgcaaagtg agtaataagg ccctgcccgc tcctatcgag | 1080 |
| aaaacaatta gcaaggccaa aggccagcct cgagaaccac aggtgtacac tctgcctcca | 1140 |
| tctcgggacg agctgactaa gaaccaggtc agtctgacct gtctggtgaa aggattctat | 1200 |
| cccagcgata tcgctgtgga gtgggaatcc aatggccagc tgagaacaa ttacaagacc | 1260 |
| acaccccctg tgctggactc tgatggcagt ttctttctgt atagtaagct gaccgtcgat | 1320 |
| aaatcacgat ggcagcaggg gaacgtgttc agctgttcag tgatgcacga agccctgcac | 1380 |
| aaccattaca cccagaagag cctgagcctg tctcccggct ga | 1422 |

<210> SEQ ID NO 17
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| | |
|---|---|
| gccacaatgg ctgtgatggc accccgaacc ctggtcctgc tgctgagtgg agcactggca | 60 |
| ctgacccaga catgggcagg cgacatccag atgacacagt cccctagctc cctgagtgcc | 120 |
| tcagtggggg acagagtcac tatcacctgc cgggcttcca gagatattaa gtcttacctg | 180 |
| aactggtatc agcagaagcc aggcaaagca cccaaggtgc tgatctacta tgccaccagt | 240 |
| ctggctgaag gagtgccttc acggttcagc ggctccgggt ctggaactga ctacacactg | 300 |
| actatttcta gtctgcagcc tgaggatttc gctacctact attgcctgca gcacggcgaa | 360 |
| tccccatgga cttttggcca ggggaccaaa gtggagatca gaggacagt ggccgctcca | 420 |
| tccgtcttca ttttcccccc ttctgacgaa cagctgaaat caggaactgc agcgtggtc | 480 |
| tgtctgctga acaatttcta ccccgcgag gcaaaagtgc agtggaaggt cgataacgcc | 540 |
| ctgcagagtg gcaattcaca ggagagcgtg acagaacagg actccaaaga ttctacttat | 600 |
| agtctgtcaa gcaccctgac actgtctaag gctgattacg agaagcacaa agtgtatgca | 660 |
| tgcgaagtca cccatcaggg gctgtcctct cccgtgacaa agagctttaa tcggggagag | 720 |
| tgttga | 726 |

<210> SEQ ID NO 18
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | |
|---|---|
| gccacaatgg ctgtgatggc tccaagaacc ctggtcctgc tgctgtccgg ggctctggct | 60 |
| ctgactcaga cctgggccgg ggaagtgcag ctggtcgaat ctggaggagg actggtgcag | 120 |
| ccaggagggt ccctgcgcct gtcttgcgcc gctagtggct caccttttac cgactacacc | 180 |
| atggattggg tgcgacaggc acctggaaag ggcctggagt gggtcgccga tgtgaaccca | 240 |
| aatagcggag ctccatctca caaccagcgg ttcaagggcc ggttcaccct gtcagtggac | 300 |
| cggagcaaaa acaccctgta tctgcagatg aatagcctgc gagccgaaga tactgctgtg | 360 |
| tactattgcg cccggaatct ggggccctcc ttctactttg actattgggg gcagggaact | 420 |

```
ctggtcaccg tgagctccgc ctccaccaag ggaccttctg tgttcccact ggctccctct        480
agtaaatcca catctggggg aactgcagcc ctgggctgtc tggtgaagga ctacttccca        540
gagcccgtca cagtgtcttg aacagtggc gctctgactt ctggggtcca cacctttcct         600
gcagtgctgc agtcaagcgg gctgtacagc ctgtcctctg tggtcaccgt gccaagttca        660
agcctgggaa cacagactta tatctgcaac gtgaatcaca agccatccaa tacaaaagtc        720
gacaagaaag tggaacccaa gtcttgtgat aaaacccata catgcccccc ttgtcctgca        780
ccagagctgc tgggaggacc aagcgtgttc ctgtttccac ccaagcctaa agatacactg        840
atgattagta ggaccccaga agtcacatgc gtggtcgtgg acgtgagcca cgaggacccc        900
gaagtcaagt ttaactggta cgtggacggc gtcgaggtgc ataatgccaa gactaaaccc        960
agggaggaac agtacaacag tacctatcgc gtcgtgtcag tcctgacagt gctgcatcag       1020
gattggctga acgggaaaga gtataagtgc aaagtgagca taaggctct gcccgcacct        1080 atcgagaaaa caatttccaa ggcaaaagga cagcctagag aaccacaggt gtacactctg       1140
cctccatcaa gggatgagct gacaaagaac caggtcagcc tgacttgtct ggtgaaagga       1200
ttctatccct ctgacattgc tgtggagtgg aaagtaatg ccagcctga aacaattac          1260 aagaccacac cccctgtgct ggactcagat ggcagcttct ttctgtatag caagctgacc       1320
gtcgacaaat cccggtggca gcaggggaat gtgtttagtt gttcagtcat gcacgaggca       1380
ctgcacaacc attacaccca gaagtcactg tcactgtcac cagggtga                   1428

<210> SEQ ID NO 19
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gccacaatgg ctgtgatggc acctagaaca ctggtcctgc tgctgagcgg ggcactggca         60
ctgacacaga cttgggccgg ggatattcag atgacccagt ccccaagctc cctgagtgcc        120
tcagtgggcg accgagtcac catcacatgc aaggcttccc aggatgtgtc tattggagtc        180
gcatggtacc agcagaagcc aggcaaagca cccaagctgc tgatctatag cgcctcctac        240
cggtataccg gcgtgccctc tagattctct ggcagtgggt caggaacaga ctttactctg        300
accatctcta gtctgcagcc tgaggatttc gctacctact attgccagca gtactatatc        360
tacccatata cctttggcca ggggacaaaa gtggagatca gaggactgt ggccgctccc         420 tccgtcttca tttttccccc ttctgacgaa cagctgaaaa gtggcacagc cagcgtggtc        480
tgtctgctga acaatttcta ccctcgcgaa gccaaagtgc agtggaaggt cgataacgct        540
ctgcagagcg gcaacagcca ggagtctgtg actgaacagg acagtaaaga ttcaacctat        600
agcctgtcaa gcacactgac tctgagcaag gcagactacg agaagcacaa agtgtatgcc        660
tgcgaagtca cacatcaggg gctgtcctct cctgtgacta gagctttaa cagaggagag        720 tgttga                                                                    726

<210> SEQ ID NO 20
<211> LENGTH: 98
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ala Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 21
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 22
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val

```
                65                  70                  75                  80
Val Leu Thr Met Thr Asn Met Asp Pro Val Asp Thr Ala Thr Tyr Tyr
                    85                  90                  95

Cys Ala His Arg
            100

<210> SEQ ID NO 23
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 24
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 25
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 25

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 26
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
                100

<210> SEQ ID NO 27
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80
```

Leu Gln Ile Cys Ser Leu Lys Ala Glu Asp Thr Ala Val Tyr Tyr Cys
                85                  90                  95

Ala Arg

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Thr Ala Ala Tyr Phe Asp Tyr Trp Gly Gln Gly Thr Leu Val Thr
1               5                   10                  15

Val Ser Ser

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Glu Tyr Phe Gln His Trp Gly Gln Gly Thr Leu Val Thr Val Ser
1               5                   10                  15

Ser

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Trp Tyr Phe Asp Leu Trp Gly Arg Gly Thr Leu Val Thr Val Ser
1               5                   10                  15

Ser

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ala Phe Asp Ile Trp Gly Gln Gly Thr Met Val Thr Val Ser Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Phe Asp Tyr Trp Gly Gln Gly Thr Leu Val Thr Val Ser Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Trp Phe Asp Pro Trp Gly Gln Gly Thr Leu Val Thr Val Ser Ser
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Tyr Tyr Tyr Tyr Gly Met Asp Val Trp Gly Gln Gly Thr Thr Val
1               5                   10                  15

Thr Val Ser Ser
            20

<210> SEQ ID NO 35
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Lys Ser Tyr
            20                  25                  30

Leu Asn Trp Tyr Gln Gln Lys Pro Gly Lys Ala Pro Lys Val Leu Ile
        35                  40                  45

Tyr Tyr Ala Thr Ser Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro
                85                  90                  95

<210> SEQ ID NO 36
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 37
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100
```

<210> SEQ ID NO 38
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 39
<211> LENGTH: 101
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 40
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 41
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
50                  55                  60
```

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Thr Phe Gly Gln Gly Thr Lys Val Glu Ile Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Thr Phe Gly Gln Gly Thr Lys Val Glu Ile Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Thr Phe Gly Gln Gly Thr Lys Leu Glu Ile Lys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Thr Phe Gly Pro Gly Thr Lys Val Asp Ile Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Thr Phe Gly Gly Gly Thr Lys Val Glu Ile Lys
1               5                   10

<210> SEQ ID NO 47
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Thr Phe Gly Gln Gly Thr Arg Leu Glu Ile Lys
1               5                   10

<210> SEQ ID NO 48
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ser Val Leu Thr Gln Pro Pro Ser Val Ser Glu Ala Pro Arg Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Asn Gly

<210> SEQ ID NO 49
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 50
<211> LENGTH: 95
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 50

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Ser Ser Thr Ala
                85                  90                  95

<210> SEQ ID NO 51
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 52
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Pro Val Leu Thr Gln Pro Pro Ser Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile

```
              65                  70                  75                  80
Leu Leu Ile Ser Gly Leu Gln Ser Glu Asp Glu Ala Asp Tyr Tyr Cys
                      85                  90                  95

Met Ile Trp Pro Ser Asn Ala Ser
                100

<210> SEQ ID NO 53
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 54
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln

<210> SEQ ID NO 55
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 55

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 56
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
            100

<210> SEQ ID NO 57
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
            85                  90                  95

Ser Ala

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Val Phe Gly Thr Gly Thr Lys Val Thr Val Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Val Val Phe Gly Gly Gly Thr Lys Leu Thr Val Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Val Phe Gly Gly Gly Thr Lys Leu Thr Val Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Phe Val Phe Gly Gly Gly Thr Gln Leu Ile Ile Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Val Phe Gly Glu Gly Thr Glu Leu Thr Val Leu
1               5                   10

<210> SEQ ID NO 63
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Val Phe Gly Ser Gly Thr Lys Val Thr Val Leu
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Val Phe Gly Gly Gly Thr Gln Leu Thr Val Leu
1               5                   10

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 66
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 67
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 68
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 69
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 69

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Tyr Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 70
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 71
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Thr Cys Asn Val Asp His Lys Pro Ser Asn Thr Lys Val Asp Lys
                 85                  90                  95

Thr Val

<210> SEQ ID NO 72
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Thr Ile Cys Asn Val Asp His Lys Pro Ser Asn Thr Lys Val Asp Lys
                85                  90                  95

Arg Val

<210> SEQ ID NO 73
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 74
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Asn Phe Leu Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

```
                    85                  90                  95

Pro Val Thr Lys Ser Phe Asn Arg Gly Glu Cys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79
```

-continued

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105
```

<210> SEQ ID NO 80
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 80

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 81
<211> LENGTH: 104
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 81

```
Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80
```

```
Arg Ser Tyr Ser Cys Gln Val Thr His Glu Gly Ser Thr Val Glu Lys
                85                  90                  95
Thr Val Ala Pro Thr Glu Cys Ser
            100

<210> SEQ ID NO 82
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Pro Lys Ala Asn Pro Thr Val Thr Leu Phe Pro Pro Ser Ser Glu
1               5                   10                  15
Glu Leu Gln Ala Asn Lys Ala Thr Leu Val Cys Leu Ile Ser Asp Phe
            20                  25                  30
Tyr Pro Gly Ala Val Thr Val Ala Trp Lys Ala Asp Gly Ser Pro Val
        35                  40                  45
Lys Ala Gly Val Glu Thr Thr Lys Pro Ser Lys Gln Ser Asn Asn Lys
    50                  55                  60
Tyr Ala Ala Ser Ser Tyr Leu Ser Leu Thr Pro Glu Gln Trp Lys Ser
65                  70                  75                  80
His Arg Ser Tyr Ser Cys Gln Val Thr His Glu Gly Ser Thr Val Glu
                85                  90                  95
Lys Thr Val Ala Pro Thr Glu Cys Ser
            100                 105

<210> SEQ ID NO 83
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Pro Lys Ala Ala Pro Ser Val Thr Leu Phe Pro Pro Ser Ser Glu
1               5                   10                  15
Glu Leu Gln Ala Asn Lys Ala Thr Leu Val Cys Leu Ile Ser Asp Phe
            20                  25                  30
Tyr Pro Gly Ala Val Thr Val Ala Trp Lys Ala Asp Ser Ser Pro Val
        35                  40                  45
Lys Ala Gly Val Glu Thr Thr Thr Pro Ser Lys Gln Ser Asn Asn Lys
    50                  55                  60
Tyr Ala Ala Ser Ser Tyr Leu Ser Leu Thr Pro Glu Gln Trp Lys Ser
65                  70                  75                  80
His Arg Ser Tyr Ser Cys Gln Val Thr His Glu Gly Ser Thr Val Glu
                85                  90                  95
Lys Thr Val Ala Pro Thr Glu Cys Ser
            100                 105

<210> SEQ ID NO 84
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 84

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
            35                  40                  45

Ala Gly Val Glu Thr Thr Thr Pro Ser Lys Gln Ser Asn Asn Lys Tyr
50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 85
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Lys Val Ala Trp Lys Ala Asp Gly Ser Pro Val
            35                  40                  45

Asn Thr Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Ala Thr Glu Cys Ser
            100                 105
```

ENGINEERED IMMUNOGLOBULIN HEAVY CHAIN-LIGHT CHAIN PAIRS AND USES THEREOF

CROSS REFERENCE TO RELATED APPLICATIONS

This application is the divisional of U.S. patent application Ser. No. 14/648,222, filed May 28, 2015, which is the U.S. National Entry of PCT/CA2013/050914, filed Nov. 28, 2018, which claims the benefit of U.S. Provisional Application No. 61/730,906, filed Nov. 28, 2012, U.S. Provisional Application No. 61/761,641, filed Feb. 6, 2013, U.S. Provisional Application No. 61/818,874, filed May 2, 2013, and U.S. Provisional Application No. 61/869,200, filed Aug. 23, 2013, the entire disclosure of each of which is hereby incorporated by reference in its entirety for all purposes.

SEQUENCE LISTING

The instant application contains a Sequence Listing which has been submitted via EFS-Web and is hereby incorporated by reference in its entirety. Said ASCII copy, created on Jan. 30, 2014, is named 24897PCT_CRF_sequencelisting.txt, and is 91,025 bytes in size.

BACKGROUND

Bi-specific antibodies are capable of binding to two different epitopes. The epitopes can be on the same antigen, or each epitope can be on a different antigen. This feature of bi-specific antibodies makes them an attractive tool for various therapeutic applications where there is a therapeutic benefit to targeting or recruiting more than one molecule in the treatment of disease. One of the approaches to form bi-specific antibody would involve concomitant expression of two unique antibody heavy chains and two unique antibody light chains. Correctly forming bi-specific antibodies in a format that is similar to wild-type remains a challenge, since antibody heavy chains have evolved to bind antibody light chains in a relatively promiscuous manner. As a result of this promiscuous pairing, concomitant expression of two antibody heavy chains and two antibody light chains naturally leads to a scrambling of heavy chain—light chain pairings. This mispairing remains a major challenge for the generation of bi-specific therapeutics, where homogeneous pairing is an essential requirement for good manufacturability and biological efficacy.

Several approaches have been described to prepare bi-specific antibodies in which specific antibody light chains or fragment pair with specific antibody heavy chains or fragments. A review of various approaches to address this problem can be found in Klein et al., (2012) mAbs 4:6, 1-11. International Patent Application No. PCT/EP2011/056388 (WO 2011/131746) describes an in vitro method for generating a heterodimeric protein in which asymmetrical mutations are introduced into the CH3 regions of two monospecific starting proteins in order to drive directional "Fab-arm" or "half-molecule" exchange between two monospecific IgG4- or IgG4-like antibodies upon incubation under reducing conditions.

Schaefer et al. (Roche Diagnostics GmbH), describe a method to assemble two heavy and two light chains, derived from two existing antibodies, into human bivalent bi-specific IgG antibodies without use of artificial linkers (PNAS (2011) 108(27): 11187-11192). The method involves exchanging heavy chain and light chain domains within the antigen-binding fragment (Fab) of one half of the bi-specific antibody.

Strop et al. (Rinat-Pfizer Inc.), describe a method of producing stable bi-specific antibodies by expressing and purifying two antibodies of interest separately, and then mixing them together under specified redox conditions (J. Mol. Biol. (2012) 420:204-19).

Zhu et al. (Genentech) have engineered mutations in the VL/VH interface of a diabody construct consisting of variant domain antibody fragments completely devoid of constant domains, and generated a heterodimeric diabody (Protein Science (1997) 6:781-788). Similarly, Igawa et al. (Chugai) have also engineered mutations in the VL/VH interface of a single-chain diabody to promote selective expression and inhibit conformational isomerization of the diabody (Protein Engineering, Design & Selection (2010) 23:667-677).

US Patent Publication No. 2009/0182127 (Novo Nordisk, Inc.) describes the generation of bi-specific antibodies by modifying amino acid residues at the Fc interface and at the CH1:CL interface of light-heavy chain pairs that reduce the ability of the light chain of one pair to interact with the heavy chain of the other pair.

SUMMARY

Described herein is an isolated antigen binding polypeptide construct comprising at least a first heterodimer and a second heterodimer, the first heterodimer comprising a first immunoglobulin heavy chain polypeptide sequence (H1), and a first immunoglobulin light chain polypeptide sequence (L1); and the second heterodimer comprising a second immunoglobulin heavy chain polypeptide sequence (H2), and a second immunoglobulin light chain polypeptide sequence (L2), wherein at least one of the H1 or L1 sequences of the first heterodimer is distinct from the corresponding H2 or L2 sequence of the second heterodimer, and wherein H1 and H2 each comprise at least a heavy chain variable domain ($V_H$ domain) and a heavy chain constant domain ($C_{H1}$ domain); L1 and L2 each comprise at least a light chain variable domain ($V_L$ domain) and a light chain constant domain ($C_L$ domain); and at least one of H1, H2, L1 and L2 comprises at least one amino acid modification of at least one constant domain and/or at least one variable domain, wherein H1 preferentially pairs with L1 as compared to L2 and H2 preferentially pairs with L2 as compared to L1.

In some aspects, the construct further comprises a heterodimeric Fc, the Fc comprising at least two $C_{H3}$ sequences, wherein the Fc is coupled, with or without one or more linkers, to the first heterodimer and the second heterodimer, wherein the dimerized $C_{H3}$ sequences have a melting temperature (Tm) of about 68° C. or higher as measured by differential scanning calorimetry (DSC), and wherein the construct is bispecific.

In some aspects, the at least one amino acid modification of is selected from at least one amino acid modification shown in the Tables or Examples.

In some aspects, H1 pairs preferentially with L1 as compared to L2, and H2 pairs preferentially with L2 as compared to L1, when H1, H2, L1 and L2 are co-expressed in a cell or a mammalian cell, or when H1, H2, L1 and L2 are co-expressed in a cell-free expression system, or when H1, H2, L1 and L2 are co-produced, or when H1, H2, L1 and L2 are co-produced via a redox production system.

In some aspects, at least one of H1, H2, L1 and L2 comprises at least one amino acid modification of a $V_H$ and/or $V_L$ domain and at least one amino acid modification of a $C_{H1}$ and/or $C_L$ domain such that H1 pairs preferentially with L1 as compared to L2, and/or H2 pairs preferentially with L2 as compared to L1.

In some aspects, if H1 comprises at least one amino acid modification in the $C_{H1}$ domain, then at least one of L1 and L2 comprise at least one amino acid modification in the $C_L$ domain; and/or if H1 comprises at least one amino acid modification in the $V_H$ domain, then at least one of L1 and L2 comprise at least one amino acid modification in the $V_L$ domain.

In some aspects, H1, L1, H2, and/or L2 comprises at least 1, 2, 3, 4, 5, 6, 7, 8, 9, or 10 amino acid mutations. In some aspects, at least one of H1, H2, L1 and L2 comprises at least 2, 3, 4, 5, 6, 7, 8, 9, or 10 amino acid modifications of at least one constant domain and/or at least one variable domain.

In some aspects, when both L1 and L2 are co-expressed with at least one of H1 and H2, the relative pairing of the at least one of H1-L1 and H2-L2 heterodimer pair to that of the respective corresponding H1-L2 or H2-L1 heterodimer pair is greater than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, and wherein the relative pairing of the modified H1-L1 or H2-L2 heterodimer pair is greater than the respective relative pairing observed in the corresponding H1-L1 or H2-L2 heterodimer pair without the at least one amino acid modification.

In some aspects, the thermal stability as measured by the melting temperature (Tm) as measured by DSC of at least one of the first and second heterodimers is within about 0, 1, 2, 3, 4, 5, 6, 7, 8, 9, or 10° C. of the Tm of the corresponding heterodimer without the at least one amino acid modification. In some aspects, the thermal stability as measured by the melting temperature (Tm) as measured by DSC of each heterodimer comprising at least one amino acid modification is within about 0, 1, 2, 3, 4, 5, 6, 7, 8, 9, or 10° C. of the Tm of the corresponding heterodimer without the at least one amino acid modification.

In some aspects, the affinity of each heterodimer for the antigen to which it binds is within about 1, 2, 3, 4, 5, 6, 7, 8, 9, 10, 20, 25, 30, 35, 40, 45, or 50-fold of the affinity of the respective unmodified heterodimer for the same antigen as measured by surface plasmon resonance (SPR) or FACS.

In some aspects, at least one of H1 and L1 comprises at least one domain comprising at least one amino acid modification resulting in greater steric complementarity of amino acids when H1 pairs with L1 as compared to L2. In some aspects, at least one of H2 and L2 comprises at least one domain comprising at least one amino acid modification resulting in greater steric complementarity of amino acids when H2 pairs with L2 as compared to L1. In some aspects, at least one of H1 and L1 comprises at least one domain comprising at least one amino acid modification resulting in greater electrostatic complementarity between charged amino acids when H1 pairs with L1 as compared to L2. In some aspects, at least one of H2 and L2 comprises at least one domain comprising at least one amino acid modification resulting in greater electrostatic complementarity between charged amino acids when H2 pairs with L2 as compared to L1.

In some aspects, the at least one amino acid modification of is a set of mutations shown in at least one of the Tables or Examples. In some aspects, the at least one modification is not H1-Q39E, L1-Q38K, H2-Q39K, and L2-Q38E. In some aspects, the at least one modification is not H1-Q39E, L1-Q38E, H2-Q39K, and L2-Q38K.

In some aspects, the construct further comprises an Fc comprising at least two $C_{H3}$ sequences, wherein the Fc is coupled, with or without one or more linkers, to the first heterodimer and the second heterodimer.

In some aspects, the Fc is a human Fc, a human IgG1 Fc, a human IgA Fc, a human IgG Fc, a human IgD Fc, a human IgE Fc, a human IgM Fc, a human IgG2 Fc, a human IgG3 Fc, or a human IgG4 Fc. In some aspects, the Fc is a heterodimeric Fc. In some aspects, the Fc comprises one or more modifications in at least one of the $C_{H3}$ sequences. In some aspects, the dimerized $C_{H3}$ sequences have a melting temperature (Tm) as measured by DSC of about 68, 69, 70, 71, 72, 73, 74, 75, 76, 77, 77.5, 78, 79, 80, 81, 82, 83, 84, or 85° C. or higher. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when produced; or wherein the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed or when expressed via a single cell. In some aspects, the Fc comprises one or more modifications in at least one of the $C_{H3}$ sequences that promote the formation of a heterodimeric Fc with stability comparable to a wild-type homodimeric Fc. In some aspects, the Fc further comprises at least one $C_{H2}$ sequence. In some aspects, the $C_{H2}$ sequence(s) of the Fc comprises one or more modifications. In some aspects, the Fc comprises one or more modifications to promote selective binding of Fc-gamma receptors.

In some aspects, the Fc is coupled to the heterodimers by one or more linkers, or wherein the Fc is coupled to H1 and H2 by one or more linkers. In some aspects, the one or more linkers are one or more polypeptide linkers. In some aspects, the one or more linkers comprises one or more antibody hinge regions. In some aspects, the one or more linkers comprises one or more IgG1 hinge regions. In some aspects, the one or more linkers comprises one or more modifications. In some aspects, the one or more modifications to the one or more linkers promote selective binding of Fc-gamma receptors.

In some aspects, the at least one amino acid modification is at least one amino acid mutation or wherein the at least one amino acid modification is at least one amino acid substitution.

In some aspects, the sequences of each of H1, H2, L1, and L2 are derived from human sequences.

In some aspects, the construct is multispecific or bispecific. In some aspects, the construct is multivalent or bivalent.

Also described herein is an isolated polynucleotide or set of isolated polynucleotides comprising at least one sequence that encodes a construct described herein. In some aspects, the polynucleotide or set of polynucleotides is cDNA.

Also described herein is a vector or set of vectors comprising one or more of the polynucleotides or sets of polynucleotides described herein. In some aspects, the vector or set of vectors is selected from the group consisting of a plasmid, a multi-cistronic vector, a viral vector, a non-episomal mammalian vector, an expression vector, and a recombinant expression vector.

Also described herein is an isolated cell comprising a polynucleotide or set of polynucleotides described herein or a vector or set of vectors described herein. In some aspects, the cell is a hybridoma, a Chinese Hamster Ovary (CHO) cell, or a HEK293 cell.

Also described herein is a pharmaceutical composition comprising a construct described herein and a pharmaceutically acceptable carrier. In some aspects, the composition further comprises one or more substances selected from the group consisting of a buffer, an antioxidant, a low molecular weight molecule, a drug, a protein, an amino acid, a carbohydrate, a lipid, a chelating agent, a stabilizer, and an excipient.

Also described herein is a use of a construct described herein or a pharmaceutical composition described herein for the treatment of a disease or disorder or cancer or vascular disease in a subject or in the manufacture of a medicine.

Also described herein is a method of treatment of a subject having a disease or disorder or cancer or vascular disease comprising administering to the subject a construct described herein or a composition described herein.

Also described herein is a method of inhibiting, reducing or blocking a signal within or to a cell, comprising contacting the cell with a construct described herein or a composition described herein.

Also described herein is a method of obtaining a construct described herein from a host cell culture, the method comprising the steps of: (a) obtaining a host cell culture comprising at least one host cell comprising one or more nucleic acid sequences encoding the construct; and (b) recovering the construct from the host cell culture.

Also described herein is a method of obtaining a construct described herein comprising the steps of: (a) obtaining H1, L1, H2, and L2; (b) allowing H1 to pair preferentially with L1 as compared to L2 and H2 to pair preferentially with L2 as compared to L1; and (c) obtaining the construct.

Also described herein is a method of preparing a construct described herein comprising: obtaining a polynucleotide or set of polynucleotides encoding at least one construct; determining the optimal ratios of each of the polynucleotide or set of polynucleotides for introduction into at least one host cell, wherein the optimal ratios are determined by assessing the amount of H1-L1 and H2-L2 heterodimer pairs formed upon expression of H1, L1, H2, and L2 as compared to mispaired H1-L2 and H2-L1 heterodimer pairs formed upon expression of H1, L1, H2, and L2; selecting a preferred optimal ratio, wherein transfection of at least one host cell with the preferred optimal ratio of the polynucleotide or set of polynucleotides results in expression of the construct; transfecting the at least one host cell with the optimal ratio of the polynucleotide or set of polynucleotides; and culturing the at least one host cell to express the construct.

In some aspects, selecting the optimal ratio is assessed by transfection in a transient transfection system. In some aspects, transfection of the at least one host cell with the preferred optimal ratio of the polynucleotide or set of polynucleotides results in optimal expression of the construct. In some aspects, the construct comprises an Fc comprising at least two $C_{H3}$ sequences, wherein the Fc is coupled, with or without one or more linkers, to the first heterodimer and the second heterodimer. In some aspects, the Fc is a heterodimer, optionally comprising one or more amino acid modifications.

Also described herein is a computer-readable storage medium storing a dataset comprising data representing complementary mutations in a first heterodimer comprising a first immunoglobulin heavy chain polypeptide sequence (H1) and a first immunoglobulin light chain polypeptide sequence (L1); and a second heterodimer comprising a second immunoglobulin heavy chain polypeptide sequence (H2) and a second immunoglobulin light chain polypeptide sequence (L2), wherein H1 and H2 each comprise at least a heavy chain variable domain ($V_H$ domain) and a heavy chain constant domain ($C_{H1}$ domain); wherein L1 and L2 each comprise at least a light chain variable domain ($V_L$ domain) and a light chain constant domain ($C_L$ domain), and wherein the dataset of complementary mutations comprises data representing those mutations listed in the Tables or Examples or a subset of those mutations; and computer executable code for determining the likelihood that H1 will pair preferentially with L1 as compared to L2 and/or H2 will pair preferentially with L2 as compared to L1.

Also described herein is a computer implemented method for determining preferential pairing, comprising: obtaining a dataset comprising data representing complementary mutations in a first heterodimer comprising a first immunoglobulin heavy chain polypeptide sequence (H1) and a first immunoglobulin light chain polypeptide sequence (L1); and a second heterodimer comprising a second immunoglobulin heavy chain polypeptide sequence (H2) and a second immunoglobulin light chain polypeptide sequence (L2), wherein H1 and H2 each comprise at least a heavy chain variable domain ($V_H$ domain) and a heavy chain constant domain ($C_{H1}$ domain); wherein L1 and L2 each comprise at least a light chain variable domain ($V_L$ domain) and a light chain constant domain ($C_L$ domain), and wherein the dataset of complementary mutations comprises data representing those mutations listed in the Tables or Examples or a subset of those mutations; and determining, by a computer processor, the likelihood that H1 will pair preferentially with L1 as compared to L2 and/or H2 will pair preferentially with L2 as compared to L1. In some aspects, the method further comprises producing a construct described herein.

Also described herein is a method of producing a bi-specific antigen binding polypeptide construct, said bi-specific construct comprising a first heterodimer comprising a first immunoglobulin heavy chain polypeptide sequence (H1), and a first immunoglobulin light chain polypeptide sequence (L1) from a first mono-specific antigen binding polypeptide; and a second heterodimer comprising a second immunoglobulin heavy chain polypeptide sequence (H2), and a second immunoglobulin light chain polypeptide sequence (L2) from a second mono-specific antigen binding polypeptide, wherein H1 and H2 each comprise at least a heavy chain variable domain ($V_H$ domain) and a heavy chain constant domain ($C_{H1}$ domain); wherein L1 and L2 each comprise at least a light chain variable domain ($V_L$ domain) and a light chain constant domain ($C_L$ domain), the method comprising: obtaining a dataset comprising data representing a set of amino acid modifications within H1, H2, L1 and L2 such that upon introduction of a subset of the modifications into H1, H2, L1 and/or L2, H1 pairs preferentially with L1 as compared to L2 and H2 pairs preferentially with L2 as compared to L1 in a test system; introducing a subset of one or more modifications from the dataset into the first heterodimer and/or the second heterodimer; and co-expressing the first heterodimer and the second heterodimer in at least one host cell to produce an expression product comprising the bi-specific construct.

In some aspects, the method further comprises determining the amount of the bi-specific construct in the expression product relative to other polypeptide products. In some aspects, the bi-specific construct is produced with a purity of greater than 70% compared to the other polypeptide products. In some aspects, the dataset is a dataset described herein. In some aspects, the method further comprises the step of adding additional amino acid modifications to at least one of H1, H2, L1, or L2 to increase the purity of the bi-specific construct compared to the other polypeptide products. In some aspects, the construct comprises an Fc comprising at least two $C_{H3}$ sequences, wherein the Fc is coupled, with or without one or more linkers, to the first heterodimer and the second heterodimer. In some aspects, the Fc is a heterodimer, optionally comprising one or more amino acid modifications. In some aspects, the antigen binding polypeptide is an antibody, a Fab, or a scFv.

BRIEF DESCRIPTION OF THE FIGURES

FIG. 1 provides a Table showing the preferential pairing of heterodimers, from antigen-binding constructs described herein, in LCCA design sets where amino acid modifications have been made to the $V_H$ or $V_L$ domains.

FIG. 2 provides a Table showing the preferential pairing of heterodimers in LCCA design sets where amino acid modifications have been made to the $C_{H1}$ or $C_L$ domains.

FIG. 3 provides a Table showing the thermal stability and affinity for antigen for selected preferentially paired or mispaired heterodimers from antigen-binding constructs described herein.

FIGS. 6A-E depicts D3H44 heavy chain and light chain amino acid sequences aligned against canonical human germline sequences for Variable, Constant and J-region segments. (Notations in figs: * sequence identity, #Interface hotspots (specificity drivers), +mutated residues tested in designs). FIG. 6A depicts Human VH germline subgroups (one representative sequence is displayed for each family). Sequence identity based on an alignment of D3H44 against VH3 and IGHJ3*02. FIG. 6A discloses SEQ ID NOS 20-34, respectively, in order of appearance. FIG. 6B depicts Human kappa VL germline subgroups (one representative sequence is displayed from each family). Sequence identity based on an alignment of D3H44 against VKI and IGKJ1*01. FIG. 6B discloses SEQ ID NOS 35-47, respectively, in order of appearance. FIG. 6C depicts Human lambda VL germline subgroups (one representative sequence is displayed from each family). Sequence identity based on an alignment of D3H44 against VL1 and IGLJ1*01. FIG. 6C discloses SEQ ID NOS 35, 48-57, 42, and 58-64, respectively, in order of appearance. FIG. 6D depicts human $C_{H1}$ allele sequences. FIG. 6D discloses SEQ ID NOS 65-74, respectively, in order of appearance. FIG. 6E depicts Human kappa and lambda allele sequences. FIG. 6E discloses SEQ ID NOS 75-80, 75, and 81-85, respectively, in order of appearance.

FIG. 11 depicts an exemplary set of H1, L1, H2, L2 chains which have been designed such that H1 preferentially pairs with L1 over L2 and H2 preferentially pairs with L2 over L1. A cartoon representation of the 3D crystal structure of the variable region heavy and light chain interface is presented. The mutations introduced at the interface achieve electrostatic and steric complementarity in the two set of variable region interface respectively for the preferentially forming obligate pair. On the other hand, there is unfavorable steric and electrostatic mismatch in the incorrect pair that would result in reduced pairing propensity for the mismatched pair as well as reduced stability.

FIG. 13A shows non-reducing SDS-PAGE analysis of the H1-L1 and H2-L2 pairs before and after protein A purification, and the yield of product is shown at the bottom of the gels; FIG. 13B shows the DSC thermograms of the H1-L1 and H2-L2 paired products; and FIG. 13C shows UPLC-SEC (H2-L2) profile for the H2-L2 pair.

FIG. 16A shows a Coomassie stained non-reducing SDS-PAGE of the SMCA variant, along with a control variant composed of Her2 binding Mab with a heterodimeric Fc. The purity of the SMCA variant, after protein A (ProtA) purification, is high and is qualitatively equivalent to the control. The estimated post-ProtA yield of the SMCA variant is 20 mg/L and is comparable to the control yield of 40 mg/ml. Right panel (FIG. 16B) depicts the SEC profile of the aforementioned bispecific construct. The main peak (>90% total peak area) observed runs at a molecular weight of ~150 KDa and is composed of Mab monomers. The observed minor peak runs at ~75 KDa and consists of half-antibodies. No significant higher molecular weight peaks (potentially indicative of aggregate species) are observed.

FIG. 17B Upper panel depicts SPR data showing monospecific binding for tissue factor (TF) or Her2 antigen by the bispecific construct based on design set depicted in FIG. 11 (Note: This SMCA design utilizes the same H1-L1 and H2-L2 MCA designs as depicted in. FIG. 11). Lower panel depicts SPR data showing simultaneous bispecific binding of TF and Her2 antigens by the bispecific antigen binding construct.

DETAILED DESCRIPTION

Figure 4:
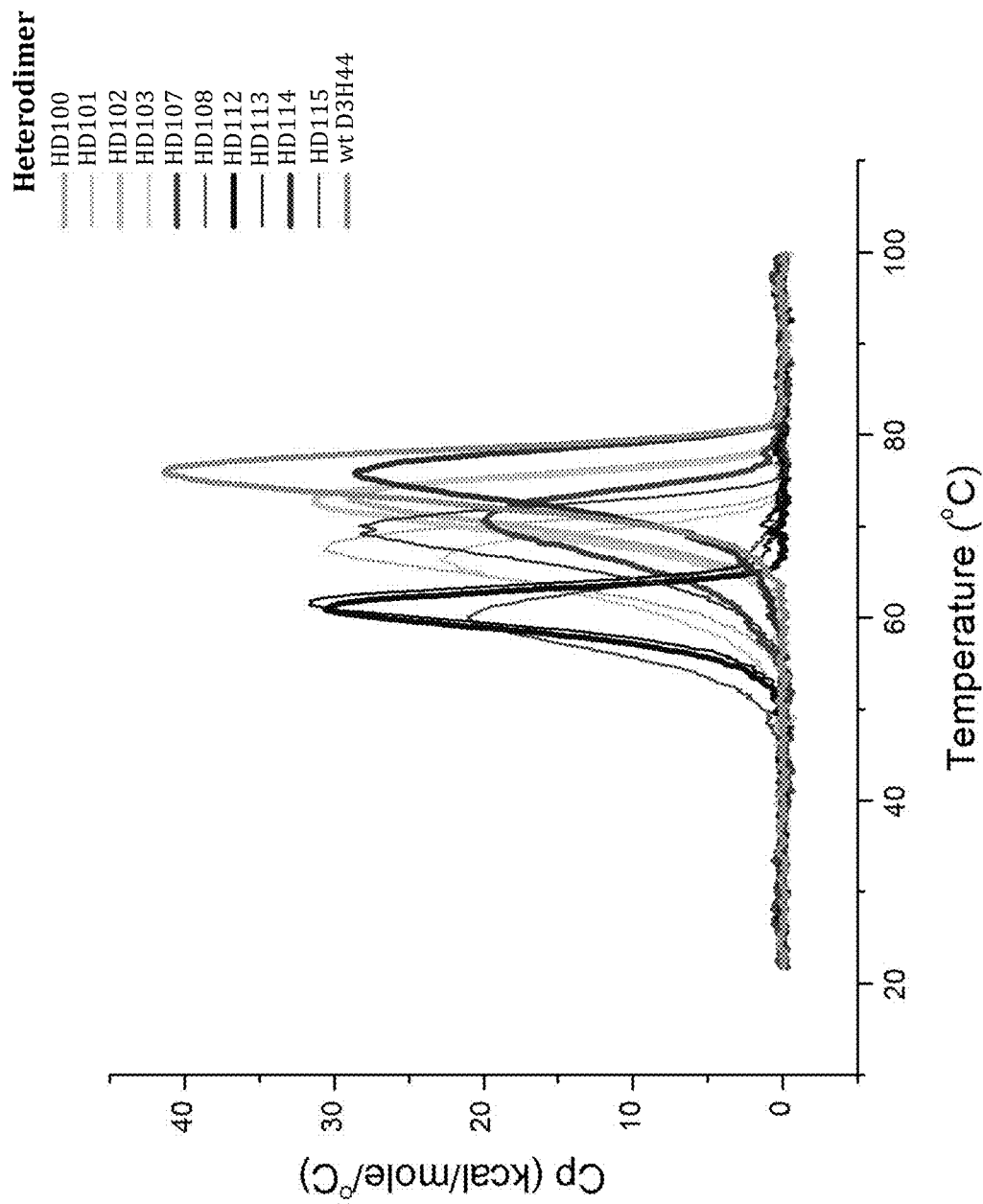
FIG. 4 provides thermal unfolding curves for selected heterodimers.

Provided herein are antigen binding polypeptide constructs (also referred to as heterodimer pairs) which can comprise a first heterodimer and a second heterodimer wherein each heterodimer comprises an immunoglobulin heavy chain or fragment thereof and an immunoglobulin light chain. At least one of the heterodimers can comprise one or more amino acid modifications in the immunoglobulin heavy chain constant domain 1 ($C_{H1}$) and one or more amino acid modifications in the immunoglobulin light chain constant domain ($C_L$); one or more amino acid modifications in the immunoglobulin heavy chain variable domain ($V_H$) and one or more amino acid modifications in the immunoglobulin light chain variable domain ($V_L$); or a combination of the preceding amino acid modifications to both the constant and variable domains of the heavy and light chains. The amino acids that are modified are typically part of the interface between the light chain and heavy chain and are modified to create preferential pairing between each heavy chain and the desired light chain such that the heavy chain of the first heterodimer preferentially pairs with one of the light chains rather than the other. Likewise, the heavy chain of the second heterodimer can preferentially pair with the second light chain rather than first.

As noted above, specific combinations of the amino acid modifications described herein promote preferential pairing of heavy chains with specific light chains, thus enabling bi-specific monoclonal antibody (Mab) expression to occur with negligible or limited mispairing, and minimizing the need to purify the desired heterodimers from undesired, or mispaired products. The heterodimers can exhibit comparable thermal stability to heterodimers that do not include the amino acid modifications, and can also demonstrate binding affinity for antigen that is comparable to heterodimers that do not include the amino acid modifications.

The designs of the first and second heterodimers, can be used to create bi-specific antibodies targeting two different therapeutic targets or targeting two distinct epitopes (overlapping or non-overlapping) within the same antigen.

The invention further provides methods of preparing the heterodimer pairs according to the invention.

Definitions

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or immunoglobulin constructs derived from various combinations of the structures and substituents described herein are disclosed by the present application to the same extent as if each single chain polypeptide or heterodimer were set forth individually. Thus, selection of particular components to form individual single chain polypeptides or heterodimers is within the scope of the present disclosure The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

In the present application, amino acid names and atom names (e.g. N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985). The term "amino acid residue" is primarily intended to indicate an amino acid residue contained in the group consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "nucleotide sequence" or "nucleic acid sequence" is intended to indicate a consecutive stretch of two or more nucleotide molecules. The nucleotide sequence may be of genomic, cDNA, RNA, semisynthetic or synthetic origin, or any combination thereof.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing a nucleic acid sequence into a cell.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as alanine, ornithine, etc.; and chemically synthesized compounds having properties known in the art to be characteristic of amino acids. Examples of non-naturally occurring amino acids include, but are not limited to, □-methyl amino acids (e.g. methyl alanine), D-amino acids, histidine-like amino acids (e.g., 2-amino-histidine, hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);

3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins: Structures and Molecular Properties (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 50% identity, about 55% identity, 60% identity, about 65%, about 70%, about 75%, about 80%, about 85%, about 90%, about 95% or about 99% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

As used herein, an "isolated" polypeptide or construct means a construct or polypeptide that has been identified and separated and/or recovered from a component of its natural cell culture environment. Contaminant components of its natural environment are materials that would typically interfere with diagnostic or therapeutic uses for the heteromultimer, and may include enzymes, hormones, and other proteinaceous or non-proteinaceous solutes.

In certain embodiments, as used herein, "isolated" antigen-binding constructs described herein comprise heterodimer pairs or "isolated" heterodimer pairs that comprise a heterodimer or heterodimer pair that has been identified and separated and/or recovered from a component of its natural cell culture environment. Contaminant components of its natural environment are materials that would interfere with diagnostic or therapeutic uses for the heterodimer or antigen-binding construct, and may include enzymes, hormones, and other proteinaceous or non-proteinaceous solutes.

The heterodimers and antigen-binding constructs and heterodimer pairs are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homodimers). Expressed in terms of purity, substantial homogeneity means that the amount of by-products does not exceed 10%, and preferably is below 5%, more preferably below 1%, most preferably below 0.5%, wherein the percentages are by weight.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

As used herein, the terms "antibody" and "immunoglobulin" or "antigen binding polypeptide" are used interchangeably. An "antigen binding polypeptide" refers to a polypeptide substantially encoded by an immunoglobulin gene or immunoglobulin genes, or one or more fragments thereof, which specifically bind an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin isotypes, IgG, IgM, IgA, IgD, and IgE, respectively. Further, the antibody can belong to one of a number of subtypes, for instance, the IgG can belong to the IgG1, IgG2, IgG3, or IgG4 subclasses.

An exemplary immunoglobulin (antibody) structural unit is composed of two pairs of polypeptide chains, each pair having one "light" (about 25 kD) and one "heavy" chain (about 50-70 kD). The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains. The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subclasses), IgA (including IgA1 and IgA2 subclasses), IgM and IgE. The term "variable region" or "variable domain" refers to a portion of the light and/or heavy chains of an antibody generally responsible for antigen recognition, typically including approximately the amino-terminal 120 to 130 amino acids in the heavy chain (VH) and about 100 to 110 amino terminal amino acids in the light chain (VL). A "complementarity determining region" or "CDR" is an amino acid sequence that contributes to antigen binding specificity and affinity. "Framework" regions (FR) can aid in maintaining the proper conformation of the CDRs to promote binding between the antigen binding region and an antigen. Structurally, framework regions can be located in antibodies between CDRs. The variable regions typically exhibit the same general structure of relatively conserved framework regions (FR) joined by three hyper variable regions, CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), unless stated otherwise. In certain embodiments, the immunoglobulin constructs comprise at least one immunoglobulin domain from IgG, IgM, IgA, IgD, or IgE connected to a therapeutic polypeptide. In some embodiments, the immunoglobulin domain comprised in an immunoglobulin construct provided herein, is from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

A "bi-specific," "dual-specific" or "bifunctional" antigen binding protein or antibody is a hybrid antigen binding protein having two different antigen binding sites. Bispecific antigen binding proteins and antibodies are a species of multispecific antigen binding protein antibody. The two binding sites of a bispecific antigen binding protein or antibody will bind to two different epitopes, which can reside on the same or different molecular targets. A "multispecific antigen binding protein" or "multispecific antibody" is one that targets more than one antigen or epitope. A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

The term "preferential pairing" is used herein to describe the pairing pattern of a first polypeptide with a second polypeptide, e.g., an immunoglobulin heavy chain with an immunoglobulin light chain in the antigen-binding constructs and heterodimer pairs described herein. As such, "preferential pairing" refers to the preferred pairing of a first polypeptide with a second polypeptide when one or more additional, distinct polypeptides are present at the same time as the pairing occurs between the first and second polypeptide. Typically preferential pairing occurs as a result of the modification (e.g., amino acid modification) of one or both of the first and second polypeptide. Typically preferential pairing results in the paired first and second polypeptide being the most abundant dimer present after pairing occurs. It is known in the art that an immunoglobulin heavy chain (H1) will if co-expressed with two different immunoglobulin light chains (L1 and L2), statistically pair equally with both light chains, resulting in an approximate 50:50 mixture of H1 paired with L1 and H1 paired with L2. In this context, "preferential pairing" would occur between, for example, H1 and L1, if the amount of the H1-L1 heavy chain-light chain heterodimer was greater than the amount of the H1-L2 heterodimer when H1 is co-expressed with both L1 and L2. Thus, in this case, H1 preferentially pairs with L1 relative to L2.

Antibody heavy chains pair with antibody light chains and meet or contact one another at an "interface." The "interface" includes one or more "contact" amino acid residues in a first polypeptide that interact with one or more "contact" amino acid residues of a second polypeptide. In one context, the term interface can be used to describe the interface of the dimerized CH3 domain of an Fc, where the Fc is preferably derived from an IgG antibody such as IgG1 and most preferably a human IgG1 antibody.

The antibody heavy chain that is to be associated with an antibody light chain typically meet or contact each other at an "interface." The immunoglobulin light chain operatively associates with the immunoglobulin heavy chain via the "interface". The "interface" comprises those one or more "contact" amino acid residues in the immunoglobulin heavy chain that interact with one or more "contact" amino acid residues in the interface of the immunoglobulin light chain. As used herein, the interface can comprise the VH and CH1 domains of the immunoglobulin heavy chain and the VL and CL domains of the immunoglobulin light chain. The "interface" can be derived from an IgG antibody and most preferably a human IgG1 antibody.

The term "amino acid modifications" as used herein includes, but is not limited to, amino acid mutations, insertions, deletions, substitutions, chemical modifications, physical modifications, and rearrangements.

Antigen Binding Constructs and Heterodimer Pairs

The antigen-binding constructs described herein can comprise a first heterodimer and a second heterodimer; each heterodimer obtained by pairing an immunoglobulin heavy chain with an immunoglobulin light chain. The structure and organization of the constant and variable domains of immunoglobulin heavy and light chains are well known in the art. Immunoglobulin heavy chains typically comprise one variable (VH) domain, and three constant domains, CH1, CH2, and CH3. Immunoglobulin light chains typically comprise one variable (VL) domain and one constant (CL) domain. Various modifications to these typical formats can be made.

The antigen-binding constructs and heterodimer pairs described herein can comprise a first heterodimer and a second heterodimer, each heterodimer comprising an immunoglobulin/antibody heavy chain or fragment thereof having at least a VH and CH1 domain, and an immunoglobulin/antibody light chain having a VL domain and a CL domain. In one embodiment, both heterodimers of the heterodimer pair and antigen-binding construct comprise a full-length immunoglobulin heavy chain. In another embodiment, both heterodimers of the heterodimer pair or antigen-binding construct comprise a fragment of the immunoglobulin heavy chain that includes at least a VH and a CH1 domain. In one embodiment, both heterodimers of the heterodimer pair comprise an amino terminal fragment of the immunoglobulin heavy chain that comprises at least a VH and a CH1 domain. In another embodiment, both heterodimers of the heterodimer pair comprise a carboxy terminal fragment of the immunoglobulin heavy chain that comprises at least a VH and a CH1 domain.

Each heterodimer of the heterodimer pair can bind specifically to an antigen or epitope. In one embodiment, the immunoglobulin heavy chain and the immunoglobulin light chain of each heterodimer is derived or engineered from a known therapeutic antibody. A therapeutic antibody is one that is effective in treating a disease or disorder in a mammal with or predisposed to the disease or disorder. Suitable therapeutic antibodies from which each heterodimer can be derived include, but are not limited to abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, PROXINIUM™, RENCAREX™, ustekinumab, and zalutumumab.

In one embodiment, the immunoglobulin heavy chain and the immunoglobulin light chain of each heterodimer are derived or engineered from an antibody that binds a molecule including, but not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (alpha-IFN), beta interferon (beta-IFN) and gamma interferon (gamma-IFN); protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as AFGF and PFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNF-alpha, superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p 150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD18, CD61, CD104, beta5, beta6, beta7 and beta8; Integrin subunit combinations including but not limited to, alphaVbeta3, alphaVbeta5 and alpha4beta7; a member of an apoptosis pathway; IgE; blood group antigens; flk2/flt3 receptor; obesity (OB) receptor; mp1 receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIb.alpha., GPIIb/IIIa and CD200; and fragments of any of the above-listed polypeptides.

In an embodiment, the immunoglobulin heavy and light chains of each heterodimer are derived or engineered from antibodies that specifically bind cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 514 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; Va4-D5; D156-22 found in colorectal cancer; TRA-1-85 (blood group H); SCP-1 found in testis and ovarian cancer;

C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 valiant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1) and fragments of any of the above-listed polypeptides.

Human antibodies can be grouped into isotypes including IgG, IgA, IgE, IgM, and IgD. In one embodiment, an Fc is derived from an IgG isotype. In another embodiment, an Fc is derived from an IgA isotype. In another embodiment, an Fc is derived from an IgE isotype. In another embodiment, an Fc is derived from an IgM isotype. In another embodiment, an Fc is derived from an IgD isotype.

Human IgG antibodies can also be divided into the subclasses IgG1, IgG2, IgG3, and IgG4. Thus, in some embodiments, it is contemplated an Fc can be derived from an IgG1, IgG2, IgG3, or IgG4 subclass of antibodies.

Each heterodimer of the heterodimer pair can bind specifically to an epitope or antigen. In one embodiment, each heterodimer of the heterodimer pair binds to the same epitope. In another embodiment, the first heterodimer of the heterodimer pair specifically binds to an epitope on one antigen and the second heterodimer of the heterodimer pair binds specifically to a different epitope on the same antigen. In another embodiment, the first heterodimer of the heterodimer pair specifically binds to an epitope on a first antigen, and the second heterodimer of the heterodimer pair specifically binds to an epitope on a second antigen that is different from the first antigen. For example, in one embodiment, the first heterodimer binds specifically to Tissue Factor, while the second heterodimer binds specifically to antigen Her2(ErbB2). In another embodiment, the first heterodimer binds specifically to a molecule or cancer antigen described above. In another embodiment, the second heterodimer binds specifically to a molecule or cancer antigen described above. In yet another embodiment, the first heterodimer binds specifically to antigen CD3, while the second heterodimer binds specifically to antigen CD19.

As indicated above, in some embodiments, the immunoglobulin heavy chain and the immunoglobulin light chain of each heterodimer can be derived or engineered from a known therapeutic antibody, or from an antibody that binds various target molecules or cancer antigens. The amino acid and nucleotide sequences of numerous such molecules are readily available (see for example, GenBank: AJ308087.1 (Humanized anti-human tissue factor antibody D3H44 light chain variable region and CL domain); GenBank. AJ308086.1 (humanized anti-human tissue factor antibody D3H44 heavy chain variable region and $C_{H1}$ domain); GenBank: HC359025.1 (Pertuzumab Fab light chain gene module); GenBank: HC359024.1 (Pertuzumab Fab heavy chain gene module); GenBank: GM685465.1 (Antibody Trastuzumab (=Herceptin)—wildtype; light chain); GenBank: GM685463.1 (Antibody Trastuzumab (=Herceptin)—wildtype; heavy chain); GenBank: GM685466.1 (Antibody Trastuzumab (=Herceptin)—GC-optimized light chain); and GenBank: GM685464.1 (Antibody Trastuzumab (=Herceptin)—GC-optimized heavy chain. The sequences of each of the GenBank numbers described herein are available from the NCBI website as of Nov. 28, 2012 and are each incorporated by reference in its entirety for all purposes.

In some aspects, an isolated antigen-binding construct comprises an amino acids sequence that is at least 80, 85, 90, 91, 92, 93, 94, 95, 96, 97, 98, 99, or 100% identical to an amino acid sequence or fragment thereof set forth in the Tables or accession numbers disclosed herein. In some aspects, an isolated antigen-binding construct comprises an amino acids sequence encoded by a polynucleotide that is at least 80, 85, 90, 91, 92, 93, 94, 95, 96, 97, 98, 99, or 100% identical to a nucleotide sequence or fragment thereof set forth in Tables or accession numbers disclosed herein.

Amino Acid Modifications to Immunoglobulin Heavy and Light Chains

At least one of the heterodimers of a heterodimer pair can comprise one or more amino acid modifications to their immunoglobulin heavy and/or immunoglobulin light chains such that the heavy chain of the first heterodimer preferentially pairs with one of the light chains rather than the other. Likewise, the heavy chain of the second heterodimer can preferentially pair with the second light chain rather than the first. This preferential pairing of one heavy chain with one of two light chains can be based on design sets comprising one immunoglobulin heavy chain and two immunoglobulin light chains where the immunoglobulin heavy chain preferentially pairs with one of the two immunoglobulin light chains over the other when the immunoglobulin heavy chain is co-expressed with both immunoglobulin light chains. Thus, a LCCA design set can comprise one immunoglobulin heavy chain, a first immunoglobulin light chain and a second immunoglobulin light chain.

In one embodiment, the one or more amino acid modifications comprise one or more amino acid substitutions.

In one embodiment, the preferential pairing demonstrated in the LCCA design set is established by modifying one or more amino acids that are part of the interface between the light chain and heavy chain. In one embodiment, the preferential pairing demonstrated in the LCCA design set is established by modifying one or more amino acids in at least one of the CH1 domain of the immunoglobulin heavy chain, the CL domain of a first immunoglobulin light chain and the CL domain of the second immunoglobulin light chain.

In one embodiment the one or amino acid modifications are limited to the conserved framework residues of the variable (VH, VL) and constant (CH1, CL) domains as indicated by the Kabat numbering of residues. For example, Almagro [Frontiers In Bioscience (2008) 13: 1619-1633] provides a definition of the framework residues on the basis of Kabat, Chotia, and IMGT numbering schemes.

In one embodiment, at least one of the heterodimers comprises one or more mutations introduced in the immunoglobulin heavy and immunoglobulin light chains that are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces. In one embodiment, at least one of the heterodimers comprises one or more mutations where the mutations introduced in the immunoglobulin heavy and immunoglobulin light chains introduce a new hydrogen bond across the light and heavy chain at the interface. In one embodiment, at least one of the heterodimers comprises one or more mutations where the mutations introduced in the immunoglobulin heavy and immunoglobulin light chains introduce a new salt bridge across the light and heavy chain at the interface.

Non-limiting examples of suitable LCCA design sets are shown in Table 1, showing amino acid modifications in one immunoglobulin heavy chain $C_{H1}$ domain (H1) and the two immunoglobulin light chain CL domains (L1 and L2) of the heterodimers, where H1 preferentially pairs with L1 when H1, L1 and L2 are co-expressed. The amino acid modifications shown in these LCCA design sets are based on the amino acid sequence of anti-tissue factor antibody D3H44 immunoglobulin heavy and light chains.

TABLE 1

Selected LCCA design sets with constant domain modifications to one immunoglobulin heavy chain (H1) and two immunoglobulin light chains, L1 and L2, where H1 preferentially pairs with L1

| Set # | H1_mutation* | L1_mutation | L2_mutation |
|---|---|---|---|
| C500 | WT# | WT | F116A |
| C503 | WT | WT | F98L |
| C505 | A139W_V190S | F116S | F118W_V133S |
| C507 | A139W_V190S | F116A | F118W_V133S |
| C509 | A139W | WT | F116A |
| C510 | A139V_V190S | F116A | F118W_V133S |
| C511 | A139V_V190S | WT | F118W_V133S |
| C513 | A139I_V190S | F116A | F118W_V133S |
| C514 | A139I_V190S | WT | F118W_V133S |
| C515 | A139G_V190A | L135W_N137A | F116A_L135A |
| C517 | A139G_V190A | L135W | F116A_L135A |
| C519 | A139G_V190A | L135W | F116A_L135V |
| C521 | S188I | WT | S176V_T178L |
| C523 | V190G | F116A | F118W_V133S |
| C524 | V190G | F116S | F118W_V133S |
| C525 | S188L_V190Y | V133S | S176L |
| C527 | F174V_P175S_S188G | S176L | WT |
| C530 | D146G_Q179R | Q124E_Q160E_T178D | Q160K_T178R |
| C532 | L143A_D144G_Q179R | Q124E_V133W_Q160E_T180E | V133A_Q160K_T178R |

*Kabat numbering;
WT refers to a wild-type immunoglobulin chain without amino acid mutations Additional non-limiting examples of suitable LCCA design sets are shown in Table 2, showing amino acid modifications in one immunoglobulin heavy chain $C_{H1}$ domain (H2) and the two immunoglobulin light chain $C_L$ domains (L1 and L2) of the heterodimers, where H2 preferentially pairs with L2 when H2, L1 and L2 are co-expressed:

TABLE 2

Selected LCCA design sets with constant domain modifications to one immunoglobulin heavy chain (H2) and two immunoglobulin light chains, L1 and L2, where H2 preferentially pairs with L2

| Set # | H2_mutation* | L1_mutation | L2_mutation |
|---|---|---|---|
| C501 | A139W_V190S | WT# | F116A |
| C502 | A139W_V190A | WT | F116A |
| C504 | F100W | WT | F98L |
| C506 | A139W | F116S | F118W_V133S |
| C508 | A139V | F116A | F118W_V133S |
| C512 | A139I | WT | F118W_V133S |
| C516 | A139W | L135W_N137A | F116A_L135A |
| C518 | A139W | L135W | F116A_L135A |
| C520 | A139W | L135W | F116A_L135V |
| C522 | WT | WT | S176V_T178L |
| C526 | F174V_P175S_S188G | V133S | S176L |
| C528 | F174V_S188L | S176L | WT |

TABLE 2-continued

Selected LCCA design sets with constant domain modifications to one immunoglobulin heavy chain (H2) and two immunoglobulin light chains, L1 and L2, where H2 preferentially pairs with L2

| Set # | H2_mutation* | L1_mutation | L2_mutation |
|---|---|---|---|
| C529 | S188L | S176L | WT |
| C531 | K145T_Q179D_S188L | Q124E_Q160E_T178D | Q160K_T178R |
| C533 | K145T_Q179D_S188F | Q124E_V133W_Q160E_T180E | V133A_Q160K_T178R |

*Kabat numbering;
WT refers to a wild-type immunoglobulin chain without amino acid mutations Additional non-limiting examples of suitable LCCA design sets are described in the Examples, Tables, and Figs.

In one embodiment, the LCCA design sets comprises an immunoglobulin heavy chain with at least one amino acid modification in the CH1 domain, a first immunoglobulin light chain with at least one amino acid modification in the CL domain, and a second immunoglobulin light chain without any amino acid modifications in the CL domain. In another embodiment, the LCCA design set comprises an immunoglobulin heavy chain with at least one amino acid modification in the CH1 domain, a first immunoglobulin light chain with at least one amino acid modification in the CL domain, and a second immunoglobulin light chain with at least one amino acid modification in the CL domain. In another embodiment, the LCCA design set comprises an immunoglobulin heavy chain with at least one amino acid modification in the CH1 domain, a first immunoglobulin light chain with at least two amino acid modifications in the CL domain, and a second immunoglobulin light chain with at least two amino acid modifications in the CL domain. In another embodiment, the LCCA design set comprises an immunoglobulin heavy chain with at least one amino acid modification in the CH1 domain, a first immunoglobulin light chain with at least two amino acid modifications in the CL domain, and a second immunoglobulin light chain with at least one amino acid modification in the CL domain.

In one embodiment, the LCCA design set comprises an immunoglobulin heavy chain with no amino acid modifications in the CH1 domain, a first immunoglobulin light chain with no amino acid modifications in the CL domain, and a second immunoglobulin light chain with at least one amino acid modification in the CL domain. In one embodiment, the LCCA design set comprises an immunoglobulin heavy chain with no amino acid modifications in the CH1 domain, a first immunoglobulin light chain with no amino acid modifications in the CL domain, and a second immunoglobulin light chain with at least two amino acid modifications in the CL domain.

In one embodiment, the LCCA design set comprises an immunoglobulin heavy chain with at least two amino acid modifications in the CH1 domain, a first immunoglobulin light chain with no amino acid modifications in the CL domain, and a second immunoglobulin light chain with at least one amino acid modification in the CL domain. In one embodiment, the LCCA design set comprises an immunoglobulin heavy chain with at least two amino acid modifications in the CH1 domain, a first immunoglobulin light chain with at least one amino acid modifications in the CL domain, and a second immunoglobulin light chain with at least one amino acid modification in the CL domain. In one embodiment, the LCCA design set comprises an immunoglobulin heavy chain with at least two amino acid modifications in the CH1 domain, a first immunoglobulin light chain with at least one amino acid modifications in the CL domain, and a second immunoglobulin light chain with at least two amino acid modifications in the CL domain. In one embodiment, the LCCA design set comprises an immunoglobulin heavy chain with at least two amino acid modifications in the CH1 domain, a first immunoglobulin light chain with at least two amino acid modifications in the CL domain, and a second immunoglobulin light chain with at least two amino acid modifications in the CL domain. In one embodiment, the LCCA design set comprises an immunoglobulin heavy chain with at least two amino acid modifications in the CH1 domain, a first immunoglobulin light chain with at least three amino acid modifications in the CL domain, and a second immunoglobulin light chain with at least two amino acid modifications in the CL domain.

In one embodiment, the LCCA design set comprises an immunoglobulin heavy chain with at least three amino acid modifications in the CH1 domain, a first immunoglobulin light chain with no amino acid modifications in the CL domain, and a second immunoglobulin light chain with at least one amino acid modifications in the CL domain. In one embodiment, the LCCA design set comprises an immunoglobulin heavy chain with at least three amino acid modifications in the CH1 domain, a first immunoglobulin light chain with at least one amino acid modification in the CL domain, and a second immunoglobulin light chain with at least one amino acid modification in the CL domain. In one embodiment, the LCCA design set comprises an immunoglobulin heavy chain with at least three amino acid modifications in the CH1 domain, a first immunoglobulin light chain with at least three amino acid modifications in the CL domain, and a second immunoglobulin light chain with at least two amino acid modifications in the CL domain. In one embodiment, the LCCA design set comprises an immunoglobulin heavy chain with at least three amino acid modifications in the CH1 domain, a first immunoglobulin light chain with at least four amino acid modifications in the CL domain, and a second immunoglobulin light chain with at least three amino acid modifications in the CL domain.

In one embodiment, the preferential pairing demonstrated in the LCCA design set is established by modifying one or more amino acids in at least one of the VH domain of the immunoglobulin heavy chain, the VL domain of a first immunoglobulin light chain and the VL domain of the second immunoglobulin light chain. Non-limiting examples of suitable LCCA design sets are shown in Table 3, showing amino acid modifications in one immunoglobulin heavy chain VH domain (H1) and the two immunoglobulin light chain VL domains (L1 and L2) of the heterodimers, where H1 preferentially pairs with L1 when H1, L1 and L2 are co-expressed:

TABLE 3

Selected LCCA design sets with variable domain modifications to one immunoglobulin heavy chain and two immunoglobulin light chains, where H1 preferentially pairs with L1

| Set # | H1_mutation* | L1_mutation | L2_mutation |
|---|---|---|---|
| V001 | V37W_W103H | F98L | F98W |
| V004 | V37W_W103H | F98L | P44W |
| V005 | V37A_W103H | P44W | F98L |
| V006 | V37W_W103F | F98L | F98W |
| V007 | V37W | F98A | F98W |
| V009 | V37W | F98A | WT# |
| V011 | V37I | WT | F98L |
| V013 | V37A_W103V | P44W | F98A |
| V015 | V37A_W103H | P44W | F98A |
| V016 | V37A_W103H | P44W | F98W |
| V020 | L45W | Y87G | P44W |
| V022 | WT | F98W | F98A |
| V023 | WT | WT | F98A |
| V024 | Q39R | Q38E | F98A |
| V026 | Q39R | Q38E | WT |
| V028 | Q39R | Q38E | Q38R |
| V030 | Q39R | Q38D | Q38R |
| V032 | Q39M | Q38M | Q38E |
| V034 | Q39K | Q38N_T85E | Q38N_T85K |
| V037 | Q39E | Q38R | F98A |
| V039 | Q39D | Q38R | Q38D |
| V040 | V37E | L89R_F98T | WT |
| V042 | V37E_F100D | L89R_F98W | WT |
| V044 | V37E_F100D | L89R_F98W | F98Y |

*Kabat numbering;
WT refers to a wild-type immunoglobulin chain without amino acid mutations Additional non-limiting examples of suitable LCCA design sets are depicted in Table 4, showing amino acid modifications in one immunoglobulin heavy chain VH domain (H2) and the two immunoglobulin light chain VL domains (L1 and L2) of the heterodimers, where H2 preferentially pairs with L2 when H2, L1 and L2 are co-expressed:

TABLE 4

Selected LCCA design sets with variable domain modifications to one immunoglobulin heavy chain and two immunoglobulin light chains, where H2 preferentially pairs with L2

| Set # | H2_mutation* | L1_mutation | L2_mutation |
|---|---|---|---|
| V002 | V37I | F98L | F98W |
| V003 | WT# | F98L | F98W |
| V005 | V37A_W103H | F98L | P44W |
| V007 | V37W | F98W | F98A |
| V008 | V37I | F98A | F98W |
| V009 | V37W | WT | F98A |
| V010 | V37I | F98A | WT |
| V012 | F100W | WT | F98L |
| V014 | V37W | P44W | F98A |
| V017 | V37A_W103V | P44W | F98W |
| V018 | V37A_W103V | P44W | F98L |
| V019 | V37I_F100W | P44W | F98L |
| V021 | V37A_W103H | Y87G | P44W |
| V025 | V37W | Q38E | F98A |
| V027 | WT | Q38E | WT |
| V029 | Q39E | Q38E | Q38R |
| V030 | Q39R | Q38R | Q38D |
| V031 | Q39E | Q38D | Q38R |
| V033 | Q39R | Q38M | Q38E |
| V035 | Q39D | Q38N_T85E | Q38N_T85K |
| V036 | Q39E | Q38N_T85E | Q38N_T85K |
| V038 | V37W | Q38R | F98A |
| V041 | WT | L89R_F98T | WT |
| V043 | WT | L89R_F98W | WT |
| V045 | V37S_A97K | L89R_F98W | F98Y |

*Kabat numbering;
WT refers to a wild-type immunoglobulin chain without amino acid mutations In one embodiment, the LCCA design set comprises an immunoglobulin heavy chain with no amino acid modifications in the VH domain, a first immunoglobulin light chain with no amino acid modifications in the VL domain, and a second immunoglobulin light chain with at least one amino acid modification in the VL domain. In one embodiment, the LCCA design set comprises an immunoglobulin heavy chain with no amino acid modifications in the VH domain, a first immunoglobulin light chain with no amino acid modifications in the VL domain, and a second immunoglobulin light chain with at least two amino acid modifications in the VL domain.

In one embodiment, the LCCA design set comprises an immunoglobulin heavy chain with at least one amino acid modification in the VH domain, a first immunoglobulin light chain with no amino acid modifications in the VL domain, and a second immunoglobulin light chain with at least one amino acid modification in the VL domain. In one embodiment, the LCCA design set comprises an immunoglobulin heavy chain with at least one amino acid modification in the VH domain, a first immunoglobulin light chain with at least one amino acid modification in the VL domain, and a second immunoglobulin light chain with at least one amino acid modification in the VL domain. In one embodiment, the LCCA design set comprises an immunoglobulin heavy chain with at least one amino acid modification in the VH domain, a first immunoglobulin light chain with at least two amino acid modifications in the VL domain, and a second immunoglobulin light chain with at least two amino acid modifications in the VL domain.

In one embodiment, the LCCA design set comprises an immunoglobulin heavy chain with at least two amino acid modifications in the VH domain, a first immunoglobulin light chain with no amino acid modifications in the VL domain, and a second immunoglobulin light chain with at least one amino acid modification in the VL domain. In one embodiment, the LCCA design set comprises an immunoglobulin heavy chain with at least two amino acid modifications in the VH domain, a first immunoglobulin light chain with at least two amino acid modifications in the VL domain, and a second immunoglobulin light chain with at least one amino acid modification in the VL domain. In one embodiment, the LCCA design set comprises an immunoglobulin heavy chain with at least two amino acid modifications in the VH domain, a first immunoglobulin light chain with at least one amino acid modification in the VL domain, and a second immunoglobulin light chain with at least one amino acid modification in the VL domain.

In one embodiment, the LCCA design sets shown in Tables 1 to 4 are combined to provide a combination comprising two distinct immunoglobulin heavy chains (H1 and H2) and two distinct immunoglobulin light chains (L1 and L2), where H1 preferentially pairs with L1 and H2 preferentially pairs with L2 when H1, H2, L1, and L2 are co-expressed. In one embodiment, a LCCA design set from Table 1, comprising modifications to the $C_{H1}$ domain of the heavy chain and/or the CL domain of the light chains is combined with a LCCA design set from Table 2, also comprising modifications to the CH1 domain of the heavy chain and/or the CL domain of the light chains.

Non-limiting examples of design sets derived from combinations of LCCA design sets are shown in Table 5:

TABLE 5

Design sets comprising constant domain modifications

| Set # | Set # | H1_mutation* | L1_mutation | H2_mutation | L2_mutation |
|---|---|---|---|---|---|
| C500 | C501 | WT# | WT | A139W_V190S | F116A |
| C500 | C502 | WT | WT | A139W_V190A | F116A |
| C503 | C504 | WT | WT | F100W | F98L |
| C505 | C506 | A139W_V190S | F116S | A139W | F118W_V133S |
| C507 | C508 | A139W_V190S | F116A | A139V | F118W_V133S |
| C509 | C501 | A139W | WT | A139W_V190S | F116A |
| C509 | C502 | A139W | WT | A139W_V190A | F116A |
| C510 | C508 | A139V_V190S | F116A | A139V | F118W_V133S |
| C511 | C512 | A139V_V190S | WT | A139I | F118W_V133S |
| C513 | C508 | A139I_V190S | F116A | A139V | F118W_V133S |
| C514 | C512 | A139I_V190S | WT | A139I | F118W_V133S |
| C515 | C516 | A139G_V190A | L135W_N137A | A139W | F116A_L135A |
| C517 | C518 | A139G_V190A | L135W | A139W | F116A_L135A |
| C519 | C520 | A139G_V190A | L135W | A139W | F116A_L135V |
| C521 | C522 | S188I | WT | WT | S176V_T178L |
| C523 | C508 | V190G | F116A | A139V | F118W_V133S |
| C524 | C506 | V190G | F116S | A139W | F118W_V133S |
| C525 | C526 | S188L_V190Y | V133S | F174V_P175S_S188G | S176L |
| C527 | C528 | F174V_P175S_S188G | S176L | F174V_S188L | WT |
| C527 | C529 | F174V_P175S_S188G | S176L | S188L | WT |
| C530 | C531 | D146G_Q179R | Q124E_Q160E_T178D | K145T_Q179D_S188L | Q160K_T178R |
| C532 | C533 | L143A_D144G_Q179R | Q124E_V133W_Q160E_T180E | K145T_Q179D_S188F | V133A_Q160K_T178R |

*Kabat numbering;
WT refers to a wild-type immunoglobulin chain without amino acid mutations In one embodiment, a LCCA design set from Table 3, comprising modifications to the $V_H$ domain of the heavy chain and/or the $V_L$ domain of the light chains is combined with a LCCA design set from Table 4, also comprising modifications to the $V_H$ domain of the heavy chain and/or the $V_L$ domain of the light chains. Non-limiting examples of design sets derived from such combinations of LCCA design sets are shown in Table 6:

Transferability of Specific Amino Acid Modifications Identified Herein to Other Antibodies:

Although the specific amino acid modifications to immunoglobulin heavy and light chains identified above have been described with respect to the D3H44 anti-tissue factor extracellular domain antibody immunoglobulin heavy and light chains, it is contemplated and demonstrated herein (see Examples, Figs, and Tables) that these amino acid modifi-

TABLE 6

Design sets comprising variable domain modifications

| Set # | Set # | H1_mutation* | L1_mutation | H2_mutation | L2_mutation |
|---|---|---|---|---|---|
| V001 | V002 | V37W_W103H | F98L | V37I | F98W |
| V001 | V003 | V37W_W103H | F98L | WT# | F98W |
| V004 | V005 | V37W_W103H | F98L | V37A_W103H | P44W |
| V006 | V002 | V37W_W103F | F98L | V37I | F98W |
| V006 | V003 | V37W_W103F | F98L | WT | F98W |
| V007 | V008 | V37W | F98A | V37I | F98W |
| V009 | V010 | V37W | F98A | V37I | WT |
| V011 | V012 | V37I | WT | F100W | F98L |
| V013 | V014 | V37A_W103V | P44W | V37W | F98A |
| V015 | V014 | V37A_W103H | P44W | V37W | F98A |
| V016 | V017 | V37A_W103H | P44W | V37A_W103V | F98W |
| V005 | V018 | V37A_W103H | P44W | V37A_W103V | F98L |
| V005 | V019 | V37A_W103H | P44W | V37I_F100W | F98L |
| V020 | V021 | L45W | Y87G | V37A_W103H | P44W |
| V022 | V007 | WT | F98W | V37W | F98A |
| V023 | V009 | WT | WT | V37W | F98A |
| V024 | V025 | Q39R | Q38E | V37W | F98A |
| V026 | V027 | Q39R | Q38E | WT | WT |
| V028 | V029 | Q39R | Q38E | Q39E | Q38R |
| V030 | V031 | Q39R | Q38D | Q39E | Q38R |
| V032 | V033 | Q39M | Q38M | Q39R | Q38E |
| V034 | V035 | Q39K | Q38N_T85E | Q39D | Q38N_T85K |
| V034 | V036 | Q39K | Q38N_T85E | Q39E | Q38N_T85K |
| V037 | V038 | Q39E | Q38R | V37W | F98A |
| V039 | V030 | Q39D | Q38R | Q39R | Q38D |
| V040 | V041 | V37E | L89R_F98T | WT | WT |
| V042 | V043 | V37E_F100D | L89R_F98W | WT | WT |
| V044 | V045 | V37E_F100D | L89R_F98W | V37S_A97K | F98Y |

*Kabat numbering;
WT refers to a wild-type immunoglobulin chain without amino acid mutations cations are transferable to other immunoglobulin heavy and light chains, resulting in similar patterns of preferential pairing of one immunoglobulin heavy chain with one of the two immunoglobulin light chains in view of the following.

The VH:VL and CH1:CL interface residues in the interface between immunoglobulin heavy and light chains are relatively well conserved (Padlan et al., 1986, Mol. Immunol. 23(9): 951-960). This sequence conservation, a result of evolutionary constraints, increases the likelihood that functionally active antibody binding domains will be formed during combinatorial pairing of light and heavy chains. As a result of this sequence conservation, it follows that sequence modifications in the specific examples noted above for D3H44, which drive preferential pairing, could transfer to other heavy and light chain pair heterodimers with approximately equivalent results being obtained with respect to preferential pairing, since this region displays high sequence conservation across antibodies; Further, when sequence differences do occur, these usually lie distal to the CH1:CL interface. This is particularly the case for the CH1 and CL domains. There is, however, some sequence variability at the antigen-binding site with respect to CDR (complementarity-determining regions) loop residues (and length), particularly for CDR-H3. Thus, in one embodiment, the heterodimer pairs according to the invention comprise heterodimers where at least one heterodimer comprises one or more amino acid modifications in the VH and/or VL domains that lie distal to the CDR loops when the amino acid sequence of the antigen-binding site is significantly different from that of the D3H44 antibody. In another embodiment, the heterodimer pairs according to the invention comprise heterodimers where at least one heterodimer comprises one or more amino acid modifications in the VH and/or VL domains that lie proximal or distal to the CDR loops, when the amino acid sequence of the antigen-binding site is substantially the same as that of the D3H44 antibody.

In one embodiment, the amino acid modifications described herein are transferable to the immunoglobulin heavy and light chains of antibodies based on human or humanized IgG1/κ. Non-limiting examples of such IgG1/κchains include Ofatumumab (for human) or Trastuzumab, Pertuzumab or Bevacizumab (for humanized).

In another embodiment, the amino acid modifications described herein are transferable to the immunoglobulin heavy and light chains of antibodies utilizing commonly used VH and VL subgroups. Non-limiting examples of such antibodies include Peruzumab.

In one embodiment, the amino acid modifications described herein are transferable to the immunoglobulin heavy and light chains of antibodies having a framework close to germline. Examples of such antibodies include Obinutuzumab.

In one embodiment, the amino acid modifications described herein are transferable to the immunoglobulin heavy and light chains of antibodies having a VH:VL interdomain angle close to the average observed for heavy and light chain pairs. An example of this type of antibody includes, but is not limited to Pertuzumab. In another embodiment, the amino acid modifications described herein are transferable to the immunoglobulin heavy and light chains of antibodies having canonical CL and CH1 domains. Suitable examples of such antibodies include, but are not limited to Trastuzumab.

In some embodiments, certain subsets of the amino acid modifications described herein are utilized in variant domains in antigen binding constructs provided above.

The Examples, Figs, and Tables demonstrate that amino acid modifications (e.g., within one or more Fab fragments comprising a variable region and a constant region) are transferable to other immunoglobulin heavy and light chains, resulting in similar patterns of preferential pairing of one immunoglobulin heavy chain with one of the two immunoglobulin light chains.

Preferential Pairing

As described above, at least one heterodimer of the antigen binding construct/heterodimer pairs according to the invention can comprise one or more amino acid modifications to their immunoglobulin heavy and/or immunoglobulin light chains such that the heavy chain of the one heterodimer, for example H1, preferentially pairs with one of the light chains, for example L1, rather than the other light chain, L2, and the heavy chain of the other heterodimer, H2, preferentially pairs with the light chain, L2, rather than the light chain L1. In other words, the desired, preferential pairing is considered to be between H1 and L1, and between H2 and L2. Preferential pairing between, for example, H1 and L1 is considered to occur if the yield of the H1-L1 heterodimer is greater than the yield of the mispaired H1-L2 heterodimer when H1 is combined with L1 and L2, relative to the respective pairing of corresponding H1/L1 pair to H2/L2 pair without the one or more amino acid modifications. Likewise, preferential pairing between H2 and L2 is considered to occur if the yield of the H2-L2 heterodimer is greater than the yield of the mispaired H2-L1 heterodimer when H2 is combined with L1 and L2, relative to the respective pairing of corresponding H1-L1 pair to H2-L2 pair without the one or more amino acid modifications. In this context, an heterodimer comprising H1 and L1 (H1-L1), or H2 and L2 (H2-L2), is referred to herein as a preferentially paired, correctly paired, obligate pair, or desired heterodimer, while a heterodimer comprising H1 and L2 (H1-L2), or H2 and L1 (H2-L1), is referred to herein as a mispaired heterodimer. The set of mutations corresponding to the two heavy chains and the two light chains meant to achieve selective pairing of H1-L1 and H2-L2 is referred to as a design set.

Thus, in one embodiment, when one immunoglobulin heavy chain of a heterodimer is co-expressed with two immunoglobulin light chains, the relative yield of the desired heterodimer is greater than 55%. In another embodiment, when one immunoglobulin heavy chain of a heterodimer is co-expressed with two immunoglobulin light chains, the relative yield of the desired heterodimer is greater than 60%. In another embodiment, when one immunoglobulin heavy chain of a heterodimer is co-expressed with two immunoglobulin light chains, the relative yield of the desired heterodimer is greater than 70%. In another embodiment, when one immunoglobulin heavy chain of a heterodimer is co-expressed with two immunoglobulin light chains, the relative yield of the desired heterodimer is greater than 80%. In another embodiment, when one immunoglobulin heavy chain of a heterodimer is co-expressed with two immunoglobulin light chains, the relative yield of the desired heterodimer is greater than 90%. In another embodiment, when one immunoglobulin heavy chain of a heterodimer is co-expressed with two immunoglobulin light chains, the relative yield of the desired heterodimer is greater than 95%.

In the above example, preferential pairing between H1-L1 is considered to occur if the amount of the desired H1-L1 heterodimer is greater than the amount of the mispaired H1-L2 heterodimer when H1 is co-expressed with L1 and L2. Similarly, preferential pairing between H2-L2 is considered to occur if the amount of the desired H2-L2 heterodimer is greater than the amount of the mispaired H2-L2 heterodimer when H2 is co-expressed with L1 and L2. Thus, in one embodiment, when one immunoglobulin heavy chain of a heterodimer is co-expressed with two immunoglobulin light chains, the ratio of the desired heterodimer to the mispaired heterodimer is greater than 1.25:1. In one embodiment, when one immunoglobulin heavy chain of a heterodimer is co-expressed with two immunoglobulin light chains, the ratio of the desired heterodimer to the mispaired heterodimer is greater than 1.5:1. In another embodiment, when one immunoglobulin heavy chain of a heterodimer is co-expressed with two immunoglobulin light chains, the ratio of the desired heterodimer to the mispaired heterodimer is greater than 2:1. In another embodiment, when one immunoglobulin heavy chain of a heterodimer is co-expressed with two immunoglobulin light chains, the ratio of the desired heterodimer to the mispaired heterodimer is greater than 3:1. In another embodiment, when one immunoglobulin heavy chain of a heterodimer is co-expressed with two immunoglobulin light chains, the ratio of the desired heterodimer to the mispaired heterodimer is greater than 5:1. In another embodiment, when one immunoglobulin heavy chain of a heterodimer is co-expressed with two immunoglobulin light chains, the ratio of the desired heterodimer to the mispaired heterodimer is greater than 10:1. In another embodiment, when one immunoglobulin heavy chain of a heterodimer is co-expressed with two immunoglobulin light chains, the ratio of the desired heterodimer to the mispaired heterodimer is greater than 25:1. In another embodiment, when one immunoglobulin heavy chain of a heterodimer is co-expressed with two immunoglobulin light chains, the ratio of the desired heterodimer to the mispaired heterodimer is greater than 50:1.

Thermal Stability of Heterodimers

In one embodiment, each heterodimer of the heterodimer pair according to the invention has a thermal stability that is comparable to that of a heterodimer comprising the same immunoglobulin heavy and light chains but without the amino acid modifications to the $C_{H1}$, CL, VH, or VL domains described herein. In one embodiment, thermal stability is determined by measurement of melting temperature, or Tm. Thus, in one embodiment, the thermal stability of a heterodimer according to the invention is within about 10° C. of that of a heterodimer comprising the same immunoglobulin heavy and light chains without the amino acid modifications to the CH1, CL, VH, or VL domains described herein. Thus, in one embodiment, the thermal stability of a heterodimer according to the invention is within about 5° C. of that of a heterodimer comprising the same immunoglobulin heavy and light chains without the amino acid modifications to the CH1, CL, VH, or VL domains described herein. In another embodiment, the thermal stability of a heterodimer according to the invention is within about 3° C. of that of a heterodimer comprising the same immunoglobulin heavy and light chains without the amino acid modifications to the CH1, CL, VH, or VL domains described herein. In another embodiment, the thermal stability of a heterodimer according to the invention is within about 2° C. of that of a heterodimer comprising the same immunoglobulin heavy and light chains without the amino acid modifications to the CH1, CL, VH, or VL domains described herein. In another embodiment, the thermal stability of a heterodimer according to the invention is within about 1.5° C. of that of a heterodimer comprising the same immunoglobulin heavy and light chains without the amino acid modifications to the CH1, CL, VH, or VL domains described herein. In another embodiment, the thermal stability of a heterodimer according to the invention is within about 1° C. of that of a heterodimer comprising the same immunoglobulin heavy and light chains without the amino acid modifications to the CH1, CL, VH, or VL domains described herein. In another embodiment, the thermal stability of a heterodimer according to the invention is within about 0.5° C. of that of a heterodimer comprising the same immunoglobulin heavy and light chains without the amino acid modifications to the CH1, CL, VH, or VL domains described herein. In another embodiment, the thermal stability of a heterodimer according to the invention is within about 0.25° C. of that of a heterodimer comprising the same immunoglobulin heavy and light chains without the amino acid modifications to the CH1, CL, VH, or VL domains described herein.

Affinity of Heterodimers for Antigen

In one embodiment, each heterodimer of the heterodimer pair has an affinity for its respective antigen that is the same or comparable to that of a heterodimer comprising the same immunoglobulin heavy and light chains but without the amino acid modifications to the CH1, CL, VH, or VL domains described herein. In one embodiment, a heterodimer of the heterodimer pair has an affinity for its respective antigen that is within about 50 fold, or one order of magnitude, of that of a heterodimer comprising the same immunoglobulin heavy and light chains without the amino acid modifications to the CH1, CL, VH, or VL domains described herein. In one embodiment, a heterodimer of the heterodimer pair has an affinity for its respective antigen that is within about 25 fold, or one order of magnitude, of that of a heterodimer comprising the same immunoglobulin heavy and light chains without the amino acid modifications to the CH1, CL, VH, or VL domains described herein. In one embodiment, a heterodimer of the heterodimer pair has an affinity for its respective antigen that is within about 10 fold, or one order of magnitude, of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 5 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 2.5 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 2 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 1.5 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about the same as that of a heterodimer comprising the same immunoglobulin heavy and light chains without the amino acid modifications to the CH1, CL, VH, or VL domains described herein.

Additional Optional Modifications

In one embodiment, the immunoglobulin heavy and light chains of the heterodimer pairs according to the invention may be further modified (i.e., by the covalent attachment of various types of molecules) such that covalent attachment does not interfere with the preferential pairing between heavy chain and light chains or affect the ability of the heterodimer to bind to its antigen, or affect its stability. Such modification include, for example, but not by way of limitation, glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc.

In another embodiment, the immunoglobulin heavy and light chains of the heterodimer pairs according to the invention may be conjugated (directly or indirectly) to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), *pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, in an alternate embodiment, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

In some embodiments, the immunoglobulin heavy and light chains of the heterodimer are expressed as fusion proteins comprising a tag to facilitate purification and/or testing etc. As referred to herein, a "tag" is any added series of amino acids which are provided in a protein at either the C-terminus, the N-terminus, or internally that contributes to the identification or purification of the protein. Suitable tags include but are not limited to tags known to those skilled in the art to be useful in purification and/or testing such as albumin binding domain (ABD), His tag, FLAG tag, glutathione-s-transferase, haemaglutinin (HA) and maltose binding protein. Such tagged proteins may also be engineered to comprise a cleavage site, such as a thrombin, enterokinase or factor X cleavage site, for ease of removal, of the tag before, during or after purification.

In some embodiments, one or more of the cysteine residues at the bottom of the Fab domain in the light (position 214, Kabat numbering) and heavy (position 233, Kabat numbering) chain that form an interchain disulphide bond can be modified to serine or alanine or a non-cysteine or a distinct amino acid.

It is contemplated that additional amino acid modifications can be made to the immunoglobulin heavy chains in order to increase the level of preferential pairing, and/or the thermal stability of the heterodimer pairs. For example, additional amino acid modifications can be made to the immunoglobulin heavy chain Fc domain in order to drive preferential pairing between heterodimer pairs relative to homodimer pairs. Such amino acid modifications are known in the art and include, for example, those described, in US Patent Publication No. 2012/0149876. Alternatively, alternate strategies for driving preferential pairing between heterodimer pairs relative to homodimer pairs such as, for example, "knobs into holes", charged residues with ionic interactions, and strand-exchange engineered domain (SEED) technologies can also be employed. The latter strategies have been described in the art and are reviewed in Klein et al, supra. Further discussion of Fc domains follows below.

Fc Domains

The constructs described herein can further include an Fc. In some aspects, the Fc comprises at least one or two $C_{H3}$ domain sequences. In some aspects, the Fc is coupled, with or without one or more linkers, to a first heterodimer and/or a second heterodimer. In some aspects, the Fc is a human Fc. In some aspects, the Fc is a human IgG or IgG1 Fc. In some aspects, the Fc is a heterodimeric Fc. In some aspects, the Fc comprises at least one or two $C_{H2}$ domain sequences.

In some aspects, the Fc comprises one or more modifications in at least one of the $C_{H3}$ domain sequences. In some aspects, the Fc comprises one or more modifications in at least one of the $C_{H2}$ domain sequences. In some aspects, an Fc is a single polypeptide. In some aspects, an Fc is multiple peptides, e.g., two polypeptides.

In some aspects, the Fc comprises one or more modifications in at least one of the $C_{H3}$ sequences. In some aspects, the Fc comprises one or more modifications in at least one of the $C_{H2}$ sequences. In some aspects, an Fc is a single polypeptide. In some aspects, an Fc is multiple peptides, e.g., two polypeptides.

In some aspects, Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

In some aspects, a construct described herein comprises a heterodimeric Fc comprising a modified CH3 domain that has been asymmetrically modified. The heterodimeric Fc can comprise two heavy chain constant domain polypeptides: a first heavy chain polypeptide and a second heavy chain polypeptide, which can be used interchangeably provided that Fc comprises one first heavy chain polypeptide and one second heavy chain polypeptide. Generally, the first heavy chain polypeptide comprises a first CH3 sequence and the second heavy chain polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table X provides the amino acid sequence of the human IgG Fc sequence, corresponding to amino acids 231 to 447 of the full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table X. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE X

| Human IgG1 Fc sequence 231-447 (EU-numbering) | APELLGGPSVFLFPPKPKDTLMISRTPEVTCVVVD SHEDPEVKFNWYVDGVEVHNAKTKPREEQYNSTYR VVSVLTVLHQDWLNGKEYKCKVSNKALPAPIEKTI SKAKGQPREPQVYTLPPSRDELTKNQVSLTCLVKG FYPSDIAVEWESNGQPENNYKTTPPVLDSDGSFFL YSKLTVDKSRWQQGNVFSCSVMHEALHNHYTQKSL SLSPGK (SEQ ID NO: 1) |
|---|---|

| Variant IgG1 Fc sequence (231-447) | | ChainMutations |
|---|---|---|
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T411E, T411D, K409E, K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modifications to the first CH3 sequence, and "B" represents the amino acid modifications to the second CH3 sequence:
A:L351Y_F405A_Y407V, B:T366L_K392M_T394W,
A:L351Y_F405A_Y407V, B:T366L_K392L_T394W,
A:T350+_351Y_F405A_Y407V,
B:T350V_T366L_K392L_T394W,
A:T350V_L351Y_F405A_Y407V,
B:T350V_T366L_K392M_T394W,
A:T350V_L351Y_S400E_F405A_Y407V, and/or
B:T350V_T366L_N390R_K392M_T394W.

The one or more asymmetric amino acid modifications can promote the formation of a heterodimeric Fc in which the heterodimeric CH3 domain has a stability that is comparable to a wild-type homodimeric CH3 domain. In an embodiment, the one or more asymmetric amino acid modifications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some aspects, the Fc comprises one or more modifications in at least one of the $C_{H3}$ sequences that promote the formation of a heterodimeric Fc with stability comparable to a wild-type homodimeric Fc.

In one embodiment, the stability of the CH3 domain can be assessed by measuring the melting temperature of the CH3 domain, for example by differential scanning calorimetry (DSC). Thus, in a further embodiment, the CH3 domain has a melting temperature of about 68° C. or higher. In another embodiment, the CH3 domain has a melting temperature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher. In some aspects, the dimerized $C_{H3}$ sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments, a heterodimeric Fc comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in International Patent Publication No. WO 96/027011 (knobs into holes), in Gunasekaran et al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Labrijn et al [Efficient generation of stable bispecific IgG1 by controlled Fab-arm exchange. Labrijn A F, Meesters J I, de Goeij B E, van den Bremer E T, Neijssen J, van Kampen M D, Strumane K, Verploegen S, Kundu A, Gramer M J, van Berkel P H, van de Winkel J G, Schuurman J, Parren P W. Proc Natl Acad Sci USA. 2013 Mar. 26; 110(13):5145-50.

In some embodiments an isolated construct described herein comprises an antigen binding construct which binds an antigen; and a dimeric Fc polypeptide construct that has superior biophysical properties like stability and ease of manufacture relative to an antigen binding construct which does not include the same Fc polypeptide. A number of mutations in the heavy chain sequence of the Fc are known in the art for selectively altering the affinity of the antibody Fc for the different Fcgamma receptors. In some aspects, the Fc comprises one or more modifications to promote selective binding of Fc-gamma receptors.

The CH2 domain is amino acid 231-340 of the sequence shown in Table X. Exemplary mutations are listed below:

S298A/E333A/K334A, S298A/E333A/K334A/K326A (Lu Y, Vernes J M, Chiang N, et al. J Immunol Methods. 2011 Feb. 28; 365(1-2):132-41);

F243L/R292P/Y3001/V305I/P396L, F243L/R292P/Y300L/L235V/P396L (Stavenhagen J B, Gorlatov S, Tuaillon N, et al. Cancer Res. 2007 Sep. 15; 67(18):8882-90: Nordstrom J L, Gorlatov S, Zhang W, et al Breast Cancer Res. 2011 Nov. 30; 13(6):R123);

F243L (Stewart R. Thom G, Levens M, et al. Protein Eng Des Se. 2011 September; 24(9): 671-8.), S298A1E333 A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11): 4005-10);

S239D/S267E, S267E/L328F (Chu S Y, Vostiar I, Karki S, et al. Mol Immunol. 2008 September; 45(15):3926-33);

S239D/D265S/S298A/I332E, S239E/S298A/K326A/A327H, G237F/S298A/A330L/I 332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila N M. Strohl, Woodhead Publishing series in Biomedicine No 11, ISBN 1 907568 37 9, Oct. 2012) lists mutations on page 283.

In some embodiments a CH2 domain comprises one or more asymmetric amino acid modifications. In some embodiments a CH2 domain comprises one or more asymmetric amino acid modifications to promote selective binding of a FcγR. In some embodiments the CH2 domain allows for separation and purification of an isolated construct described herein.

FcRn Binding and PK Parameters

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport. Thus, in one embodiment, the constructs of the invention are able to bind FcRn.

Additional Modifications to Improve Effector Function

In some embodiments a construct described herein can be modified to improve its effector function. Such modifications are known in the art and include afucosylation, or engineering of the affinity of the Fc portion of antibodies towards an activating receptor, mainly FCGR3a for ADCC, and towards Clq for CDC. The following Table Y summarizes various designs reported in the literature for effector function engineering.

TABLE Y

| Reference | Mutations | Effect |
| --- | --- | --- |
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Thus, in one embodiment, a construct described herein can include a dimeric Fc that comprises one or more amino acid modifications as noted in the above table that confer improved effector function. In another embodiment, the construct can be afucosylated to improve effector function.

Linkers

The constructs described herein can include one or more heterodimers described herein operatively coupled to an Fc described herein. In some aspects, Fc is coupled to the one or more heterodimers with or without one or more linkers. In some aspects, Fc is directly coupled to the one or more heterodimers. In some aspects, Fc is coupled to the one or more heterodimers by one or more linkers. In some aspects, Fc is coupled to the heavy chain of each heterodimer by a linker.

In some aspects, the one or more linkers are one or more polypeptide linkers. In some aspects, the one or more linkers comprise one or more antibody hinge regions. In some aspects, the one or more linkers comprise one or more IgG1 hinge regions.

Methods of Preparing Heterodimer Pairs

As described above, the heterodimer pairs according to the invention can comprise a first heterodimer and a second heterodimer, each heterodimer comprising an immunoglobulin heavy chain or fragment thereof having at least a VH and CH1 domain, and an immunoglobulin light chain having a VL domain and a CL domain. The immunoglobulin heavy chains and immunoglobulin light chains of the heterodimer can readily be prepared using recombinant DNA technology known in the art. Standard techniques such as, for example, those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Short Protocols in Molecular Biology (Ausubel et al., John Wiley and Sons, New York, 4th ed., 1999); and Glick and Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression. Alternatively, the heterodimers and heterodimer pairs according to the invention can be chemically synthesized.

The nucleic acid and amino acid sequences of the immunoglobulin heavy and light chains of the antibodies from which the heterodimers are derived are either known in the art or can be readily determined using nucleic acid and/or protein sequencing methods. Methods of genetically fusing the tags described herein to the immunoglobulin heavy and/or light chains are known in the art, and some are described below and in the Examples.

For example, methods of expressing and co-expressing immunoglobulin heavy and light chains in a host cell are well known in the art. In addition, methods of tagging heavy chains and/or light chains using recombinant DNA technology are also well known in the art. Expression vectors and host cells suitable for expression of the heavy and light chains are also well known in the art as described below.

Bispecific antibody production methods that do not rely on the use only a single clonal or transient cell line expressing all four chains are known in the art (Gramer, et al. (2013) mAbs 5, 962; Strop et al. (2012) J Mol Biol 420, 204.). These methods rely on a post production arm exchange under redox conditions of the two pairs of light and heavy chain involved in the formation of bispecific antibody (Redox production). In this approach the H1:L1 and H2:L2 pairs can be expressed in two different cell lines to independently produce the two Fab arms. Subsequently, the two Fab arms are mixed under select redox conditions to achieve re-association of the two unique heavy chain H1 and H2 to form the bispecific antibody comprising L1:H1:H2:L2 chains. One can envision the use of the library/dataset of designs described herein in the production of bispecific antibodies using the Redox production method or modified versions of that method.

In certain embodiments, cell-free protein expression systems are utilized to co-express polypeptides (e.g., heavy and light chain polypeptides) without the use of living cells. Instead, all components needed to transcribe DNA to RNA and translate the RNA to protein (e.g. ribosomes, tRNAs, enzymes, cofactors, amino acids) are provided in solution for use in vitro. In certain embodiments, the in vitro expression requires (1) the genetic template (mRNA or DNA) encoding the heavy and light chain polypeptides and (2) a reaction solution containing the necessary transcriptional and translational molecular machinery. In certain embodiments, cell extracts substantially supply components of the reaction solution, for instance: RNA polymerases for mRNA transcription, ribosomes for polypeptide translation, tRNA, amino acids, enzymatic cofactors, an energy source, and cellular components essential for proper protein folding. Cell-free protein expression systems can be prepared using lysates derived from bacterial cells, yeast cells, insect cells, plant cells, mammalian cells, human cells or combinations thereof. Such cell lysates can provide the correct composition and proportion of enzymes and building blocks required for translation. In some embodiments, cell membranes are removed to leave only the cytosolic and organelle components of the cell.

Several cell-free protein expression systems are known in the art as reviewed in Carlson et al. (2012) Biotechnol. Adv. 30:1185-1194. For example, cell-free protein expression systems are available based on prokaryotic or eukaryotic cells. Examples of prokaryotic cell-free expression systems include those from *E. coli*. Eukaryotic cell-free protein expression systems are available based on extracts from rabbit reticulocytes, wheat germ, and insect cells, for example. Such prokaryotic and eukaryotic cell-free protein expression systems are commercially available from companies such as Roche, Invitrogen, Qiagen, and Novagen. One skilled in the art would readily be able to select suitable cell-free protein expression systems that would produce polypeptides (e.g., heavy chain and light chain polypeptides) that are capable of pairing with each other. Further, the cell-free protein expression system can also be supplemented with chaperones (e.g. BiP) and isomerases (e.g. disulphide isomerase) to improve the efficiency of IgG folding.

In some embodiments, cell-free expression systems are utilized to co-express the heavy and light chain polypeptides from DNA templates (transcription and translation) or mRNA templates (translation only).

Vectors and Host Cells

Recombinant expression of heavy and light chains requires construction of an expression vector containing a polynucleotide that encodes the heavy or light chain (e.g., antibody, or fusion protein). Once a polynucleotide encoding the heavy or light chain has been obtained, the vector for the production of the heavy or light chain may be produced by recombinant DNA technology using techniques well known in the art. Thus, methods for preparing a protein by expressing a polynucleotide containing the heavy or light chain encoding nucleotide sequence are described herein. Methods that are well known to those skilled in the art can be used to construct expression vectors containing heavy or light chain coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding heavy or light chains, operably linked to a promoter.

The expression vector is transferred to a host cell by conventional techniques and the transfected cells are then cultured by conventional techniques to produce the modified heavy or light chains for use in the method of the invention. In specific embodiments the heavy and light chains for use in the method are co-expressed in the host cell for expression of the entire immunoglobulin molecule, as detailed below.

A variety of host-expression vector systems may be utilized to express the modified heavy and light chains. Such host-expression systems represent vehicles by which the coding sequences of interest may be produced and subsequently purified, but also represent cells which may, when transformed or transfected with the appropriate nucleotide coding sequences, express the modified heavy and light chains in situ. These include but are not limited to microorganisms such as bacteria (e.g., *E. coli* and *B. subtilis*) transformed with recombinant bacteriophage DNA, plasmid DNA or cosmid DNA expression vectors containing the modified heavy and light chain coding sequences; yeast (e.g., *Saccharomyces Pichia*) transformed with recombinant yeast expression vectors containing modified heavy and light chain coding sequences; insect cell systems infected with recombinant virus expression vectors (e.g., baculovirus) containing modified heavy and light chain coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing modified heavy and light chain coding sequences; or mammalian cell systems (e.g., COS, CHO, BHK, HEK-293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of modified heavy and light chains, which is a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding the immunoglobulin heavy and light chains of each heterodimer is regulated by a constitutive promoter, inducible promoter or tissue specific promoter.

In mammalian host cells, a number of viral-based expression systems may be utilized. In cases where an adenovirus is used as an expression vector, the modified heavy and light chain coding sequences of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the modified heavy and light chains in infected hosts (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of the immunoglobulin heavy and light chains of the heterodimers may be controlled by any promoter or enhancer element known in the art. Promoters which may be used to control the expression of the gene encoding modified heavy and light chains (e.g., antibody or fusion protein) include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78.1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al, 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, HEK-293, 3T3, WI38, NSO, and in particular, neuronal cell lines such as, for example, SK-N-AS, SK—N—FI, SK-N-DZ human neuroblastomas (Sugimoto et al., 1984, J. Natl. Cancer Inst. 73: 51-57), SK—N—SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321 N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161:370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines that stably express the modified heavy and light chains of the invention (e.g., antibody or fusion protein) may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Co-Expression of Heavy Chains and Light Chains

The immunoglobulin heavy chains and light chains of the heterodimer pairs according to the invention can be co-expressed in mammalian cells, as noted above. In one embodiment, one heavy chain is co-expressed with two different light chains in a LCCA design set as described above, where the heavy chain preferentially pairs with one of the two light chains. In another embodiment, two heavy chains are co-expressed with two different light chains, where each heavy chain preferentially pairs with one of the light chains.

Testing of Heterodimer Pairs

As described above, at least one heterodimer of the heterodimer pairs according to the invention can comprise one or more amino acid modifications to their immunoglobulin heavy and/or immunoglobulin light chains such that when the two heavy chains and two light chains of the heterodimer pair are co-expressed in a mammalian cell, the heavy chain of the first heterodimer preferentially pairs with one of the light chains rather than the other. Likewise, the heavy chain of the second heterodimer preferentially pairs with the second light chain rather than the first. The degree of preferential pairing can be assessed, for example, by using the methods described below. The affinity of each heterodimer of the heterodimer pair for its respective antigen can be tested as described below. The thermal stability of each heterodimer of the heterodimer pair can also be tested as described below.

Methods to Measure Preferential Pairing

LCCA

In one embodiment, preferential pairing between immunoglobulin heavy and light chains is determined by performing a Light Chain Competition Assay (LCCA). Co-owned patent application PCT/US2013/063306, filed Oct. 3, 2013, describes various embodiments of LCCA and is herein incorporated by reference in its entirety for all purposes. The method allows quantitative analysis of the pairing of heavy chains with specific light chains within the mixture of co-expressed proteins and can be used to determine if one particular immunoglobulin heavy chain selectively associates with either one of two immunoglobulin light chains when the heavy chain and light chains are co-expressed. The method is briefly described as follows: At least one heavy chain and two different light chains are co-expressed in a cell, in ratios such that the heavy chain is the limiting pairing reactant; optionally separating the secreted proteins from the cell; separating the immunoglobulin light chain polypeptides bound to heavy chain from the rest of the secreted proteins to produce an isolated heavy chain paired fraction; detecting the amount of each different light chain in the isolated heavy chain fraction; and analyzing the relative amount of each different light chain in the isolated heavy chain fraction to determine the ability of the at least one heavy chain to selectively pair with one of the light chains.

The method provides reasonable throughput and is robust (i.e. insensitive to minor changes in operation, such as user or flow rate) and accurate. The method provides a sensitive assay that can measure the effects of small variations in the protein sequences. Promiscuous protein—protein; domain-domain; chain—chain interactions over large surface areas usually require multiple mutations (swaps) in order to introduce selectivity. The protein products do not need to be isolated and purified which enables more efficient screening. Further details regarding an embodiment of this method are described in the Examples.

Alternative Methods to Determine Preferential Pairing

Alternative methods for detecting preferential pairing include using LC-MS (Liquid chromatography—Mass spectrometry) to quantify the relative heterodimer populations including each light chain using differences in their molecular weight to identify each distinct species. An antigen activity assay could also be used to quantify relative heterodimer populations containing each light chain whereby the degree of binding measured (relative to controls) would be used to estimate each respective heterodimer population.

Additional methods such as SMCA are described in the Examples, Figs, and Tables.

Thermal Stability

The thermal stability of the heterodimers can be determined according to methods known in the art. The melting temperature of each heterodimer is indicative of its thermal stability. The melting point of the heterodimer may be measured using techniques such as differential scanning calorimetry (Chen et al (2003) Pharm Res 20:1952-60; Ghirlando et al (1999) Immunol Lett 68:47-52). Alternatively, the thermal stability of the heterodimer may be measured using circular dichroism (Murray et al. (2002) J. Chromatogr Sci 40:343-9).

Affinity for Antigen

The binding affinity of the heterodimers for their respective antigens and the off-rate of the interaction can be determined by competitive binding assays according to methods well known in the art. One example of a competitive binding assay is a radioimmunoassay comprising the incubation of labeled antigen (e.g., 3H or 125I with a molecule of interest (e.g., heterodimers of the present invention) in the presence of increasing amounts of unlabeled antigen, and the detection of the molecule bound to the labeled ligand. The affinity of the heterodimer of the present invention for the antigen and the binding off-rates can be determined from the saturation data by Scatchard analysis.

The kinetic parameters of a heterodimer according to the invention may also be determined using surface plasmon resonance (SPR) based assays known in the art (e.g., BIAcore kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention. FACS can also be used to measured affinity, as is known in the art.

Pharmaceutical Compositions

The present invention also provides pharmaceutical compositions comprising the heterodimers or heterodimer pairs described herein. Such compositions comprise a therapeutically effective amount of the heterodimer or heterodimer pair, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the heterodimer or heterodimer pair is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Uses of Heterodimer Pairs

As described above, the heterodimer pairs according to the invention can comprise a first heterodimer and a second heterodimer, where the immunoglobulin heavy chain and the immunoglobulin light chain of each heterodimer is derived or engineered from a known therapeutic antibody or from a known antibody that binds a molecule. Thus, it is contemplated that heterodimers derived or engineered from these antibodies could be used for the treatment or prevention of the same disease, disorder, or infection that the known therapeutic antibody or known antibody can be used for.

Thus, in one embodiment, heterodimer pairs according to the invention that comprise a heterodimer with heavy and light chains derived from a therapeutic antibody that can be used for the treatment and/or prevention of cancer and related disorders, can also be used for the treatment and/or prevention of cancer and related disorders.

In another embodiment, heterodimer pairs according to the invention that comprise a heterodimer with heavy and light chains derived from a therapeutic antibody that can be used for preventing, treating, or managing the symptoms of an inflammatory disorder in a subject, can also be used for preventing, treating, or managing the symptoms of an inflammatory disorder in a subject.

In another embodiment, heterodimer pairs according to the invention that comprise a heterodimer with heavy and light chains derived from a therapeutic antibody that can be used for the treatment or prevention of autoimmune disease or inflammatory disease in a subject, can also be used for the treatment or prevention of autoimmune disease or inflammatory disease in a subject.

In another embodiment, heterodimer pairs according to the invention that comprise a heterodimer with heavy and light chains derived from a therapeutic antibody that can be used for the treatment or prevention of an infectious disease in a subject, can also be used for the treatment or prevention of an infectious disease in a subject.

In another embodiment, heterodimer pairs according to the invention that comprise a heterodimer with heavy and light chains derived from a therapeutic antibody that can be used for the treatment of vascular disease in a subject, can also be used for the treatment of vascular disease in a subject.

In another embodiment, the heterodimer pairs according to the invention may also be advantageously utilized in combination with other therapeutic agents known in the art for the treatment or prevention of a cancer, autoimmune disease, inflammatory disorders or infectious diseases. In a specific embodiment, the heterodimer pairs according to the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The heterodimer pairs according to the invention may also be advantageously utilized in combination with one or more drugs used to treat a disease, disorder, or infection such as, for example anti-cancer agents, anti-inflammatory agents or anti-viral agents.

Kits

The present invention additionally provides for kits comprising one or more heterodimer pairs. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the heterodimer pairs.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits of the invention also may comprise an instrument for assisting with the administration of the composition to a patient. Such an instrument may be an inhalant, nasal spray device, syringe, pipette, forceps, measured spoon, eye dropper or similar medically approved delivery vehicle.

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B(1992).

Example 1: Preparation of Constructs Encoding D3H44 IgG Heavy Chains and D3H44 IgG Light Chains The wild-type heavy and light chains of the anti-tissue factor antibody D3H44 for use in the co-expression sets described herein were prepared as follows. D3H44 Fab light (AJ308087.1) and heavy (AJ308086.1) chain sequences were taken from GenBank (Tables A, A1, and A2), gene synthesized and codon optimized for mammalian expression. Light chain vector inserts, consisting of a 5'-EcoRI cutsite—HLA-A signal peptide—HA or FLAG tag—Light chain Ig clone—'TGA stop'—BamH1 cutsite-3', were ligated into a pTT5 vector (Durocher Y et al., Nucl. Acids Res. 2002; 30, No. 2 e9). The resulting vector+insert were sequenced to confirm correct reading frame and sequence of the coding DNA. Likewise, heavy chain vector inserts, consisting of a 5'-EcoRIcutsite—HLA-A signal peptide—heavy chain clone (terminating at T238; see Table A1)—$ABD_2$-$His_6$tag—TGA stop—BamH1 cutsite-3' ("$His_6$" disclosed as SEQ ID NO: 2), were ligated into a pTT5 vector (ABD; albumin binding domain). The resulting vector+insert were also sequenced to confirm correct reading frame and sequence of the coding DNA. The various D3H44 constructs were generated either by gene synthesis or by site-directed mutagenesis (Braman J, Papworth C & Greener A., Methods Mol. Biol. (1996) 57:31-44).

Heavy and light chains were tagged at the C- and N-terminals respectively, in order to facilitate the assessment of preferential pairing via a competition assay-SPR screen. The $ABD_2$-$His_6$ heavy chain tag ("$His_6$" disclosed as SEQ ID NO: 2) specifically allowed HC-LC complexes to be captured on an anti-his tag SPR chip surface, whilst FLAG and HA light chain tags allowed the relative LC1 and LC2 populations to be quantified.

Example 2: Assessment of Preferential Pairing of Heterodimers in Co-Expression Sets Comprising Variable Domain Modifications in D3H44 IgG Light and/or Heavy Chains The ability of heterodimers to preferentially pair in co-expression sets comprising D3H44 heavy and light chains with modified $V_L$ and/or $V_H$ domains was determined and the results are shown in FIG. 1. The results provided in FIG. 1 are preliminary and a more complete set of results is provided below. The amino acid modifications shown in FIGS. 1-3 are identified with reference to the amino acid sequence of D3H44 heavy chain and D3H44 light chain. See Tables A, A1, and A2.

Figure 8:
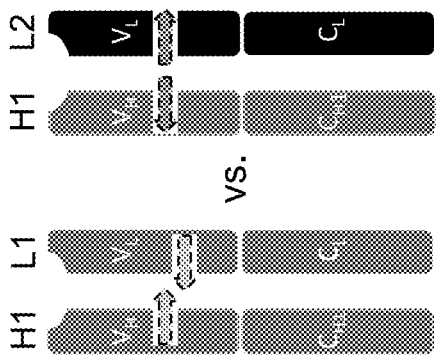
FIG. 8 illustrates a high level schematic overview of the engineering requirements for forming a bispecific Mab (monoclonal antibody), and the assay requirements needed to quantify heavy chain light chain pairs. The design goal of engineering a bispecific Mab with high purity (i.e., little or no mispaired H-L associations) can be achieved by rationally engineering (via the introduction of specific amino acid mutations) the preferential pairing of two unique heavy chains for their unique cognate light chains. This process is shown schematically; here H1 has been engineered to preferentially pair with L1 and not L2. Likewise, H2 has been engineered to preferentially pair with L2 and not L1. The experimental screening of bispecific Mab designs requires an assay capable of simultaneously quantifying H1-L1:H1-L2 and H2-L2:H2-L1. These assay requirements can be simplified by assuming that each bispecific Fab arm can be independently engineered. In this case, the assay would only need to quantify H1-L1:H1-L2 or H2-L2:H2-L1, and not both simultaneously.

One D3H44 heavy chain construct was co-expressed with two unique D3H44 light chain constructs and the relative light chain pairing specificity (e.g. H1-L1:H1-L2) was determined from a competition assay-SPR screen (Column entitled "Competition assay screen results" in FIG. 1). Selected heterodimer hits were verified via a light chain competition assay verification whereby L1:L2 DNA ratios were varied by 40:60, 50:50 and 60:40 during transfection (Column entitled "Competition assay verification results" in FIG. 1). Heavy chain were kept in limiting quantities (i.e. HC<L1+L2) for both competition assay screens and verifications. A schematic representing the design of the assay is shown in FIG. 8.

Figure 9:
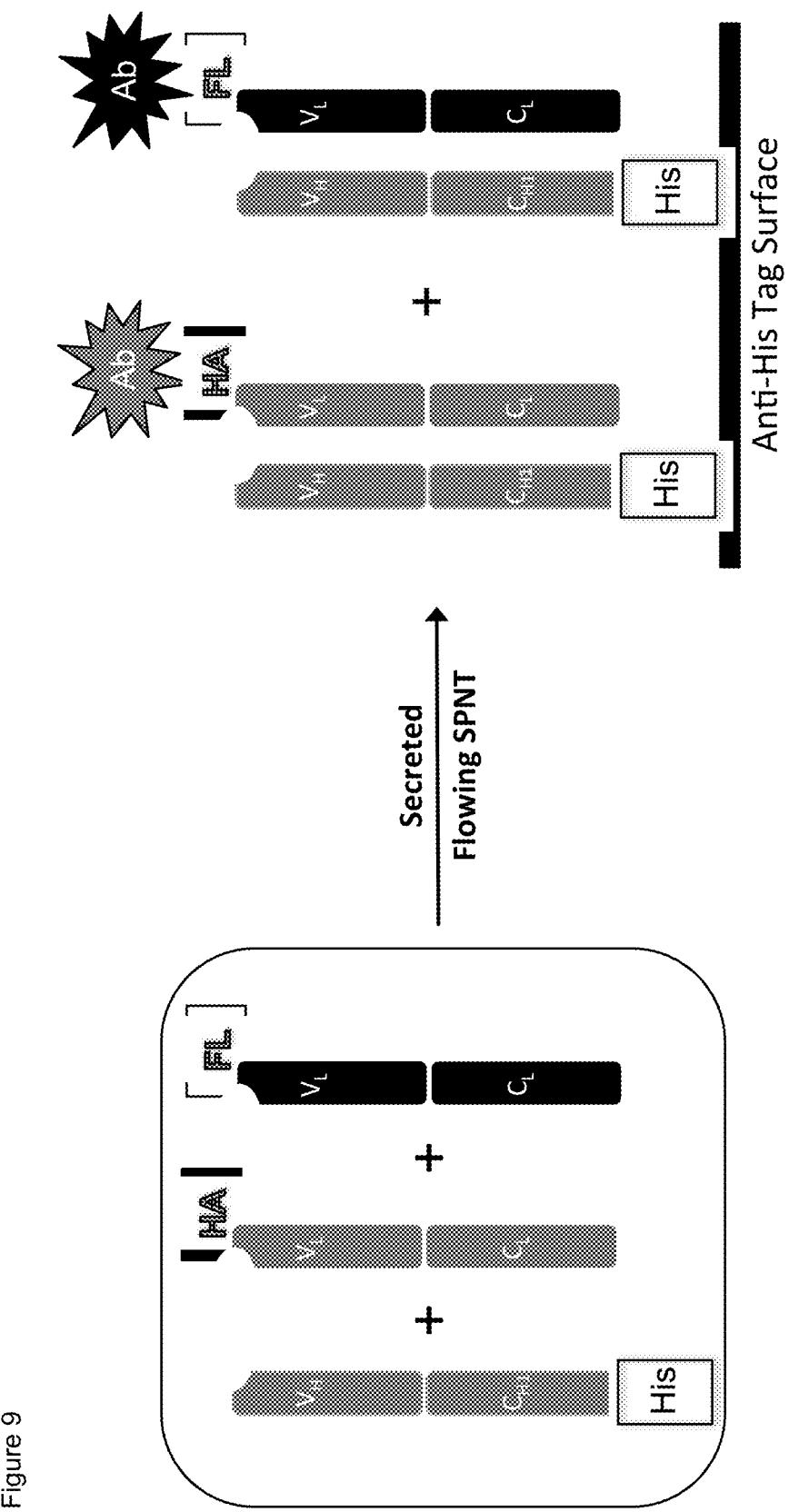
FIG. 9 provides a schematic depicting how heavy chains and light chains are tagged and preferential pairing is determined. In this schematic, the circle represents a cell in which 3 constructs are transfected. The expression products are secreted from the cell and the supernatant (SPNT) is flowed over a detection device, in this case an SPR chip. Based on the detection level of the two different tags fused to the two light chains competing for heavy chain pairing, a quantitative estimate of the preferential pairing of the heavy chain to the two light chains can be estimated.

The methods were carried out as follows: The Light Chain Competition Assay (LCCA) quantifies the relative pairing of one heavy chain for at least two unique light chains. The assay and the preceding steps can be summarized as follows: 1. Concomitant expression of heavy and light chains, with the heavy chain being in limiting amounts (e.g. HC:LC1: LC2=1:1:1), 2. Isolation of HC-LC complexes—achieved by binding heavy chains to the SPR chip via a his-tag pull-down, and 3) Quantification of relative HC-LC populations (i.e. H1-L1:H1-L2). In the SPR format, antibodies specific for unique light chain-tagged populations are used for the quantification. Note: This assay can be carried out with or without the H-L disulphide. A schematic diagram representing the method is shown in FIG. 9.

Transfection Method

Co-expression sets comprising one heavy chain and two light chain constructs prepared as described in Example 1 were transfected into CHO-3E7 cells as follows. CHO-3E7 cells, at a density of $1.7-2 \times 10^6$ cells/ml, were cultured at 37° C. in FREESTYLE™ F17 medium (Invitrogen cat #A-1383501) supplemented with 4 mM glutamine and 0.1% Pluronic F-68 (Invitrogen cat #24040-032). A total volume of 2 ml were transfected with a total of 2 ug DNA using PEIPRO® (Polyplus cat #115-010) at a DNA:PEI ratio of 1:2.5. Twenty-four hours after the addition of the DNA-PEI mixture, the cells were transferred to 32° C. Supernatants were tested for expression on day 7 by non-reducing SDS-PAGE analysis followed by Coommassie blue staining to visualize the bands. HC: LC ratios are as indicated in Table 7.

TABLE 7

| HC:L1:L2 ratio | Experiment | DNA quantity used for transfection (ng) | | | |
| --- | --- | --- | --- | --- | --- |
| | | HC | LC1 | LC2 | Stuffer^ DNA |
| 1:1:1 | Competition assay screen | 333 | 333 | 333 | 1000 |
| 1:1:1 | Competition assay verification | 333 | 333 | 333 | 1000 |
| 1:0.8:1.2 | Competition assay verification | 333 | 266 | 400 | 1000 |
| 1:1:1 | Competition assay verification | 333 | 333 | 333 | 1000 |
| 1:1.2:0.8 | Competition assay verification | 333 | 400 | 266 | 1000 |

^Stuffer DNA: pTT5 vector without a DNA insert.

Competition Assay SPR Method

The degree of preferential D3H44 light chain pairing to D3H44 heavy chain in co-expression sets was assessed using an SPR-based readout of unique epitope tags located at the N-terminus of each light chain.

Surface Plasmon resonance (SPR) supplies. GLM sensorchips, the Biorad PROTEON™ amine coupling kit (1-ethyl-3-(3-dimethylaminopropyl) carbodiimide hydrochloride (EDC), N-hydroxysulfosuccinimide (sNHS) and ethanolamine), and 10 mM sodium acetate buffers were purchased from Bio-Rad Laboratories (Canada) Ltd. (Mississauga, ON). Recombinant Her-2 protein was purchased from eBioscience (San Diego, Calif.). 4-(2-hydroxyethyl)-1-piperazineethanesulfonic acid (HEPES) buffer, ethylenediaminetetraacetic acid (EDTA), and NaCl were purchased from Sigma-Aldrich (Oakville, ON). 10% Tween 20 solution was purchased from Teknova (Hollister, Calif.).

SPR biosensor assays. All surface plasmon resonance assays were carried out using a BioRad PROTEON™ XPR36 instrument (Bio-Rad Laboratories (Canada) Ltd. (Mississauga, ON)) with PBST running buffer (PBS Teknova Inc with 0.05% Tween20) at a temperature of 25° C. The anti-penta His (SEQ ID NO: 3) capture surface was generated using a GLM sensorchip activated by a 1:5 dilution of the standard BioRad sNHS/EDC solutions injected for 140 s at 100 μL/min in the analyte (horizontal) direction. Immediately after the activation, a 25 μg/mL solution of anti-penta His antibody (SEQ ID NO: 3) (Qiagen Inc.) in 10 mM NaOAc pH 4.5 was injected in the analyte (vertical) direction at a flow rate of 25 μL/min until approximately 3000 resonance units (RUs) were immobilized. Remaining active groups were quenched by a 140 s injection of 1M ethanolamine at 100 μL/min in the analyte direction, and this also ensures mock-activated interspots are created for blank referencing.

The screening of the heterodimers for binding to the anti-FLAG (Sigma Inc.) and anti-HA (Roche Inc.) monoclonal antibodies occurred in two steps: an indirect capture of the heterodimers onto the anti-penta His surface (SEQ ID NO: 3) in the ligand direction followed by an anti-FLAG and anti-HA injection in the analyte direction. First, one buffer injection for 30 s at 100 uL/min in the ligand direction was used to stabilize the baseline. For each heterodimer capture, unpurified heterodimers in cell-culture media were diluted to 4% in PBST. One to five heterodimers or controls (i.e. controls containing either 100% HA-light chain or 100% FLAG-light chain) were simultaneously injected in individual ligand channels for 240 s at flow 25 μL/min. This resulted in a saturating heterodimer capture of approximately 300 to 400 RUs onto the anti-penta His surface (SEQ ID NO: 3). The first ligand channel was left empty to use as a blank control if required. This heterodimer capture step was immediately followed by two buffer injections in the analyte direction to stabilize the baseline, and then 5 nM anti-FLAG and 5 nM anti-HA were each injected in duplicate at 50 μL/min for 120 s with a 180 s dissociation phase, resulting in a set of binding sensorgrams with a buffer reference for each of the captured heterodimer. Where possible, the antigen to which the heterodimer binds can also be injected over the last remaining analyte channel as an activity control. The heterodimers were regenerated by an 18 s pulse of 0.85% phosphoric acid for 18 s at 100 μL/min to prepare the anti-penta His surface (SEQ ID NO: 3) for the next injection cycle. Sensorgrams were aligned and double-referenced using the buffer blank injection and interspots, and the resulting sensorgrams were analyzed using PROTEON™ Manager software v3.0.

The total percentage of L1 and L2 should, theoretically, add up to 100%. In practice, it was observed for some variants that the total amount of L1 and L2 added up to significantly less than 100%. This discrepancy in total light chain percentage is believed to be due in part to the occurrence of variable non-specific binding during initial heterodimer capture on the SPR chip.

Example 3: Assessment of Preferential Pairing of Heterodimers in Co-Expression Sets Comprising Constant ($C_L$ or $C_{h1}$) Domain Modifications in D3H44 IgG Light and/or Heavy Chains The ability of heterodimers to preferentially pair in co-expression sets comprising D3H44 heavy and light chains with modified $C_L$ and/or $C_{H1}$ domains was determined as described for heterodimers with variable domain modifications in Example 2, and the results are shown in FIG. 2. One D3H44 heavy chain construct was co-expressed with two unique D3H44 light chain constructs and the relative light chain pairing specificity (e.g. H1-L1:H1-L2) was determined from a competition assay-SPR screen (Column entitled "Competition assay screen results" in FIG. 2). Selected heterodimer hits were confirmed via a modified competition assay verification where DNA ratios of L1:L2 were varied by 40:60, 50:50 and 60:40 during transfection (Column entitled "Competition assay verification results" in FIG. 2). As described in Example 2, heavy chain was kept in limiting quantities (i.e. HC<L1+L2) for both competition assay screens and verifications. Assessment of preferential pairing was carried out as described in Example 2.

Example 4: Scale Up for Biophysical Characterization

Selected heterodimers, both paired and mispaired, were scaled up (typically to 50 ml) and purified as follows in order to test for thermal stability and antigen binding. Heterodimers HD100-HD 115, as shown in FIG. 3 were expressed and purified. The heavy and light chain of each heterodimer was expressed in 50 ml cultures of CHO-3E7 cells under the culture conditions described above. Cells were centrifuged and heterodimers purified by loading the supernatant on Fractogel column charged with Nickel as described below.

Purification on Fractogel Column Charged with Nickel (his)

Charging the column with Nickel: Sequentially wash with 5 column volumes (CV) of 0.5 M NaCl (no pH adjustment), followed by 4 CV 200 mM of $NiCl_2$ (Nickel) and 2 CV of 0.5 M NaCl pH 5.0. Sample loading and elution: Equilibrate column with 10 CV PBS. Load sample and wash with 10 CV of wash buffer #1 (50 mM sodium phosphate pH 7.0, 300 mM NaCl) followed by 10 CV of wash buffer #2 (50 mM sodium phosphate pH 7.0, 300 mM NaCl, 25 mM Imidazole) to remove impurities bound to the column. The heterodimers were eluted in fractions with wash buffer #1+300 mM Imidazole. The protein content of each fraction was tested by Bradford protein assay. Fractions containing protein were pooled. The purified heterodimers were then assayed for antigen binding and thermal stability as described in Example 5.

Example 5: Thermal Stability and Antigen Affinity Measurements of Heterodimers

The thermal stability and antigen affinity of selected heterodimer pairs was measured in order to compare these features with that of wild type, unmodified heavy chain-light chain pair. Correctly paired and mispaired heterodimers from co-expression sets were individually scaled up, purified (i.e. His tag affinity purification) and assessed for thermal stability and antigen binding as described below. The results are shown in FIG. 3.

Measurement of Thermal Stability

The thermal stability of selected heterodimer pairs was measured using differential scanning calorimetry (DSC) as follows.

Each heterodimer was purified as described in Example 3 and diluted to 0.2 mg/mL in PBS, and a total of 400 μL was used for DSC analysis with a VP-Capillary DSC (GE Healthcare). At the start of each DSC run, 5 buffer blank injections were performed to stabilize the baseline, and a buffer injection was placed before each heterodimer injection for referencing. Each sample was scanned from 20 to 100° C. at a 60° C./hr rate, with low feedback, 8 sec filter, 5 min preTstat, and 70 psi nitrogen pressure. The resulting thermograms were referenced and analyzed using Origin 7 software.

Thermal unfolding curves for the heterodimers tested are shown in FIG. 4. The results indicate that the correctly paired heterodimer (from a design perspective) is usually significantly more stable than the intended mispaired heterodimer (e.g. HD107 versus HD108). In addition, many of the correctly paired heterodimer exhibit a thermal stability close to wild-type Fab (e.g. HD 114).

Measurement of Antigen Affinity

The affinity of the heterodimer pairs for antigen (tissue factor extracellular domains) was measured using surface plasmon resonance (SPR) assays. All surface plasmon resonance assays were carried out using a BioRad PROTEON™ XPR36 instrument (Bio-Rad Laboratories (Canada) Ltd. (Mississauga, ON) with PBST running buffer (PBS Teknova Inc with 0.05% Tween20) at a temperature of 25° C. A purified tissue factor (TF) surface was generated using a GLM sensorchip activated by a 1:10 dilution of the standard BioRad sNHS/EDC solutions injected for 140 s at 100 μL/min in the ligand (vertical) direction. Immediately after the activation, a 25 μg/mL solution of TF in 10 mM NaOAc pH 4.5 was injected in the ligand direction at a flow rate of 25 μL/min until approximately 1000 resonance units (RUs) were immobilized (or enough for a 100 RU maximum response when flowing 60 nM FAB). Remaining active groups were quenched by a 140 s injection of 1M ethanolamine at 100 μL/min in the analyte direction. For each injection series, two buffer blank injections in the horizontal injection preceded the purified heterodimer. A 3-fold dilution series of each heterodimer (60 nM, 20 nM, 6.7 nM, 2.2 nM) with a blank buffer control was simultaneously injected at 50 μL/min for 120 s with a 20 minute dissociation, resulting in a set of binding sensorgrams with a buffer reference for each of the heterodimers. The heterodimer:TF complexes on the SPR surface were regenerated by an 18 s pulse of 0.85% phosphoric acid for 18 s at 100 μL/min to prepare the TF surface for the next injection cycle. Sensorgrams were aligned and double-referenced using the buffer blank injection and interspots, and the resulting sensorgrams were analyzed using a 1:1 binding model within the PROTEON™ Manager software v3.0.

The results indicate that the correctly paired heterodimer (from a design perspective) exhibits a range of affinities for antigen, with some designs showing wild-type like binding affinity for antigen (e.g. HD107 and HD 114).

Example 6: Size Exclusion Chromatography (SEC) Profiles of Wild-Type Tagged D3H44 Heterodimers and a Representative Sample of Individual Preferentially Paired Heterodimers Wild-type D3H44 heterodimer (one heavy chain and one light chain) with a C-terminus ABD2-$His_6$ tag ("$His_6$" disclosed as SEQ ID NO: 2) on the heavy chain and an N-terminus FLAG tag on the light chain were expressed and purified according to methods known in the art and similar to those described in Examples 1 and 4. Preferentially or correctly paired heterodimers from co-expression sets (heterodimers HD100, HD105, and HD107, shown in FIG. 3) were individually scaled up and purified via His tag affinity purification as described in Example 4 and SEC.

SEC was carried out as follows. Heterodimer samples were separated using a Superdex 200 HR 10/30 Pharmacia (GE Healthcare) column mounted on a Pharmacia (GE Healthcare) ÄKTA Purifier system. Heterodimer samples (0.3-0.5 ml) in PBS were manually loaded into a 0.5 ml loop filled with PBS. Samples were than automatically injected onto the column and resolved at 0.5 ml/min with a 1 CV elution volume. Protein elution was monitored at $OD_{280}$ and collected in 1 ml fractions.

Figure 5:
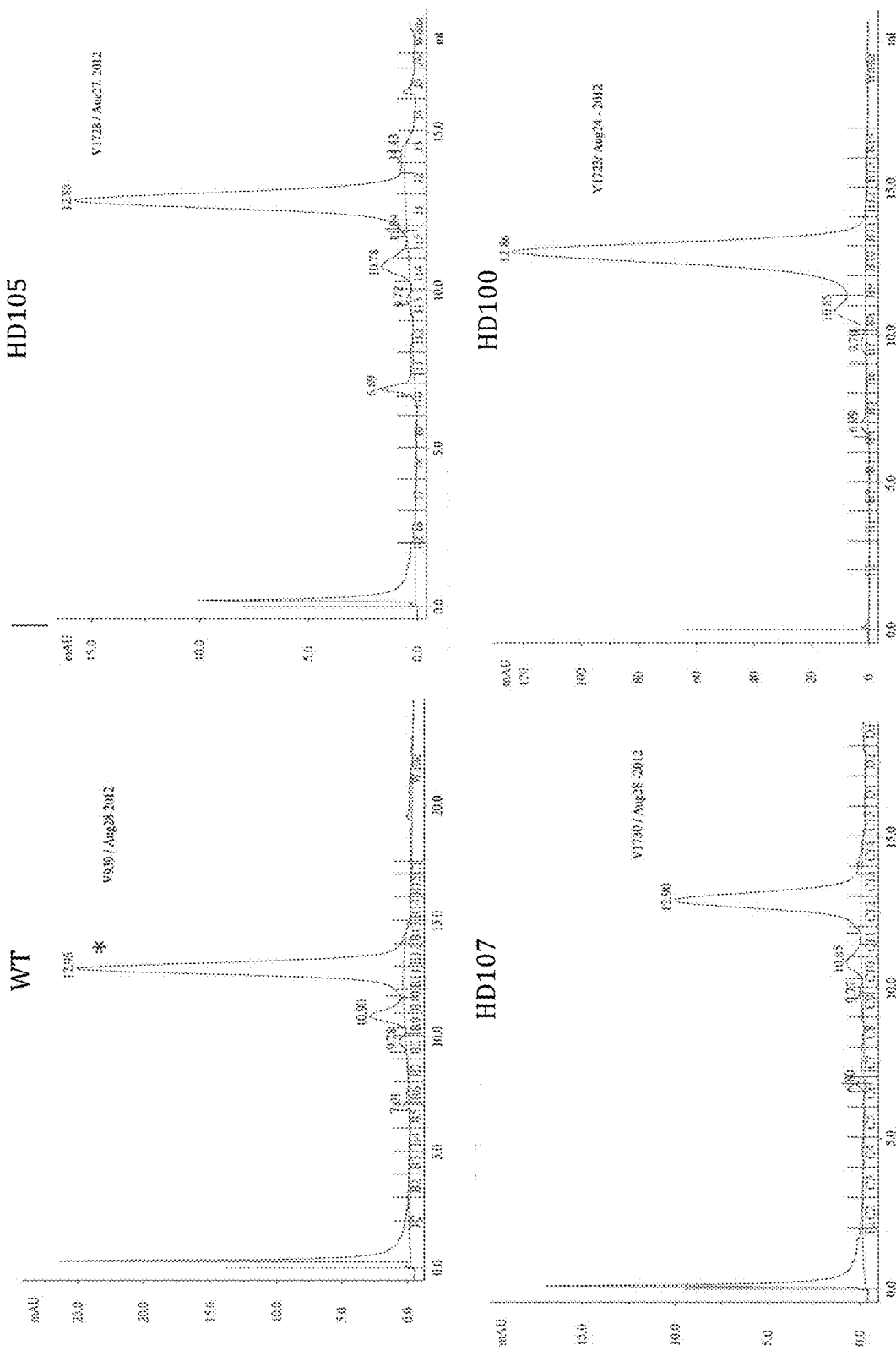
FIG. 5 provides size exclusion chromatography profiles for selected heterodimers.
Figure 7:
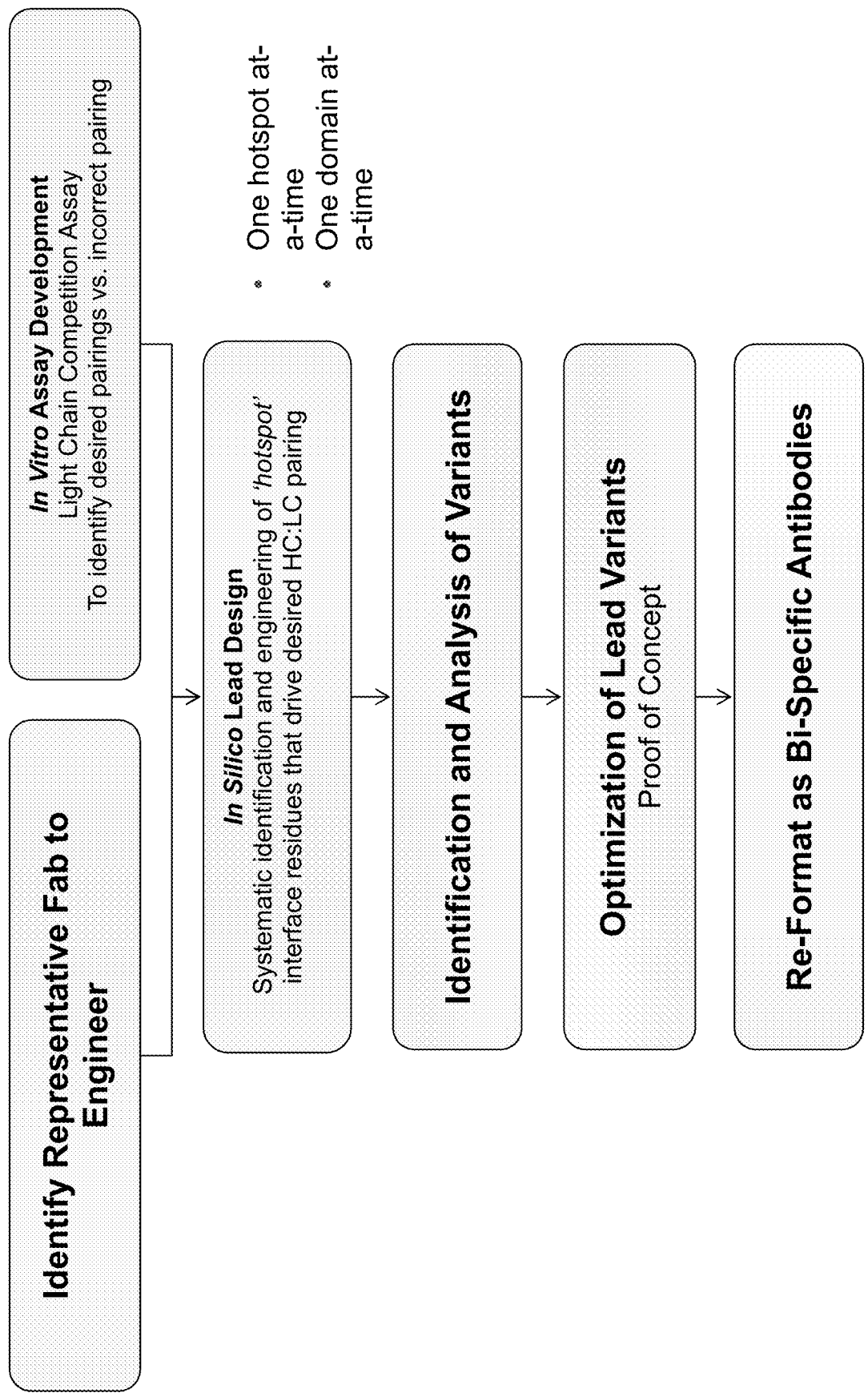
FIG. 7 depicts a flow chart outlining a strategy for designing a bi-specific antibody.

As shown in FIG. 5, correctly paired heterodimers displayed SEC profiles close to that observed for wild-type heterodimer without amino acid modifications (Main peak [*]:heterodimer). Equivalent results are obtained when the light chain of the wild-type heterodimer has a N-terminus HA tag.

Example 7: Additional Data Relating to the Stability of Heterodimers

Designs shown in Table 8 were highlighted as combinations of design drivers with improved HC-LC selectivities.

TABLE 8

| Design | Set # | Set # | H1_mutation | L1_mutation | H2_mutation | L2_mutation |
|---|---|---|---|---|---|---|
| 11 | C525 | C526 | S188L_V190Y | V133S | F174V_P175S_S188G | S176L |

TABLE 8-continued

| Design | Set # | Set # | H1_mutation | L1_mutation | H2_mutation | L2_mutation |
|---|---|---|---|---|---|---|
| 12 | V042 | V043 | V37E_F100D | L89R_F98W | WT | WT |
| 13 | C532 | C533 | L143A_D144G_Q179R | Q124E_V133W_Q160E_T180E | K145T_Q179D_S188F | V133A_Q160K_T178R |
| 14 | | | D146G_S186R | Q124E_Q160E_T178D | K145E_D146G_Q179D_S188L | Q124R_Q160K_T178R |
| 15 | C530 | C531 | D146G_Q179R | Q124E_Q160E_T178D | K145T_Q179D_S188L | Q160K_T178R |

Residue numbering follows Kabat nomenclature (Kabat E. A. et al., (1983) Sequence of Proteins of Immunological Interest National Institutes of Health, Bethesda).

The majority of the designs retained wild-type like thermal stability (Tm) and TF binding affinity as shown in Table 9.

TABLE 9

| | Tm (° C.) | | TF Binding KD (nM) | | H1 Readout | | H2 Readout | |
|---|---|---|---|---|---|---|---|---|
| Design | H1-L1 Tm | H2-L2 Tm | H1-L1 | H2-L2 | H1-L1 | H1-L2 | H2-L2 | H2-L1 |
| 11 | 74.7 | 73.3 | 0.043 | 0.040 | 83 | 24 | 98 | 1 |
| 12 | 76.2 | 76.0 | | 0.052 | 99 | 10 | 88 | 15 |
| 13 | 67.5 | 71.5 | 0.087 | 0.086 | 104 | 1 | 87 | 14 |
| 14 | | | | | 84 | 1 | 74 | 2 |
| 15 | 70.1 | 76.3 | 0.082 | 0.071 | 93 | 1 | 83 | 24 |

Design 12 contains a wild-type H2-L2 pairing (see Table 8). As a result, H2-L2 Fab retains wild-type binding affinity. Wild-type anti-TF D3H44 Fab Tm=~76° C. (data not shown).

Example 8: Additional Heterodimers and Testing of Same

Additional heterodimer pairs as described in Table 10 were prepared and tested. These heterodimers were designed to increase Fab hotspot coverage.

TABLE 10

| Design | H1_mutation* | L1_mutation | H2_mutation | L2_mutation |
|---|---|---|---|---|
| 26 | A141G_V185A | L135W | A141W_K147Y_Q175E | F116A_S131K_L135A |
| 27 | A141I_K147T_D148G_Q175E_S183G_V185S | F116A_V133G_S176F_T178A | S181K_S183H_V185G | F118W_Q124E_V133S_S176A_T178S_T180E |
| 28 | A141V_K147L_Q175E_S183G_V185S | F116A_S131K_V133G_S176F_T178A | A141W_S181K_S183A | F118W_V133S_S176A_T180E |
| 29 | L145K_D148G | Q124E_V133D | L145E_K147T | Q124R |
| 30 | D148G_Q175K | Q124E_Q160E_T180E | L145E_K147T | Q160K_T178R |
| 31 | Q39D_A141G_V185A | Q38R_L135W | Q39R_A141W | Q38D_F116A_L135A |
| 32 | Q39E | Q38R | Q39R | Q38E_F98W |

*Residue numbering in Table 10 follows the convention used for residues in the crystal structure of D3H44 Fab (PDB ID = 1JPT [Faelber K et al., J. Mol. Biol. (2001) 313: 83-97]; www.resb.org/pdb/explore/explore.do?structureId=1JPT).

The stability, ability to bind to target, and the ability to selectively pair for these heterodimers was determined as described in Example 5 and are shown in Table 11.

TABLE 11

| Design | Tm (° C.) H1-L1 Tm | Tm (° C.) H2-L2 Tm | TF Binding KD (nM) H1-L1 | TF Binding KD (nM) H2-L2 | H1 Readout H1-L1 | H1 Readout H1-L2 | H2 Readout H2-L2 | H2 Readout H2-L1 |
|---|---|---|---|---|---|---|---|---|
| 26 | 67.8 | 73.6 | | | 92 | 1 | 106 | 1 |
| 27 | 71.0 | | | | 67 | 1 | 85 | 12 |
| 28 | | | | | 85 | 4 | 94 | 1 |
| 29 | 64.1 | 68.3 | | | 93 | 1 | 102 | 1 |
| 30 | 67.0 | 75.5 | 0.024 | 0.060 | 96 | 1 | 102 | 1 |
| 31 | 74.3 | | 0.025 | | 106 | 1 | 78 | 1 |
| 32 | | | | | 98 | 1 | 93 | 1 |

Wild-type anti-TF D3H44 Fab KD=0.052 nM; Wild-type anti-TF Fab Tm=~76° C.

Example 9: Additional Heterodimers

The following heterodimer pairs were also prepared and tested for their ability to selectively pair.

TABLE 12

| Designs | Region | Design Strategy | Heavy Chain 1 | Light Chain 1 | Heavy Chain 2 | Light Chain 2 |
|---|---|---|---|---|---|---|
| ZW #1 | Variable | Steric | Q39R | Q38E | V37W | F98A |
| ZW #2 | Variable | Combo | — | F98W | V37W | F98A |
| ZW #3 | Variable | Combo | Q39R | Q38E | V37W_Q39E | Q38R_F98A |
| ZW #4 | Variable | Combo | V37I_Q39R | Q38D_F98W | V37W_Q39E | Q38R_F98A |
| ZW #5 | Variable | Combo | V37I_Q39D | Q38R_F98W | V37W_Q39R_W107F | Q38E_F98L |
| ZW #6 | Constant | Electrostatic | D148G_Q175R | Q124E_Q160E_T178D | K147T_Q175D_S183L | Q160K_T178R |
| ZW #7 | Constant | Electrostatic | L145K_D148G | Q124E_V133D | L145E_K147T | Q124R |
| ZW #8 | Constant | Electrostatic | D148G_Q175K | Q124_Q160E_T180E | L145E_K147T | Q124R_Q160K_T178R |
| ZW #9 | Constant | Electrostatic | K147L_Q175E | S131K | D148G_Q175K | Q124E_Q160E_T180E |
| ZW #10 | Constant | Electrostatic | S181R | Q124E_Q160E_T178D | K147L_Q175E | S131K |

Residue numbering in Table 12 follows the convention used for residues in the crystal structure of D3H44 Fab (PDB ID=1JPT [Faelber K et al., J. Mol. Biol. (2001) 313:83-97]; www.rcsb.org/pdb/explore/explore.do?structureId=1JPT).

TABLE 13

| Design | H1_mutation | L1_mutation | H2_mutation | L2_mutation |
|---|---|---|---|---|
| 4691 | S181R | Q124E_Q160E_T180E | K147L_Q175E | S131K |
| 4686 | D148G_Q175K | Q124E_Q160E_T180E | L145E_K147T | Q124R_Q160K_T178R |
| 5838 | Q39E_S181R | Q38R_Q124E_Q160E_T180E | Q39R_K147L_Q175E | Q38E_S131K |
| 5826 | Q39E_S181R | Q38R_Q160E_T180E | Q39R_K147T_Q175E | Q38E_S131K |
| Design 1 | L145K_D148G | Q124E_V133D | L145E_K147T | Q124R |
| Design 2 | D148G_Q175K | Q124E_Q160E_T180E | L145E_K147T | Q124R_Q160K_T178R |
| Design 3 | S181R | Q124E_Q160E_T178D | K147L_Q175E | S131K |
| | K147L_Q175E | S131K | D148G_Q175K | Q124E_Q160E_T180E |
| Design 4 | V37I_Q39R | Q38D_F98W | V37W_Q39E | Q38R_F98A |
| Design 5 | Q39R | Q38E | V37W_Q39E | Q38R_F98A |
| Design 6 | V37I_Q39D | Q38R_F98W | V37W_Q39R_W107F | Q38E_F98L |

Residue numbering in Table 13 follows the convention used for residues in the crystal structure of D3H44 Fab (PDB ID=1JPT [Faelber K et al., J. Mol. Biol. (2001) 313:83-97]; www.rcsb.org/pdb/explore/explore.do?structureId=1JPT)

Example 10: Assessment of Preferential Pairing of Heterodimers in Co-Expression Sets Comprising Constant Domain and/or Variable Domain Modifications in D3H44 Heavy and Light Chain Fab Format Co-expression sets in addition to those shown in FIGS. 1 and 2 were designed. Constructs encoding the D3H44 IgG heavy and light chains in Fab format comprising amino acid modifications according to the design of the co-expression set were prepared as described in Example 1. The ability of the D3H44 heavy and light chain Fab pairs to preferentially pair was assessed as described in Examples 2 and 3. The stability and binding affinity of the designs was determined as described in Example 5. The results shown in Tables 14 and 15 are cumulative and include results for designs shown in FIGS. 1 and 2 in addition to new designs. The amino acid modifications shown in these tables are identified with reference to the amino acid sequence of D3H44 heavy chain and D3H44 light chain. See Tables A, A1, and A2.

Note that "Design" or "Design set" in this application is referring to a set of mutations on H1, L1, H2, and L2 chains. "LCCA design" refers to set of mutations in H1, L1 and L2.

Each unique set of H1, L1 and L2 mutations (LCCA format) was assigned a unique number, or so called 'unique identifier'. When data is presented in H1 L1 H2 L2 format (Fab pair format or SMCA), such a design set is consequently denoted with a 'unique identifier set' comprised of unique identifiers for the two constituent LCCAs (e.g. 1-2). Designs featured in the D3H44 LCCA data set were assigned first. Designs that are not present in this set, but are present in different homogeneous or mixed system data or/and in different formats (MCA) are in addition denoted with *. In this exercise of assigning unique identifiers, via automatic processing of numerous tables, some redundancy has arisen. Cases where different WT amino acids in systems other than D3H44 occupy the same position are: 309*=319*=47, 316*=101, 317*=183, 318*=182, 310*=48, 311*=102, 323*=180, 324*=179. Cases where additional mutations were incorporated for LC/MS are: 442*=326*, and 443*=23.

Note that the majority of LCCA experiments were performed on constructs lacking interchain Fab disulfide bond(s) located in the constant domain (H/C233S-L/C214S).

In Table 14 provided are designs that exhibit correct pairing specificity of 55%: 45% (H1-L1:H1-L2 and H2-L2:H2-L1) or greater. For the purposes of highlighting a particular design's success with respect to preferential pairing, two complementary LCCA sets (H1, L1, L2 and H2, L2, L1) are represented in a pair Fab format.

Presence of tags (L: HA and FLAG and H: ABD2) does not affect the expected neutral pairing of ~50%: 50% for D3H44 WT (this is further supported by pairing results for the actual designs; hence tag information is not included in this table).

In the table, the measured amount of relevant Fab species (H1-L1, H1-L2 and that of H2-L2, H2-L1) was included in ratio format (H1-L1:H1-L2 and H2-L2:H2-L1). In the majority of cases, several LCCA experimental repeats were performed (screening and verification). A summary column in the format of a normalized ratio (i.e. to 100% H1-L1 and H1-L2 sum) for the median H1-L1:H1-L2 and H2-L2:H2-L1 is also provided.

Data was clustered according to thermal stability data (Tm) and antigen affinity (in table buckets, the 'TF' notation is used for tissue factor affinity) categories:

Tm1 (x=>71° C.); Tm2 (71° C.>x=>66° C.); Tm3 (66° C.>x). Tm3 category also includes ND (experiment not performed) cases.

For reference, the Tm of D3H44 WT Fab (without disulfide bond) is ~76° C.

TF1 (x=<5×KD of WT median value); TF2 (5<x=<20× KD of WT median value); and miscellaneous category that includes cases of x>20×KD of WT median value where NB cases (no binding: for KD greater than 500 nM, which is ~10000×KD of WT median) were labeled separately. This last category also includes ND cases (experiment not performed).

For reference, the median KD of D3H44 WT Fab is 0.06 nM (with a range of 0.1).

Note: In Table columns referring to antigen affinity and thermal stability, range (min-max reading) is indicated if the number of experiments performed was greater than 1 (n>1).

Within each bucket, designs are ordered in descending pairing specificity of H1-L1:H1-L2 followed by that of H2-L2:H2-L1.

An example of reading bucket categories in the table:
Tm1 only (both H1-L1 and H2-L2 Tm belong to Tm1 category)
Tm1/Tm2 (H1-L1 or H2-L2 Tm belongs to Tm1 and the other to Tm2 category)
The same logic applies to 'TF' categories.

An additional set of LCCA results (Table 15), also presented in the Fab pair format, obtained following an additional design cycle is included in a separate table. This set of data is arranged in the order of decreasing pairing specificity and contains somewhat limited data with respect to thermal stability.

Results in Table 14 and 15 demonstrate that our in silico design approach led to achievement of preferential pairing of H1-L1 over H1-L2 and that of H2-L2 over H2-L1 across a diverse set of designs and their variations. These designs generally fell into two main categories: electrostatic (based on specificity drivers that utilize hydrogen bonding or charge-charge interactions) and steric complementarity. Specificity of such pairing ranged from moderate to 100% correct pairing for both LCCA designs. As evident from the table, some of these designs did not impact thermal stability (Tm) or antigen binding affinity, while some exhibited various degrees of impact on these two properties. Furthermore, successful designs were present in both constant and variable domain, as well as in domain design combination formats.

Example 11: Assessment of Preferential Pairing of Heterodimers in Co-Expression Sets Comprising Constant Domain and/or Variable Domain Modifications in Mixed Ab or Pure Ab Heavy and Light Chain Fab Format Certain designs described in the previous examples were tested in a system where the heterodimer pairs were derived from a different Ab (cf. to D3H44) or two different antibodies, to assess whether the design of the co-expression set resulted in preferential pairing in these types of systems. A number of different systems were tested. In one example, one heterodimer pair was derived from D3H44 heavy and light chains in the Fab format and the second heterodimer pair was derived from pertuzumab heavy and light chains in the Fab format. In another example, one heterodimer pair was derived from D3H44 heavy and light chains in the Fab format and the second heterodimer pair was derived from trastuzumab heavy and light chains in the Fab format.

Constructs encoding the D3H44 IgG, pertuzumab, and trastuzumab heavy and light chains in Fab format comprising amino acid modifications according to the design of the co-expression set were prepared as described in Example 1. The base DNA sequence for the heavy chain of pertuzumab, the base DNA sequence for the light chain of pertuzumab, the base DNA sequence for the heavy chain of trastuzumab, and the base DNA sequence for the light chain of trastuzumab are shown in Tables A, A1, and A2. Amino acid modifications were introduced into these sequences by site directed mutagenesis, or the DNA sequences were synthesized including the amino acid modifications from the base sequences as described in Example 1.

The ability of the heterodimer designs to preferentially pair was assessed as described in Examples 2 and 3, except for the fact that when mixed systems were tested the non-obligate chain employed belonged to a different Fab.

The results are shown in Table 16. The amino acid modifications shown in Table 16 are identified with reference to the amino acid sequence of D3H44 heavy chain and D3H44 light chain; pertuzumab heavy chain and pertuzumab light chain; trastuzumab heavy chain and trastuzumab light chain. See Tables A, A1, and A2.

A representative and diverse subset of designs, that exhibited successful preferential pairing in D3H44 system, were tested in different systems (Trastuzumab (TRAS) and Pertuzumab (PERT), as well as in mixed systems (D3H44/TRAS, D3H44/PERT and TRAS/PERT) (as with D3H44 LCCA, constructs lacked Fab disulfide).

Data is presented in both LCCA (Table 16) and Fab pair formats (Table 17). LCCA data reflects the minimal 'competition unit' (i.e. H1-L1:H1-L2) and is the optimal format for interpreting whether an LCCA design can successfully transfer across Fabs. Analysis in the Fab pair format including the second Fab pair (i.e. H2-L2:H2-L1) further illustrated the degree of translation into whole design (i.e. H1-L1 and H2-L2) and its efficacy in these different Fab systems. Apart from the ratio of H1-L1:H1-L2, we present the relative propensity for correct pairing relative to incorrect pairing as a scalar, where Scalar=ln(H1-L1:H1-L2).

In some of the mixed systems, an inherent cross-system pairing preference (e.g. H_D3H44 pairs preferentially with L_PERT than L_D3H44) was observed (Table 17). In the same example, H_D3H44 preferential pairing with L_PERT was also supported by thermal stability measurements (Tm), which indicated that H_D3H44-L_PERT species was more stable than H_D3H44-L_D3H44. Hence, along with reporting the actual species amounts measured, the normalized data to respective WT LCCA system (REF) behavior is presented in the form of ΔScalar(VAR-REF_WT) where ΔScalar=ln (H1-L1:H1-L2/H2-L2:H2-L1). This metric is an indicator of the actual effectiveness of the LCCA design. Data included in the tables comprise designs that yielded an equivalent of 55%: 45% or greater pairing specificity (i.e. ΔScalar (VAR-REF_WT)>0.2).

Unlike in the D3H44 system, certain species ratios appear to be at times affected by the light chain tag in WT PERT only and WT TRAS (to a lesser degree) systems (Table 18). This appears to be due to random events of HA-tag cleavage (LC/MS evidence available when systems are tested in Mab format), rather than tag interference with pairing. Hence tags were taken into account when presenting results in the relevant tables.

A summary of the results, in both LCCA and Fab pair format, across the different systems is reported in Tables 19 and 20. The results indicate design transferability across different tested Fab systems. These results do not necessarily reflect that some of the designs are better than others; nor do they reflect a more comprehensive transferability estimate. Successful LCCA designs (e.g., median ΔScalar (VAR-REF_WT)>0.2) in two systems or more, presented in Table 19, constitute app. 30% of tested LCCA designs in these different systems. This is indicative of transferability, dependent on the particular system and design. Thus, having a collection of unique designs allowed for the creation of bispecific pairs for a number of systems and highlights the utility of a library of design set that can be evaluated in the context of any antibody (or antibody pair) of interest. This example indicates that mutation/design sets can be used to achieve preferential pairing of heterodimers in co-expression sets comprising constant domain and/or variable domain modifications in mixed Ab or pure Ab heavy and light chain Fab format.

Example 12: Assessment of Preferential Pairing of Heterodimers in Co-Expression Sets Comprising Constant Domain and/or Variable Domain Modifications in D3H44 Heavy and Light Chain, in Full-Length Heavy Chain (Mab) Format The heterodimer co-expression set designs were assessed to determine if they also allowed for preferential pairing in a format (Mab format) where the heavy chain is a full-length heavy chain and not a Fab portion.

Preparation of Constructs:

Constructs encoding the D3H44 IgG heavy and light chains comprising amino acid modifications according to the design of the co-expression set were prepared as follows. D3H44 Fab light chain constructs were prepared as described in Example 1. D3H44 heavy chain sequences were prepared as described in Example 1, except a full-length D3H44 heavy chain was created by appending the IgG1*01 DNA sequence, encoding the hinge-CH2-CH3 domains, onto the C-terminus of the D3H44 Fab heavy chain. Of note, the canonical C-terminal heavy chain lysine residue was removed in order to prevent LC-MS signal heterogeneity due to C-terminal lysine clipping (Lawrence W. Dick Jr. et al., *Biotechnol. Bioeng.* (2008) 100:1132-43).

Mab Assay Format

Figure 10:
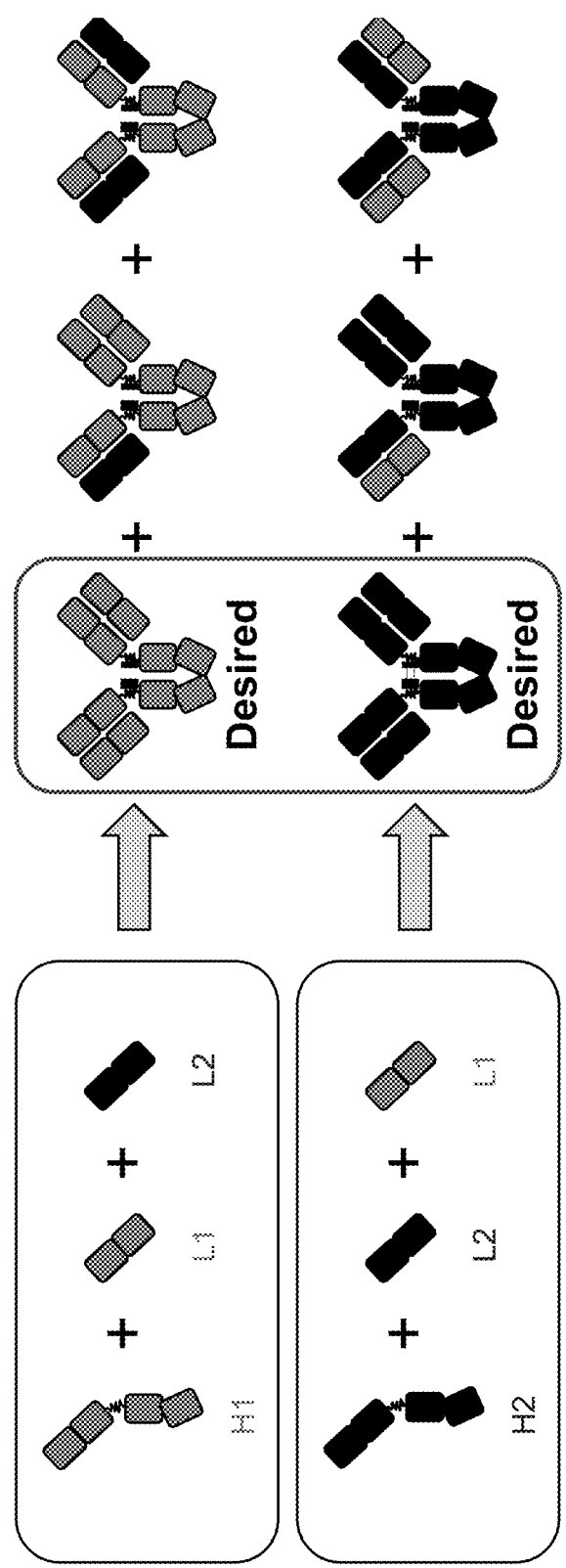
FIG. 10 depicts the heavy chain associated products expected when each of two full-length heavy chains is independently co-expressed with two different light chains. Preferential pairing is assessed using MCA.

The ability of the D3H44 heavy and light chains to preferentially pair was assessed as follows: One full-length D3H44 heavy chain construct was co-expressed with two unique D3H44 light chain constructs, yielding three possible antibody species: H1-L1:H1-L1, H1-L2:H1-L2 and H1-L1:H1-L2 (see FIG. 10). The relative light chain pairing specificity in terms of the amount of preferred H1-L1:H1-L1 species vs. others was determined using LC-MS after protein A (pA) purification. Where possible, chains were left untagged, provided the three possible Mab species resulting from co-transfection of the three chains differed by at least 50 Da from each other. When mass differences precluded this possibility, at least one of the light chains was constructed with an N-terminal HA or FLAG tag fusion in order to provide sufficient mass differentiation between species. As described in Example 2, heavy chain was kept in limiting quantities (i.e. HC<L1+L2).

Transfection Method for Mab Assay Format

Co-expression sets comprising one heavy chain and two light chain constructs prepared as described in Example 12 were transfected into CHO-3E7 cells as follows. CHO-3E7 cells, at a density of 1.7-2×10$^6$ cells/ml, were cultured at 37° C. in FREESTYLE™ F17 medium (Invitrogen cat #A-1383501) supplemented with 4 mM glutamine and 0.1% Pluronic F-68 (Invitrogen cat #24040-032). A total volume 50 ml were transfected with a total of 50 ug DNA using PEIPRO® (Polyplus cat #115-010) at a DNA:PEI ratio of 1:2.5. Twenty-four hours after the addition of the DNA-PEI mixture, the cells were transferred to 32° C. Supernatants were tested for expression on day 7 by non-reducing SDS-PAGE analysis followed by Coommassie blue staining to visualize the bands. HC: L1:L2 ratios used were 1:1:1.

Mass Spectrometry Method for Mab Assay Format

The degree of preferential D3H44 light chain pairing to D3H44 heavy chain in co-expression sets was assessed using mass spectrometry after protein A purification and deglycosylation The purified samples were de-glycosylated with PNGaseF as follows: 0.2 U PNGaseF/g of antibody in 50 mM Tris-HCl pH 8.0, overnight incubation at 37° C., final protein concentration was 0.45 mg/mL. The protein samples were analyzed by LC-MS using an Agilent 1100 HPLC system coupled to an LTQ-Orbitrap XL hybrid mass spectrometer (ThermoFisher Scientific) via a high-flow electrospray interface. The samples (2.5 g) were injected onto a 2.1×10 mm POROS™ R2 column (Applied Biosystems) and eluted using the following gradient conditions: 0-3 min: 20% solvent B; 3-6 min: 20-90% solvent B. Solvent A was 0.1% formic acid aq. and solvent B was 65% ACN, 25% THF, 9.9% ddH2O, 0.1% formic acid. The flow rate was 1 mL/min. The flow was split post-column to direct 100 µL/min into the electrospray interface. The column and solvent were heated to 80° C. to improve protein peak shape. The LTQ-Orbitrap XL was calibrated using ThermoFisher Scientific's LTQ Positive Ion ESI calibration solution (caffeine, MRFA and ULTRAMARK® 1621), and tuned using a 10 mg/mL solutions of CsI. The cone voltage (source fragmentation setting) was 40 V, the FT resolution was 7,500 and the scan range was m/z 400-4,000.

The protein spectra were deconvoluted using the MaxEnt module of the MassLynx instrument control and data analysis algorithm (Waters). Briefly, the raw protein LC-MS data were first opened in QualBrower, the spectrum viewing module of Xcalibur (Thermo Scientific) and converted to be compatible with MassLynx using Databridge, a file conversion program provided by Waters. The converted protein spectra were viewed in the Spectrum module of MassLynx and deconvoluted using MaxEnt. The abundances of the different antibody species in each sample were determined directly from the resulting molecular weight profiles.

The results are shown in Table 21. The amino acid modifications shown in Table 21 are identified with reference to the amino acid sequence of D3H44 heavy chain and D3H44 light chain. See Tables A, A1, and A2.

A subset of designs that exhibited successful preferential pairing in D3H44 system, which are also representatives of a diverse design set, were chosen for assessment of format transferability, i.e., from LCCA with Fab structures to Mab competition assay (MCA) based on Mab structures.

As shown in Table 21, D3H44 WT used in a Mab competition assay exhibited deviation from the expected theoretical species distribution of 50% H1-L1_H1-L2 and 25% of each H1-L1_H1-L1 and H1-L2_H1-L2, where light chains were distinguished by the presence or absence of a tag (HA or FLAG). This deviation is likely a result of tag dependent expression levels rather than tag dependent pairing (e.g., based on experiments performed at different WT H1:L1:L2 ratios, as well as indirect observation on the basis of design behavior). Median values for all the measured species across experimental repeats and/or variants differing by tag identity were included as well.

Figure 12:
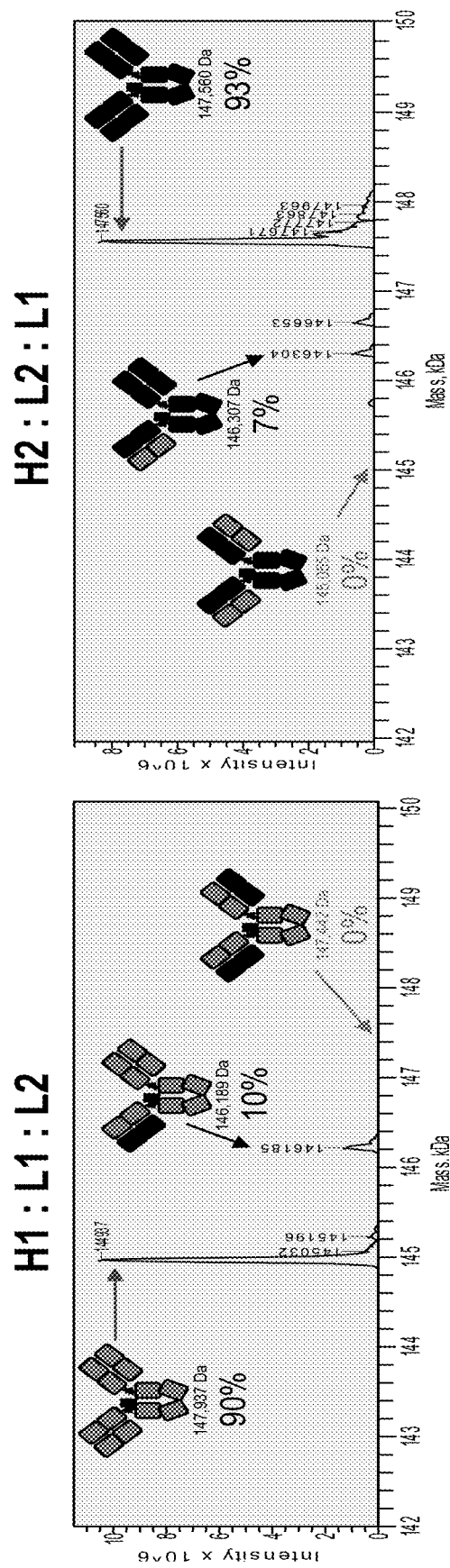
FIG. 12 depicts LC/MS spectra resulting when H1, L1 and L2 are co-expressed (left panel) and when H2, L1, and L2 are co-expressed (right panel), based on the exemplary set of H1, L1, H2, L2 chains shown in FIG. 11.
Figure 13:
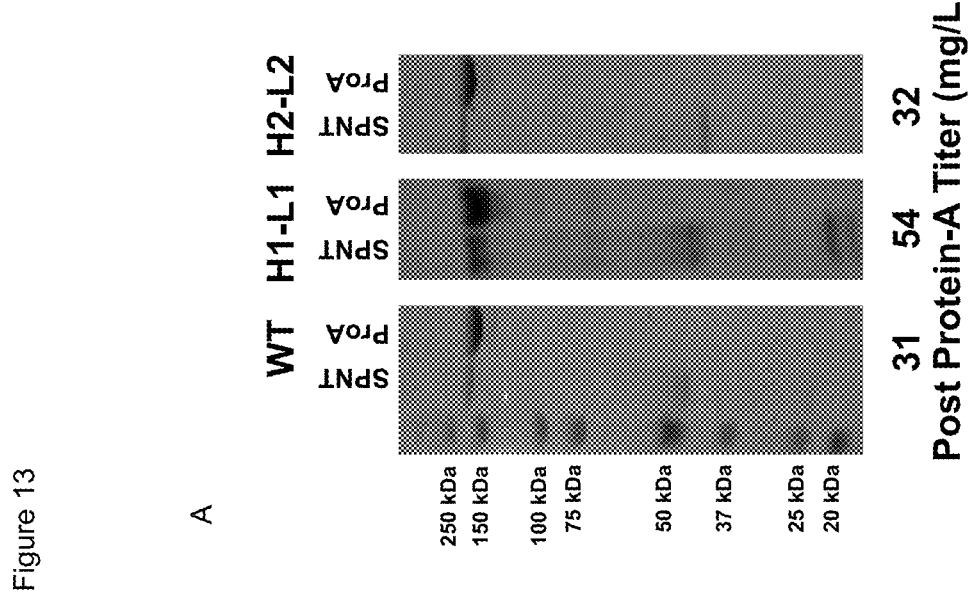
FIGS. 13 A-C depicts assessment of the biophysical properties of the H1-L1 and H2-L2 pairs based on the design shown in FIG. 11.

An example of LC/MS spectra of two successful Mab assay variants (FIG. 11) that comprise a given design are found in FIG. 12. In the case of these variants a majority of the measured species corresponded to the desired H1-L1_H1-L1 species. Expression profiles, UPLC-SEC (shown only for H2-L2_H2-L2 species (in the Fig. denoted as H2-L2)), and DSC thermograms reported in FIG. 13 are typical for characterization of the variants carried out for certain hits. In this particular case these demonstrated well-expressed, homogeneous species with relatively minor impact on Fab stability.

The results in Table 21 demonstrate that transferability into the Mab format was achieved with notable success among the LCCA designs. 11 out of the 12 LCCA designs tested exhibited equal to or greater than the theoretical 25% correctly paired species. This data indicates that the LCCA format used as an initial screen of design library is suitable for assessing and/or predicting design success in the Mab format.

Example 13: Assessment of Preferential Pairing of Heterodimers in Co-Expression Sets Comprising Constant Domain and/or Variable Domain Modifications in a Bi-Specific Antibody Format The heterodimer co-expression set designs were assessed to determine if they also allowed for preferential pairing in a bi-specific Mab antibody format. In this example, the Fc region of the full-length heavy chain of each heterodimer was asymmetrically modified to promote heterodimerization of the unique heavy chains compared to homodimerization.

Preparation of Constructs:

The heterodimer co-expression set designs were tested in the context of the following bi-specific antibodies: a) D3H44/pertuzumab, b) D3H44/trastuzumab, c) D3H44/ramucirumab, and d) trastuzumab/ramucirumab. The D3H44, pertuzumab, and trastuzumab heavy and light chains comprising amino acid modifications in the constant and/or variable domains were prepared as described in Example 12, except complementary Fc heterodimerization mutations were introduced into each two heavy chain of a co-expression design set. The ramucirumab heavy and light chains were prepared based on the base DNA sequence for the ramucirumab heavy chain and light chain. See Table A. The CH3 sequences of the heavy chains included the following amino acid modifications:

a) D3H44/pertuzumab: Chain A: T371V_T389L_K420L_T422W, Chain B: T371V_L372Y_F436A_Y438V
b) D3H44/trastuzumab: Chain A: T371V_T389L_K420L_T422W, Chain B: T371V_L372Y_F436A_Y438V
c) D3H44/ramucirumab: Chain A: T371V_T389L_K420L_T422W, Chain B: T371V_L372Y_F436A_Y438V
d) Trastuzumab/ramucirumab: Chain A: T371V_T389L_K420L_T422W, Chain B: T371V_L372Y_F436A_Y438V Assay Format (SMCA)

Figure 14:
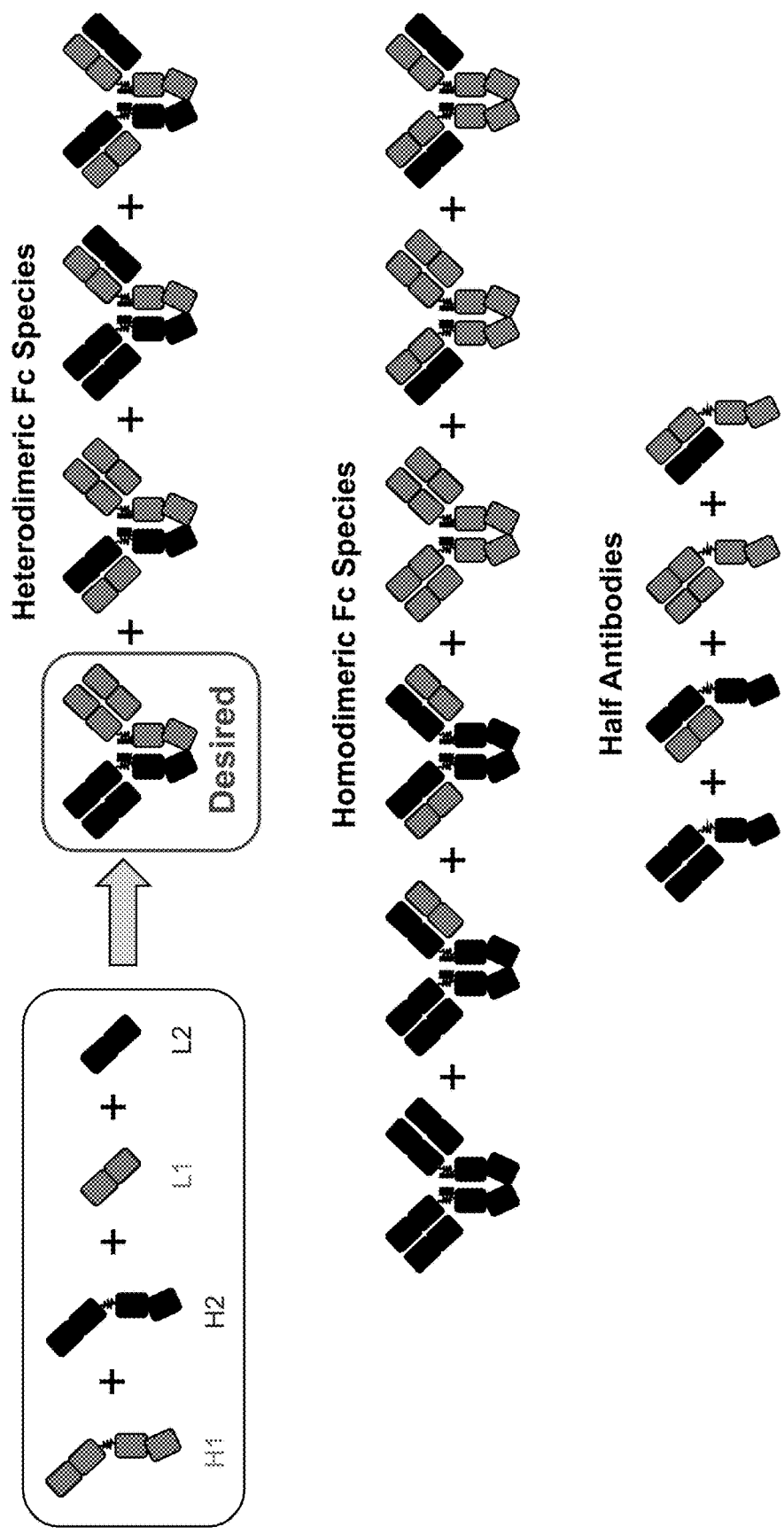
FIG. 14 depicts the heavy chain associated products expected when two different light chains are co-expressed with two different heavy chains in a cell. Preferential pairing is assessed using an SMCA (monoclonal antibody competition assay).

The ability of the heterodimer co-expression set designs to preferentially pair to form a bi-specific antibody was assessed as described below. The assay is based on co-expressing the four chains (two from Ab1 and two from Ab2) and detecting the presence of correctly formed bispecific antibody using mass spectrometry (LC-MS). The assay was carried out as follows. FIG. 14 provides a schematic depicting the four starting polypeptide chains and the potential products resulting from co-expression of these starting polypeptide chains in the absence of preferential pairing between heavy and light chains of the heterodimer pairs. Two full-length heavy chain constructs were co-expressed with two unique light chain constructs, yielding ten possible antibody species: H1-L1:H1-L1, H1-L2:H1-L2, H1-L1:H1-L2, H2-L1:H2-L1, H2-L2:H2-L2, H2-L1:H2-L2, H1-L1:H2-L1, H1-L2:H2-L2, H1-L2:H2-L1 and H1-L1:H2-L2. The latter species is the correctly paired heterodimer (see Fig. below). The relative pairing specificity in terms of amount of preferred species H1-L1:H2-L2 vs. others was determined using LC-MS after pA purification. When possible, chains were left untagged, provided all Mab and half-Ab species differed from each other by at least 50 Da. When mass differences precluded this possibility, one of the light chains was constructed with an N-terminal HA tag fusion in order to provide sufficient mass differentiation between species. We refer to this assay involving the expression and screening steps of a bispecific antibody as SMCA.

Transfection Method

Co-expression sets comprising two heavy chains and two light chain constructs prepared as described in Example 1 were transfected into CHO-3E7 cells as follows. CHO-3E7 cells, at a density of $1.7-2 \times 10^6$ cells/ml, were cultured at 37° C. in FREESTYLE™ F17 medium (Invitrogen cat #A-1383501) supplemented with 4 mM glutamine and 0.1% Pluronic F-68 (Invitrogen cat #24040-032). A total volume of 20 ml were transfected with a total of 20 ug DNA using PEIPRO® (Polyplus cat #115-010) at a DNA:PEI ratio of 1:2.5. Twenty-four hours after the addition of the DNA-PEI mixture, the cells were transferred to 32° C. Supernatants were tested for expression on day 7 by non-reducing SDS-PAGE analysis followed by Coommassie blue staining to visualize the bands. H1:H2: L1:L2 ratios used were initially kept neutral (15:15:35:35) to assess expression efficiency. A set of H1:H2:L1:L2 DNA ratios was then tested in CHO expressions to assess which condition(s) produced a mixture reflecting the theoretical distribution of the different species when all chains are wild-type. These ratios compensate for natural differences in expression levels and/or intrinsic pairing biases between heavy and light chains of the two different antibodies.

SPR Biosensor Assays

EDC: I-ethyl-3-(3-dimethylaminopropyl) carbodiimide hydrochloride; sNHS: N-hydroxysulfosuccinimide; SPR: surface plasmon resonance; EDTA: ethylenediaminetetraacetic acid; HEPES: 4-(2-hydroxyethyl)-1-piperazineethanesulfonic acid; TF: tissue factor.

SPR supplies. GLC sensorchips, the Biorad PROTEON™ amine coupling kit (EDC, sNHS and ethanolamine), and IOmM sodium acetate buffers were purchased from Bio-Rad Laboratories (Canada) Ltd. (Mississauga, ON). Recombinant Her-2 protein was purchased from eBioscience (San Diego, Calif.). PBS running buffer with 0.05% Tween20 (PBST) was purchased from Teknoca Inc. (Hollister, Calif.). Goat polyclonal anti-human Fc antibody was purchased from Jackson Immuno Research Laboratories Inc. (West Grove, Pa.).

All surface plasmon resonance assays were carried out using a BioRad PROTEON™ XPR36 instrument (Bio-Rad Laboratories (Canada) Ltd. (Mississauga, ON)) with PBST running buffer at a temperature of 25° C. The anti-human Fc capture surface was generated using a GLC sensorchip activated by a 1:5 dilution of the standard BioRad sNHS/EDC solutions injected for 140 s at 100 µL/min in the analyte (horizontal) direction. Immediately after the activation, a 10 ug/mL solution of anti-human Fc antibody in 10 mM NaOAc pH 4.5 was injected in the ligand (vertical) direction at a flow rate of 25 µL/min until approximately 3000 resonance units (RUs) were immobilized. Remaining active groups were quenched by a 140 s injection of 1M ethanolamine at 100 µL/min in the analyte direction, and this also ensures mock-activated interspots are created for blank referencing. The screening of the antibody variants for binding to Her2 or TF antigen targets occurred in two steps: an indirect capture of the antibody variants onto the anti-human Fc antibody surface in the ligand direction followed by the simultaneous injection of 5 concentrations of purified antigen and one buffer blank for double referencing in the analyte direction. Firstly, one buffer injection for 30 s at 100 uL/min in the ligand direction was used to stabilize the baseline. For each antibody variant capture, unpurified variants in cell-culture media were diluted to 4% in PBST. One to five variants or controls were simultaneously injected in individual ligand channels for 240 s at flow 25 µL/min. This resulted in a capture of approximately 400 to 600 RUs onto the anti-human Fc surface. The first ligand channel was left empty to use as a blank control if required. This capture step was immediately followed by two buffer injections in the analyte direction to stabilize the baseline, and then 60 nM, 20 nM, 6.7 nM, 2.2 nM and 0.74 nM antigen (TF or Her2) along with a buffer blank was simultaneously injected at 50 µL/min for 120 s with a 300 s dissociation phase. The captured antibody surfaces were regenerated by an 18 s pulse of 0.85% phosphoric acid for 18 s at 100 L/min to prepare for the next injection cycle. Sensorgrams were aligned and double-referenced using the buffer blank injection and interspots, and the resulting sensorgrams were analyzed using PROTEON™ Manager software v3.1. The double-referenced sensorgrams were fit to the 1:1 binding model. Rmax values for each antigen were normalized to antibody capture levels for each variant and compared to 100% controls.

The stability of the bi-specific antibodies was tested as described in Example 5. The LCMS analysis of the bi-specific antibodies was carried out using the procedure described in Example 12.

A number of selected D3H44 LCCA designs were tested in the SMCA format. Furthermore, some designs were directly evaluated in the SMCA format only. A majority of designs were tested in the D3H44/Pertuzumab system. A subset of designs that were selected in this system (involving a variety of designs) were further tested in three additional bispecific Mab systems: D3H44/Trastuzumab, D3H44/Ramucirumab (RAMU), and Trastuzumab/Ramucirumab systems.

Inherent cross-system light/heavy chain preference observed for D3H44/Pertuzumab and D3H44/Trastuzumab in LCCA experiments (Example 11) was reproducible in the full antibody format as well. Furthermore, similar behavior, although with different cross-system pairing tendencies, was also observed for the other two systems (Table 22).

Desired bispecific species, H1-L1_H2-L2, cannot generally be distinguished experimentally on the basis of LC/MS from the mispaired type: H1-L2_H2-L1. As such, when bispecific content is reported in the tables, it cannot be completely excluded that it does not contain this type of mispaired species. However, the very low content observed for species such as H1-L2_H1-L2 and H2-L1_H2-L1 as well as H1-L2 and H2-L1 half antibodies is indicative that only minor if any contamination of the bispecific species occurred. All other species present in a particular sample measured by LC/MS are included in the table. In most cases MS peaks were accompanied by side peaks; however these were annotated only for the bispecific species. When normalizing MS peak intensities, these adduct species were not taken into account. The number represented for side peak(s) in the tables was obtained by intensity comparison with that for the main bispecific peak. Some preliminary analysis indicated the side peak as being correlated with the presence of light chain tags involving the formation of adducts or heterogeneity in the cleavage of leader peptides and it is likely representative of the main peak species.

Finally all paired species were summed up, in addition to mispaired species, to obtain the ratios reported in the paired: mispaired column. This was further used to calculate ΔScalar (VAR-REF_WT) following the mathematical approach described in Example 11 to demonstrate the strength of a particular design. Within a system, designs were ordered in descending values of the Scalar metric.

Due to the cross-system natural preference for pairing of light and heavy chains described in Example 12, DNA ratios of H1:L1:H2:L2 required alteration (e.g. over-expression of H1 (D3H44) over H2 (PERT)) to yield the highest content of desired bispecific species (H1-L1_H2-L2). Optimal ratios may also vary to some degree with a particular design as a result. DNA ratios mainly affect the actual ratio of bispecific species:paired half antibody species (usually of one type: H1-L1 or H2-L2). An example is included in Table 23, where DNA titration with this ratio varied but the overall ratio of paired:mispaired species was relatively constant.

In the case of the D3H44/Pertuzumab system, a limited set of DNA titrations was performed for the majority of designs. Data for ratios that resulted in the highest paired: mispaired species content are shown in Tables 22 and 24. For the other three systems, transfections were performed only at one ratio, as reported in the tables. If at the reported ratio the experiment was repeated, a mean value was included in the table. Information with respect to tag identity was not included as tag influence was not observed for the WT (Table 26). The WT reference provided was chosen as such to be representative of the most common DNA ratio among reported design data.

LC/MS analysis was performed on samples that were stored at pH4 as well as at pH7. Experiments on samples stored at pH7 were tested in the case of D3H44/Trastuzumab, D3H44/Ramucirumab (RAMU), and Trastuzumab/Ramucirumab systems. Hence data is presented in two tables (Table 22 (pH4) and 24 (pH7)). Satisfactory correlation was observed for paired: mispaired species ratios between the two experiments, indicating that pH did not likely play a substantial role in the LC/MS experiment, i.e., in characterization of the type of species present.

Figure 15:
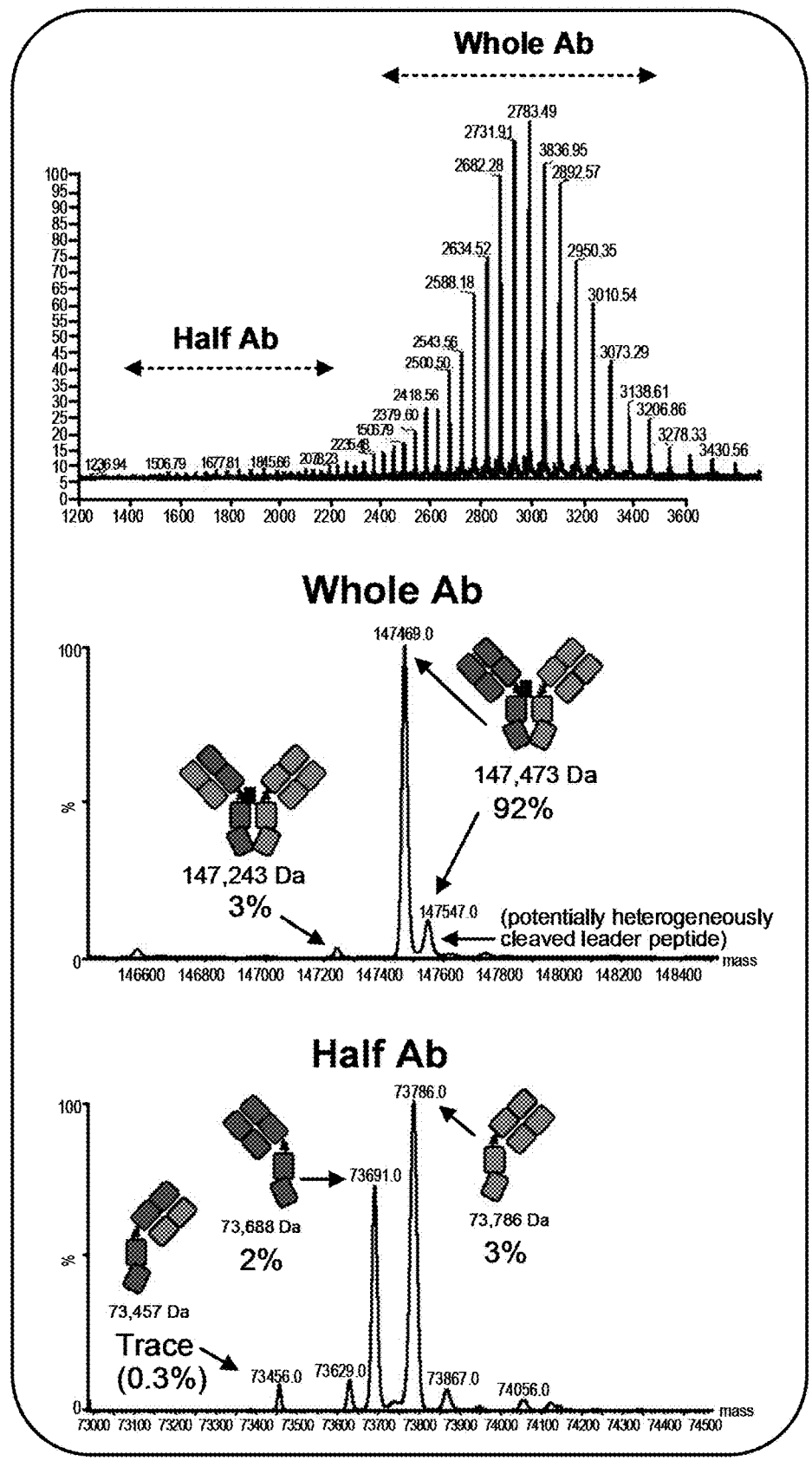
FIG. 15 depicts the LC/MS spectra for the bispecific antigen-binding construct (H1-L1_H2-L2) based on design shown in FIG. 11.
Figure 16:
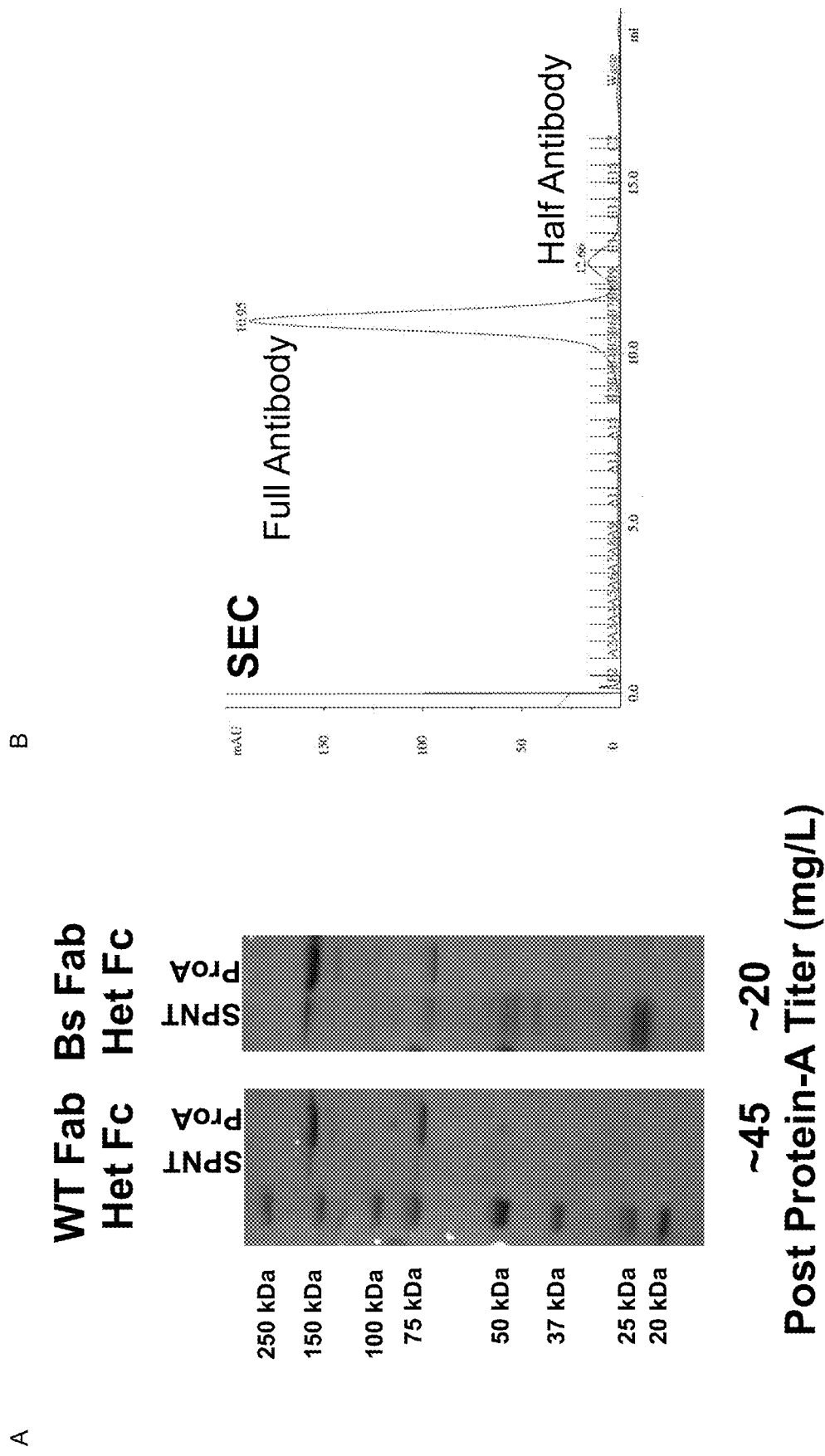
FIG. 16A Left panel depicts an assessment of the purity of the bispecific antigen-binding construct derived from design set as depicted in FIG. 11.
Figure 17A:
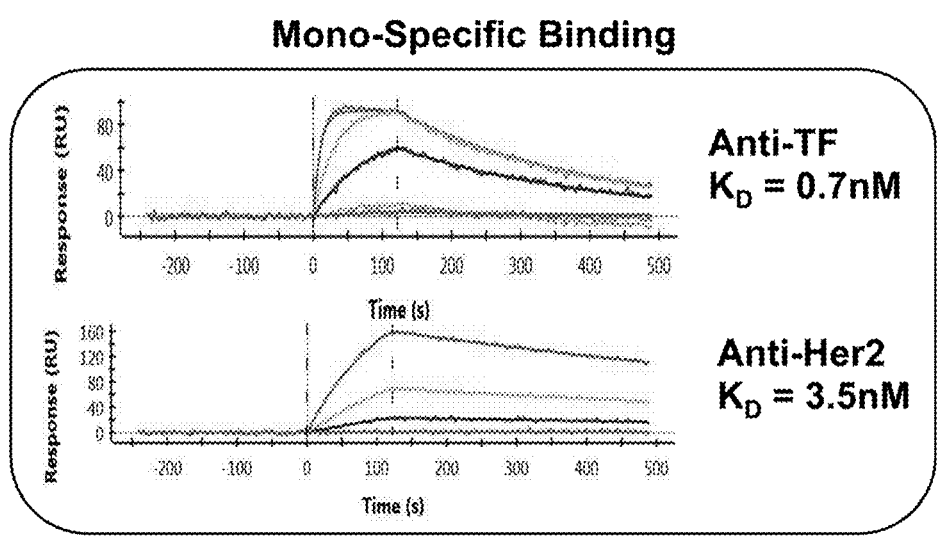
FIG. 17A Upper panel depicts SPR data showing monospecific binding for TF or Her2 antigen by the bispecific construct based on design set depicted in FIG. 11 (Note: This SMCA design utilizes the same H1-L1 and H2-L2 MCA designs as depicted in FIG. 11). Lower panel depicts SPR data showing simultaneous bispecific binding of TF and Her2 antigens by the bispecific antigen-binding construct.
Figure 17B:
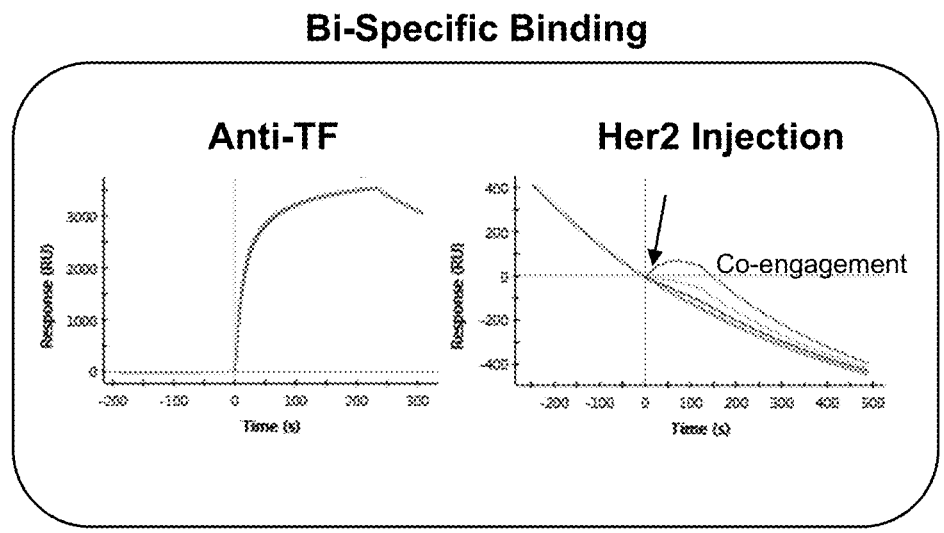

FIG. 15 presents the LC/MS analysis results of the bispecific construct targeting TF and Her2 based on the designs presented in FIG. 11 and FIG. 12 in the MCA format. Close to 92% of the preferred bispecific antibody with the correct pairing of obligate heavy and light chains was observed. FIG. 16 presents the expression profile of the protein product in the supernatant and following protein A purification in SDS PAGE as well as the SEC profile of the protein A purified compound. FIG. 17 presents the bispecific target binding features of the bispecific molecule, first to the two targets (TF and Her2 independently) and then in a sandwich (bridging) mode.

In some cases, the mutations at H/S 115 and H/S156, featured in limited set of variants, were not part of the actual design, but rather were added for practical reasons to gain necessary mass difference for the purposes of a LC/MS experiment. These amino acids are located on the surface of the constant domain, sufficiently away from the actual design set of mutations and is not expected to impact the behavior of the antibody.

Thermal stability and antigen affinity were assessed for a number of designs in the D3H4/Pertuzumab system and are presented in Table 25. Tm values (indicated in italics) were annotated manually. Homodimeric Mab controls (WT) exhibited the following stability range of thermal melting ($T_m$) for product expressed in transfection repeats (at pH 7): PERT (72.03-77.72) and for D3H44 (77.97-78.88). The wider range observed for pertuzumab is likely due to its intrinsic properties. Affinity measurements were undertaken post pA purification only. Observed KD range for Homodimeric Mabs is: TF: 0.04-0.076 nM, HER2: 1.84-6.3 nM. In most cases one would expect two melting transitions due to the above indicated different ranges for the two Fabs. In cases where only one value for Tm is reported, it potentially arose due to one of two reasons: variation of pertuzumab stability or/and destabilization of the design on the D3H44 Fab that may coincide with that of pertuzumab Fab. Results indicate that selection of SMCA variants ranges from the ones that affect thermal stability minimally as well as antigen binding to the ones that do so to varying degrees.

Some designs were tested with both possible Fc mutation placements. These are identifiable by having the same unique identifier and denoted with *D3H44 (or in Table 25 with #preceding unique identifier set). As evident from Table 22, placement of Fc mutations does not appear to influence the paired: mispaired species outcome with a limited exception.

The SMCA results show that a substantial number of designs representing a diverse set can overcome the natural cross-species pairing tendency in the Mab format. Among these, close to a quarter of the designs tested fall into the category of high paired:mispaired ratio (>=80:20) (numbers are provided for the more exhaustively tested system, D3H44/Pertuzumab). Comparison of design effectiveness across different systems reveals varying degrees of transferability. Furthermore, approximately 60% of designs, listed in Table 27, transported from the D3H44 LCCA into the SMCA format resulted in a high degree of preferential pairing (>75%: 25%) in at least one of the four tested SMCA systems.

For designs tested in systems other than D3H44/Pertuzumab, design placement was inverted with respect to the binding domains as well, e.g. H1-L1 designs on D3H44 binding domain, H2-L2 designs on TRAS as well as H1-L1 designs on TRAS and H2-L2 designs on D3H44. The results demonstrate that a design's effectiveness in a majority of cases could be impacted by such a flipped placement.

The results discussed above indicate that a design's transferability can be impacted by a combination of antigen binding domains coupled with the driving potential of design constituents (e.g. H1L1L2 driving may be better than H2L2L1). The results indicate that a large number of base core designs work across a range of Mab pairs to form a bispecific Ab with greater than 75% selective pairing.

Example 14: Molecular Modeling and Computer Guided Engineering of Fab Interface

We employed a structure and computational molecular modeling guided approach to produce a library of heavy and light chain mutation designs that can be screened in the context of other antibodies or fragments thereof to identify mutations that exhibit the desired specificity in the antibodies of interest. The design strategy for engineering preferential HC-LC pairing included first identifying a representative Ab (i.e. D3H44) to work with. Key criteria of this Ab are shown in Table 28.

TABLE 28

| Criteria | Importance |
| --- | --- |
| Human or humanized IgG1/κ | Similarity |
| Has commonly used $V_H$ and $V_L$ subgroups | |
| Framework close to germline | |
| $V_H$:$V_L$ interdomain packing angle close to observed average for Fabs | |
| Structure available for apo- and complexed Fab | Design |
| No major structural changes observed upon binding antigen | |
| Antigen binding can be readily assayed | Assay |

Figure 18:
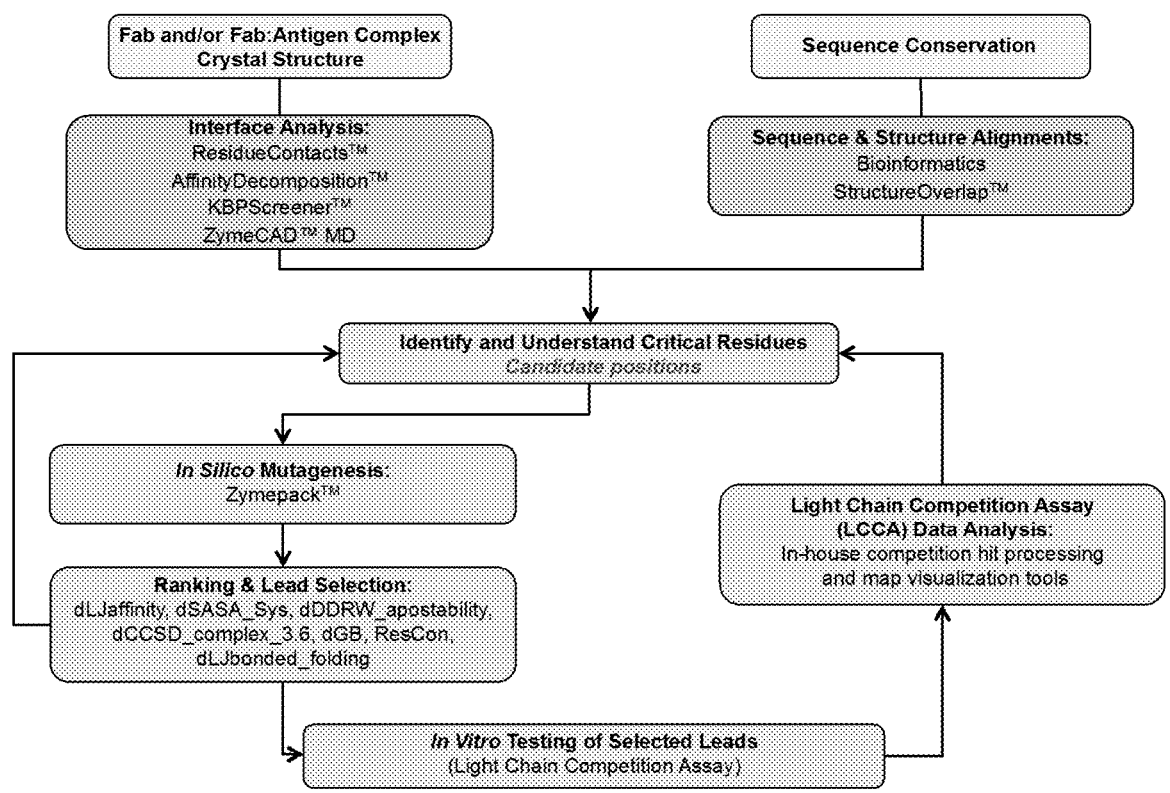
FIG. 18 depicts a flowchart for identifying critical interface residues and for computational modeling of designs with preferential heavy-light chain pairing.

As indicated in Table 28, key criteria presented by this antibody was that it was a human/humanized Ab, with commonly used VH and VL subgroups and minimal framework region mutations. In addition, structural considerations were that the VH:VL interdomain angle should be close to the average observed for Abs. After selection of the Fab, an in silico analysis of the Fab interface was carried with the aim being to identify and understand the important residues. A two-pronged approach was taken. First, a global analysis of the sequence conservation across the Fab variable and constant interfaces was carried out via sequence and structure alignments of publicly available Abs. An alignment of constant and variable domain sequences from various antibody subgroups is shown in FIG. 6. In parallel, the crystal structure interface D3H44 was analyzed using a number of molecular modeling tools listed in FIG. 18 (e.g. RESIDUE-CONTACTS™). These analyses resulted in the identification of a list of hotspot positions for engineering preferential HC-LC pairing. The hotspot positions determined from this analysis are listed in Table 29.

TABLE 29

Hotspot amino acid positions at the interface of the heavy (H) and light (L) chain in a typical Fab derived from human VH and VL kappa chains. These positions and amino acids are also mostly conserved in the VL lambda chains. These are mainly framework residues except for a few located in the CDR3 loops. The amino acids in the parent D3H44 sequences with Kabat numbering are provided in Tables A1-A2.

| H (Kabat) | L (Kabat) |
| --- | --- |
| V37 | Y36 |
| Q39 | Q38 |
| L45 | P44 |
| W47 | L89 |
| F100 | F98 |
| W103 | F116 |
| L124 | F118 |
| A139 | V133 |
| F174 | L135 |

Next, potential mutations and designs at the hotspot positions as well as positions neighboring the hotspots of interest in the 3D crystal structure were simulated and identified via in silico mutagenesis and packing/modeling with ZYMEPACK™ and scored on the basis of a number of factors including steric and electrostatic complementarity. FIG. 11 presents a limited number of hotspot positions at the heavy and light chain interface in the variable domains and how mutations can be introduced at these interface positions to facilitate selective pairing of the obligate chains while disfavoring the formation of incorrect chain pairs. Steric complementarity was modeled and also computed on the basis of energy factors such as van der Waals packing, cavitation effects and close contact of hydrophobic groups. Similarly, electrostatic interaction energies were modeled and evaluated on the basis of coulomb interactions between charges, hydrogen bonds, and desolvation effects. Both the preferred heavy and light chain pair models such as H1:L1 (or H2:L2) and incorrect pair such as H1:L2 (and H2:L1) obtained by introducing the mutations of interest were simulated to compute the relative steric and electrostatic scores. This allowed us to decide if a particular mutation set lead to favorable energies i.e. greater steric or electrostatic complementarity for the preferred (obligate) heavy—light chain pairs relative to the incorrect (non-obligate) pairs. The computed steric and electrostatic energies are components of the free energy associated with the light and heavy chain pairing. Hence greater steric and electrostatic complementarity is indicative of a larger free energy change associated with the pairing of the obligate pair relative to the pairing of the non-obligate pair. The greater steric or electrostatic complementarity results in preferential (selective) pairing of the obligate heavy and light chains relative to the non-obligate pair and can be detected in terms of the percentage of the two products (obligate paired vis-à-vis the non-obligate paired heavy and light chain) upon co-expression. The greater steric or electrostatic complementarity in the obligate pair can also be typically observed in terms of better/greater thermal stability relative to the non-obligate pair. Candidate designs were shortlisted and ranked. Designs were initially tested in vitro using the LCCA system. Moderately performing designs displaying non-optimal biophysical characteristics such as poor HC-LC pairing specificity, low thermal stability, or reduced antigen binding affinity, were further improved via additional rounds of in silico design and in vitro screening. The best designs were then tested in a bispecific Mab format; in vitro screening primarily being via the SMCA format.

Example 15: Generation of Bispecific Antibody Given Mab1 and Mab2 Using a Library of Bispecific Antibody Mutation Design Sets In one embodiment, presented here is a bispecific antibody mutation design set aimed at selectively forming bispecific antibodies given two canonical antibodies Mab1 and Mab2 comprising of the antigen binding fragments Fab1 and Fab2 respectively. The design set consists of cognate mutations corresponding to Fab1, Fab2 and Fc respectively. Mutations are introduced at the interface of light and heavy chain of Fab1 to achieve selective pairing between the two obligate chains in the presence of competing light and heavy chain of Fab2. Selective pairing is achieved by introducing favorable complementary mutations in the two obligate light and heavy chains on the basis of steric, hydrophobic or electrostatic complementarity between certain hotspot framework residues at the interface while involving these mutated residues in unfavorable interface interaction for the non-obligate chain pairs. In each design set selective pairing mutations can also be introduced at the interface of light and heavy chain of Fab2 to achieve selective pairing between these two obligate chains in the presence of competing light and heavy chain of Fab1. The mutations are aimed at reducing the mis-pairing of light chain from Fab1 with heavy chain of Fab2 and vice-versa. Mutations are introduced at the Fc interface in order to achieve selective pairing of heavy chains to form asymmetric antibody molecules comprising two different heavy chains.

Figure 19:
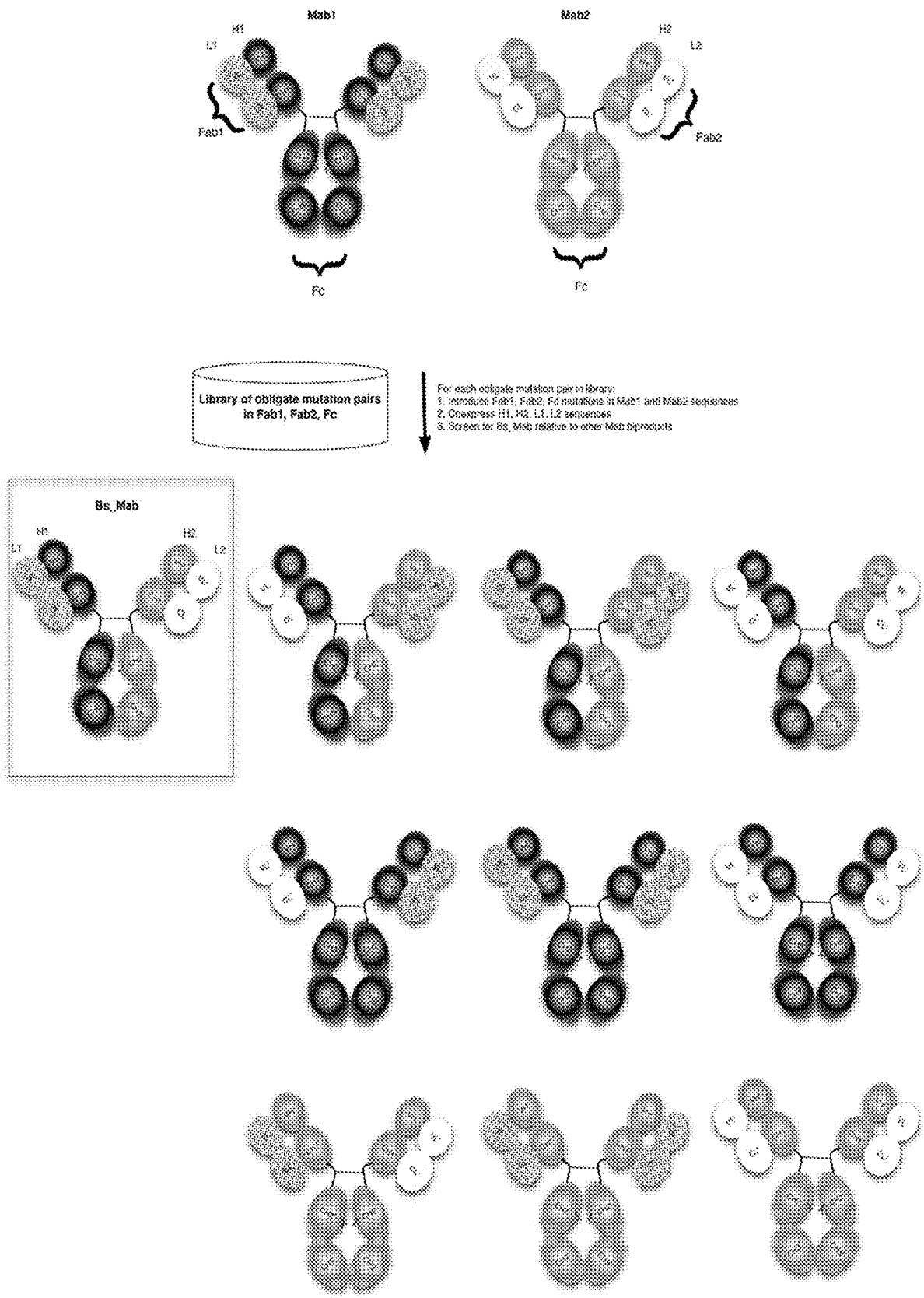
FIG. 19 presents a schematic depicting a method of preparing a bi-specific antibody using the library of obligate mutation pairs provided in this invention.

Engineering at certain interface residue positions of light and heavy chains of an antibody can often lead to detrimental effects such as loss in antigen binding affinity, stability, solubility, aggregation propensity etc of that antibody. A number of related properties can be affected such as kon and koff rates, melting temperature (Tm), stability to stress conditions like acid, base, oxidation, freeze/thaw, agitation, pressure etc. This is often impacted by the complementarity determining regions (CDR's) of the antibody of interest. Given that the CDR's of antibodies are not generally the same, the impact of the mutation design set may not be the same across all antibodies. In another embodiment, a number of different bispecific mutation design sets constituting a library of bispecific antibody mutation design sets are defined that involve mutations at different hotspot positions at the interface. A library of such bispecific antibody mutation design sets is shown in Table 30. Presented here is a method to create a bispecific antibody with noted purity relative to other contaminants containing incorrectly paired antibody-like structures, given any two available antibodies Mab1 and Mab2. The light and heavy chains of Mab1 and Mab2 are co-expressed after introducing the cognate mutations of each of the mutation design sets and the expressed antibody product is analytically screened to estimate the purity of the preferred bispecific antibody relative to other Mab like species expressed in the protein product. In some embodiments the analytical screening procedure may be based on an LC-MS technique. In some embodiments the analytical screening procedure may be based on charge based separation such as a capillary isoelectric focusing (cIEF) technique. An example of the screening technique is presented in Example 13 based on the SMCA procedure. In some embodiments the noted purity of the bispecific antibody is defined as being greater than 70% of all the obtained Mab like species in the expressed protein product. In some embodiments the noted purity of the bispecific antibody is defined as being greater than 90% of all the obtained Mab like species in the expressed protein product. The procedure for preparation and selection of bispecific Mab design set given Mab1 and Mab2 is shown schematically in FIG. 19.

All publications, patents and patent applications mentioned in this specification are herein incorporated by reference into the specification to the same extent as if each individual publication, patent or patent application was specifically and individually indicated to be incorporated herein by reference.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE A

SEQUENCES

| SEQ ID NO | DESCRIPTION | SEQUENCE |
|---|---|---|
| 4 | D3H44 light chain (Domain boundaries: VL; D1-K107, CL; R108-C214) | DIQMTQSPSSLSASVGDRVTITCRASRDIKSYLNWYQQKPGKAPKVLIYYATSLAE GVPSRFSGSGSGTDYTLTISSLQPEDFATYYCLQHGESPWTFGQGTKVEIKRTVAA PSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 5 | Pertuzumab light chain (Domain boundaries: VL; D1-K107, CL; R108-C214) | DIQMTQSPSSLSASVGDRVTITCKASQDVSIGVAWYQQKPGKAPKLLIYSASYRYT GVPSRFSGSGSGTDFTLTISSLQPEDFATYYCQQYYTYPYTFGQGTKVEIKRTVAA PSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 6 | Trastuzumab light chain (Domain boundaries: VL; D1-K107, CL; R108-C214) | DIQMTQSPSSLSASVGDRVTITCRASQDVNTAVAWYQQKPGKAPKLLIYSASFLYS GVPSRFSGSRSGTDFTLTISSLQPEDFATYYCQQHYTTPPTFGQGTKVEIKRTVAA PSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 7 | Ramucirumab light chain (Domain boundaries: VL; D1-K107, CL; G108-C214) | DIQMTQSPSSVSASIGDRVTITCRASQGIDNWLGWYQQKPGKAPKLLIYDASNLDT GVPSRFSGSGSGTYFTLTISSLQAEDFAVYFCQQAKAFPPTFGGGTKVDIKGTVAA PSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 8 | D3H44 heavy chain (Domain boundaries: VH; E1-S113, CH1; A114-K223, Hinge; E226-P243, CH2; A244-K360, CH3; G361-G477) | EVQLVESGGGLVQPGGSLRLSCAASGFNIKEYYMHWVRQAPGKGLEWVGLIDPEQG NTIYDPKFQDRATISADNSKNTAYLQMNSLRAEDTAVYYCARDTAAYFDYWGQGTL VTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKTH TCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPG |

TABLE A-continued

| SEQ ID NO | DESCRIPTION | SEQUENCE |
|---|---|---|
| 9 | Pertuzumab heavy chain (Domain boundaries: VH; E1-S113, CH1; A114-K223, Hinge; E226-P243, CH2; A244-K360, CH3; G361-G477) | EVQLVESGGGLVQPGGSLRLSCAASGFTFTDYTMDWVRQAPGKGLEWVADVNPNSG<br>GSIYNQRFKGRFTLSVDRSKNTLYLQMNSLRAEDTAVYYCARNLGPSFYFDYWGQG<br>TLVTVSSASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQKSLSLSPG |
| 10 | Trastuzumab heavy chain (Domain boundaries: VH; E1-S113, CH1; A114-K223, Hinge; E226-P243, CH2; A244-K360, CH3; G361-G477) | EVQLVESGGGLVQPGGSLRLSCAASGFNIKDTYIHWVRQAPGKGLEWVARTYPTNG<br>YTRYADSVKGRFTISADTSKNTAYLQMNSLRAEDTAVYYCSRWGGDGFYAMDYWGQ<br>GTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYTQKSLSLSP<br>G |
| 11 | Ramucirumab heavy chain (Domain boundaries: VH; E1-S113, CH1; A114-K223, Hinge; E226-P243, CH2; A244-K360, CH3; G361-G477) | EVQLVQSGGGLVKPGGSLRLSCAASGFTFSSYSMNWVRQAPGKGLEWVSSISSSSS<br>YIYYADSVKGRFTISRDNAKNSLYLQMNSLRAEDTAVYYCARVTDAFDIWQGTMV<br>TVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSLSPG |
| 12 | Trastuzumab_HC | GCCACCATGGCCGTGATGGCTCCTAGAACCCTGGTGCTGCTGCTGTCTGGAGCTCT<br>GGCTCTGACTCAGACCTGGGCTGGAGAGGTGCAGCTGGTGGAAAGCGGAGGAGGAC<br>TGGTGCAGCCAGGAGGATCTCTGCGACTGAGTTGCGCCGCTTCAGGATTCAACATC<br>AAGGACACCTACATTCACTGGGTGCGACAGGCTCCAGGAAAAGGACTGGAGTGGGT<br>GGCTCGAATCTATCCCACTAATGGATACACCCGGTATGCCGACTCCGTGAAGGGGA<br>GGTTTACTATTAGCGCCGATACATCCAAAAACACTGCTTACCTGCAGATGAACAGC<br>CTGCGAGCCGAAGATACCGCTGTGTACTATTGCAGTCGATGGGGAGGAGACGGATT<br>CTACGCTATGGATTATTGGGGACAGGGGACCCTGGTGACAGTGAGCTCCGCCTCTA<br>CCAAGGGCCCCAGTGTGTTTCCCCTGGCTCCTTCTAGTAAATCCACCTCTGGAGGG<br>ACAGCCGCTCTGGGATGTCTGGTGAAGGACTATTTCCCCGAGCCTGTGACCGTGAG<br>TTGGAACTCAGGCGCCCTGACAAGCGGAGTGCACACTTTTCCTGCTGTGCTGCAGT<br>CAAGCGGGCTGTACTCCCTGTCCTCTGTGGTGACAGTGCCAAGTTCAAGCCTGGGC<br>ACACAGACTTATATCTGCAACGTGAATCATAAGCCCTCAAATACAAAAGTGGACAA<br>GAAAGTGGAGCCCAAGAGCTGTGATAAGACCCACACCTGCCCTCCCTGTCCAGCTC<br>CAGAACTGCTGGGAGGACCTAGCGTGTTCCTGTTTCCCCCTAAGCCAAAAGACACT<br>CTGATGATTTCCAGGACTCCCGAGGTGACCTGCGTGGTGGTGGACGTGTCTCACGA<br>GGACCCCGAAGTGAAGTTCAACTGGTACGTGGATGGCGTGGAAGTGCATAATGCTA<br>AGACAAAACCAAGAGAGGAACAGTACAACTCCACTTATCGCGTCGTGAGCGTGCTG<br>ACCGTGCTGCACCAGGACTGGCTGAACGGGAAGGAGTATAAGTGCAAAGTCAGTAA<br>TAAGGCCCTGCCTGCTCCAATCGAAAAAACCATCTCTAAGGCCAAAGGCCAGCCAA<br>GGGAGCCCCAGGTGTACACACTGCCACCCAGCAGAGACGAACTGACCAAGAACCAG<br>GTGTCCCTGACATGTCTGGTGAAAGGCTTCTATCCTAGTGATATTGCTGTGGAGTG<br>GGAATCAAATGGACAGCCAGAGAACAATTACAAGACCACACCTCCAGTGCTGGACA<br>GCGATGGCAGCTTCTTCCTGTATTCCAAGCTGACAGTGGATAAATCTCGATGGCAG<br>CAGGGGAACGTGTTTAGTTGTTCAGTGATGCATGAAGCCCTGCACAATCATTACAC<br>TCAGAAGAGCCTGTCCCTGTCTCCCGGCTGA |
| 13 | Trastuzumab_LC | GCCACTATGGCTGTGATGGCCCCTAGGACCCTGGTGCTGCTGCTGTCCGGAGCTCT<br>GGCTCTGACTCAGACCTGGGCTGGAGACATCCAGATGACCCAGTCTCCATCCTCCC<br>TGTCTGCATCTGTAGGAGACAGAGTCACCATCACTTGCCGGGCAAGTCAGGACGTT<br>AACACCGCTGTAGCTTGGTATCAGCAGAAACCAGGGAAAGCCCCTAAGCTCCTGAT<br>CTATTCTGCATCCTTTTTGTACAGTGGGGTCCCATCAAGGTTCAGTGGCAGTCGAT<br>CTGGGACAGATTTCACTCTCACCATCAGCAGTCTGCAACCTGAAGATTTTGCAACT<br>TACTACTGTCAACAGCATTACACTACCCCACCCACTTTCGGCCAAGGGACCAAAGT<br>GGAGATCAAACGAACTGTGGCTGCACCATCTGTCTTCATCTTCCCGCCATCTGATG<br>AGCAGTTGAAATCTGGAACTGCCTCTGTTGTGTGCCTGCTGAATAACTTCTATCCC<br>AGAGAGGCCAAAGTACAGTGGAAGGTGGATAACGCCCTCCAATCGGGTAACTCCCA |

TABLE A-continued

SEQUENCES

| SEQ ID NO | DESCRIPTION | SEQUENCE |
|---|---|---|
| | | AGAGAGTGTCACAGAGCAGGACAGCAAGGACAGCACCTACAGCCTCAGCAGCACCC |
| | | TGACGCTGAGCAAAGCAGACTACGAGAAACACAAAGTCTACGCCTGCGAAGTCACC |
| | | CATCAGGGCCTGAGCTCGCCCGTCACAAAGAGCTTCAACAGGGGAGAGTGTTGA |
| 14 | Ramucirumab_HC | GCCACCATGGCCGTGATGGCTCCTAGAACACTGGTCCTGCTGCTGTCAGGGGCACT |
| | | GGCACTGACTCAGACTTGGGCTGGGGAGGTCCAGCTGGTCCAGTCCGGAGGAGGAC |
| | | TGGTGAAGCCTGGAGGGAGTCTGCGACTGTCATGCGCCGCTAGCGGGTTCACCTTT |
| | | AGCTCCTACAGCATGAACTGGGTGCGACAGGCACCAGGCAAAGGACTGGAATGGGT |
| | | GTCTAGTATCTCAAGCTCCTCTAGTTACATCTACTATGCAGACAGCGTGAAGGGCC |
| | | GGTTCACCATCAGCAGAGATAACGCCAAAAATTCCCTGTATCTGCAGATGAACAGC |
| | | CTGCGAGCCGAGGACACCGCTGTCTACTATTGCGCACGGGTGACAGACGCCTTCGA |
| | | TATTTGGGGACAGGGCACCATGGTCACAGTGTCAAGCGCCTCCACCAAGGGACCAA |
| | | GCGTGTTCCCACTGGCTCCATCCTCTAAAAGCACTTCCGGAGGAACCGCAGCCCTG |
| | | GGATGTCTGGTGAAGGATTACTTCCCAGAGCCCGTCACAGTGTCATGGAACAGCGG |
| | | GGCTCTGACCTCTGGAGTCCACACATTTCCAGCAGTGCTGCAGAGTTCAGGACTGT |
| | | ACAGCCTGAGCTCCGTGGTCACAGTGCCCTCTAGTTCACTGGGCACTCAGACCTAT |
| | | ATCTGCAACGTGAATCACAAGCCAAGCAATACTAAAGTCGACAAGAAAGTGGAACC |
| | | CAAGTCCTGTGATAAAACACATACTTGCCCACCTTGTCCTGCACCAGAGCTGCTGG |
| | | GAGGACCATCCGTGTTCCTGTTTCCACCCAAGCCTAAAGACACTCTGATGATTTCT |
| | | AGGACACCCGAAGTCACTTGCGTGGTCGTGGACGTGAGCCACGAGGACCCCGAAGT |
| | | CAAGTTTAACTGGTACGTGGATGGCGTCGAGGTGCATAATGCTAAGACAAAACCTA |
| | | GGGAGGAACAGTACAACAGTACATATAGAGTCGTGTCAGTCCTGACTGTGCTGCAT |
| | | CAGGACTGGCTGAACGGAAAGGAATATAAGTGCAAAGTGAGCAATAAGGCTCTGCC |
| | | CGCACCTATCGAGAAAACTATTTCCAAGGCTAAAGGCCAGCCTAGAGAACCACAGG |
| | | TGTACACCCTGCCTCCATCTAGGGACGAGCTGACTAAGAACCAGGTCAGTCTGACC |
| | | TGTCTGGTGAAAGGCTTCTATCCTAGCGATATCGCAGTGGAGTGGGAATCCAATGG |
| | | GCAGCCAGAGAACAATTACAAGACCACACCCCCTGTGCTGGACTCCGATGGGTCTT |
| | | TCTTTCTGTATAGTAAGCTGACCGTCGATAAATCACGGTGGCAGCAGGGAAACGTG |
| | | TTCAGCTGTAGTGTCATGCACGAAGCACTGCACAATCATTACACCCAGAAGAGCCT |
| | | GTCACTGTCACCCGGATGA |
| 15 | Ramucirumab_LC | GCCACCATGGCTGTGATGGCACCTAGAACACTGGTCCTGCTGCTGTCCGGGGCACT |
| | | GGCACTGACTCAGACTTGGGCTGGCGATATTCAGATGACCCAGAGTCCAAGCTCCG |
| | | TGTCCGCCTCTATCGGCGACCGAGTCACCATTACATGCAGAGCTAGCCAGGGCATC |
| | | GATAACTGGCTGGGGTGGTACCAGCAGAAGCCTGGAAAAGCCCCAAAGCTGCTGAT |
| | | CTACGACGCTTCCAATCTGGATACAGGCGTGCCCTCTAGGTTCAGTGGCTCAGGGA |
| | | GCGGAACTTACTTTACTCTGACCATCTCTAGTCTGCAGGCTGAGGACTTCGCAGTG |
| | | TATTTTTGCCAGCAGGCAAAAGCCTTCCCCCCTACCTTTGGCGGGGGAACAAAAGT |
| | | CGACATCAAGGGGACCGTGGCCGCTCCCTCAGTCTTCATTTTTCCACCCAGCGATG |
| | | AGCAGCTGAAGTCTGGAACAGCCAGTGTGGTCTGTCTGCTGAACAATTTCTACCCT |
| | | CGGGAAGCAAAAGTGCAGTGGAAGGTCGACAACGCCCTGCAGTCCGGCAACAGCCA |
| | | GGAGAGTGTGACTGAACAGGACTCAAAAGATAGCACCTATTCCCTGTCAAGCACAC |
| | | TGACTCTGTCCAAGGCTGATTACGAAAAGCACAAAGTGTATGCATGTGAGGTCACC |
| | | CATCAGGGGCTGTCAAGTCCAGTCACAAAAAGTTTCAACCGAGGAGAGTGCTGA |
| 16 | D3H44_HC | GCCACAATGGCCGTGATGGCTCCTAGAACACTGGTCCTGCTGCTGTCCGGGGCTCT |
| | | GGCTCTGACTCAGACTTGGGCTGGGGAGGTGCAGCTGGTCGAATCTGGAGGAGGAC |
| | | TGGTGCAGCCAGGAGGGTCACTGAGACTGAGCTGCGCCGCTTCCGGCTTCAACATC |
| | | AAGGAGTACTATATGCACTGGGTGAGGCAGGCACCTGGCAAAGGACTGGAGTGGGT |
| | | GGGACTGATCGACCCAGAACAGGGGAACACCATCTACGACCCTAAGTTTCAGGATA |
| | | GGGCAACCATTTCTGCCGACAACAGTAAAAATACAGCTTATCTGCAGATGAACAGC |
| | | CTGAGGGCTGAAGATACTGCAGTGTACTATTGCGCACGCGACACCGCAGCCTACTT |
| | | CGATTATTGGGGACAGGGCACCCTGGTCACAGTGAGCTCCGCATCAACTAAGGGAC |
| | | CCAGCGTGTTTCCACTGGCCCCCTCTAGTAAATCCACTTCTGGAGGCACCGCTGCA |
| | | CTGGGCTGTCTGGTGAAGGATTACTTCCCAGAGCCCGTCACAGTGAGCTGGAACTC |
| | | CGGGGCCCTGACCAGCGGAGTCCATACATTTCCTGCTGTGCTGCAGTCAAGCGGGC |
| | | TGTACTCCCTGTCCTCTGTGGTCACCGTGCCAAGTTCAAGCCTGGGAACTCAGACC |
| | | TATATCTGCAACGTGAATCACAAGCCTTCAAATACAAAAGTCGACAAGAAAGTGGA |
| | | ACCAAAGAGCTGTGATAAAACACATACTTGCCCACCTTGTCCTGCACCAGAGCTGC |
| | | TGGGGAGGACCAAGCGTGTTCCTGTTTCCACCCAAGCCCAAAGACACCCTGATGAT |
| | | TCCCGCACACCAGAAGTCACTTGCGTGGTCGTGGACGTGTCTCACGAGGACCCCGA |
| | | AGTCAAGTTCAACTGGTACGTGGATGGCGTCGAGGTGCATAATGCCAAGACAAAAC |
| | | CCCGGGAGGAACAGTACAACTCCACATATAGAGTCGTGTCTGTCCTGACTGTGCTG |
| | | CACCAGGACTGGCTGAACGGGAAGGAGTATAAGTGCAAAGTGAGTAATAAGGCCCT |
| | | GCCCGCTCCTATCGAGAAAACAATTAGCAAGGCCAAAGGCCAGCCTCGAGAACCAC |
| | | AGGTGTACACTCTGCCTCCATCTCGGGACGAGCTGACTAAGAACCAGGTCAGTCTG |
| | | ACCTGTCTGGTGAAAGGATTCTATCCCAGCGATATCGCTGTGGAGTGGGAATCCAA |
| | | TGGCCAGCCTGAGAACAATTACAAGACCACACCCCCTGTGCTGGACTCTGATGGCA |
| | | GTTTCTTTCTGTATAGTAAGCTGACCGTCGATAAATCACGATGGCAGCAGGGGAAC |
| | | GTGTTCAGCTGTTCAGTGATGCACGAAGCCCTGCACAACCATTACACCCAGAAGAG |
| | | CCTGAGCCTGTCTCCCGGCTGA |
| 17 | D3H44_LC | GCCACAATGGCTGTGATGGCACCCCGAACCCTGGTCCTGCTGCTGAGTGGAGCACT |
| | | GGCACTGACCCAGACATGGGCAGGCGACATCCAGATGACACAGTCCCCTAGCTCCC |
| | | TGAGTGCCTCAGTGGGGGACAGAGTCACTATCACCTGCCGGGCTTCCAGAGATATT |
| | | AAGTCTTACCTGAACTGGTATCAGCAGAAGCCAGGCAAAGCACCCAAGGTGCTGAT |

TABLE A-continued

SEQUENCES

| SEQ ID NO | DESCRIPTION | SEQUENCE |
|---|---|---|
|  |  | CTACTATGCCACCAGTCTGGCTGAAGGAGTGCCTTCACGGTTCAGCGGCTCCGGGT<br>CTGGAACTGACTACACACTGACTATTTCTAGTCTGCAGCCTGAGGATTTCGCTACC<br>TACTATTGCCTGCAGCACGGCGAATCCCCATGGACTTTTGGCCAGGGGACCAAAGT<br>GGAGATCAAGAGGACAGTGGCCGCTCCATCCGTCTTCATTTTTCCCCCTTCTGACG<br>AACAGCTGAAATCAGGAACTGCCAGCGTGGTCTGTCTGCTGAACAATTTCTACCCC<br>CGCGAGGCAAAAGTGCAGTGGAAGGTCGATAACGCCCTGCAGAGTGGCAATTCACA<br>GGAGAGCGTGACAGAACAGGACTCCAAAGATTCTACTTATAGTCTGTCAAGCACCC<br>TGACACTGTCTAAGGCTGATTACGAGAAGCACAAAGTGTATGCATGCGAAGTCACC<br>CATCAGGGGCTGTCCTCTCCCGTGACAAAGAGCTTTAATCGGGGAGAGTGTTGA |
| 18 | Pertuzumab_HC | GCCACAATGGCTGTGATGGCTCCAAGAACCCTGGTCCTGCTGCTGTCCGGGGCTCT<br>GGCTCTGACTCAGACCTGGGCCGGGGAAGTGCAGCTGGTCGAATCTGGAGGAGGAC<br>TGGTGCAGCCAGGAGGGTCCCTGCGCCTGTCTTGCGCCGCTAGTGGCTTCACTTTT<br>ACCGACTACACCATGGATTGGGTGCGACAGGCACCTGGAAAGGGCCTGGAGTGGGT<br>CGCCGATGTGAACCCAAATAGCGGAGGCTCCATCTACAACCAGCGGTTCAAGGGCC<br>GGTTCACCCTGTCAGTGGACCGGAGCAAAAACACCCTGTATCTGCAGATGAATAGC<br>CTGCGAGCCGAAGATACTGCTGTGTACTATTGCGCCCGGAATCTGGGGCCCTCCTT<br>CTACTTTGACTATTGGGGGCAGGGAACTCTGGTCACCGTGAGCTCCGCCTCCACCA<br>AGGGACCTTCTGTGTTCCCACTGGCTCCCTCTAGTAAATCCACATCTGGGGGAACT<br>GCAGCCCTGGGCTGTCTGGTGAAGGACTACTTCCCAGAGCCCGTCACAGTGTCTTG<br>GAACAGTGGCGCTCTGACTTCTGGGGTCCACACCTTTCCTGCAGTGCTGCAGTCAA<br>GCGGGCTGTACAGCCTGTCCTCTGTGGTCACCGTGCCAAGTTCAAGCCTGGGAACA<br>CAGACTTATATCTGCAACGTGAATCACAAGCCATCCAATACAAAAGTCGACAAGAA<br>AGTGGAACCCAAGTCTTGTGATAAAACCCATACATGCCCCCCTTGTCCTGCACCAG<br>AGCTGCTGGGAGGACCAAGCGTGTTCCTGTTTCCACCCAAGCCTAAAGATACACTG<br>ATGATTAGTAGGACCCCAGAAGTCACATGCGTGGTCGTGGACGTGAGCCACGAGGA<br>CCCCGAAGTCAAGTTTAACTGGTACGTGGACGGCGTCGAGGTGCATAATGCCAAGA<br>CTAAACCCAGGGAGGAACAGTACAACAGTACCTATCGCGTCGTGTCAGTCCTGACA<br>GTGCTGCATCAGGATTGGCTGAACGGGAAAGAGTATAAGTGCAAAGTGAGCAATAA<br>GGCTCTGCCCGCACCTATCGAGAAAACAATTTCCAAGGCAAAAGGACAGCCTAGAG<br>AACCACAGGTGTACACTCTGCCTCCATCAAGGGATGAGCTGACAAAGAACCAGGTC<br>AGCCTGACTTGTCTGGTGAAAGGATTCTATCCCTCTGACATTGCTGTGGAGTGGGA<br>AAGTAATGGCCAGCCTGAGAACAATTACAAGACCACACCCCCTGTGCTGGACTCAG<br>ATGGCAGCTTCTTTCTGTATAGCAAGCTGACCGTCGACAAATCCCGGTGGCAGCAG<br>GGGAATGTGTTTAGTTGTTCAGTCATGCACGAGGCACTGCACAACCATTACACCCA<br>GAAGTCACTGTCACTGTCACCAGGGTGA |
| 19 | Pertuzumab_LC | GCCACAATGGCTGTGATGGCACCTAGAACACTGGTCCTGCTGCTGAGCGGGGCACT<br>GGCACTGACACAGACTTGGGCCGGGGATATTCAGATGACCCAGTCCCCAAGCTCCC<br>TGAGTGCCTCAGTGGGCGACCGAGTCACCATCACATGCAAGGCTTCCCAGGATGTG<br>TCTATTGGAGTCGCATGGTACCAGCAGAAGCCAGGCAAAGCACCCAAGCTGCTGAT<br>CTATAGCGCCTCCTACCGGTATACCGGCGTGCCCTCTAGATTCTCTGGCAGTGGGT<br>CAGGAACAGACTTTACTCTGACCATCTCTAGTCTGCAGCCTGAGGATTTCGCTACC<br>TACTATTGCCAGCAGTACTATATCTACCCATATACCTTTGGCCAGGGGACAAAAGT<br>GGAGATCAAGAGGACTGTGGCCGCTCCCTCCGTCTTCATTTTTCCCCCTTCTGACG<br>AACAGCTGAAAAGTGGCACACCAGCAGCGTGGTCTGTCTGCTGAACAATTTCTACCCT<br>CGCGAAGCCAAAGTGCAGTGGAAGGTCGATAACGCTCTGCAGAGCGGCAACAGCCA<br>GGAGTCTGTGACTGAACAGGACAGTAAAGATTCAACCTATAGCCTGTCAAGCACAC<br>TGACTCTGAGCAAGGCAGACTACGAGAAGCACAAAGTGTATGCCTGCGAAGTCACA<br>CATCAGGGGCTGTCCTCTCCTGTGACTAAGAGCTTTAACAGAGGAGAGTGTTGA |

Note:
The nucleotide sequences start with the signal peptide sequence and end with the stop codon TGA. These can be removed if desired.

TABLES A1-A2

Heavy chain and light chain amino acid sequences of D3H44, Trastuzumab, Pertuzumab and Ramucirumab

Table A1
Heavy chain origin

| KABAT numbering | D3H44 (SEQ ID NO: 8) | PERTUZUMAB (SEQ ID NO: 9) | TRASTUZUMAB (SEQ ID NO: 10) | RAMUCIRUMAB (SEQ ID NO: 11) |
|---|---|---|---|---|
| 1 | E | E | E | E |
| 2 | V | V | V | V |
| 3 | Q | Q | Q | Q |
| 4 | L | L | L | L |
| 5 | V | V | V | V |
| 6 | E | E | E | Q |
| 7 | S | S | S | S |
| 8 | G | G | G | G |
| 9 | G | G | G | G |
| 10 | G | G | G | G |
| 11 | L | L | L | L |
| 12 | V | V | V | V |

TABLES A1-A2-continued

Heavy chain and light chain amino acid sequences of D3H44, Trastuzumab, Pertuzumab and Ramucirumab Table A1
Heavy chain origin

| KABAT numbering | D3H44 (SEQ ID NO: 8) | PERTUZUMAB (SEQ ID NO: 9) | TRASTUZUMAB (SEQ ID NO: 10) | RAMUCIRUMAB (SEQ ID NO: 11) |
|---|---|---|---|---|
| 13 | Q | Q | Q | K |
| 14 | P | P | P | P |
| 15 | G | G | G | G |
| 16 | G | G | G | G |
| 17 | S | S | S | S |
| 18 | L | L | L | L |
| 19 | R | R | R | R |
| 20 | L | L | L | L |
| 21 | S | S | S | S |
| 22 | C | C | C | C |
| 23 | A | A | A | A |
| 24 | A | A | A | A |
| 25 | S | S | S | S |
| 26 | G | G | G | G |
| 27 | F | F | F | F |
| 28 | N | T | N | T |
| 29 | I | F | I | F |
| 32 | K | T | K | S |
| 33 | E | D | D | S |
| 34 | Y | Y | T | Y |
| 35 | Y | T | Y | S |
| 35A | M | M | I | M |
| 35B | H | D | H | N |
| 36 | W | W | W | W |
| 37 | V | V | V | V |
| 38 | R | R | R | R |
| 39 | Q | Q | Q | Q |
| 40 | A | A | A | A |
| 41 | P | P | P | P |
| 42 | G | G | G | G |
| 43 | K | K | K | K |
| 44 | G | G | G | G |
| 45 | L | L | L | L |
| 46 | E | E | E | E |
| 47 | W | W | W | W |
| 48 | V | V | V | V |
| 49 | G | A | A | S |
| 50 | L | D | R | S |
| 51 | I | V | I | I |
| 52 | D | N | Y | S |
| 52A | P | P | P | S |
| 52B | E | N | T | S |
| 54 | Q | S | N | S |
| 55 | G | G | G | S |
| 56 | N | G | Y | Y |
| 57 | T | S | T | I |
| 58 | I | I | R | Y |
| 59 | Y | Y | Y | Y |
| 60 | D | N | A | A |
| 61 | P | Q | D | D |
| 62 | K | R | S | S |
| 63 | F | F | V | V |
| 64 | Q | K | K | K |
| 65 | D | G | G | G |
| 66 | R | R | R | R |
| 67 | A | F | F | F |
| 68 | T | T | T | T |
| 69 | I | L | I | I |
| 70 | S | S | S | S |
| 71 | A | V | A | R |
| 72 | D | D | D | D |
| 73 | N | R | T | N |
| 74 | S | S | S | A |
| 75 | K | K | K | K |
| 76 | N | N | N | N |
| 77 | T | T | T | S |
| 78 | A | L | A | L |
| 79 | Y | Y | Y | Y |
| 80 | L | L | L | L |
| 81 | Q | Q | Q | Q |
| 82 | M | M | M | M |
| 82A | N | N | N | N |
| 82B | S | S | S | S |
| 82C | L | L | L | L |
| 83 | R | R | R | R |
| 84 | A | A | A | A |
| 85 | E | E | E | E |
| 86 | D | D | D | D |
| 87 | T | T | T | T |
| 88 | A | A | A | A |
| 89 | V | V | V | V |
| 90 | Y | Y | Y | Y |
| 91 | Y | Y | Y | Y |
| 92 | C | C | C | C |
| 93 | A | A | S | A |
| 94 | R | R | R | R |
| 95 | D | N | W | V |
| 96 | T | L | G | T |
| 97 | A | G | G | D |
| 98 |  | P | D |  |
| 98 |  |  | G |  |
| 98 |  | S | F |  |
| 98 | A | F | Y |  |
| 99 | Y | Y | A | A |
| 100 | F | F | M | F |
| 101 | D | D | D | D |
| 102 | Y | Y | Y | I |
| 103 | W | W | W | W |
| 104 | G | G | G | G |
| 105 | Q | Q | Q | Q |
| 106 | G | G | G | G |
| 107 | T | T | T | T |
| 108 | L | L | L | M |
| 109 | V | V | V | V |
| 110 | T | T | T | T |
| 111 | V | V | V | V |
| 112 | S | S | S | S |
| 113 | S | S | S | S |
| 114 | A | A | A | A |
| 115 | S | S | S | S |
| 116 | T | T | T | T |
| 117 | K | K | K | K |
| 118 | G | G | G | G |
| 119 | P | P | P | P |
| 120 | S | S | S | S |
| 121 | V | V | V | V |
| 122 | F | F | F | F |
| 123 | P | P | P | P |
| 124 | L | L | L | L |
| 125 | A | A | A | A |
| 126 | P | P | P | P |
| 127 | S | S | S | S |
| 128 | S | S | S | S |
| 129 | K | K | K | K |
| 130 | S | S | S | S |
| 133 | T | T | T | T |
| 134 | S | S | S | S |
| 135 | G | G | G | G |
| 136 | G | G | G | G |
| 137 | T | T | T | T |
| 138 | A | A | A | A |
| 139 | A | A | A | A |
| 140 | L | L | L | L |
| 141 | G | G | G | G |
| 142 | C | C | C | C |
| 143 | L | L | L | L |
| 144 | V | V | V | V |
| 145 | K | K | K | K |

TABLES A1-A2-continued

Heavy chain and light chain amino acid sequences of D3H44, Trastuzumab, Pertuzumab and Ramucirumab Table A1
Heavy chain origin

| KABAT numbering | D3H44 (SEQ ID NO: 8) | PERTU-ZUMAB (SEQ ID NO: 9) | TRASTU-ZUMAB (SEQ ID NO: 10) | RAMUCIRUMAB (SEQ ID NO: 11) |
|---|---|---|---|---|
| 146 | D | D | D | D |
| 147 | Y | Y | Y | Y |
| 148 | F | F | F | F |
| 149 | P | P | P | P |
| 150 | E | E | E | E |
| 151 | P | P | P | P |
| 152 | V | V | V | V |
| 153 | T | T | T | T |
| 154 | V | V | V | V |
| 156 | S | S | S | S |
| 157 | W | W | W | W |
| 162 | N | N | N | N |
| 163 | S | S | S | S |
| 164 | G | G | G | G |
| 165 | A | A | A | A |
| 166 | L | L | L | L |
| 167 | T | T | T | T |
| 168 | S | S | S | S |
| 169 | G | G | G | G |
| 171 | V | V | V | V |
| 172 | H | H | H | H |
| 173 | T | T | T | T |
| 174 | F | F | F | F |
| 175 | P | P | P | P |
| 176 | A | A | A | A |
| 177 | V | V | V | V |
| 178 | L | L | L | L |
| 179 | Q | Q | Q | Q |
| 180 | S | S | S | S |
| 182 | S | S | S | S |
| 183 | G | G | G | G |
| 184 | L | L | L | L |
| 185 | Y | Y | Y | Y |
| 186 | S | S | S | S |
| 187 | L | L | L | L |
| 188 | S | S | S | S |
| 189 | S | S | S | S |
| 190 | V | V | V | V |
| 191 | V | V | V | V |
| 192 | T | T | T | T |
| 193 | V | V | V | V |
| 194 | P | P | P | P |
| 195 | S | S | S | S |
| 196 | S | S | S | S |
| 197 | S | S | S | S |
| 198 | L | L | L | L |
| 199 | G | G | G | G |
| 200 | T | T | T | T |
| 203 | Q | Q | Q | Q |
| 205 | T | T | T | T |
| 206 | Y | Y | Y | Y |
| 207 | I | I | I | I |
| 208 | C | C | C | C |
| 209 | N | N | N | N |
| 210 | V | V | V | V |
| 211 | N | N | N | N |
| 212 | H | H | H | H |
| 213 | K | K | K | K |
| 214 | P | P | P | P |
| 215 | S | S | S | S |
| 216 | N | N | N | N |
| 217 | T | T | T | T |
| 218 | K | K | K | K |
| 219 | V | V | V | V |
| 220 | D | D | D | D |
| 221 | K | K | K | K |
| 222 | K | K | K | K |
| 223 | V | V | V | V |
| 226 | E | E | E | E |
| 227 | P | P | P | P |
| 228 | K | K | K | K |
| 232 | S | S | S | S |
| 233 | C | C | C | C |
| 234 | D | D | D | D |
| 235 | K | K | K | K |
| 236 | T | T | T | T |
| 237 | H | H | H | H |
| 238 | T | T | I | T |
| 239 | C | C | C | C |
| 240 | P | P | P | P |
| 241 | P | p | P | P |
| 242 | C | C | C | C |
| 243 | P | P | P | P |
| 244 | A | A | A | A |
| 245 | P | P | P | P |
| 246 | E | E | E | E |
| 247 | L | L | L | L |
| 248 | L | L | L | L |
| 249 | G | G | G | G |
| 250 | G | G | G | G |
| 251 | P | P | P | P |
| 252 | S | S | S | S |
| 253 | V | V | V | V |
| 254 | F | F | F | F |
| 255 | L | L | L | L |
| 256 | F | F | F | F |
| 257 | P | P | P | P |
| 258 | P | P | P | P |
| 259 | K | K | K | K |
| 260 | P | P | P | P |
| 261 | K | K | K | K |
| 262 | D | D | D | D |
| 263 | T | T | T | T |
| 264 | L | L | L | L |
| 265 | M | M | M | M |
| 266 | I | I | I | I |
| 267 | S | S | S | S |
| 268 | R | R | R | R |
| 269 | T | T | T | T |
| 270 | P | P | P | P |
| 271 | E | E | E | E |
| 272 | V | V | V | V |
| 273 | T | T | T | T |
| 274 | C | C | C | C |
| 275 | V | V | V | V |
| 276 | V | V | V | V |
| 277 | V | V | V | V |
| 278 | D | D | D | D |
| 279 | V | V | V | V |
| 280 | S | S | S | S |
| 281 | H | H | H | H |
| 282 | E | E | E | E |
| 283 | D | D | D | D |
| 284 | P | P | P | P |
| 285 | E | E | E | E |
| 286 | V | V | V | V |
| 287 | K | K | K | K |
| 288 | F | F | F | F |
| 289 | N | N | N | N |
| 290 | W | W | W | W |
| 291 | Y | Y | Y | Y |
| 292 | V | V | V | V |
| 295 | D | D | D | D |
| 296 | G | G | G | G |
| 299 | V | V | V | V |
| 300 | E | E | E | E |
| 301 | V | V | V | V |
| 302 | H | H | H | H |

TABLES A1-A2-continued

Heavy chain and light chain amino acid sequences of D3H44, Trastuzumab, Pertuzumab and Ramucirumab Table A1
Heavy chain origin

| KABAT numbering | D3H44 (SEQ ID NO: 8) | PERTU-ZUMAB (SEQ ID NO: 9) | TRASTU-ZUMAB (SEQ ID NO: 10) | RAMUCIRUMAB (SEQ ID NO: 11) |
|---|---|---|---|---|
| 303 | N | N | N | N |
| 304 | A | A | A | A |
| 305 | K | K | K | K |
| 306 | T | T | T | T |
| 307 | K | K | K | K |
| 308 | P | P | P | P |
| 309 | R | R | R | R |
| 310 | E | E | E | E |
| 311 | E | E | E | E |
| 312 | Q | Q | Q | Q |
| 313 | Y | Y | Y | Y |
| 314 | N | N | N | N |
| 317 | S | S | S | S |
| 318 | T | T | T | T |
| 319 | Y | Y | Y | Y |
| 320 | R | R | R | R |
| 321 | V | V | V | V |
| 322 | V | V | V | V |
| 323 | S | S | S | S |
| 324 | V | V | V | V |
| 325 | L | L | L | L |
| 326 | T | T | T | T |
| 327 | V | V | V | V |
| 328 | L | L | L | L |
| 329 | H | H | H | H |
| 330 | Q | Q | Q | Q |
| 331 | D | D | D | D |
| 332 | W | W | W | W |
| 333 | L | L | L | L |
| 334 | N | N | N | N |
| 335 | G | G | G | G |
| 336 | K | K | K | K |
| 337 | E | E | E | E |
| 338 | Y | Y | Y | Y |
| 339 | K | K | K | K |
| 340 | C | C | C | C |
| 341 | K | K | K | K |
| 342 | V | V | V | V |
| 343 | S | S | S | S |
| 344 | N | N | N | N |
| 345 | K | K | K | K |
| 346 | A | A | A | A |
| 347 | L | L | L | L |
| 348 | P | P | P | P |
| 349 | A | A | A | A |
| 350 | P | P | P | P |
| 351 | I | I | I | I |
| 352 | E | E | E | E |
| 353 | K | K | K | K |
| 354 | T | T | T | T |
| 355 | I | I | I | I |
| 357 | S | S | S | S |
| 358 | K | K | K | K |
| 359 | A | A | A | A |
| 360 | K | K | K | K |
| 361 | G | G | G | G |
| 363 | Q | Q | Q | Q |
| 364 | P | P | P | P |
| 365 | R | R | R | R |
| 366 | E | E | E | E |
| 367 | P | P | P | P |
| 368 | Q | Q | Q | Q |
| 369 | V | V | V | V |
| 370 | Y | Y | Y | Y |
| 371 | T | T | T | T |
| 372 | L | L | L | L |
| 373 | P | P | P | P |
| 374 | P | P | P | P |
| 375 | S | S | S | S |
| 376 | R | R | R | R |
| 377 | D | D | D | D |
| 378 | E | E | E | E |
| 381 | L | L | L | L |
| 382 | T | T | T | T |
| 383 | K | K | K | K |
| 384 | N | N | N | N |
| 385 | Q | Q | Q | Q |
| 386 | V | V | V | V |
| 387 | S | S | S | S |
| 388 | L | L | L | L |
| 389 | T | T | T | T |
| 390 | C | C | C | C |
| 391 | L | L | L | L |
| 392 | V | V | V | V |
| 393 | K | K | K | K |
| 394 | G | G | G | G |
| 395 | F | F | F | F |
| 396 | Y | Y | Y | Y |
| 397 | P | P | P | P |
| 398 | S | S | S | S |
| 399 | D | D | D | D |
| 400 | I | I | I | I |
| 401 | A | A | A | A |
| 402 | V | V | V | V |
| 405 | E | E | E | E |
| 406 | W | W | W | W |
| 407 | E | E | E | E |
| 408 | S | S | S | S |
| 410 | N | N | N | N |
| 411 | G | G | G | G |
| 414 | Q | Q | Q | Q |
| 415 | P | P | P | P |
| 416 | E | E | E | E |
| 417 | N | N | N | N |
| 418 | N | N | N | N |
| 419 | Y | Y | Y | Y |
| 420 | K | K | K | K |
| 421 | T | T | T | T |
| 422 | T | T | T | T |
| 423 | P | P | P | P |
| 424 | P | P | P | P |
| 425 | V | V | V | V |
| 426 | L | L | L | L |
| 427 | D | D | D | D |
| 428 | S | S | S | S |
| 430 | D | D | D | D |
| 433 | G | G | G | G |
| 434 | S | S | S | S |
| 435 | F | F | F | F |
| 436 | F | F | F | F |
| 437 | L | L | L | L |
| 438 | Y | Y | Y | Y |
| 439 | S | S | S | S |
| 440 | K | K | K | K |
| 441 | L | L | L | L |
| 442 | T | T | T | T |
| 443 | V | V | V | V |
| 444 | D | D | D | D |
| 445 | K | K | K | K |
| 446 | S | S | S | S |
| 447 | R | R | R | R |
| 448 | W | W | W | W |
| 449 | Q | Q | Q | Q |
| 450 | Q | Q | Q | Q |
| 451 | G | G | G | G |
| 452 | N | N | N | N |
| 453 | V | V | V | V |
| 454 | F | F | F | F |

TABLES A1-A2-continued

Heavy chain and light chain amino acid sequences of D3H44, Trastuzumab, Pertuzumab and Ramucirumab Table A1
Heavy chain origin

| KABAT numbering | D3H44 (SEQ ID NO: 8) | PERTU-ZUMAB (SEQ ID NO: 9) | TRASTU-ZUMAB (SEQ ID NO: 10) | RAMUCIRUMAB (SEQ ID NO: 11) |
|---|---|---|---|---|
| 455 | S | S | S | S |
| 456 | C | C | C | C |
| 457 | S | S | S | S |
| 458 | V | V | V | V |
| 459 | M | M | M | M |
| 460 | H | H | H | H |
| 461 | E | E | E | E |
| 462 | A | A | A | A |
| 463 | L | L | L | L |
| 464 | H | H | H | H |
| 465 | N | N | N | N |
| 466 | H | H | H | H |
| 467 | Y | Y | Y | Y |
| 468 | T | T | T | T |
| 469 | Q | Q | Q | Q |
| 470 | K | K | K | K |
| 471 | S | S | S | S |
| 472 | L | L | L | L |
| 473 | S | S | S | S |
| 474 | L | L | L | L |
| 475 | S | S | S | S |
| 476 | P | P | P | P |
| 477 | G | G | G | G |

Variable regions: HFR1; 1-30, CDR-H1; 31-35, HFR2; 36-49, CDR-H2; 50-65, HFR3; 66-94, CDR-H3; 95-102, HFR4; 103-113 (Reference: Molecular Immunology. Volume 45, Issue 14 August 2008, Pages 3832-3839).

Table A2
Light chain origin

| KABAT numbering | D3H44 (SEQ ID NO: 4) | PERTU-ZUMAB (SEQ ID NO: 5) | TRASTU-ZUMAB (SEQ ID NO: 6) | RAMUCIRUMAB (SEQ ID NO: 7) |
|---|---|---|---|---|
| 1 | D | D | D | D |
| 2 | I | I | I | I |
| 3 | Q | Q | Q | Q |
| 4 | M | M | M | M |
| 5 | T | T | T | T |
| 6 | Q | Q | Q | Q |
| 7 | S | S | S | S |
| 8 | P | P | P | P |
| 9 | S | S | S | S |
| 10 | S | S | S | S |
| 11 | L | L | L | V |
| 12 | S | S | S | S |
| 13 | A | A | A | A |
| 14 | S | S | S | S |
| 15 | V | V | V | I |
| 16 | G | G | G | G |
| 17 | D | D | D | D |
| 18 | R | R | R | R |
| 19 | V | V | V | V |
| 20 | T | T | T | T |
| 21 | I | I | I | I |
| 22 | T | T | T | T |
| 23 | C | C | C | C |
| 24 | R | K | R | R |
| 25 | A | A | A | A |
| 26 | S | S | S | S |
| 27 | R | Q | Q | Q |
| 28 | D | D | D | G |
| 29 | I | V | V | I |
| 30 | K | S | N | D |
| 31 | S | I | T | N |
| 32 | Y | G | A | W |
| 33 | L | V | V | L |
| 34 | N | A | A | G |
| 35 | W | W | W | W |
| 36 | Y | Y | Y | Y |
| 37 | Q | Q | Q | Q |
| 38 | Q | Q | Q | Q |
| 39 | K | K | K | K |
| 40 | P | P | P | P |
| 41 | G | G | G | G |
| 42 | K | K | K | K |
| 43 | A | A | A | A |
| 44 | P | P | P | P |
| 45 | K | K | K | K |
| 46 | V | L | L | L |
| 47 | L | L | L | L |
| 48 | I | I | I | I |
| 49 | Y | Y | Y | Y |
| 50 | Y | S | S | D |
| 51 | A | A | A | A |
| 52 | T | S | S | S |
| 53 | S | Y | F | N |
| 54 | L | R | L | L |
| 55 | A | Y | Y | D |
| 56 | E | T | S | T |
| 57 | G | G | G | G |
| 58 | V | V | V | V |
| 59 | P | P | P | P |
| 60 | S | S | S | S |
| 61 | R | R | R | R |
| 62 | F | F | F | F |
| 63 | S | S | S | S |
| 64 | G | G | G | G |
| 65 | S | S | S | S |
| 66 | G | G | R | G |
| 67 | S | S | S | S |
| 68 | G | G | G | G |
| 69 | T | T | T | T |
| 70 | D | D | D | Y |
| 71 | Y | F | F | F |
| 72 | T | T | T | T |
| 73 | L | L | L | L |
| 74 | T | T | T | T |
| 75 | I | I | I | I |
| 76 | S | S | S | S |
| 77 | S | S | S | S |
| 78 | L | L | L | L |
| 79 | Q | Q | Q | Q |
| 80 | P | P | P | A |
| 81 | E | E | E | E |
| 82 | D | D | D | D |
| 83 | F | F | F | F |
| 84 | A | A | A | A |
| 85 | T | T | T | V |
| 86 | Y | Y | Y | Y |
| 87 | Y | Y | Y | F |
| 88 | C | C | C | C |
| 89 | L | Q | Q | Q |
| 90 | Q | Q | Q | Q |
| 91 | H | Y | H | A |
| 92 | G | Y | Y | K |
| 93 | E | I | T | A |
| 94 | S | Y | T | F |
| 95 | P | P | P | P |
| 96 | W | Y | P | P |
| 97 | T | T | T | T |
| 98 | F | F | F | F |
| 99 | G | G | G | G |
| 100 | Q | Q | Q | G |
| 101 | G | G | G | G |
| 102 | T | T | T | T |

Table A2
Light chain origin

| KABAT numbering | D3H44 (SEQ ID NO: 4) | PERTU-ZUMAB (SEQ ID NO: 5) | TRASTU-ZUMAB (SEQ ID NO: 6) | RAMUCIRUMAB (SEQ ID NO: 7) |
|---|---|---|---|---|
| 103 | K | K | K | K |
| 104 | V | V | V | V |
| 105 | E | E | E | D |
| 106 | I | I | I | I |
| 107 | K | K | K | K |
| 108 | R | R | R | G |
| 109 | T | T | T | T |
| 110 | V | V | V | V |
| 111 | A | A | A | A |
| 112 | A | A | A | A |
| 113 | P | P | P | P |
| 114 | S | S | S | S |
| 115 | V | V | V | V |
| 116 | F | F | F | F |
| 117 | I | I | I | I |
| 118 | F | F | F | F |
| 119 | P | P | P | P |
| 120 | P | P | P | P |
| 121 | S | S | S | S |
| 122 | D | D | D | D |
| 123 | E | E | E | E |
| 124 | Q | Q | Q | Q |
| 125 | L | L | L | L |
| 126 | K | K | K | K |
| 127 | S | S | S | S |
| 128 | G | G | G | G |
| 129 | T | T | T | T |
| 130 | A | A | A | A |
| 131 | S | S | S | S |
| 132 | V | V | V | V |
| 133 | V | V | V | V |
| 134 | C | C | C | C |
| 135 | L | L | L | L |
| 136 | L | L | L | L |
| 137 | N | N | N | N |
| 138 | N | N | N | N |
| 139 | F | F | F | F |
| 140 | Y | Y | Y | Y |
| 141 | P | P | P | P |
| 142 | R | R | R | R |
| 143 | E | E | E | E |
| 144 | A | A | A | A |
| 145 | K | K | K | K |
| 146 | V | V | V | V |
| 147 | Q | Q | Q | Q |
| 148 | W | W | W | W |
| 149 | K | K | K | K |
| 150 | V | V | V | V |
| 151 | D | D | D | D |
| 152 | N | N | N | N |
| 153 | A | A | A | A |
| 154 | L | L | L | L |
| 155 | Q | Q | Q | Q |
| 156 | S | S | S | S |
| 157 | G | G | G | G |
| 158 | N | N | N | N |
| 159 | S | S | S | S |
| 160 | Q | Q | Q | Q |
| 161 | E | E | E | E |
| 162 | S | S | S | S |
| 163 | V | V | V | V |
| 164 | T | T | T | T |
| 165 | E | E | E | E |
| 166 | Q | Q | Q | Q |
| 167 | D | D | D | D |
| 168 | S | S | S | S |
| 169 | K | K | K | K |
| 170 | D | D | D | D |
| 171 | S | S | S | S |
| 172 | T | T | T | T |
| 173 | Y | Y | Y | Y |
| 174 | S | S | S | S |
| 175 | L | L | L | L |
| 176 | S | S | S | S |
| 177 | S | S | S | S |
| 178 | T | T | T | T |
| 179 | L | L | L | L |
| 180 | T | T | T | T |
| 181 | L | L | L | L |
| 182 | S | S | S | S |
| 183 | K | K | K | K |
| 184 | A | A | A | A |
| 185 | D | D | D | D |
| 186 | Y | Y | Y | Y |
| 187 | E | E | E | E |
| 188 | K | K | K | K |
| 189 | H | H | H | H |
| 190 | K | K | K | K |
| 191 | V | V | V | V |
| 192 | Y | Y | Y | Y |
| 193 | A | A | A | A |
| 194 | C | C | C | C |
| 195 | E | E | E | E |
| 196 | V | V | V | V |
| 197 | T | T | T | T |
| 198 | H | H | H | H |
| 199 | Q | Q | Q | Q |
| 200 | G | G | G | G |
| 201 | L | L | L | L |
| 202 | S | S | S | S |
| 203 | S | S | S | S |
| 204 | P | P | P | P |
| 205 | V | V | V | V |
| 206 | T | T | T | T |
| 207 | K | K | K | K |
| 208 | S | S | S | S |
| 209 | F | F | F | F |
| 210 | N | N | N | N |
| 211 | R | R | R | R |
| 212 | G | G | G | G |
| 213 | E | E | E | E |
| 214 | C | C | C | C |

Variable regions: LFR1; 1-23, CDR-L1; 24-34, LFR2; 35-49, CDR-L2; 50-56, LFR3; 57-88, CDR-L3; 89-97, LFR4; 98-110 (Reference: Molecular Immunology. Volume 45, Issue 14 August 2008, Pages 3832-3839).

TABLE 14

| Unique identifier set | Buckets | Fab Region | Design Type | H1_mutation | L1_mutation |
|---|---|---|---|---|---|
| 1--2 | Tm1 only, TF1 only | constant | electrostatic | S186R | Q124E_Q160E_T178D |
| 3--4 | | constant | steric | F174V_P175S_S188G | S176L |
| 5--6 | | constant | electrostatic | D146G_Q179K | Q124E_Q160E_T180E |
| 7--6 | | constant | electrostatic | D146G_Q179R | Q124E_Q160E_T180E |
| 8--6 | | constant | electrostatic | D146G_S186R | Q124E_Q160E_T180E |

TABLE 14-continued

| | | | | | |
|---|---|---|---|---|---|
| 7--9 | | constant | electrostatic | D146G_Q179R | Q124E_Q160E_T180E |
| 8--9 | | constant | electrostatic | D146G_S186R | Q124E_Q160E_T180E |
| 10--11 | | constant | steric | F174V_S188L | S176G |
| 12--13 | | constant | steric | F174V_P175S_S188G | S176L |
| 12--14 | | constant | steric | F174V_P175S_S188G | S176L |
| 12--15 | | constant | steric | F174V_P175S_S188G | S176L |
| 16-17 | | variable | electrostatic | Q39D | Q38R |
| 18--11 | | constant | steric | F174W_S188L | S176G |
| 19--3 | | constant | steric | S188L_V190Y | V133S |
| 20--11 | | constant | steric | S188L | S176G |
| 21-22 | | variable | electrostatic | Q39D | Q38R |
| 23-24 | | constant | electrostatic | K145L_Q179E | S131K |
| 9--5 | | constant | electrostatic | K145T_Q179D_S188L | Q160K_T178R |
| 25-26 | Tm1 only, TF1/TF2 | variable | combination (electrostatic + steric) | V37I_Q39R | Q38E_F98W |
| 27-28 | | variable | combination (electrostatic + steric) | V37W_Q39E | Q38R_F98A |
| 29-30 | | variable | steric | V37W_A93V | F98A |
| 31-32 | | variable | steric | WT | F98W |
| 33-34 | | variable | combination (electrostatic + steric) | V37I_Q39R | Q38E |
| 35-36 | Tm1 only, remaining TF category combinations | variable | combination (electrostatic + steric) | Q39D | Q38R |
| 37-36 | | variable | combination (electrostatic + steric) | Q39E | Q38R |
| 25-38 | | variable | combination (electrostatic + steric) | V37I_Q39R | Q38E_F98W |
| 39-34 | | variable | combination (electrostatic + steric) | Q39R | Q38E |
| 39-40 | | variable | combination (electrostatic + steric) | Q39R | Q38E |
| 41-42 | | variable | combination (electrostatic + steric) | Q39D | Q38R_F98W |
| 43-17 | | variable | electrostatic | Q39E | Q38R |
| 22-44 | | variable | electrostatic | Q39R | Q38D |
| 45-28 | | variable | combination (electrostatic + steric) | V37W_Q39D | Q38R_F98A |
| 46-30 | | variable | steric | V37W | F98A |
| 47-48 | | variable | electrostatic | V37E_F100D | L89R_F98W |
| 49-42 | | variable | combination (electrostatic + steric) | V37I_Q39E | Q38R_F98W |
| 50-42 | | variable | combination (electrostatic + steric) | V37I_Q39D | Q38R_F98W |
| 51-52 | | variable | electrostatic | Q39R | Q38E |
| 53-54 | | variable | electrostatic | Q39R | Q38E |
| 33-40 | | variable | combination (electrostatic + steric) | V37I_Q39R | Q38E |
| 55-56 | | variable | electrostatic vs hydrophobic | Q39M | Q38M |
| 57-58 | Tm1/Tm2, TF1 only | constant | electrostatic | L143K_D146G | Q124E_V133D |
| 5-59 | | constant | electrostatic | D146G_Q179K | Q124E_Q160E_T180E |
| 7-59 | | constant | electrostatic | D146G_Q179R | Q124E_Q160E_T180E |
| 8-59 | | constant | electrostatic | D146G_S186R | Q124E_Q160E_T180E |
| 60-61 | | constant | electrostatic | D146G_Q179R | Q124E_Q160E_T178D |
| 62-61 | | constant | electrostatic | D146G_S186R | Q124E_Q160E_T178D |
| 63-64 | | constant | electrostatic | D146G_S186R | Q124E_Q160E_T178D |
| 63-65 | | constant | electrostatic | D146G_S186R | Q124E_Q160E_T178D |
| 66-67 | | constant | electrostatic | L143A_D146G_Q179R | Q124E_V133W_Q160E_T180E |
| 66-68 | | constant | electrostatic | L143A_D146G_Q179R | Q124E_V133W_Q160E_T180E |
| 63-69 | | constant | electrostatic | D146G_S186R | Q124E_Q160E_T178D |
| 3-70 | | constant | steric | F174V_P175S_S188G | S176L |
| 61-71 | | constant | electrostatic | L143E_K145T | Q124R_Q160K_T178R |
| 72-64 | | constant | electrostatic | D146G_Q179R | Q124E_Q160E_T178D |

TABLE 14-continued

| | | | | | |
|---|---|---|---|---|---|
| 72-65 | | constant | electrostatic | D146G_Q179R | Q124E_Q160E_T178D |
| 72-69 | | constant | electrostatic | D146G_Q179R | Q124E_Q160E_T178D |
| 73-74 | | variable | combination (electrostatic + steric) | V37I_Q39R | Q38E_F98W |
| 75-76 | | variable | electrostatic | Q39D | Q38R |
| 75-77 | | variable | electrostatic | Q39D | Q38R |
| 64-78 | | constant | electrostatic | K145E_D146G_Q179D_S188L | Q160K_T178R |
| 65-78 | | constant | electrostatic | K145T_Q179D_S188L | Q160K_T178R |
| 67-79 | | constant | electrostatic | K145T_Q179D_S188F | V133A_Q160K_T178R |
| 68-79 | | constant | electrostatic | K145T_Q179D_S188L | V133A_Q160K_T178R |
| 80-81 | | constant | electrostatic | K145T_Q179D_S188F | Q160K_T178R |
| 80-82 | | constant | electrostatic | K145T_Q179D_S188F | Q160K_T178R |
| 80-83 | | constant | electrostatic | K145T_Q179D_S188F | Q160K_T178R |
| 16-84 | | variable | electrostatic | Q39D | Q38R |
| 85-81 | | constant | electrostatic | K145T_Q179D_S188L | Q160K_T178R |
| 85-82 | | constant | electrostatic | K145T_Q179D_S188L | Q160K_T178R |
| 69-78 | | constant | electrostatic | K145T_Q179D_S188F | Q160K_T178R |
| 85-83 | | constant | electrostatic | K145T_Q179D_S188L | Q160K_T178R |
| 86-87 | | variable | electrostatic | Q39K | Q38N_T85E |
| 86-88 | | variable | electrostatic | Q39K | Q38N_T85E |
| 89-90 | Tm1/Tm2, TF1/TF2 | variable | combination (electrostatic + steric) | Q39R | Q38D_F98W |
| 73-91 | | variable | combination (electrostatic + steric) | V37I_Q39R | Q38E_F98W |
| 92-90 | | variable | combination (electrostatic + steric) | V37I_Q39R | Q38D_F98W |
| 93-26 | | variable | combination (electrostatic + steric) | Q39R | Q38E_F98W |
| 94-95 | | variable | combination (electrostatic + steric) | V37I_Q39R | Q38E_F98W |
| 96-97 | Tm1/Tm2, remaining TF category combinations | variable | combination (electrostatic + steric) | Q39D | Q38R_F98W |
| 89-98 | | variable | combination (electrostatic + steric) | Q39R | Q38D_F98W |
| 99-76 | | variable | electrostatic | Q39E | Q38R |
| 99-77 | | variable | electrostatic | Q39E | Q38R |
| 100-97 | | variable | combination (electrostatic + steric) | V37I_Q39E | Q38R_F98W |
| 101-102 | | variable | electrostatic | V37E | L89R_F98T |
| 103-104 | | constant | steric | A139G_V190A | L135W_N137A |
| 105-42 | | variable | combination (electrostatic + steric) | Q39E | Q38R_F98W |
| 106-97 | | variable | combination (electrostatic + steric) | V37I_Q39D | Q38R_F98W |
| 92-98 | | variable | combination (electrostatic + steric) | V37I_Q39R | Q38D_F98W |
| 43-84 | | variable | electrostatic | Q39E | Q38R |
| 93-38 | | constant | combination (electrostatic + steric) | Q39R | Q38E_F98W |
| 107-108 | | constant | steric | A139G_V190A | L135W |
| 109-110 | | variable | electrostatic | V37E | L89R_F98V |
| 111-112 | Tm2 only, TF1 only | combination of constant and variable | combination (electrostatic + steric) | Q39D_A139G_V190A | Q38R_L135W |
| 63-113 | | constant | electrostatic | D146G_S186R | Q124E_Q160E_T178D |
| 79-114 | | constant | electrostatic | D146G_Q179R | Q124E_V133W_Q160E_T180E |
| 66-114 | | constant | electrostatic | L143A_D146G_Q179R | Q124E_V133W_Q160E_T180E |
| 72-113 | | constant | electrostatic | D146G_Q179R | Q124E_Q160E_T178D |
| 113-78 | | constant | electrostatic | L143E_K145T | Q160K_T178R |
| 115-116 | | variable | combination (electrostatic + steric) | Q39R | Q38D_F98W |
| 117-116 | | variable | combination (electrostatic + steric) | V37I_Q39R | Q38D_F98W |

TABLE 14-continued

| | | | | |
|---|---|---|---|---|
| 118-74 | | variable | combination (electrostatic + steric) | Q39R | Q38E_F98W |
| 119-120 | Tm2 only, TF1/TF2 | variable | combination (electrostatic + steric) | Q39K | Q38N_T85E_F98W |
| 121-95 | | variable | combination (electrostatic + steric) | Q39R | Q38E_F98W |
| 115-122 | | variable | combination (electrostatic + steric) | Q39R | Q38D_F98W |
| 123-124 | | variable | combination (electrostatic + steric) | Q39R | Q38D_F98W |
| 117-122 | | variable | combination (electrostatic + steric) | V37I_Q39R | Q38D_F98W |
| 118-91 | | variable | combination (electrostatic + steric) | Q39R | Q38E_F98W |
| 125-124 | | variable | combination (electrostatic + steric) | V37I_Q39R | Q38D_F98W |
| 126-97 | Tm2 only, remaining TF category combinations | variable | combination (electrostatic + steric) | Q39E | Q38R_F98W |
| 127-128 | | variable | combination (electrostatic + steric) | Q39E | Q38N_T85K |
| 129-128 | | variable | combination (electrostatic + steric) | V37I_Q39E | Q38N_T85K |
| 130-131 | | variable | combination (electrostatic + steric) | V37I_Q39E | Q38N_T85K_F98W |
| 96-132 | Tm1/Tm3, any TF catgory combination | variable | combination (electrostatic + steric) | Q39D | Q38R_F98W |
| 3-133 | | constant | steric | F174V_P175S_S188G | S176L |
| 134-36 | | variable | combination (electrostatic + steric) | V37I_Q39E | Q38R |
| 135-136 | | variable | combination (electrostatic + steric) | Q39D | Q38R |
| 137-138 | | variable | combination (electrostatic + steric) | Q39D | Q38R_F98W |
| 100-132 | | variable | combination (electrostatic + steric) | V37I_Q39E | Q38R_F98W |
| 139-140 | | constant | combination (electrostatic + steric) | A139I_K145T_D146G_Q179E_S188G_V190S | F116A_V133G_S176F_T178A |
| 141-142 | | variable | combination (electrostatic + steric) | Q39E | Q38R |
| 73-143 | | variable | combination (electrostatic + steric) | V37I_Q39R | Q38E_F98W |
| 73-144 | | variable | combination (electrostatic + steric) | V37I_Q39R | Q38E_F98W |
| 145-146 | | variable | combination (electrostatic + steric) | Q39D | Q38R_F98W |
| 145-147 | | variable | combination (electrostatic + steric) | Q39D | Q38R_F98W |
| 106-132 | | variable | combination (electrostatic + steric) | V37I_Q39D | Q38R_F98W |
| 148-149 | | variable | combination (electrostatic + steric) | V37A_Q39R_W103V | Q38D_P44W |
| 148-150 | | variable | combination (electrostatic + steric) | V37A_Q39R_W103V | Q38D_P44W |

TABLE 14-continued

| | | | | |
|---|---|---|---|---|
| 22-151 | | variable | electrostatic | Q39R | Q38D |
| 152-153 | | variable | combination (electrostatic + steric) | V37A_Q39R_W103V | Q38E_P44W |
| 152-154 | | variable | combination (electrostatic + steric) | V37A_Q39R_W103V | Q38E_P44W |
| 155-36 | | variable | combination (electrostatic + steric) | V37I_Q39D | Q38R |
| 156-157 | | variable | steric | V37T_A93Q_W103L | P44W_F98W |
| 158-159 | | variable | combination (electrostatic + steric) | V37A_Q39R_W103V | Q38E_P44W |
| 160-146 | | variable | combination (electrostatic + steric) | V37I_Q39E | Q38R_F98W |
| 161-142 | | variable | combination (electrostatic + steric) | Q39D | Q38R |
| 160-147 | | variable | combination (electrostatic + steric) | V37I_Q39E | Q38R_F98W |
| 162-163 | | variable | combination (electrostatic + steric) | Q39D | Q38R |
| 164-165 | | constant | combination (electrostatic + steric) | A139G_K145L_Q179E_V190A | S131R_L135W |
| 166-157 | | variable | steric | V37I_W103H | P44W_F98W |
| 167-157 | | variable | steric | V37T_A93Q_W103V | P44W_F98W |
| 168-163 | | variable | combination (electrostatic + steric) | Q39E | Q38R |
| 169-157 | | variable | steric | V37T_A93Q_W103T | P44W_F98W |
| 170-171 | | variable | combination (electrostatic + steric) | Q39K | Q38N_T85E |
| 170-172 | | variable | combination (electrostatic + steric) | Q39K | Q38N_T85E |
| 173-174 | | variable | combination (electrostatic + steric) | V37A_Q39R_W103V | Q38D_P44W |
| 94-175 | | variable | combination (electrostatic + steric) | V37I_Q39R | Q38E_F98W |
| 157-176 | | variable | steric | V37W | F98A |
| 177-157 | | variable | steric | V37A_W103H | P44W_F98W |
| 157-178 | | variable | steric | V37W | F98A |
| 179-180 | | variable | steric | V37W_F100W | F98A |
| 181-138 | | variable | combination (electrostatic + steric) | V37I_Q39E | Q38R_F98W |
| 182-183 | | variable | electrostatic | V37E_F100D | L89R_F98W |
| 86-184 | | variable | electrostatic | Q39K | Q38N_T85E |
| 185-138 | | variable | combination (electrostatic + steric) | V37I_Q39D | Q38R_F98W |
| 186-187 | | variable | steric | WT | F98W |
| 187-188 | | variable | steric | V37W_W103H | F98L |
| 189-157 | | variable | steric | V37A_W103V | P44W_F98W |
| 190-191 | | variable | combination (electrostatic + steric) | Q39E | Q38R |
| 192-193 | Remaining categories | combination of constant and variable | combination (electrostatic + steric) | Q39D_A139W | Q38R_F116A_L135A |
| 194-195 | | combination of constant and variable | combination (steric) | A139G_V190A | F98W_L135W |
| 196-197 | | combination of constant and variable | combination (steric) | A139W | F98W_F116A_L135A |
| 198-199 | | combination of constant and variable | combination (electrostatic + steric) | V37A_Q39E_W103H | Q38N_P44W_T85K |
| 200-146 | | variable | combination (electrostatic + steric) | Q39E | Q38R_F98W |

TABLE 14-continued

| | | | | |
|---|---|---|---|---|
| 81-201 | constant | electrostatic | D146G_Q179R | Q124E_V133W_Q160E_T180E |
| 82-201 | constant | electrostatic | L143A_D146G_Q179R | Q124E_V133W_Q160E_T180E |
| 202-203 | variable | steric | F100M_W103V | P44W_L89W |
| 204-179 | variable | steric | V37T_A93Q_W103V | P44W_L89W_F98A |
| 202-205 | variable | steric | F100M_W103V | P44W_L89W |
| 200-147 | variable | combination (electrostatic + steric) | Q39E | Q38R_F98W |
| 206-136 | variable | combination (electrostatic + steric) | Q39E | Q38R |
| 126-132 | variable | combination (electrostatic + steric) | Q39E | Q38R_F98W |
| 207-203 | variable | steric | F100M_W103H | P44W_L89W |
| 207-205 | variable | steric | F100M_W103H | P44W_L89W |
| 208-209 | constant | combination (steric) | A139G_S188G_V190A | L135W_S176L_T178S |
| 210-138 | variable | combination (electrostatic + steric) | Q39E | Q38R_F98W |
| 121-175 | variable | combination (electrostatic + steric) | Q39R | Q38E_F98W |
| 211-212 | constant | combination (electrostatic + steric) | A139S | L135R |
| 213-214 | variable | combination (electrostatic + steric) | V37A_Q39K_W103H | Q38N_P44W_T85E |
| 215-216 | constant | combination (steric) | A139G_S188G_V190A | V133G_L135W_S176F_T178A |
| 115-217 | variable | combination (electrostatic + steric) | Q39R | Q38D_F98W |
| 115-218 | variable | combination (electrostatic + steric) | Q39R | Q38D_F98W |
| 123-219 | variable | combination (electrostatic + steric) | Q39R | Q38D_F98W |
| 117-217 | variable | combination (electrostatic + steric) | V37I_Q39R | Q38D_F98W |
| 117-218 | variable | combination (electrostatic + steric) | V37I_Q39R | Q38D_F98W |
| 220-199 | variable | combination (electrostatic + steric) | V37A_Q39E_W103V | Q38N_P44W_T85K |
| 118-143 | variable | combination (electrostatic + steric) | Q39R | Q38E_F98W |
| 118-144 | variable | combination (electrostatic + steric) | Q39R | Q38E_F98W |
| 221-222 | variable | combination (steric) | V37A_W103H_A139G_V190A | P44W_L135W |
| 223-179 | variable | steric | V37T_A93Q_W103T | P44W_L89W_F98A |
| 224-225 | constant | steric | A139V_V190S | WT |
| 226-227 | variable | combination (electrostatic + steric) | Q39K | Q38N_T85E_F98W |
| 226-228 | variable | combination (electrostatic + steric) | Q39K | Q38N_T85E_F98W |
| 229-230 | variable | electrostatic | V37E | L89R_F98V |
| 201-83 | constant | electrostatic | K145E_D146G_Q179D_S188F | Q160K_T178R |
| 231-232 | constant | combination (electrostatic + steric) | A139I_K145T_D146G_S188G_V190S | F116A_V133G_S176F_T178A |
| 233-131 | variable | combination (electrostatic + steric) | Q39E | Q38N_T85K_F98W |
| 234-235 | constant | electrostatic | K145E_D146G_Q179D_S188L | T178R |
| 236-237 | constant | combination (electrostatic + steric) | A139G_K145L_Q179E_V190A | S131R_L135W |

TABLE 14-continued

| | | | | | |
|---|---|---|---|---|---|
| 234-238 | | constant | electrostatic | K145E_D146G_Q179D_S188L | T178R |
| 239-240 | | variable | combination (electrostatic + steric) | Q39E | Q38N_T85K_F98W |
| 241-242 | | variable | steric | V37W_W103H | F98L |
| 239-243 | | variable | combination (electrostatic + steric) | Q39E | Q38N_T85K_F98W |
| 242-244 | | variable | steric | V37A_W103H | P44W |
| 179-245 | | variable | steric | V37W_F100W | F98A |
| 246-225 | | constant | steric | A139I_V190S | WT |
| 247-248 | | variable | steric | V37W_F100W | F98A |
| 125-219 | | variable | combination (electrostatic + steric) | V37I_Q39R | Q38D_F98W |
| 249-250 | | variable | steric | L45W | Y87G |
| 251-240 | | variable | combination (electrostatic + steric) | V37I_Q39E | Q38N_T85K_F98W |
| 252-227 | | variable | combination (electrostatic + steric) | V37I_Q39K | Q38N_T85E_F98W |
| 251-243 | | variable | combination (electrostatic + steric) | V37I_Q39E | Q38N_T85K_F98W |
| 252-228 | | variable | combination (electrostatic + steric) | V37I_Q39K | Q38N_T85E_F98W |
| 253-120 | | variable | combination (electrostatic + steric) | V37I_Q39K | Q38N_T85E_F98W |
| 254-255 | | constant | steric | F174G_S188A | WT |
| 250-256 | | variable | steric | V37A_W103H | P44W |

| Unique identifier set | H2_mutation | L2_mutation | Presence of H-L disulfide bond (C233-C214) (y/n) | Screening only/ Verification only/ Screening and verification data for H1-L1:H1-L2 (s/v/s_v) | H1-L1:H1-L2 |
|---|---|---|---|---|---|
| 1--2 | K145L_Q179E | S131K | n | v | 99:01 |
| 3--4 | S188L | V133S | n | s, v | 101:1_102:2_103:1_67:3_81:1_ 83:1_90:1_93:1_99:1 |
| 5--6 | K145E_D146G_Q179D_S188L | Q160K_T178R | n | s, v | 116:1_96:1 |
| 7--6 | K145E_D146G_Q179D_S188L | Q160K_T178R | n | s, v | 100:2_116:1 |
| 8--6 | K145E_D146G_Q179D_S188L | Q160K_T178R | n | s, v | 104:1_99:1 |
| 7--9 | K145T_Q179D_S188L | Q160K_T178R | n | s, v | 100:2_116:1 |
| 8--9 | K145T_Q179D_S188L | Q160K_T178R | n | s, v | 104:1_99:1 |
| 10--11 | F174V_P175S_S188G | S176L | n | s, v | 91:10_92:10_84:15_107:19 |
| 12--13 | F174V_S188L | WT | n | s, v | 53:10_67:11 |
| 12--14 | S188L | WT | n | s, v | 53:10_67:11 |
| 12--15 | F174W_S188L | WT | n | s, v | 53:10_67:11 |
| 16--17 | V37I_Q39R | Q38E_F98W | n | s, v | 70:25_86:11 |
| 18--11 | F174V_P175S_S188G | S176L | n | s, v | 71:26_79:15_87:23_94:13 |
| 19--3 | F174V_P175S_S188G | S176L | n | s, v | 75:27_76:34_77:27_79:25_79:36_ 80:24_82:12_83:25_90:8 |
| 20--11 | F174V_P175S_S188G | S176L | n | s, v | 70:29_78:25_78:30 |
| 21--22 | Q39R | Q38D | n | s, v | 62:31_67:35 |
| 23--24 | D146G_Q179K | Q124E_Q160E_T180E | n | v | 75:43 |
| 9--5 | D146G_Q179K | Q124E_Q160E_T180E | n | s, v | 54:43_57:31 |
| 25--26 | V37W_Q39E | Q38R_F98A | n | s, v | 85:6_99:2 |
| 27--28 | Q39R | Q38D | n | s, v | 71:18_87:9 |
| 29--30 | WT | L89F_F98W | n | s, v | 64:17_88:7_89:18 |
| 31--32 | V37W_A93V | F98A | n | s, v | 101:20_17:83_62:27_67:29_67:29_ 78:17_82:18_83:18_83:21_83:23_ 85:21_86:14_86:20 |
| 33--34 | V37W_Q39E | Q38R_F98A | n | s, v | 56:34_74:24 |
| 35--36 | V37W_Q39R | Q38E_F98A | n | s | 102:01 |
| 37--36 | V37W_Q39R | Q38E_F98A | n | s, v | 103:1_82:8 |
| 25--38 | V37W_Q39D | Q38R_F98A | n | s, v | 85:6_99:2 |
| 39--34 | V37W_Q39E | Q38R_F98A | n | s, v | 104:1_60:18 |
| 39--40 | V37W_Q39D | Q38R_F98A | n | s, v | 104:1_60:18 |
| 41--42 | V37W_Q39R | Q38E_F98A | n | s, v | 103:1_84:5_99:8 |
| 43--17 | V37I_Q39R | Q38E_F98W | n | s, v | 88:16_96:9 |
| 22--44 | Q39E | Q38R | n | s, v | 72:17_73:11_85:11 |
| 45--28 | Q39R | Q38D | n | s, v | 101:16_80:15 |

TABLE 14-continued

| | | | | | |
|---|---|---|---|---|---|
| 46-30 | WT | L89F_F98W | n | s, v | 62:13_92:19_92:4 |
| 47-48 | WT | WT | n | s, v | 117:4_21:81_68:26_76:20_76:26_76:28_86:16_87:21_99:4 |
| 49-42 | V37W_Q39R | Q38E_F98A | n | s | 81:24 |
| 50-42 | V37W_Q39R | Q38E_F98A | n | s, v | 68:20_73:24 |
| 51-52 | Q39E | Q38R | n | s, v | 70:32_71:23_72:24_73:30_75:20_76:24_78:24_81:15_85:8 |
| 53-54 | WT | WT | n | s, v | 65:38_66:19_69:22_73:38_74:29_74:31_77:27_77:36_78:30 |
| 33-40 | V37W_Q39D | Q38R_F98A | n | s, v | 56:34_74:24 |
| 55-56 | Q39R | Q38E | n | s, v | 59:41_60:31_70:33 |
| 57-58 | L143E_K145T | Q124R | n | s, v | 100:1_103:1_90:1_91:1_95:1_96:1_98:1_99:1 |
| 5-59 | L143E_K145T | Q160K_T178R | n | s, v | 116:1_96:1 |
| 7-59 | L143E_K145T | Q160K_T178R | n | s, v | 100:2_116:1 |
| 8-59 | L143E_K145T | Q160K_T178R | n | s, v | 104:1_99:1 |
| 60-61 | L143E_K145T | Q124R_Q160K_T178R | n | s, v | 102:1_105:1 |
| 62-61 | L143E_K145T | Q124R_Q160K_T178R | n | s, v | 104:1_92:1 |
| 63-64 | K145E_D146G_Q179D_S188L | Q160K_T178R | n | s, v | 112:1_116:1 |
| 63-65 | K145T_Q179D_S188L | Q160K_T178R | n | s, v | 112:1_116:1 |
| 66-67 | K145T_Q179D_S188F | V133A_Q160K_T178R | n | s, v | 101:1_104:1_107:1_111:2_112:1_115:1_94:1_97:1_99:1 |
| 66-68 | K145T_Q179D_S188L | V133A_Q160K_T178R | n | s, v | 101:1_104:1_107:1_111:2_112:1_115:1_94:1_97:1_99:1 |
| 63-69 | K145T_Q179D_S188F | Q160K_T178R | n | s, v | 112:1_116:1 |
| 3-70 | F174V_S188L | V133S | n | s, v | 101:1_102:2_103:1_67:3_81:1_83:1_90:1_93:1_99:1 |
| 61-71 | D146G_Q179K | Q124E_Q160E_T178D | n | s, v | 77:1_88:3 |
| 72-64 | K145E_D146G_Q179D_S188L | Q160K_T178R | n | s, v | 102:6_110:1_110:3_112:2_87:1_88:5_94:4_95:3_99:1 |
| 72-65 | K145T_Q179D_S188L | Q160K_T178R | n | s, v | 102:6_110:1_110:3_112:2_87:1_88:5_94:4_95:3_99:1 |
| 72-69 | K145T_Q179D_S188F | Q160K_T178R | n | s, v | 102:6_110:1_110:3_112:2_87:1_88:5_94:4_95:3_99:1 |
| 73-74 | V37W_Q39E_W103F | Q38R_F98L | n | s, v | 83:7_84:5 |
| 75-76 | Q39R | Q38D_F98W | n | s, v | 81:18_83:2 |
| 75-77 | V37I_Q39R | Q38D_F98W | n | s, v | 81:18_83:2 |
| 64-78 | D146G_Q179K | Q124E_Q160E_T178D | n | s, v | 84:15_91:4 |
| 65-78 | D146G_Q179K | Q124E_Q160E_T178D | n | s, v | 72:4_75:20_80:18_88:12_88:12_92:10_92:13_93:13_94:15 |
| 67-79 | D146G_Q179R | Q124E_V133W_Q160E_T180E | n | s, v | 76:24_78:20_80:16_83:12_86:1_86:21_88:13_93:11_94:17 |
| 68-79 | D146G_Q179R | Q124E_V133W_Q160E_T180E | n | s, v | 62:25_87:11 |
| 80-81 | D146G_Q179R | Q124E_V133W_Q160E_T180E | n | s, v | 72:18_77:15 |
| 80-82 | L143A_D146G_Q179R | Q124E_V133W_Q160E_T180E | n | s, v | 72:18_77:15 |
| 80-83 | D146G_Q179K | Q124E_V133W_Q160E_T180E | n | s, v | 72:18_77:15 |
| 16-84 | Q39R | Q38E_F98W | n | s, v | 70:25_86:11 |
| 85-81 | D146G_Q179R | Q124E_V133W_Q160E_T180E | n | s, v | 63:24_81:11 |
| 85-82 | L143A_D146G_Q179R | Q124E_V133W_Q160E_T180E | n | s, v | 63:24_81:11 |
| 69-78 | D146G_Q179K | Q124E_Q160E_T178D | n | s, v | 76:18_82:19 |
| 85-83 | D146G_Q179K | Q124E_V133W_Q160E_T180E | n | s, v | 63:24_81:11 |
| 86-87 | Q39E | Q38N_T85K | n | s, v | 55:30_66:22 |
| 86-88 | V37I_Q39E | Q38N_T85K | n | s, v | 55:30_66:22 |
| 89-90 | V37W_Q39E | Q38R_F98A | n | s, v | 87:2_96:2 |
| 73-91 | V37W_Q39D_W103F | Q38R_F98L | n | s, v | 83:7_84:5 |
| 92-90 | V37W_Q39E | Q38R_F98A | n | s, v | 82:6_91:11 |
| 93-26 | V37W_Q39E | Q38R_F98A | n | s, v | 71:24_75:13_75:19_76:3_79:12_82:12_83:6_89:6_97:1 |
| 94-95 | V37W_W103F | F98L | n | s, v | 71:17_73:24 |
| 96-97 | V37W_Q39R_W103F | Q38E_F98L | n | s, v | 100:1_92:1 |
| 89-98 | V37W_Q39D | Q38R_F98A | n | s, v | 87:2_96:2 |
| 99-76 | Q39R | Q38D_F98W | n | s, v | 108:1_80:8 |
| 99-77 | V37I_Q39R | Q38D_F98W | n | s, v | 108:1_80:8 |
| 100-97 | V37W_Q39R_W103F | Q38E_F98L | n | s, v | 85:10_85:2 |
| 101-102 | WT | WT | n | s, v | 101:6_101:8_107:4_54:25_86:8_91:14_91:17_97:6_98:5 |
| 103-104 | A139W | F116A_L135A | n | s | 70:05 |
| 105-42 | V37W_Q39R | Q38E_F98A | n | s, v | 74:15_90:3 |
| 106-97 | V37W_Q39R_W103F | Q38E_F98L | n | s, v | 92:15_97:6 |
| 92-98 | V37W_Q39D | Q38R_F98A | n | s, v | 82:6_91:11 |

TABLE 14-continued

| | | | | | |
|---|---|---|---|---|---|
| 43-84 | Q39R | Q38E_F98W | n | s, v | 88:16_96:9 |
| 93-38 | V37W_Q39D | Q38R_F98A | n | s, v | 71:24_75:13_75:19_76:3_79:12_82:12_83:6_89:6_97:1 |
| 107-108 | A139W | F116A_L135A | n | s, v | 56:20_61:12_63:7_65:10_67:16_68:10_69:11_69:11_69:12_74:15 |
| 109-110 | WT | WT | n | s, v | 62:27_67:25_74:27 |
| 111-112 | Q39R_A139W | Q38D_F116A_L135A | n | s, v | 111:1_85:1 |
| 63-113 | L143E_K145T | Q160K_T178R | n | s, v | 112:1_116:1 |
| 79-114 | K145E_D146G_Q179D_S188F | V133A_Q160K_T178R | n | s, v | 108:1_93:2 |
| 66-114 | K145E_D146G_Q179D_S188F | V133A_Q160K_T178R | n | s, v | 101:1_104:1_107:1_111:2_112:1_115:1_94:1_97:1_99:1 |
| 72-113 | L143E_K145T | Q160K_T178R | n | s, v | 102:6_110:1_110:3_112:2_87:1_88:5_94:4_95:3_99:1 |
| 113-78 | D146G_Q179K | Q124E_Q160E_T178D | n | s, v | 74:6_93:3_94:1 |
| 115-116 | V37W_Q39E_W103F | Q38R_F98L | n | s, v | 55:16_89:3 |
| 117-116 | V37W_Q39E_W103F | Q38R_F98L | n | s, v | 85:8_86:13 |
| 118-74 | V37W_Q39E_W103F | Q38R_F98L | n | s, v | 78:13_80:10_92:2 |
| 119-120 | V37W_Q39E | Q38N_T85K_F98A | n | s, v | 56:9_69:1 |
| 121-95 | V37W_W103F | F98L | n | s, v | 71:15_93:3 |
| 115-122 | V37W_Q39D_W103F | Q38R_F98L | n | s, v | 55:16_89:3 |
| 123-124 | V37W_W103F | F98L | n | s, v | 70:17_80:3 |
| 117-122 | V37W_Q39D_W103F | Q38R_F98L | n | s, v | 85:8_86:13 |
| 118-91 | V37W_Q39D_W103F | Q38R_F98L | n | s, v | 78:13_80:10_92:2 |
| 125-124 | V37W_W103F | F98L | n | s, v | 60:30_79:23 |
| 126-97 | V37W_Q39R_W103F | Q38E_F98L | n | s, v | 101:1_82:16 |
| 127-128 | V37W_Q39K | Q38N_T85E_F98A | n | s, v | 101:2_86:13 |
| 129-128 | V37W_Q39K | Q38N_T85E_F98A | n | s, v | 73:13_74:25 |
| 130-131 | V37W_Q39K | Q38N_T85E_F98A | n | s, v | 57:30_62:23 |
| 96-132 | V37W_Q39R_W103H | Q38E_F98L | n | s, v | 100:1_92:1 |
| 3-133 | F174W_S188L | V133S | n | s, v | 101:1_102:2_103:1_67:3_81:1_83:1_90:1_93:1_99:1 |
| 134-36 | V37W_Q39R | Q38E_F98A | n | s | 103:02 |
| 135-136 | V37W_Q39R | Q38D_F98A | n | s | 104:01 |
| 137-138 | V37W_Q39R | Q38D_F98A | n | s, v | 100:1_93:7 |
| 100-132 | V37W_Q39R_W103H | Q38E_F98L | n | s, v | 85:10_85:2 |
| 139-140 | S186K_S188H_V190G | F118W_Q124E_V133S_S176A_T178S_T180E | n | s, v | 101:7_69:4 |
| 141-142 | V37A_Q39R_W103V | Q38D_P44W | n | s, v | 92:5_99:6 |
| 73-143 | V37W_Q39D_W103H | Q38R_F98L | n | s, v | 83:7_84:5 |
| 73-144 | V37W_Q39E_W103H | Q38R_F98L | n | s, v | 83:7_84:5 |
| 145-146 | V37W_Q39R_W103H | Q38D_F98L | n | s, v | 36:73_86:3_87:8 |
| 145-147 | V37W_Q39R_W103F | Q38D_F98L | n | s, v | 36:73_86:3_87:8 |
| 106-132 | V37W_Q39R_W103H | Q38E_F98L | n | s, v | 92:15_97:6 |
| 148-149 | V37W_Q39D | Q38R_F98A | n | s, v | 68:6_69:9 |
| 148-150 | V37W_Q39E | Q38R_F98A | n | s, v | 68:6_69:9 |
| 22-151 | V37I_Q39R | Q38R | n | s, v | 72:17_73:11_85:11 |
| 152-153 | V37W_Q39D | Q38R_F98A | n | s, v | 61:19_63:5 |
| 152-154 | V37W_Q39E | Q38R_F98A | n | s, v | 61:19_63:5 |
| 155-36 | V37W_Q39R | Q38E_F98A | n | s, v | 58:32_94:6 |
| 156-157 | V37W | F98A | n | s, v | 50:17_76:8 |
| 158-159 | V37W | F98A | n | s, v | 66:13_77:15 |
| 160-146 | V37W_Q39R_W103H | Q38D_F98L | n | s | 88:18 |
| 161-142 | V37A_Q39R_W103V | Q38D_P44W | n | s, v | 102:8_56:29 |
| 160-147 | V37W_Q39R_W103F | Q38D_F98L | n | s | 88:18 |
| 162-163 | V37A_Q39R_W103V | Q38E_P44W | n | s, v | 77:23_98:16 |
| 164-165 | A139W | F116A_L135A | n | s, v | 48:21_49:14_50:12_51:10_68:1 |
| 166-157 | V37W | F98A | n | s, v | 55:20_61:10 |
| 167-157 | V37W | F98A | n | s, v | 50:21_74:10 |
| 168-163 | V37A_Q39R_W103V | Q38E_P44W | n | s, v | 60:32_91:10 |
| 169-157 | V37W | F98A | n | s, v | 54:26_68:9 |
| 170-171 | V37A_Q39E_W103H | Q38N_P44W_T85K | n | s, v | 66:34_92:13 |
| 170-172 | V37A_Q39E_W103V | Q38N_P44W_T85K | n | s, v | 66:34_92:13 |
| 173-174 | V37W | F98A | n | s, v | 61:12_74:26 |
| 94-175 | V37W_W103H | F98L | n | s, v | 71:17_73:24 |
| 157-176 | W103H | P44W_F98W | n | s, v | 63:37_86:12 |
| 177-157 | V37W | F98A | n | s | 66:19 |
| 157-178 | W103V | P44W_F98W | n | s, v | 63:37_86:12 |
| 179-180 | W103V | P44W_L89W_F98A | n | s, v | 64:26_69:26_69:28_75:25_77:26_78:26_83:22_86:16_95:8 |
| 181-138 | V37W_Q39R | Q38D_F98A | n | s | 84:29 |
| 182-183 | V37S_A93K | F98Y | n | s, v | 65:34_68:24_75:27_77:18_77:18_79:31_81:28_86:21_91:16 |
| 86-184 | Q39D | Q38N_T85K | n | s, v | 55:30_66:22 |
| 185-138 | V37W_Q39R | Q38D_F98A | n | s | 67:31 |
| 186-187 | V37W_W103H | F98L | n | s, v | 50:36_51:24_74:28 |
| 187-188 | V37I | F98W | n | s, v | 57:30_62:31 |
| 189-157 | V37W | F98A | n | s | 69:39 |
| 190-191 | V37W | F98A | n | s, v | 48:30_57:32_75:7 |
| 192-193 | Q39R_A139G_V190A | Q38D_L135W | n | s | 103:01 |

TABLE 14-continued

| | | | | | |
|---|---|---|---|---|---|
| 194-195 | V37W_W103H_A139W | F98L_F116A_L135A | n | s | 81:01 |
| 196-197 | V37W_W103H_A139G_V190A | F98L_L135W | n | s | 71:01 |
| 198-199 | V37W_Q39K | Q38N_T85E_F98A | n | s, v | 67:1_76:1 |
| 200-146 | V37W_Q39R_W103H | Q38D_F98L | n | s, v | 102:2_96:1 |
| 81-201 | K145E_D146G_Q179D_S188F | Q160K_T178R | n | s, v | 102:1_113:3 |
| 82-201 | K145E_D146G_Q179D_S188F | Q160K_T178R | n | s, v | 103:1_97:3 |
| 202-203 | V37W_F100W | F98A | n | s, v | 86:5_87:2_97:1 |
| 204-179 | V37W_F100W | F98A | n | s, v | 87:2_88:1 |
| 202-205 | V37W_F100W_W103L | F98A | n | s, v | 86:5_87:2_97:1 |
| 200-147 | V37W_Q39R_W103F | Q38D_F98L | n | s, v | 102:2_96:1 |
| 206-136 | V37W_Q39R | Q38D_F98A | n | s, v | 104:2_93:1 |
| 126-132 | V37W_Q39R_W103H | Q38E_F98L | n | s, v | 101:1_82:16 |
| 207-203 | V37W_F100W | F98A | n | s, v | 92:5_93:6_98:1 |
| 207-205 | V37W_F100W_W103L | F98A | n | s, v | 92:5_93:6_98:1 |
| 208-209 | A139W_S188H_V190S | F116S_L135A_S176A | n | s | 85:06 |
| 210-138 | V37W_Q39R | Q38D_F98A | n | s, v | 100:4_74:8 |
| 121-175 | V37W_W103H | F98L | n | s, v | 71:15_93:3 |
| 211-212 | A139I | F118W_V133S | n | s | 60:05 |
| 213-214 | V37W_Q39E | Q38N_T85E_F98A | n | s, v | 60:11_76:3 |
| 215-216 | A139W_S188A | F116S_L135A_S176A | n | s | 84:07 |
| 115-217 | V37W_Q39D_W103H | Q38R_F98L | n | s, v | 55:16_89:3 |
| 115-218 | V37W_Q39E_W103H | Q38R_F98L | n | s, v | 55:16_89:3 |
| 123-219 | V37W_W103H | F98L | n | s, v | 70:17_80:3 |
| 117-217 | V37W_Q39D_W103H | Q38R_F98L | n | s, v | 85:8_86:13 |
| 117-218 | V37W_Q39E_W103H | Q38R_F98L | n | s, v | 85:8_86:13 |
| 220-199 | V37W_Q39K | Q38N_T85E_F98A | n | s, v | 72:12_91:7 |
| 118-143 | V37W_Q39D_W103H | Q38R_F98L | n | s, v | 78:13_80:10_92:2 |
| 118-144 | V37W_Q39E_W103H | Q38R_F98L | n | s, v | 78:13_80:10_92:2 |
| 221-222 | V37W_A139W | F98A_F116A_L135A | y | s | 68:10 |
| 223-179 | V37W_F100W | F98A | n | s | 85:12 |
| 224-225 | A139I | F118W_V133S | n | s, v | 52:9_57:9_59:35 |
| 226-227 | V37W_Q39E_W103H | Q38N_T85K_F98L | n | s, v | 37:27_67:12_80:9 |
| 226-228 | V37W_Q39E_W103F | Q38N_T85K_F98L | n | s, v | 37:27_67:12_80:9 |
| 229-230 | V37S_A93K | F98Y | n | s, v | 110:16_76:21 |
| 201-83 | D146G_Q179K | Q124E_V133W_Q160E_T180E | n | s, v | 69:21_86:10 |
| 231-232 | S186K_S188H_V190G | F118W_V133S_S176A_T178S_T180E | n | s | 69:16 |
| 233-131 | V37W_Q39K | Q38N_T85E_F98A | n | s, v | 49:28_88:10 |
| 234-235 | D146G_S186R | Q124E_Q160E_T178D | n | s, v | 67:25_78:15 |
| 236-237 | A139W | F116S_L135A | n | s | 54:14 |
| 234-238 | D146G_Q179R | Q124E_Q160E_T178D | n | s, v | 67:25_78:15 |
| 239-240 | V37W_Q39K_W103H | Q38N_T85E_F98L | n | s, v | 72:29_86:15 |
| 241-242 | V37A_W103H | P44W | n | s, v | 48:29_54:22_56:21_75:10_81:14_88:9 |
| 239-243 | V37W_Q39K_W103F | Q38N_T85E_F98L | n | s, v | 72:29_86:15 |
| 242-244 | V37T_A93Q_W103T | F98L | n | s, v | 36:25_41:25_58:7_67:6 |
| 179-245 | W103H | P44W_L89W_F98A | n | s, v | 64:26_69:26_69:28_75:25_77:26_78:26_83:22_86:16_95:8 |
| 246-225 | A139I | F118W_V133S | n | s, v | 67:28_69:24_77:8 |
| 247-248 | V37W_F100W_W103L | L89W_F98A | n | s, v | 67:30_71:22 |
| 125-219 | V37W_W103H | F98L | n | s, v | 60:30_79:23 |
| 249-250 | V37A_W103H | P44W | n | s, v | 55:24_58:31 |
| 251-240 | V37W_Q39K_W103H | Q38N_T85E_F98L | n | s, v | 62:38_64:27 |
| 252-227 | V37W_Q39E_W103H | Q38N_T85K_F98L | n | s | 68:35 |
| 251-243 | V37W_Q39K_W103F | Q38N_T85E_F98L | n | s, v | 62:38_64:27 |
| 252-228 | V37W_Q39E_W103F | Q38N_T85K_F98L | n | s | 68:35 |
| 253-120 | V37W_Q39E | Q38N_T85K_F98A | n | s | 67:36 |
| 254-255 | F174A_S188G | S176W | n | s, v | 73:30_78:30_66:32_61:36_65:37_70:38_59:40_62:40_54:45 |
| 250-256 | V37T_A93Q_W103T | Y87G | n | s, v | 43:26_43:27_53:19 |

| Unique identifier set | Normalized Median H1-L1:H1-L2 | Screening only/Verification only/Screening and verification data for H2-L2:H2-L1 (s/v/s_v) | H2-L2:H2-L1 | Normalized Median H2-L2:H2-L1 | H1-L1 Tm (Range if n > 1) (° C.) | H2-L2 Tm (Range if n > 1) (° C.) | H1-L1 Antigen Affinity (KD) (Range if n > 1) (nM) | H2-L2 Antigen Affinity (KD) (Range if n > 1) (nM) |
|---|---|---|---|---|---|---|---|---|
| 1--2 | 99:01 | v | 100:06 | 95:05 | 72.52 | 74.38 | 0.125 | 0.066 |
| 3--4 | 99:01 | s, v | 73:10_80:14 | 87:13 | 73.3 | 73.22 | 0.0399 | 0.0144 |
| 5--6 | 99:01 | s, v | 61:30_64:32 | 67:33 | 74.32 | 74.95 | 0.0245 | 0.0415 |
| 7--6 | 99:01 | s, v | 61:30_64:32 | 67:33 | 71.85 | 74.95 | 0.078 | 0.0415 |
| 8--6 | 99:01 | s, v | 61:30_64:32 | 67:33 | 72.57 | 74.95 | 0.0671 | 0.0415 |

TABLE 14-continued

| | | | | | | | | |
|---|---|---|---|---|---|---|---|---|
| 7--9 | 99:01 | s, v | 54:43_57:31 | 60:40 | 71.85 | 76.31 | 0.078 | 0.0705 |
| 8--9 | 99:01 | s, v | 54:43_57:31 | 60:40 | 72.57 | 76.31 | 0.0671 | 0.0705 |
| 10--11 | 88:12 | s | 85:30 | 74:26 | 73.88 | 73.3 | 0.0949 | 0.0399 |
| 12--13 | 86:14 | s, v | 103:6_76:23_92:22_94:6 | 89:11 | 73.3 | 71.62 | 0.0399 | 0.0377 (0.0386) |
| 12--14 | 86:14 | s, v | 60:37_83:10_92:9_97:33 | 83:17 | 73.3 | 76.91 | 0.0399 | 0.0342 (0.0372) |
| 12--15 | 86:14 | s, v | 76:21_78:18 | 80:20 | 73.3 | 73.01 | 0.0399 | 0.0271 |
| 16-17 | 82:18 | s, v | 58:25_59:45 | 64:36 | 73.03 | 72.38 | 0.077 | 0.144 |
| 18--11 | 81:19 | s | 85:30 | 74:26 | 72.21 | 73.3 | 0.0155 | 0.0399 |
| 19--3 | 76:24 | s, v | 101:1_102:2_103:1_67:3_81:1_83:1_90:1_93:1_99:1 | 99:01 | 74.73 | 73.3 | 0.0428 | 0.0399 |
| 20--11 | 72:28 | s | 85:30 | 74:26 | 77.09 | 73.3 | 0.0866 | 0.0399 |
| 21-22 | 66:34 | s, v | 72:17_73:11_85:11 | 87:13 | 73.03 | 71.68 | 0.077 | 0.0229 |
| 23-24 | 64:36 | v | 126:01 | 99:01 | 74.38 | 74.32 | 0.066 | 0.0245 |
| 9--5 | 60:40 | s, v | 116:1_96:1 | 99:01 | 76.31 | 74.32 | 0.0705 | 0.0245 |
| 25-26 | 96:04 | s, v | 101:4_71:18_73:17_85:12_85:18_86:9_88:7_89:10_99:2 | 90:10 | 72.38 | 73.07 | 0.144 | 0.902 |
| 27-28 | 86:14 | s | 99:02 | 98:02 | 73.07 | 71.68 | 0.902 | 0.0229 |
| 29-30 | 83:17 | s, v | 31:60_56:31_82:25_97:17 | 71:29 | 76.47 | 74.7 | 0.697 | 0.239 |
| 31-32 | 80:20 | s, v | 37:57_56:19_72:39_83:18 | 70:30 | 74.74 | 76.47 | 0.0109 | 0.697 |
| 33-34 | 69:31 | s, v | 67:13_90:8 | 88:12 | 73.6 | 73.07 | 0.123 | 0.902 |
| 35-36 | 99:01 | s, v | 62:26_62:29 | 69:31 | 73.64 | 71.29 | 0.0524 | 3.18 |
| 37-36 | 97:03 | s, v | 62:26_62:29 | 69:31 | 73.02 (0.22) | 71.29 | ND | 3.18 |
| 25-38 | 96:04 | s, v | 107:10_80:11 | 90:10 | 72.38 | 73.21 | 0.144 | 1.73 |
| 39-34 | 95:05 | s, v | 67:13_90:8 | 88:12 | 72.78 (0.006) | 73.07 | ND | 0.902 |
| 39-40 | 95:05 | s, v | 86:15_91:27 | 82:18 | 72.78 (0.006) | 73.21 | ND | 1.73 |
| 41-42 | 95:05 | s, v | 57:18_65:24 | 75:25 | 71.9 | 71.29 | 0.127 | 3.18 |
| 43-17 | 89:11 | s, v | 58:25_59:45 | 64:36 | 73.02 (0.22) | 72.38 | ND | 0.144 |
| 22-44 | 87:13 | s | 60:18 | 77:23 | 71.68 | 73.02 (0.22) | 0.0229 | ND |
| 45-28 | 85:15 | s | 99:02 | 98:02 | 73.21 | 71.68 | 1.73 | 0.0229 |
| 46-30 | 83:17 | s, v | 31:60_56:31_82:25_97:17 | 71:29 | 76.9 | 74.7 | 3.44 | 0.239 |
| 47-48 | 80:20 | s, v | 76:25_78:27_83:14_85:18_85:6_86:14_90:10_91:16 | 85:15 | 75.84 (0.7) | 75.83 (2.1884) | NB | 0.056 (0.1017) |
| 49-42 | 77:23 | s, v | 57:18_65:24 | 75:25 | 72.87 | 71.29 | 0.0729 | 3.18 |
| 50-42 | 76:24 | s, v | 57:18_65:24 | 75:25 | 73.78 | 71.29 | 0.177 | 3.18 |
| 51-52 | 76:24 | s, v | 63:30_65:30_71:31_76:35_77:31_81:35_91:26_91:27_97:15 | 70:30 | 72.78 (0.006) | 73.02 (0.22) | ND | ND |
| 53-54 | 72:28 | s, v | 58:37_59:33_60:45_74:34_77:32_79:30_81:34_82:34 | 70:30 | 72.78 (0.006) | 75.83 (2.1884) | ND | 0.056 (0.1017) |
| 33-40 | 69:31 | s, v | 86:15_91:27 | 82:18 | 73.6 | 73.21 | 0.123 | 1.73 |
| 55-56 | 66:34 | s, v | 68:24_71:27_83:17 | 74:26 | 72.58 | 72.78 (0.06) | 0.0273 | ND |
| 57-58 | 99:01 | s, v | 106:1_107:1_107:2_112:1_112:1_117:2_120:1_123:1_92:2 | 99:01 | 67.04 | 75.45 | 0.0243 | 0.0596 |
| 5-59 | 99:01 | s, v | 73:5_83:1_83:2 | 98:02 | 74.32 | 69.6 | 0.0245 | 0.0236 |
| 7-59 | 99:01 | s, v | 73:5_83:1_83:2 | 98:02 | 71.85 | 69.6 | 0.078 | 0.0236 |
| 8-59 | 99:01 | s, v | 73:5_83:1_83:2 | 98:02 | 72.57 | 69.6 | 0.0671 | 0.0236 |
| 60-61 | 99:01 | s, v | 77:1_88:3 | 98:02 | 70.11 | 72.7 | 0.0816 | 0.0769 |
| 62-61 | 99:01 | s, v | 77:1_88:3 | 98:02 | 66.67 | 72.7 | 0.0511 | 0.0769 |
| 63-64 | 99:01 | s, v | 84:15_91:4 | 92:08 | 66.67 | 74.95 | 0.0511 | 0.0415 |
| 63-65 | 99:01 | s, v | 72:4_75:20_80:18_88:12_88:12_92:10_92:13_93:13_94:15 | 88:12 | 66.67 | 76.31 | 0.0511 | 0.0705 |
| 66-67 | 99:01 | s, v | 76:24_78:20_80:16_83:12_86:1_86:21_88:13_93:11_94:17 | 85:15 | 67.53 | 71.45 | 0.0871 | 0.0856 |
| 66-68 | 99:01 | s, v | 62:25_87:11 | 82:18 | 67.53 | 73.14 | 0.0871 | 0.0423 |
| 63-69 | 99:01 | s, v | 76:18_82:19 | 81:19 | 66.67 | 74.3 | 0.0511 | 0.111 |
| 3-70 | 99:01 | s, v | 70:24_80:28 | 74:26 | 73.3 | 66.245 (0.99) | 0.0399 | 0.0201 |
| 61-71 | 98:02 | v | 102:01 | 99:01 | 72.7 | 69.16 | 0.0769 | 0.0525 |
| 72-64 | 98:02 | s, v | 84:15_91:4 | 92:08 | 70.11 | 74.95 | 0.0816 | 0.0415 |
| 72-65 | 98:02 | s, v | 72:4_75:20_80:18_88:12_88:12_92:10_92:13_93:13_94:15 | 88:12 | 70.11 | 76.31 | 0.0816 | 0.0705 |
| 72-69 | 98:02 | s, v | 76:18_82:19 | 81:19 | 70.11 | 74.3 | 0.0816 | 0.111 |
| 73-74 | 93:07 | s, v | 79:10_86:8 | 90:10 | 72.38 | 66.23 | 0.144 | 0.172 |
| 75-76 | 93:07 | s, v | 72:13_83:11 | 87:13 | 73.03 | 67.79 | 0.077 | 0.127 |
| 75-77 | 93:07 | s, v | 59:41_67:32 | 63:37 | 73.03 | 69.62 | 0.077 | 0.101 |
| 64-78 | 92:08 | v | 81:03 | 97:03 | 74.95 | 69.16 | 0.0415 | 0.0525 |
| 65-78 | 88:12 | v | 81:03 | 97:03 | 76.31 | 69.16 | 0.0705 | 0.0525 |
| 67-79 | 85:15 | s, v | 108:1_93:2 | 99:01 | 71.45 | 67.01 | 0.0856 | 0.0631 |
| 68-79 | 82:18 | s, v | 108:1_93:2 | 99:01 | 73.14 | 67.01 | 0.0423 | 0.0631 |
| 80-81 | 82:18 | s, v | 102:1_113:3 | 98:02 | 74.3 | 67.01 | 0.111 | 0.0631 |
| 80-82 | 82:18 | s, v | 103:1_97:3 | 98:02 | 74.3 | 67.53 | 0.111 | 0.0871 |

TABLE 14-continued

| | | | | | | | | |
|---|---|---|---|---|---|---|---|---|
| 80-83 | 82:18 | v | 84:03 | 96:04 | 74.3 | 68.37 | 0.111 | 0.0828 |
| 16-84 | 82:18 | s, v | 80:17_85:12 | 85:15 | 73.03 | 70.69 | 0.077 | 0.1785 (0.007) |
| 85-81 | 81:19 | s, v | 102:1_113:3 | 98:02 | 76.31 | 67.01 | 0.0705 | 0.0631 |
| 85-82 | 81:19 | s, v | 103:1_97:3 | 98:02 | 76.31 | 67.53 | 0.0705 | 0.0871 |
| 69-78 | 81:19 | v | 81:03 | 97:03 | 74.3 | 69.16 | 0.111 | 0.0525 |
| 85-83 | 81:19 | v | 84:03 | 96:04 | 76.31 | 68.37 | 0.0705 | 0.0828 |
| 86-87 | 70:30 | s, v | 59:33_72:30 | 67:33 | 71.25 | 68.83 | 0.0213 | 0.0201 |
| 86-88 | 70:30 | s | 73:37 | 66:34 | 71.25 | 69.8 | 0.0213 | 0.0182 |
| 89-90 | 98:02 | s, v | 74:12_93:4 | 92:08 | 67.79 | 73.07 | 0.127 | 0.902 |
| 73-91 | 93:07 | s, v | 115:11_99:4 | 94:06 | 72.38 | 67.39 | 0.144 | 0.924 |
| 92-90 | 91:09 | s, v | 74:12_93:4 | 92:08 | 69.62 | 73.07 | 0.101 | 0.902 |
| 93-26 | 87:13 | s, v | 101:4_71:18_73:17_85:12_85:18_86:9_88:7_89:10_99:2 | 90:10 | 70.69 | 73.07 | 0.1785 (0.007) | 0.902 |
| 94-95 | 78:22 | s, v | 61:12_83:13 | 85:15 | 72.38 | 69.42 | 0.144 | 0.955 (1.05) |
| 96-97 | 99:01 | s, v | 72:10_99:2 | 95:05 | 71.9 | 67.14 | 0.127 | 1.11 |
| 89-98 | 98:02 | s, v | 90:8_93:7 | 92:08 | 67.79 | 73.21 | 0.127 | 1.73 |
| 99-76 | 97:03 | s, v | 72:13_83:11 | 87:13 | 73.02 (0.22) | 67.79 | ND | 0.127 |
| 99-77 | 97:03 | s, v | 59:41_67:32 | 63:37 | 73.02 (0.22) | 69.62 | ND | 0.101 |
| 100-97 | 95:05 | s, v | 72:10_99:2 | 95:05 | 72.87 | 67.14 | 0.0729 | 1.11 |
| 101-102 | 93:07 | s, v | 75:28_78:2_81:23_84:21_85:23_86:13_86:18_88:5_91:16 | 83:17 | 68 | 75.83 (2.1884) | 2.41 | 0.056 (0.1017) |
| 103-104 | 93:07 | s | 74:20 | 79:21 | 70.65 | 71.86 | ND | ND |
| 105-42 | 92:08 | s, v | 57:18_65:24 | 75:25 | 70.74 | 71.29 | 0.163 | 3.18 |
| 106-97 | 91:09 | s, v | 72:10_99:2 | 95:05 | 73.78 | 67.14 | 0.177 | 1.11 |
| 92-98 | 91:09 | s, v | 90:8_93:7 | 92:08 | 69.62 | 73.21 | 0.101 | 1.73 |
| 43-84 | 89:11 | s, v | 80:17_85:12 | 85:15 | 73.02 (0.22) | 70.69 | ND | 0.1785 (0.007) |
| 93-38 | 87:13 | s, v | 107:10_80:11 | 90:10 | 70.69 | 73.21 | 0.1785 (0.007) | 1.73 |
| 107-108 | 86:14 | s, v | 100:11_77:17_79:10_90:17_93:11_96:10_96:15_96:6_99:12 | 89:11 | 70.88 (0.32) | 71.86 | 0.0586 | ND |
| 109-110 | 73:27 | s, v | 70:3_74:29 | 88:12 | 69.875 (0.03) | 75.83 (2.1884) | NB | 0.056 (0.1017) |
| 111-112 | 99:01 | s, v | 101:1_84:2 | 99:01 | 69.22 | 66.73 | 0.117 | 5.64E−09 |
| 63-113 | 99:01 | s, v | 74:6_93:3_94:1 | 97:03 | 66.67 | 69.6 | 0.0511 | 0.0236 |
| 79-114 | 99:01 | s, v | 66:24_93:11 | 83:17 | 67.01 | 68.64 | 0.0631 | 0.0219 |
| 66-114 | 99:01 | s, v | 66:24_93:11 | 83:17 | 67.53 | 68.64 | 0.0871 | 0.0219 |
| 72-113 | 98:02 | s, v | 74:6_93:3_94:1 | 97:03 | 70.11 | 69.6 | 0.0816 | 0.0236 |
| 113-78 | 97:03 | v | 81:03 | 97:03 | 69.6 | 69.16 | 0.0236 | 0.0525 |
| 115-116 | 91:09 | s, v | 75:8_89:8 | 91:09 | 67.79 | 66.23 | 0.127 | 0.172 |
| 117-116 | 90:10 | s, v | 75:8_89:8 | 91:09 | 69.62 | 66.23 | 0.101 | 0.172 |
| 118-74 | 89:11 | s, v | 79:10_86:8 | 90:10 | 70.69 | 66.23 | 0.1785 (0.007) | 0.172 |
| 119-120 | 95:05 | s, v | 61:35_74:19 | 72:28 | 66.94 | 67.29 | 0.0134 | 0.861 |
| 121-95 | 93:07 | s, v | 61:12_83:13 | 85:15 | 70.69 | 69.42 | 0.1785 (0.007) | 0.955 (1.05) |
| 115-122 | 91:09 | s, v | 114:5_91:2 | 97:03 | 67.79 | 67.39 | 0.127 | 0.924 |
| 123-124 | 91:09 | s, v | 75:8_85:8 | 91:09 | 67.79 | 69.42 | 0.127 | 0.955 (1.05) |
| 117-122 | 90:10 | s, v | 114:5_91:2 | 97:03 | 69.62 | 67.39 | 0.101 | 0.924 |
| 118-91 | 89:11 | s, v | 115:11_99:4 | 94:06 | 70.69 | 67.39 | 0.1785 (0.007) | 0.924 |
| 125-124 | 72:28 | s, v | 75:8_85:8 | 91:09 | 69.62 | 69.42 | 0.101 | 0.955 (1.05) |
| 126-97 | 96:04 | s, v | 72:10_99:2 | 95:05 | 70.74 | 67.14 | 0.163 | 1.11 |
| 127-128 | 95:05 | s, v | 64:29_70:21 | 73:27 | 68.83 | 68.63 | 0.0201 | 1.78 |
| 129-128 | 80:20 | s, v | 64:29_70:21 | 73:27 | 69.8 | 68.63 | 0.0182 | 1.78 |
| 130-131 | 69:31 | s, v | 81:16_88:10 | 87:13 | 68.1 | 68.63 | 0.1247 (0.0646) | 1.78 |
| 96-132 | 99:01 | s, v | 76:6_95:3 | 95:05 | 71.9 | 58.03 | 0.127 | 2.99 |
| 3-133 | 99:01 | s, v | 68:21_72:24 | 76:24 | 73.3 | 65.53 | 0.0399 | 0.0172 |
| 134-36 | 99:01 | s, v | 62:26_62:29 | 69:31 | ND | 71.29 | ND | 3.18 |
| 135-136 | 99:01 | s, v | 47:31_53:39_93:38 | 60:40 | 73.64 | ND | 0.0524 | ND |
| 137-138 | 97:03 | s, v | 46:21_46:34_97:20 | 69:31 | 71.9 | ND | 0.127 | ND |
| 100-132 | 95:05 | s, v | 76:6_95:3 | 95:05 | 72.87 | 58.03 | 0.0729 | 2.99 |
| 139-140 | 94:06 | s, v | 90:1_98:5 | 98:02 | 65 | 72.57 | 0.0406 | 0.0615 |
| 141-142 | 94:06 | s, v | 61:18_69:16 | 79:21 | 73.02 (0.22) | ND | ND | ND |
| 73-143 | 93:07 | s, v | 94:1_97:1 | 99:01 | 72.38 | 58.76 | 0.144 | 7.89 |
| 73-144 | 93:07 | s, v | 105:3_57:5_97:1 | 97:03 | 72.38 | ND | 0.144 | ND |
| 145-146 | 92:08 | s, v | 83:6_98:3 | 95:05 | 71.9 | 60.35 | 0.127 | 5.62 |
| 145-147 | 92:08 | s, v | 48:24_63:33 | 66:34 | 71.9 | ND | 0.127 | ND |
| 106-132 | 91:09 | s, v | 76:6_95:3 | 95:05 | 73.78 | 58.03 | 0.177 | 2.99 |
| 148-149 | 90:10 | s, v | 101:3_99:3 | 97:03 | ND | 73.21 | ND | 1.73 |
| 148-150 | 90:10 | s, v | 74:8_84:4 | 93:07 | ND | 73.07 | ND | 0.902 |
| 22-151 | 87:13 | s | 54:34 | 61:39 | 71.68 | ND | 0.0229 | ND |

TABLE 14-continued

| | | | | | | | | |
|---|---|---|---|---|---|---|---|---|
| 152-153 | 86:14 | s, v | 101:5_116:4 | 96:04 | 60.29 | 73.21 | 0.977 | 1.73 |
| 152-154 | 86:14 | s, v | 86:12_91:3 | 93:07 | 60.29 | 73.07 | 0.977 | 0.902 |
| 155-36 | 85:15 | s, v | 62:26_62:29 | 69:31 | ND | 71.29 | ND | 3.18 |
| 156-157 | 84:16 | s, v | 63:37_86:12 | 77:23 | 53.23 | 76.9 | NB | 3.44 |
| 158-159 | 84:16 | s, v | 58:38_87:31 | 68:32 | 60.29 | 76.9 | 0.977 | 3.44 |
| 160-146 | 83:17 | s, v | 83:6_98:3 | 95:05 | 72.87 | 60.35 | 0.0729 | 5.62 |
| 161-142 | 83:17 | s, v | 61:18_69:16 | 79:21 | 73.03 | ND | 0.077 | ND |
| 160-147 | 83:17 | s, v | 48:24_63:33 | 66:34 | 72.87 | ND | 0.0729 | ND |
| 162-163 | 82:18 | s, v | 42:33_67:12_69:8 | 85:15 | 73.03 | 60.29 | 0.077 | 0.977 |
| 164-165 | 81:19 | s, v | 104:2_105:1_107:1_108:1_110:1_ 111:1_115:1_117:1_120:1 | 99:01 | ND | 71.86 | ND | ND |
| 166-157 | 81:19 | s, v | 63:37_86:12 | 77:23 | 59.34 | 76.9 | 0.24 | 3.44 |
| 167-157 | 81:19 | s, v | 63:37_86:12 | 77:23 | 54.89 | 76.9 | 0.192 | 3.44 |
| 168-163 | 80:20 | s, v | 42:33_67:12_69:8 | 85:15 | 73.02 (0.22) | 60.29 | ND | 0.977 |
| 169-157 | 80:20 | s, v | 63:37_86:12 | 77:23 | 53.64 | 76.9 | 1.33 | 3.44 |
| 170-171 | 79:21 | s, v | 63:3_75:7 | 94:06 | 71.25 | 55.37 | 0.0213 | NB |
| 170-172 | 79:21 | s, v | 60:17_70:17 | 79:21 | 71.25 | 59.74 | 0.0213 | 0.55 |
| 173-174 | 79:21 | s, v | 101:28_61:40 | 70:30 | ND | 76.9 | ND | 3.44 |
| 94-175 | 78:22 | s, v | 79:12_85:7 | 90:10 | 72.38 | 60.9 | 0.144 | ND |
| 157-176 | 77:23 | s, v | 65:6_66:12 | 88:12 | 76.9 | 58.86 | 3.44 | 0.212 |
| 177-157 | 77:23 | s, v | 63:37_86:12 | 77:23 | ND | 76.9 | ND | 3.44 |
| 157-178 | 77:23 | s, v | 52:18_64:21 | 75:25 | 76.9 | 63.59 | 3.44 | 0.174 |
| 179-180 | 75:25 | s, v | 102:4_104:3_105:2_81:3_92:3_ 96:1_96:3_99:2_99:3 | 97:03 | 27.52 | 74.17 | NB | 4.125 (0.35) |
| 181-138 | 75:25 | s, v | 46:21_46:34_97:20 | 69:31 | 72.87 | ND | 0.0729 | ND |
| 182-183 | 74:26 | s, v | 66:12_69:15_69:7_72:1_72:11_ 75:12_76:9_80:8_82:7 | 89:11 | 75.84 (0.7) | 61.7 | NB | 0.42 |
| 86-184 | 70:30 | s | 72:27 | 72:28 | 71.25 | ND | 0.0213 | ND |
| 185-138 | 69:31 | s, v | 46:21_46:34_97:20 | 69:31 | 73.78 | ND | 0.177 | ND |
| 186-187 | 68:32 | s, v | 57:30_62:31 | 66:34 | 74.74 | 60.9 | 0.0109 | ND |
| 187-188 | 66:34 | s | 66:22 | 75:25 | 60.9 | 75.745 (0.11) | ND | ND |
| 189-157 | 64:36 | s, v | 63:37_86:12 | 77:23 | ND | 76.9 | ND | 3.44 |
| 190-191 | 64:36 | s, v | 48:27_49:27_53:33 | 64:36 | ND | 76.9 | ND | 3.44 |
| 192-193 | 99:01 | s | 88:01 | 99:01 | ND | ND | ND | ND |
| 194-195 | 99:01 | s | 69:01 | 99:01 | ND | ND | ND | ND |
| 196-197 | 99:01 | s | 66:03 | 96:04 | ND | ND | ND | ND |
| 198-199 | 99:01 | s, v | 68:15_74:21 | 80:20 | 55.37 | 68.63 | NB | 1.78 |
| 200-146 | 98:02 | s, v | 83:6_98:3 | 95:05 | 70.74 | 60.35 | 0.163 | 5.62 |
| 81-201 | 98:02 | s, v | 69:21_86:10 | 84:16 | 67.01 | ND | 0.0631 | ND |
| 82-201 | 98:02 | s, v | 69:21_86:10 | 84:16 | 67.53 | ND | 0.0871 | ND |
| 202-203 | 98:02 | s, v | 79:28_80:14 | 80:20 | 70.92 | 27.52 | 1.54 | NB |
| 204-179 | 98:02 | s, v | 64:26_69:26_69:28_75:25_77:26_ 78:26_83:22_86:16_95:8 | 75:25 | 64.69 | 27.52 | NB | NB |
| 202-205 | 98:02 | s, v | 60:33_77:17 | 74:26 | 70.92 | 64.56 | 1.54 | 1.22 |
| 200-147 | 98:02 | s, v | 48:24_63:33 | 66:34 | 70.74 | ND | 0.163 | ND |
| 206-136 | 98:02 | s, v | 47:31_53:39_93:38 | 60:40 | ND | ND | ND | ND |
| 126-132 | 96:04 | s, v | 76:6_95:3 | 95:05 | 70.74 | 58.03 | 0.163 | 2.99 |
| 207-203 | 95:05 | s, v | 79:28_80:14 | 80:20 | ND | 27.52 | ND | NB |
| 207-205 | 95:05 | s, v | 60:33_77:17 | 74:26 | ND | 64.56 | ND | 1.22 |
| 208-209 | 94:06 | s | 89:03 | 97:03 | ND | ND | ND | ND |
| 210-138 | 94:06 | s, v | 46:21_46:34_97:20 | 69:31 | 70.74 | ND | 0.163 | ND |
| 121-175 | 93:07 | s, v | 79:12_85:7 | 90:10 | 70.69 | 60.9 | 0.1785 (0.007) | ND |
| 211-212 | 92:08 | s | 88:02_122:01 | 98:01 | ND | 68.62 | ND | 0.052 |
| 213-214 | 92:08 | s, v | 51:35_66:14_76:32 | 70:30 | 55.83 | 67.29 | 0.832 | 0.861 |
| 215-216 | 92:08 | s | 66:35 | 66:34 | ND | ND | ND | ND |
| 115-217 | 91:09 | s, v | 79:2_97:2 | 98:02 | 67.79 | 58.76 | 0.127 | 7.89 |
| 115-218 | 91:09 | s, v | 62:11_94:3 | 93:07 | 67.79 | ND | 0.127 | ND |
| 123-219 | 91:09 | s, v | 80:13_91:7 | 90:10 | 67.79 | 60.9 | 0.127 | ND |
| 117-217 | 90:10 | s, v | 79:2_97:2 | 98:02 | 69.62 | 58.76 | 0.101 | 7.89 |
| 117-218 | 90:10 | s, v | 62:11_94:3 | 93:07 | 69.62 | ND | 0.101 | ND |
| 220-199 | 90:10 | s, v | 68:15_74:21 | 80:20 | 59.74 | 68.63 | 0.55 | 1.78 |
| 118-143 | 89:11 | s, v | 94:1_97:1 | 99:01 | 70.69 | 58.76 | 0.1785 (0.007) | 7.89 |
| 118-144 | 89:11 | s, v | 105:3_57:5_97:1 | 97:03 | 70.69 | ND | 0.1785 (0.007) | ND |
| 221-222 | 88:12 | s | 71:42 | 63:37 | ND | ND | ND | ND |
| 223-179 | 87:13 | s, v | 64:26_69:26_69:28_75:25_77:26_ 78:26_83:22_86:16_95:8 | 75:25 | ND | 27.52 | ND | NB |
| 224-225 | 86:14 | s | 52:29 | 64:36 | ND | 68.62 | ND | 0.052 |
| 226-227 | 85:15 | s, v | 73:19_91:7 | 87:13 | 66.94 | ND | 0.0134 | ND |
| 226-228 | 85:15 | s, v | 67:31_72:20 | 74:26 | 66.94 | 61.43 | 0.0134 | 2.51 |
| 229-230 | 84:16 | s, v | 76:2_79:1 | 98:02 | 69.875 (0.03) | 61.7 | NB | 0.42 |
| 201-83 | 84:16 | v | 84:03 | 96:04 | ND | 68.37 | ND | 0.0828 |
| 231-232 | 82:18 | s | 92:07 | 93:07 | ND | ND | ND | ND |
| 233-131 | 80:20 | s, v | 81:16_88:10 | 87:13 | 65.72 | 68.63 | 0.0348 | 1.78 |
| 234-235 | 79:21 | s, v | 102:1_106:2 | 99:01 | ND | 66.67 | ND | 0.0511 |

TABLE 14-continued

| | | | | | | | | |
|---|---|---|---|---|---|---|---|---|
| 236-237 | 79:21 | s | 108:02 | 98:02 | ND | ND | ND | ND |
| 234-238 | 79:21 | s | 98:04 | 97:03 | ND | 70.11 | ND | 0.0816 |
| 239-240 | 79:21 | s | 79:10 | 89:11 | 65.72 | ND | 0.0348 | ND |
| 241-242 | 79:21 | s, v | 36:25_41:25_58:7_67:6 | 78:22 | 60.9 | 56.17 | ND | ND |
| 239-243 | 79:21 | s, v | 54:24_69:18 | 75:25 | 65.72 | 62.29 | 0.0348 | 0.984 |
| 242-244 | 78:22 | s, v | 53:17_59:27_67:19 | 75:25 | 56.17 | ND | ND | ND |
| 179-245 | 75:25 | s, v | 79:3_89:1 | 98:02 | 27.52 | 67.82 | NB | 3.4 (2.52) |
| 246-225 | 74:26 | s | 52:29 | 64:36 | ND | 68.62 | ND | 0.052 |
| 247-248 | 73:27 | s, v | 50:32_56:22 | 67:33 | 27.52 | ND | NB | ND |
| 125-219 | 72:28 | s, v | 80:13_91:7 | 90:10 | 69.62 | 60.9 | 0.101 | ND |
| 249-250 | 67:33 | s, v | 43:26_43:27_53:19 | 62:38 | 66.54 | ND | 0.197 | ND |
| 251-240 | 66:34 | s | 79:10 | 89:11 | 68.1 | ND | 0.1247 (0.0646) | ND |
| 252-227 | 66:34 | s, v | 73:19_91:7 | 87:13 | ND | ND | ND | ND |
| 251-243 | 66:34 | s, v | 54:24_69:18 | 75:25 | 68.1 | 62.29 | 0.1247 (0.0646) | 0.984 |
| 252-228 | 66:34 | s, v | 67:31_72:20 | 74:26 | ND | 61.43 | ND | 2.51 |
| 253-120 | 65:35 | s, v | 61:35_74:19 | 72:28 | ND | 67.29 | ND | 0.861 |
| 254-255 | 64:36 | s, v | 73:2_41:33 | 88:12 | 63.91 | ND | 0.0792 | ND |
| 250-256 | 62:38 | s, v | 59:20_63:19_74:11 | 77:23 | ND | ND | ND | ND |

TABLE 15

| Unique identifier set | Fab Region | Design Type | H1_mutation | L1_mutation | H2_mutation | L2_mutation |
|---|---|---|---|---|---|---|
| 257-258 | constant | electrostatic | L143E_K145T | Q124R_Q160K_T178R | S186R | Q124E_Q160E_T180E |
| 259-260 | constant | electrostatic | L143E_K145T | Q124K_T178R | S186R | Q124E_Q160E_T180E |
| 261-262 | constant | combination (electrostatic + steric) | L124E_H172R | V133G_S176R | L124R_H172A | V133G_S174W_S176D |
| 263-264 | constant | electrostatic | L124E | V133G_S176R | L124R | V133G_S176D |
| 265-266 | constant | electrostatic | L143E_K145T | Q124K_T178R | S186R | Q124R |
| 267-268 | constant | combination (electrostatic + steric) | L124E_H172R | V133G_S176R | L124R_H172A | V133A_S174W_S176D |
| 269-270 | constant | combination (electrostatic + steric) | L124E_H172W | V133G_S176R | L124R_H172T | V133G_S174R_S176D |
| 271-272 | constant | combination (electrostatic + steric) | L124E_H172R | V133A_S176K | L124R_H172A | V133A_S174W_S176D |
| 273-274 | variable | combination (electrostatic + steric) | Q39E | Q38R_F98W | Q39R_F100W_W103F | Q38E_F98M |
| 275-276 | constant | combination (electrostatic + steric) | L124E_H172W | V133A_S176K | L124R_H172T | V133G_S174R_S176D |
| 277-278 | constant | electrostatic | L143E_K145T | Q124R | L143R | Q124E |
| 277-279 | constant | electrostatic | L143E_K145T | Q124R | WT | Q124E |
| 277-280 | constant | electrostatic | L143E_K145T | Q124E | S186R | Q124E |
| 277-281 | constant | electrostatic | L143E_K145T | Q124R | L143K | Q124E |
| 282-283 | constant | electrostatic | L143E_K145T | Q124R | S186R | T178E |
| 284-285 | constant | electrostatic | L143E_K145T | Q124R | S186R | Q124E_Q160E_T180E |
| 286-287 | constant | combination (electrostatic + steric) | L124E_H172W | V133G_S176R | L124R_H172T | V133A_S174R_S176D |
| 288-289 | constant | electrostatic and steric | L124E | V133G_S176R | L124R | V133A_S176D |
| 290-291 | constant | electrostatic | L143E_K145T_S188L | Q124K | L143K | Q124E |
| 290-292 | constant | electrostatic | L143E_K145T_S188L | Q124K | S186R | Q124E |
| 290-293 | constant | electrostatic | L143E_K145T_S188L | Q124K | L143R | Q124E |
| 294-295 | constant | electrostatic and steric | L124E | V133A_S176K | L124R | V133G_S176D |
| 296-297 | variable | steric | F100W | F98M | W103F | Y36W |
| 298-297 | variable | steric | F100W_W103F | F98M | W103F | Y36W |
| 299-300 | variable | steric | L45A | P44F | V37W | F98A |
| 301-302 | variable | electrostatic | Q39E | Q38N_T85R | Q39R | Q38E_T85E |
| 303-278 | constant | electrostatic | L143E_K145T_S188L | Q124R | L143R | Q124E |

TABLE 15-continued

| Unique identifier set | | | | | |
|---|---|---|---|---|---|
| 303-279 | constant | electrostatic | L143E_K145T_S188L Q124R | WT | Q124E |
| 303-280 | constant | electrostatic | L143E_K145T_S188L Q124R | S186R | Q124E |
| 303-281 | constant | electrostatic | L143E_K145T_S188L Q124R | L143K | Q124E |

| Unique identifier set | Presence of H-L disulfide bond (C233-C214) (y/n) | Screening only/Verification only/Screening and verification data for H1-L1:H1-L2 (s/v/s_v) | H1-L1:H1-L2 | Normalized medain H1-L1:H1-L2 | Screening only/Verification only/Screening and verification data for H2-L2:H2-L1 (s/v/s_v) | H2-L2:H2-L1 |
|---|---|---|---|---|---|---|
| 257-258 | n | s | 93:3 | 97:3 | v | 94:11 |
| 259-260 | n | v | 90:6 | 94:6 | v | 91:29 |
| 261-262 | n | v_s | 99:8_94:8 | 93:7 | v_s | 48:21_58:15 |
| 263-264 | n | v_s | 95:5_68:25 | 88:12 | v_s | 70:29_101:9 |
| 265-266 | n | v | 90:13 | 87:13 | v | 96:6 |
| 267-268 | n | v_s_s | 86:12_80:12_85:19 | 87:13 | v_s | 52:22_51:16 |
| 269-270 | n | v_s | 82:15_76:13 | 85:15 | v_s | 89:13_84:11 |
| 271-272 | n | v_s | 90:19_74:16 | 82:18 | v_s | 49:35_46:19 |
| 273-274 | n | v_s | 73:11_54:19 | 81:19 | v_s | 56:45_80:4 |
| 275-276 | n | v_s | 75:18_60:15 | 80:20 | v_s | 82:21_79:18 |
| 277-278 | n | v | 93:26 | 78:22 | s | 77:20 |
| 277-279 | n | v | 93:26 | 78:22 | v_v_s | 81:24_76:22_77:8 |
| 277-280 | n | v | 93:26 | 78:22 | v | 86:30 |
| 277-281 | n | v | 93:26 | 78:22 | v_s_s | 70:29_97:10_31:35 |
| 282-283 | n | v | 92:28 | 77:23 | v | 68:30 |
| 284-285 | n | v | 82:26 | 76:24 | v | 94:9 |
| 286-287 | n | v_s | 68:30_64:21 | 72:28 | v_s | 83:18_83:14 |
| 288-289 | n | v_s | 58:46_59:16 | 68:32 | v_s | 83:12_81:8 |
| 290-291 | n | v_s | 75:26_47:32 | 68:32 | s | 88:6 |
| 290-292 | n | v_s | 75:26_47:32 | 68:32 | v | 87:7 |
| 290-293 | n | v_s | 75:26_47:32 | 68:32 | v_s | 84:20_87:25 |
| 294-295 | n | v_s | 69:35_49:30 | 64:36 | v_s | 68:40_42:22 |
| 296-297 | n | v_s | 70:38_65:38 | 64:36 | v_s | 53:41_77:43 |
| 298-297 | n | v_s | 67:45_62:36 | 62:38 | v_s | 53:41_77:43 |
| 299-300 | n | v_s | 59:48_60:33 | 60:40 | v_s | 92:11_81:17 |
| 301-302 | n | v_s_s | 66:44_45:31_62:31 | 60:40 | v_s | 64:39_86:27 |
| 303-278 | n | v_s_s | 70:52_59:41_76:27 | 59:41 | s | 77:20 |
| 303-279 | n | v_s_s | 70:52_59:41_76:27 | 59:41 | v_v_s | 81:24_76:22_77:8 |
| 303-280 | n | v_s_s | 70:52_59:41_76:27 | 59:41 | v | 86:30 |
| 303-281 | n | v_s_s | 70:52_59:41_76:27 | 59:41 | v_s_s | 70:29_97:10_31:35 |

| Unique identifier set | Normalized median H2-L2:H2-L1 | H1-L1 Tm (° C.) | H2-L2 Tm (° C.) |
|---|---|---|---|
| 257-258 | 89:11 | ND | ND |
| 259-260 | 76:24 | ND | ND |
| 261-262 | 75:25 | 77.7 | 76 |
| 263-264 | 84:16 | 76.96 | ND |
| 265-266 | 94:6 | | ND |
| 267-268 | 73:27 | 77.7 | ND |
| 269-270 | 88:12 | 76.43 | 77.04 |
| 271-272 | 65:35 | 76.49 | ND |
| 273-274 | 84:16 | 74.32 | 70.41 |
| 275-276 | 80:20 | 75.62 | 77.04 |
| 277-278 | 79:21 | ND | 76.56 |
| 277-279 | 78:22 | ND | ND |
| 277-280 | 74:26 | ND | ND |
| 277-281 | 71:29 | ND | ND |
| 282-283 | 70:30 | ND | 76.03 |
| 284-285 | 92:8 | ND | ND |
| 286-287 | 84:16 | 76.43 | 77.12 |
| 288-289 | 89:11 | 76.96 | 77.45 |
| 290-291 | 93:7 | 76.95 | ND |
| 290-292 | 92:8 | 76.95 | ND |
| 290-293 | 79:21 | 76.95 | 76.56 |
| 294-295 | 64:36 | 76.07 | ND |
| 296-297 | 61:39 | 72.27 | 73.15 |
| 298-297 | 61:39 | 71.38 | 73.15 |
| 299-300 | 86:14 | 71.4 | 78.545 |
| 301-302 | 69:31 | ND | 71.37 |
| 303-278 | 79:21 | ND | 76.56 |
| 303-279 | 78:22 | ND | ND |
| 303-280 | 74:26 | ND | ND |
| 303-281 | 71:29 | ND | ND |

TABLE 16

| Unique identifier | REF_WT or VAR | Design Type | H1_Ab | H1_mutation | L1_Ab | L1_mutation | L1_tag | L2_Ab | L2_mutation | L2_tag |
|---|---|---|---|---|---|---|---|---|---|---|
|  | A |  | TRAS |  | TRAS |  | FLAG | TRAS |  | HA |
| 58 |  | electrostatic | TRAS | L143E_K145T | TRAS | Q124R | FLAG | TRAS | Q124E_V133D | HA |
| 304* |  | combination (steric + electrostatic) | TRAS | A139W_S186K | TRAS | F116A_Q124E_L135A_T180E | FLAG | TRAS | L135W | HA |
| 305* |  | combination (steric + electrostatic) | TRAS | V37W | TRAS | F98A | FLAG | TRAS | Q38E | HA |
| 26 |  | combination (steric + electrostatic) | TRAS | V37W_Q39E | TRAS | Q38R_F98A | FLAG | TRAS | Q38E_F98W | HA |
| 57 |  | electrostatic | TRAS | L143K_D146G | TRAS | Q124E_V133D | HA | TRAS | Q124R | FLAG |
| 306* |  | combination (steric + electrostatic) | TRAS | A139G_K145T_D146G_Q179E_V190A | TRAS | L135W | HA | TRAS | F116A_Q124E_L135A_T180E | FLAG |
| 307* |  | combination (steric + electrostatic) | TRAS | Q39R | TRAS | Q38E | HA | TRAS | F98A | FLAG |
| 93 |  | combination (steric + electrostatic) | TRAS | Q39R | TRAS | Q38E_F98W | HA | TRAS | Q38R_F98A | FLAG |
| 72 |  | electrostatic | TRAS | D146G_Q179R | TRAS | Q124E_Q160E_T178D | FLAG | TRAS | Q160K_T178R | HA |
| 3 |  | steric | TRAS | F174V_P175S_S188G | TRAS | S176L | FLAG | TRAS | V133S | HA |
| 108 |  | steric | TRAS | A139W | TRAS | F116A_L135A | FLAG | TRAS | L135W | HA |
| 308* |  | steric | TRAS | L124W | TRAS | F118A | FLAG | TRAS | WT | HA |
| 52 |  | electrostatic | TRAS | Q39E | TRAS | Q38R | FLAG | TRAS | Q38E | HA |
| 309* |  | electrostatic | TRAS | V37E_M100D | TRAS | Q89R_F98W | FLAG | TRAS | WT | HA |
| 54 |  | electrostatic | TRAS | WT | TRAS | WT | FLAG | TRAS | Q38E | HA |
| 65 |  | electrostatic | TRAS | K145T_Q179D_S188L | TRAS | Q160K_T178R | HA | TRAS | Q124E_Q160E_T178D | FLAG |
| 19 |  | steric | TRAS | S188L_V190Y | TRAS | V133S | HA | TRAS | S176L | FLAG |
| 107 |  | steric | TRAS | A139G_V190A | TRAS | L135W | HA | TRAS | F116A_L135A | FLAG |
| 51 |  | electrostatic | TRAS | Q39E | TRAS | Q38E | HA | TRAS | Q38R | FLAG |
| 310* |  | electrostatic | TRAS | WT | TRAS | WT | HA | TRAS | Q89R_F98W | FLAG |
| 311* |  | electrostatic | TRAS | WT | TRAS | WT | HA | TRAS | Q89R_F98T | FLAG |
| 53 |  | electrostatic | TRAS | Q39R | TRAS | Q38E | HA | TRAS | WT | FLAG |
| 312* |  | steric | TRAS | WT | TRAS | WT | HA | TRAS | F98A | FLAG |
|  | B |  | TRAS |  | TRAS |  | FLAG | D3H44 |  | HA |
|  | C |  | TRAS |  | TRAS |  | HA | D3H44 |  | FLAG |
| 67 |  | electrostatic | TRAS | K145T_Q179D_S188F | TRAS | V133A_Q160K_T178R | FLAG | D3H44 | Q124E_V133W_Q160E_T180E | HA |
| 58 |  | electrostatic | TRAS | L143E_K145T | TRAS | Q124R | FLAG | D3H44 | Q124E_V133D | HA |
| 66 |  | electrostatic | TRAS | L143A_D146G_Q179R | TRAS | Q124E_V133W_Q160E_T180E | FLAG | D3H44 | V133A_Q160K_T178R | HA |
| 304* |  | combination (steric + electrostatic) | TRAS | A139W_S186K | TRAS | F116A_Q124E_L135A_T180E | FLAG | D3H44 | L135W | HA |
| 165 |  | combination (steric + electrostatic) | TRAS | A139W | TRAS | F116A_L135A | FLAG | D3H44 | S131R_L135W | HA |
| 307* |  | combination (steric + electrostatic) | TRAS | Q39R | TRAS | Q38E | FLAG | D3H44 | F98A | HA |
| 26 |  | combination (steric + electrostatic) | TRAS | V37W_Q39E | TRAS | Q38R_F98A | FLAG | D3H44 | Q38E_F98W | HA |
| 313* |  | steric | TRAS | V37W | TRAS | F98A | FLAG | D3H44 | P44W | HA |
| 306* |  | combination (steric + electrostatic) | TRAS | A139G_K145T_D146G_Q179E_V190A | TRAS | L135W | HA | D3H44 | F116A_Q124E_L135A_T180E | FLAG |
| 57 |  | electrostatic | TRAS | L143K_D146G | TRAS | Q124E_V133D | HA | D3H44 | Q124R | FLAG |
| 93 |  | combination (steric + electrostatic) | TRAS | Q39R | TRAS | Q38E_F98W | HA | D3H44 | Q38R_F98A | FLAG |
| 3 |  | steric | TRAS | F174V_P175S_S188G | TRAS | S176L | FLAG | D3H44 | V133S | HA |
| 108 |  | steric | TRAS | A139W | TRAS | F116A_L135A | FLAG | D3H44 | L135W | HA |
| 314* |  | combination (steric + electrostatic) | TRAS | A139V_K145L_Q179E_S188G_V190S | TRAS | F116A_S131K_V133G_S176F_T178A | FLAG | D3H44 | F118W_V133S_S176A_T180E | HA |
| 164 |  | combination (steric + electrostatic) | TRAS | A139G_K145L_Q179E_V190A | TRAS | S131R_L135W | FLAG | D3H44 | F116A_L135A | HA |

TABLE 16-continued

| | | | | | | | | | | |
|---|---|---|---|---|---|---|---|---|---|---|
| 72 | | electrostatic | TRAS | D146G_Q179R | TRAS | Q124E_Q160E_T178D | FLAG | D3H44 | Q160K_T178R | HA |
| 315* | | combination (steric + electrostatic) | TRAS | A139W_S186K_S188A | TRAS | F118W_V133S_S176A_T180E | FLAG | D3H44 | F116A_S131K_V133G_S176F_T178A | HA |
| 51 | | electrostatic | TRAS | Q39R | TRAS | Q38E | FLAG | D3H44 | Q38R | HA |
| 309* | | electrostatic | TRAS | V37E_M100D | TRAS | Q89R_F98W | FLAG | D3H44 | WT | HA |
| 316* | | electrostatic | TRAS | V37E | TRAS | Q89R_F98T | FLAG | D3H44 | WT | HA |
| 317* | | electrostatic | TRAS | V37S_S93K | TRAS | F98Y | FLAG | D3H44 | L89R_F98W | HA |
| 318* | | electrostatic | TRAS | V37E_M100D | TRAS | Q89R_F98W | FLAG | D3H44 | F98Y | HA |
| 19 | | steric | TRAS | S188L_V190Y | TRAS | V133S | HA | D3H44 | S176L | FLAG |
| 107 | | steric | TRAS | A139G_V190A | TRAS | L135W | HA | D3H44 | F116A_L135A | FLAG |
| 102 | | electrostatic | TRAS | WT | TRAS | WT | HA | D3H44 | L89R_F98T | FLAG |
| | D | | PERT | | TRAS | | FLAG | TRAS | | HA |
| 58 | | electrostatic | PERT | L143E_K145T | PERT | Q124R | FLAG | TRAS | Q124E_V133D | HA |
| 304* | | combination (steric + electrostatic) | PERT | A139W_S186K | PERT | F116A_Q124E_L135A_T180E | FLAG | TRAS | L135W | HA |
| 26 | | combination (steric + electrostatic) | PERT | V37W_Q39E | PERT | Q38R_F98A | FLAG | TRAS | Q38E_F98W | HA |
| 72 | | electrostatic | PERT | D146G_Q179R | PERT | Q124E_Q160E_T178D | FLAG | TRAS | Q160K_T178R | HA |
| 3 | | steric | PERT | F174V_P175S_S188G | PERT | S176L | FLAG | TRAS | V133S | HA |
| 108 | | steric | PERT | A139W | PERT | F116A_L135A | FLAG | TRAS | L135W | HA |
| 308* | | steric | PERT | L124W | PERT | F118A | FLAG | TRAS | WT | HA |
| 52 | | electrostatic | PERT | Q39E | PERT | Q38R | FLAG | TRAS | Q38E | HA |
| 319* | | electrostatic | PERT | V37E_F100D | PERT | Q89R_F98W | FLAG | TRAS | WT | HA |
| | E | | PERT | | PERT | | FLAG | PERT | | HA |
| 72 | | electrostatic | PERT | D146G_Q179R | PERT | Q124E_Q160E_T178D | FLAG | PERT | Q160K_T178R | HA |
| 58 | | electrostatic | PERT | L143E_K145T | PERT | Q124R | FLAG | PERT | Q124E_V133D | HA |
| 3 | | steric | PERT | F174V_P175S_S188G | PERT | S176L | FLAG | PERT | V133S | HA |
| 304* | | combination (steric + electrostatic) | PERT | A139W_S186K | PERT | F116A_Q124E_L135A_T180E | FLAG | PERT | L135W | HA |
| 308* | | steric | PERT | L124W | PERT | F118A | FLAG | PERT | WT | HA |
| 52 | | electrostatic | PERT | Q39E | PERT | Q38R | FLAG | PERT | Q38E | HA |
| 319* | | electrostatic | PERT | V37E_F100D | PERT | Q89R_F98W | FLAG | PERT | WT | HA |
| 305* | | combination (steric + electrostatic) | PERT | V37W | PERT | F98A | FLAG | PERT | Q38E | HA |
| 26 | | combination (steric + electrostatic) | PERT | V37W_Q39E | PERT | Q38R_F98A | FLAG | PERT | Q38E_F98W | HA |
| 65 | | electrostatic | PERT | K145T_Q179D_S188L | PERT | Q160K_T178R | HA | PERT | Q124E_Q160E_T178D | FLAG |
| 57 | | electrostatic | PERT | L143K_D146G | PERT | Q124E_V133D | HA | PERT | Q124R | FLAG |
| 107 | | steric | PERT | A139G_V190A | PERT | L135W | HA | PERT | F116A_L135A | FLAG |
| 306* | | combination (steric + electrostatic) | PERT | A139G_K145T_D146G_Q179E_V190A | PERT | L135W | HA | PERT | F116A_Q124E_L135A_T180E | FLAG |
| 51 | | electrostatic | PERT | Q39R | PERT | Q38E | HA | PERT | Q38R | FLAG |
| 310* | | electrostatic | PERT | WT | PERT | WT | HA | PERT | Q89R_F98W | FLAG |
| 311* | | electrostatic | PERT | WT | PERT | WT | HA | PERT | Q89R_F98T | FLAG |
| 307* | | combination (steric + electrostatic) | PERT | Q39R | PERT | Q38E | HA | PERT | F98A | FLAG |
| 53 | | electrostatic | PERT | Q39R | PERT | Q38E | HA | PERT | WT | FLAG |
| 312* | | steric | PERT | WT | PERT | WT | HA | PERT | F98A | FLAG |
| 93 | | combination (steric + electrostatic) | PERT | Q39R | PERT | Q38E_F98W | HA | PERT | Q38R_F98A | FLAG |
| 108 | | steric | PERT | A139W | PERT | F116A_L135A | FLAG | PERT | L135W | HA |
| 19 | | steric | PERT | S188L_V190Y | PERT | V133S | HA | PERT | S176L | FLAG |
| 320* | | steric | PERT | L124S | PERT | WT | HA | PERT | F118A | FLAG |
| | F | | PERT | | PERT | | FLAG | D3H44 | | HA |
| | G | | PERT | | PERT | | HA | D3H44 | | FLAG |
| 58 | | electrostatic | PERT | L143E_K145T | PERT | Q124R | FLAG | D3H44 | Q124E_V133D | HA |
| 3 | | steric | PERT | F174V_P175S_S188G | PERT | S176L | FLAG | D3H44 | V133S | HA |
| 108 | | steric | PERT | A139W | PERT | F116A_L135A | FLAG | D3H44 | L135W | HA |
| 66 | | electrostatic | PERT | L143A_D146G_Q179R | PERT | Q124E_V133W_Q160E_T180E | FLAG | D3H44 | V133A_Q160K_T178R | HA |
| 304* | | combination (steric + electrostatic) | PERT | A139W_S186K | PERT | F116A_Q124E_L135A_T180E | FLAG | D3H44 | L135W | HA |

TABLE 16-continued

| # | | type | | H chain A mutations | | H chain B mutations | H chain A tag | | H chain C mutations | H chain C tag |
|---|---|---|---|---|---|---|---|---|---|---|
| 315* | | combination (steric + electrostatic) | PERT | A139W_S186K_S188A | PERT | F118W_V133S_S176A_T180E | FLAG | D3H44 | F116A_S131K_V133G_S176F_T178A | HA |
| 165 | | combination (steric + electrostatic) | PERT | A139W | PERT | F116A_L135A | FLAG | D3H44 | S131R_L135W | HA |
| 51 | | electrostatic | PERT | Q39R | PERT | Q38E | FLAG | D3H44 | Q38R | HA |
| 307* | | combination (steric + electrostatic) | PERT | Q39R | PERT | Q38E | FLAG | D3H44 | F98A | HA |
| 26 | | combination (steric + electrostatic) | PERT | V37W_Q39E | PERT | Q38R_F98A | FLAG | D3H44 | Q38E_F98W | HA |
| 65 | | electrostatic | PERT | K145T_Q179D_S188L | PERT | Q160K_T178R | HA | D3H44 | Q124E_Q160E_T178D | FLAG |
| 306* | | combination (steric + electrostatic) | PERT | A139G_K145T_D146G_Q179E_V190A | PERT | L135W | HA | D3H44 | F116A_Q124E_L135A_T180E | FLAG |
| 57 | | electrostatic | PERT | L143K_D146G | PERT | Q124E_V133D | HA | D3H44 | Q124R | FLAG |
| 93 | | combination (steric + electrostatic) | PERT | Q39R | PERT | Q38E_F98W | HA | D3H44 | Q38R_F98A | FLAG |
| 314* | | combination (steric + electrostatic) | PERT | A139V_K145L_Q179E_S188G_V190S | PERT | F116A_S131K_V133G_S176F_T178A | FLAG | D3H44 | F118W_V133S_S176A_T180E | HA |
| 72 | | electrostatic | PERT | D146G_Q179R | PERT | Q124E_Q160E_T178D | FLAG | D3H44 | Q160K_T178R | HA |
| 53 | | electrostatic | PERT | Q39R | PERT | Q38E | FLAG | D3H44 | WT | HA |
| 321* | | steric | PERT | V37W_L45W | PERT | Y87A_F98A | FLAG | D3H44 | Y87W_G101I | HA |
| 52 | | electrostatic | PERT | Q39E | PERT | Q38E | FLAG | D3H44 | Q38E | HA |
| 48 | | electrostatic | PERT | WT | PERT | WT | FLAG | D3H44 | L89R_F98W | HA |
| 322* | | steric | PERT | L45A | PERT | Y87W_G101I | FLAG | D3H44 | Y87A_F98A | HA |
| 323* | | steric | PERT | W103V | PERT | P44W_Q89W_F98A | FLAG | D3H44 | F98A | HA |
| 19 | | steric | PERT | S188L_V190Y | PERT | V133S | HA | D3H44 | S176L | FLAG |
| 107 | | steric | PERT | A139G_V190A | PERT | L135W | HA | D3H44 | F116A_L135A | FLAG |
| 320* | | steric | PERT | L124S | PERT | WT | HA | D3H44 | F118A | FLAG |
| 102 | | electrostatic | PERT | WT | PERT | WT | HA | D3H44 | L89R_F98T | FLAG |
|  | H |  | D3H44 |  | D3H44 |  | FLAG |

TABLE 16-continued

| Unique identifier | Presence of H-L disulfide bond (C233-C214) (y/n) | Observed Trends for REF_WT | Number of screening experiments | H1-L1:H1-L2 | Normalized Median H1-L1:H1-L2 | H1-L1:H1-L2 Scalar (Median) | REF_WT for VAR | REF_WT H1-L1:H1-L2 | Normalized Median REF_WT H1-L1:H1-L2 Scalar (Median) | Δ(VAR-(REF_WT)) H1-L1:H1-L2 Scalar |
|---|---|---|---|---|---|---|---|---|---|---|
|  | n | Apparent tag dependence. Likely similar issue with HA-tag as with PERT system, but to a lesser extent | 6 | 66:34_57:36_ 66:43_54:36_ 58:43_58:43 | 61:39 | 0.4295 | N/A | N/A | N/A | N/A |
| 58 | n |  | 2 | 104:1_77:2 | 99:01 | 4.288 | A | 61:39 | 0.4295 | 3.86 |
| 304* | n |  | 2 | 103:1_92:1 | 99:01 | 4.548 | A | 61:39 | 0.4295 | 4.12 |
| 305* | n |  | 2 | 73:17_73:20 | 80:20 | 1.402 | A | 61:39 | 0.4295 | 0.97 |
| 26 | n |  | 2 | 87:1_79:1 | 99:01 | 4.423 | A | 61:39 | 0.4295 | 3.99 |
| 57 | n |  | 2 | 89:1_89:1 | 99:01 | 4.488 | A | 39:61 | −0.4295 | 4.92 |
| 306* | n |  | 2 | 76:1_69:2 | 98:02 | 3.797 | A | 39:61 | −0.4295 | 4.23 |
| 307* | n |  | 2 | 92:1_74:2 | 98:02 | 4.1395 | A | 39:61 | −0.4295 | 4.57 |
| 93 | n |  | 2 | 103:1_73:1 | 99:01 | 4.4615 | A | 39:61 | −0.4295 | 4.89 |
| 72 | n |  | 1 | 66:13 | 84:16 | 1.644 | A | 61:39 | 0.4295 | 1.21 |
| 3 | n |  | 1 | 92:02 | 98:02 | 4.016 | A | 61:39 | 0.4295 | 3.59 |
| 108 | n |  | 1 | 70:14 | 83:17 | 1.584 | A | 61:39 | 0.4295 | 1.15 |
| 308* | n |  | 1 | 66:28 | 70:30 | 0.864 | A | 61:39 | 0.4295 | 0.43 |
| 52 | n |  | 1 | 73:18 | 80:20 | 1.413 | A | 61:39 | 0.4295 | 0.98 |
| 309* | n |  | 1 | 78:17 | 82:18 | 1.499 | A | 61:39 | 0.4295 | 1.07 |
| 54 | n |  | 1 | 63:15 | 81:19 | 1.459 | A | 61:39 | 0.4295 | 1.03 |
| 65 | n |  | 1 | 56:33 | 63:37 | 0.529 | A | 39:61 | −0.4295 | 0.96 |
| 19 | n |  | 1 | 59:35 | 63:37 | 0.527 | A | 39:61 | −0.4295 | 0.96 |
| 107 | n |  | 1 | 58:19 | 75:25 | 1.122 | A | 39:61 | −0.4295 | 1.55 |
| 51 | n |  | 1 | 55:35 | 61:39 | 0.451 | A | 39:61 | −0.4295 | 0.88 |
| 310* | n |  | 1 | 87:06 | 94:06 | 2.7 | A | 39:61 | −0.4295 | 3.13 |
| 311* | n |  | 1 | 92:01 | 99:01 | 4.52 | A | 39:61 | −0.4295 | 4.95 |
| 53 | n |  | 1 | 59:32 | 65:35 | 0.613 | A | 39:61 | −0.4295 | 1.04 |
| 312* | n |  | 1 | 84:05 | 94:06 | 2.814 | A | 39:61 | −0.4295 | 3.24 |
|  | n | Preference of H_TRAS for L_TRAS over L_D3H44 | 5 | 70:16_84:21_ 84:21_72:44_ 66:50 | 80:20 | 1.369 | N/A | N/A | N/A | N/A |
|  | n |  | 5 | 107:15_107:18_ 86:17_89:18_ 61:19 | 84:16 | 1.622 | N/A | N/A | N/A | N/A |
| 67 | n |  | 2 | 115:1_104:1 | 99:01 | 4.6925 | B | 80:20 | 1.369 | 3.32 |
| 58 | n |  | 2 | 105:1_94:1 | 99:01 | 4.5975 | B | 80:20 | 1.369 | 3.23 |
| 66 | n |  | 2 | 102:1_83:2 | 99:01 | 4.246 | B | 80:20 | 1.369 | 2.88 |
| 304* | n |  | 2 | 98:1_68:1 | 99:01 | 4.3965 | B | 80:20 | 1.369 | 3.03 |
| 165 | n |  | 2 | 103:1_83:1 | 99:01 | 4.5225 | B | 80:20 | 1.369 | 3.15 |
| 307* | n |  | 2 | 102:2_73:9 | 96:04 | 3.0565 | B | 80:20 | 1.369 | 1.69 |
| 26 | n |  | 2 | 91:2_87:1 | 95:05 | 2.9825 | B | 80:20 | 1.369 | 1.61 |
| 313* | n |  | 2 | 92:3_91:11 | 94:06 | 2.801 | B | 80:20 | 1.369 | 1.43 |
| 306* | n |  | 2 | 108:1_90:1 | 99:01 | 4.59 | C | 84:16 | 1.622 | 2.97 |
| 57 | n |  | 2 | 104:1_88:1 | 99:01 | 4.56 | C | 84:16 | 1.622 | 2.94 |
| 93 | n |  | 2 | 96:1_87:1 | 99:01 | 4.5175 | C | 84:16 | 1.622 | 2.9 |
| 3 | n |  | 1 | 77:02 | 97:03 | 3.499 | B | 80:20 | 1.369 | 2.13 |
| 108 | n |  | 1 | 80:01 | 99:01 | 4.377 | B | 80:20 | 1.369 | 3.01 |
| 314* | n |  | 1 | 88:01 | 99:01 | 4.477 | B | 80:20 | 1.369 | 3.11 |
| 164 | n |  | 1 | 84:01 | 99:01 | 4.426 | B | 80:20 | 1.369 | 3.06 |
| 72 | n |  | 1 | 72:01 | 99:01 | 4.275 | B | 80:20 | 1.369 | 2.91 |
| 315* | n |  | 1 | 107:03 | 97:03 | 3.426 | B | 80:20 | 1.369 | 2.06 |
| 51 | n |  | 1 | 73:12 | 86:14 | 1.825 | B | 80:20 | 1.369 | 0.46 |
| 309* | n |  | 1 | 110:05 | 95:05 | 3.009 | B | 80:20 | 1.369 | 1.64 |
| 316* | n |  | 1 | 97:10 | 91:09 | 2.278 | B | 80:20 | 1.369 | 0.91 |
| 317* | n |  | 1 | 72:12 | 86:14 | 1.791 | B | 80:20 | 1.369 | 0.42 |
| 318* | n |  | 1 | 99:07 | 94:06 | 2.689 | B | 80:20 | 1.369 | 1.32 |
| 19 | n |  | 1 | 92:13 | 87:13 | 1.943 | C | 84:16 | 1.622 | 0.32 |
| 107 | n |  | 1 | 86:02 | 98:02 | 4.053 | C | 84:16 | 1.622 | 2.43 |
| 102 | n |  | 1 | 111:01 | 99:01 | 4.708 | C | 84:16 | 1.622 | 3.09 |
|  | n | Likely no preference of H_PERT for L_PERT over L_TRAS | 5 | 68:43_66:42_ 55:56_56:58_ 48:60 | 49:51 | −0.026 | N/A | N/A | N/A | N/A |
| 58 | n |  | 2 | 84:5_70:23 | 88:12 | 1.981 | D | 49:51 | −0.026 | 2.01 |
| 304* | n |  | 2 | 77:22_75:23 | 77:23 | 1.221 | D | 49:51 | −0.026 | 1.25 |
| 26 | n |  | 2 | 82:10_79:12 | 88:12 | 1.9955 | D | 49:51 | −0.026 | 2.02 |

TABLE 16-continued

| | | | | | | | | | | |
|---|---|---|---|---|---|---|---|---|---|---|
| 72 | n | | 1 | 83:13 | 87:13 | 1.891 | D | 49:51 | −0.026 | 1.92 |
| 3 | n | | 1 | 72:12 | 86:14 | 1.794 | D | 49:51 | −0.026 | 1.82 |
| 108 | n | | 1 | 78:32 | 71:29 | 0.897 | D | 49:51 | −0.026 | 0.92 |
| 308* | n | | 1 | 62:36 | 64:36 | 0.557 | D | 49:51 | −0.026 | 0.58 |
| 52 | n | | 1 | 62:35 | 64:36 | 0.573 | D | 49:51 | −0.026 | 0.6 |
| 319* | n | | 1 | 92.01 | 99:01 | 4.524 | D | 49:51 | −0.026 | 4.55 |
| | n | Apparent tag dependence observed. Observed ratios are likely due to HA-tag cleavage rather than tag interference with pairing | 10 | 81:20_79:20_ 70:29_78:34_ 78:47_57:35_ 56:36_65:53_ 65:53_53:50 | 62:38 | 0.4975 | N/A | N/A | N/A | N/A |
| 72 | n | | 2 | 101:1_79:8 | 97:03 | 3.477 | E | 62:38 | 0.4975 | 2.98 |
| 58 | n | | 2 | 99:1_97:1 | 99:01 | 4.4065 | E | 62:38 | 0.4975 | 3.91 |
| 3 | n | | 2 | 102:1_94:1 | 99:01 | 4.585 | E | 62:38 | 0.4975 | 4.09 |
| 304* | n | | 2 | 97:1_101:3 | 98:02 | 3.981 | E | 62:38 | 0.4975 | 3.48 |
| 308* | n | | 2 | 72:21_69:23 | 76:24 | 1.17 | E | 62:38 | 0.4975 | 0.67 |
| 52 | n | | 2 | 82:8_96:10 | 91:09 | 2.323 | E | 62:38 | 0.4975 | 1.83 |
| 319* | n | | 2 | 76:1_94:2 | 98:02 | 4.0915 | E | 62:38 | 0.4975 | 3.59 |
| 305* | n | | 2 | 90:9_79:17 | 87:13 | 1.9365 | E | 62:38 | 0.4975 | 1.44 |
| 26 | n | | 2 | 101:1_98:1 | 99:01 | 4.6015 | E | 62:38 | 0.4975 | 4.1 |
| 65 | n | | 2 | 97:8_73:13 | 89:11 | 2.106 | E | 38:62 | −0.4975 | 2.6 |
| 57 | n | | 2 | 110:1_94:1 | 99:01 | 4.6195 | E | 38:62 | −0.4975 | 5.12 |
| 107 | n | | 2 | 92:3_78:2 | 97:03 | 3.546 | E | 38:62 | −0.4975 | 4.04 |
| 306* | n | | 2 | 102:1_96:1 | 99:01 | 4.5905 | E | 38:62 | −0.4975 | 5.09 |
| 51 | n | | 2 | 125:6_75:15 | 91:09 | 2.312 | E | 38:62 | −0.4975 | 2.81 |
| 310* | n | | 2 | 110:9_75:13 | 89:11 | 2.1055 | E | 38:62 | −0.4975 | 2.6 |
| 311* | n | | 2 | 126:2_88:3 | 98:02 | 3.7895 | E | 38:62 | −0.4975 | 4.29 |
| 307* | n | | 2 | 124:1_95:1 | 99:01 | 4.688 | E | 38:62 | −0.4975 | 5.19 |
| 53 | n | | 2 | 112:8_70:33 | 85:15 | 1.7115 | E | 38:62 | −0.4975 | 2.21 |
| 312* | n | | 2 | 105:20_66:35 | 76:24 | 1.146 | E | 38:62 | −0.4975 | 1.64 |
| 93 | n | | 2 | 103:1_82:1 | 99:01 | 4.522 | E | 38:62 | −0.4975 | 5.02 |
| 108 | n | | 1 | 63:27 | 70:30 | 0.857 | E | 62:38 | 0.4975 | 0.36 |
| 19 | n | | 2 | 81:45_60:41 | 62:38 | 0.472 | E | 38:62 | −0.4975 | 0.97 |
| 320* | n | | 2 | 53:34_63:44 | 60:40 | 0.405 | E | 38:62 | −0.4975 | 0.9 |
| | n | Preference of H_PERT for L_PERT over L_D3H44 | 7 | 106:1_104:1_ 123:2_105:6_ 126:9_102:7_ 113:15 | 94:06 | 2.804 | N/A | N/A | N/A | N/A |
| | n | | 5 | 98:26_68:23_ 68:25_65:44_ 67:46 | 73:27 | 0.998 | N/A | N/A | N/A | N/A |
| 58 | n | | 2 | 112:1_99:10 | 97:03 | 3.515 | F | 94:06 | 2.804 | 0.71 |
| 3 | n | | 6 | 111:1_105:1_ 104:1_97:1_ 94:1_90:1 | 99:01 | 4.6135 | F | 94:06 | 2.804 | 1.81 |
| 108 | n | | 6 | 96:1_92:1_ 103:1_109:2_ 113:3_102:3 | 99:01 | 4.2365 | F | 94:06 | 2.804 | 1.43 |
| 66 | n | | 2 | 117:1_110:1 | 99:01 | 4.731 | F | 94:06 | 2.804 | 1.93 |
| 304* | n | | 2 | 106:1_84:1 | 99:01 | 4.55 | F | 94:06 | 2.804 | 1.75 |
| 315* | n | | 2 | 111:1_115:25 | 96:04 | 3.12 | F | 94:06 | 2.804 | 0.32 |
| 165 | n | | 2 | 109:1_109:12 | 97:03 | 3.46 | F | 94:06 | 2.804 | 0.66 |
| 51 | n | | 6 | 106:1_106:2_ 98:2_97:2_ 110:3_97:3 | 98:02 | 3.7925 | F | 94:06 | 2.804 | 0.99 |
| 307* | n | | 6 | 113:1_97:1_ 83:1_108:2_ 100:2_115:2 | 99:01 | 4.2825 | F | 94:06 | 2.804 | 1.48 |
| 26 | n | | 2 | 101:1_84:1 | 99:01 | 4.4435 | F | 94:06 | 2.804 | 1.64 |
| 65 | n | | 2 | 98:1_63:1 | 99:01 | 4.3665 | G | 73:27 | 0.998 | 3.37 |
| 306* | n | | 2 | 119:1_112:1 | 99:01 | 4.7495 | G | 73:27 | 0.998 | 3.75 |
| 57 | n | | 2 | 125:1_107:1 | 99:01 | 4.7505 | G | 73:27 | 0.998 | 3.75 |
| 93 | n | | 2 | 89:1_88:6 | 97:03 | 3.5745 | G | 73:27 | 0.998 | 2.58 |
| 314* | n | | 1 | 108:01 | 99:01 | 4.684 | F | 94:06 | 2.804 | 1.88 |
| 72 | n | | 1 | 95:01 | 99:01 | 4.328 | F | 94:06 | 2.804 | 1.52 |
| 53 | n | | 1 | 116:02 | 98:02 | 3.927 | F | 94:06 | 2.804 | 1.12 |
| 321* | n | | 1 | 90:03 | 97:03 | 3.496 | F | 94:06 | 2.804 | 0.69 |
| 52 | n | | 1 | 105:01 | 99:01 | 4.654 | F | 94:06 | 2.804 | 1.85 |
| 48 | n | | 1 | 112:01 | 99:01 | 4.336 | F | 94:06 | 2.804 | 1.53 |
| 322* | n | | 1 | 97:01 | 99:01 | 4.575 | F | 94:06 | 2.804 | 1.77 |
| 323* | n | | 1 | 71:01 | 99:01 | 4.267 | F | 94:06 | 2.804 | 1.46 |
| 19 | n | | 1 | 101:15 | 87:13 | 1.927 | G | 73:27 | 0.998 | 0.93 |
| 107 | n | | 1 | 102:01 | 99:01 | 4.623 | G | 73:27 | 0.998 | 3.63 |

TABLE 16-continued

| | | | | | | | | | | |
|---|---|---|---|---|---|---|---|---|---|---|
| 320* | n | | 1 | 79:06 | 93:07 | 2.573 | G | 73:27 | 0.998 | 1.58 |
| 102 | n | | 1 | 113:03 | 97:03 | 3.52 | G | 73:27 | 0.998 | 2.52 |
| | n | Preference of H_D3H44 for L_TRAS over L_D3H44 | 5 | 36:59_36:59_ 35:86_31:87_ 20:67 | 29:71 | −0.894 | N/A | N/A | N/A | N/A |
| | n | | 5 | 50:58_49:61_ 34:68_21:71_ 21:76 | 33:67 | −0.701 | N/A | N/A | N/A | N/A |
| 57 | n | | 2 | 100:1_85:4 | 98:02 | 3.832 | I | 33:67 | −0.701 | 4.53 |
| 72 | n | | 1 | 67:36 | 65:35 | 0.633 | H | 29:71 | −0.894 | 1.53 |
| 66 | n | | 1 | 92:20 | 82:18 | 1.549 | I | 33:67 | −0.701 | 2.25 |
| 182 | n | | 1 | 83:03 | 97:03 | 3.41 | I | 33:67 | −0.701 | 4.11 |
| 47 | n | | 1 | 84:02 | 97:03 | 3.55 | I | 33:67 | −0.701 | 4.25 |
| 324* | n | | 1 | 77:25 | 75:25 | 1.116 | I | 33:67 | −0.701 | 1.82 |
| | n | Inconsistency in observed ratios of H_D3H44 towards FLAG_L_ D3H44 or HA_L_PERT likely due to HA-tag issue, as preference of H_D3H44 for FLAG_L_PERT over HA_L_D3H44 is consistent | 5 | 92:4_88:8_ 58:52_43:60_ 47:70 | 53:47 | 0.119 | N/A | N/A | N/A | N/A |
| | n | | 7 | 34:65_29:70_ 27:67_29:73_ 27:73_2:101_ 1:98 | 29:71 | −0.909 | N/A | N/A | N/A | N/A |
| 26 | n | | 2 | 96:1_69:32 | 94:06 | 2.673 | J | 53:47 | 0.119 | 2.55 |
| 66 | n | | 2 | 82:4_92:24 | 90:10 | 2.164 | K | 29:71 | −0.909 | 3.07 |
| 57 | n | | 2 | 90:3_85:4 | 96:04 | 3.1675 | K | 29:71 | −0.909 | 4.08 |
| 165 | n | | 2 | 97:4_58:30 | 87:13 | 1.8885 | K | 29:71 | −0.909 | 2.8 |
| 313* | n | | 2 | 108:1_82:27 | 94:06 | 2.7655 | K | 29:71 | −0.909 | 3.67 |
| 305* | n | | 6 | 102:3_99:3_ 101:4_121:5_ 110:10_85:24 | 96:04 | 3.2045 | K | 29:71 | −0.909 | 4.11 |
| 93 | n | | 2 | 76:24_70:31 | 73:27 | 0.9895 | K | 29:71 | −0.909 | 1.9 |
| 307* | n | | 2 | 80:34_70:33 | 69:31 | 0.799 | K | 29:71 | −0.909 | 1.71 |
| 310* | n | | 1 | 74:39 | 65:35 | 0.638 | K | 29:71 | −0.909 | 1.55 |
| 311* | n | | 1 | 75:25 | 75:25 | 1.109 | K | 29:71 | −0.909 | 2.02 |
| 182 | n | | 1 | 74:03 | 96:04 | 3.093 | K | 29:71 | −0.909 | 4 |
| 325* | n | | 6 | 74:24_84:29_ 74:26_78:32 78:36_66:51 | 73:27 | 0.979 | K | 29:71 | −0.909 | 1.89 |
| 47 | n | | 1 | 82:02 | 97:03 | 3.519 | K | 29:71 | −0.909 | 4.43 |
| 324* | n | | 1 | 92:17 | 84:16 | 1.675 | K | 29:71 | −0.909 | 2.58 |

TABLE 17

| Unique identifier set | REF_WT or VAR1 | REF_WT or VAR2 | Design Type | H1_Ab | H1_mutation | L1_Ab |
|---|---|---|---|---|---|---|
| 58-57 | | | electrostatic | PERT | L143E_K145T | PERT |
| 3-19 | | | steric | PERT | F174V_P175S_S188G | PERT |
| 108-107 | | | steric | PERT | A139W | PERT |
| 308*-320* | | | steric | PERT | L124W | PERT |
| 319*-310* | | | electrostatic | PERT | V37E_F100D | PERT |
| 26-93 | | | combination (steric + electrostatic) | PERT | V37W_Q39E | PERT |
| 65-72 | | | electrostatic | PERT | K145T_Q179D_S188L | PERT |
| 306*-304* | | | combination (steric + electrostatic) | PERT | A139G_K145T_D146G_ Q179E_V190A | PERT |
| 51-52 | | | electrostatic | PERT | Q39R | PERT |
| 307*-305* | | | combination (steric + electrostatic) | PERT | Q39R | PERT |
| 58-57 | | | electrostatic | TRAS | L143E_K145T | TRAS |
| 3-19 | | | steric | TRAS | F174V_P175S_S188G | TRAS |
| 108-107 | | | steric | TRAS | A139W | TRAS |
| 309*-310* | | | electrostatic | TRAS | V37E_M100D | TRAS |
| 26-93 | | | combination (steric + electrostatic) | TRAS | V37W_Q39E | TRAS |

TABLE 17-continued

| Unique identifier set | | | | | | | |
|---|---|---|---|---|---|---|---|
| 65-72 | | | electrostatic | TRAS | K145T_Q179D_S188L | | TRAS |
| 306*-304* | | | combination (steric + electrostatic) | TRAS | A139G_K145T_D146G_Q179E_V190A | | TRAS |
| 51-52 | | | electrostatic | TRAS | Q39R | | TRAS |
| 307*-305* | | | combination (steric + electrostatic) | TRAS | Q39R | | TRAS |
| 53-54 | | | electrostatic | TRAS | Q39R | | TRAS |
| | I | B | N/A | D3H44 | | | D3H44 |
| 66-67 | | | electrostatic | D3H44 | L143A_D146G_Q179R | | D3H44 |
| 57-58 | | | electrostatic | D3H44 | L143K_D146G | | D3H44 |
| 182-317* | | | electrostatic | D3H44 | V37E_F100D | | D3H44 |
| | K | F | N/A | D3H44 | | | D3H44 |
| 57-58 | | | electrostatic | D3H44 | L143K_D146G | | D3H44 |
| 305*-307* | | | combination (steric + electrostatic) | D3H44 | V37W | | D3H44 |
| 93-26 | | | combination (steric + electrostatic) | D3H44 | Q39R | | D3H44 |
| 48-47 | | | electrostatic | PERT | WT | | PERT |
| 323*-324* | | | steric | PERT | W103V | | PERT |
| | J | G | N/A | D3H44 | | | D3H44 |
| 93-26 | | | combination (steric + electrostatic) | PERT | Q39R | | PERT |

| Unique identifier set | L1_mutation | L1_tag | H2_Ab | H2_mutation | L2_Ab | L2_mutation | L2_tag | Presence of H-L disulfide bond (C233-C214) (y/n) |
|---|---|---|---|---|---|---|---|---|
| 58-57 | Q124R | FLAG | PERT | L143K_D146G | PERT | Q124E_V133D | HA | n |
| 3-19 | S176L | FLAG | PERT | S188L_V190Y | PERT | V133S | HA | n |
| 108-107 | F116A_L135A | FLAG | PERT | A139G_V190A | PERT | L135W | HA | n |
| 308*-320* | F118A | FLAG | PERT | L124S | PERT | WT | HA | n |
| 319*-310* | Q89R_F98W | FLAG | PERT | WT | PERT | WT | HA | n |
| 26-93 | Q38R_F98A | FLAG | PERT | Q39R | PERT | Q38E_F98W | HA | n |
| 65-72 | Q160K_T178R | HA | PERT | D146G_Q179R | PERT | Q124E_Q160E_T178D | FLAG | n |
| 306*-304* | L135W | HA | PERT | A139W_S186K | PERT | F116A_Q124E_L135A_T180E | FLAG | n |
| 51-52 | Q38E | HA | PERT | Q39E | PERT | Q38R | FLAG | n |
| 307*-305* | Q38E | HA | PERT | V37W | PERT | F98A | FLAG | n |
| 58-57 | Q124R | FLAG | TRAS | L143K_D146G | TRAS | Q124E_V133D | HA | n |
| 3-19 | S176L | FLAG | TRAS | S188L_V190Y | TRAS | V133S | HA | n |
| 108-107 | F116A_L135A | FLAG | TRAS | A139G_V190A | TRAS | L135W | HA | n |
| 309*-310* | Q89R_F98W | FLAG | TRAS | WT | TRAS | WT | HA | n |
| 26-93 | Q38R_F98A | FLAG | TRAS | Q39R | TRAS | Q38E_F98W | HA | n |
| 65-72 | Q160K_T178R | HA | TRAS | D146G_Q179R | TRAS | Q124E_Q160E_T178D | FLAG | n |
| 306*-304* | L135W | HA | TRAS | A139W_S186K | TRAS | F116A_Q124E_L135A_T180E | FLAG | n |
| 51-52 | Q38E | HA | TRAS | Q39E | TRAS | Q38R | FLAG | n |
| 307*-305* | Q38E | HA | TRAS | V37W | TRAS | F98A | FLAG | n |
| 53-54 | Q38E | HA | TRAS | WT | TRAS | WT | FLAG | |
| | | HA | TRAS | | TRAS | | FLAG | n |
| 66-67 | Q124E_V133W_Q160E_T180E | HA | TRAS | K145T_Q179D_S188F | TRAS | V133A_Q160K_T178R | FLAG | n |
| 57-58 | Q124E_V133D | HA | TRAS | L143E_K145T | TRAS | Q124R | FLAG | n |
| 182-317* | L89R_F98W | HA | TRAS | V37S_S93K | TRAS | F98Y | FLAG | n |
| | | HA | PERT | | PERT | | FLAG | n |
| 57-58 | Q124E_V133D | HA | PERT | L143E_K145T | PERT | Q124R | FLAG | n |
| 305*-307* | F98A | HA | PERT | Q39R | PERT | Q38E | FLAG | n |
| 93-26 | Q38E_F98W | HA | PERT | V37W_Q39E | PERT | Q38R_F98A | FLAG | n |
| 48-47 | WT | FLAG | D3H44 | V37E_F100D | D3H44 | L89R_F98W | HA | n |
| 323*-324* | P44W_Q89W_F98A | FLAG | D3H44 | V37W_F100W | D3H44 | F98A | HA | n |
| | | FLAG | PERT | | PERT | | HA | n |
| 93-26 | Q38E_F98W | HA | D3H44 | V37W_Q39E | D3H44 | Q38R_F98A | FLAG | n |

| Unique identifier set | Observed Trends for REF_WTs | H1-L1:H1-L2 | Normalized Median H1-L1: H1-L2 | H1-L1: H1-L2 Scalar (Median) | REF_WT for VAR1 | Normalized Median REF_WT for VAR1 H1-L1: H1-L2 | REF_WT for VAR1 H1-L1: H1-L2 Scalar (Median) | Δ (VAR1-REF_WT) H1-L1: H1-L2 Scalar |
|---|---|---|---|---|---|---|---|---|
| 58-57 | | 99:1_97:1 | 99:01 | 4.4065 | E | 62:38 | 0.4975 | 3.91 |
| 3-19 | | 102:1_94:1 | 99:01 | 4.585 | E | 62:38 | 0.4975 | 4.09 |
| 108-107 | | 63:27 | 70:30 | 0.857 | E | 62:38 | 0.4975 | 0.36 |
| 308*-320* | | 72:21_69:23 | 76:24 | 1.17 | E | 62:38 | 0.4975 | 0.67 |
| 319*-310* | | 76:1_94:2 | 98:02 | 4.0915 | E | 62:38 | 0.4975 | 3.59 |

TABLE 17-continued

| | | | | | | | | |
|---|---|---|---|---|---|---|---|---|
| 26-93 | | 101:1_98:1 | 99:01 | 4.6015 | E | 62:38 | 0.4975 | 4.1 |
| 65-72 | | 97:8_73:13 | 89:11 | 2.106 | E | 38:62 | -0.4975 | 2.6 |
| 306*-304* | | 102:1_96:1 | 99:01 | 4.5905 | E | 38:62 | -0.4975 | 5.09 |
| 51-52 | | 125:6_75:15 | 91:09 | 2.312 | E | 38:62 | -0.4975 | 2.81 |
| 307*-305* | | 124:1_95:1 | 99:01 | 4.688 | E | 38:62 | -0.4975 | 5.19 |
| 58-57 | | 104:1_77:2 | 99:01 | 4.288 | A | 61:39 | 0.4295 | 3.86 |
| 3-19 | | 92:02 | 98:02 | 4.016 | A | 61:39 | 0.4295 | 3.59 |
| 108-107 | | 70:14 | 83:17 | 1.584 | A | 61:39 | 0.4295 | 1.15 |
| 309*-310* | | 78:17 | 82:18 | 1.499 | A | 61:39 | 0.4295 | 1.07 |
| 26-93 | | 87:1_79:1 | 99:01 | 4.423 | A | 61:39 | 0.4295 | 3.99 |
| 65-72 | | 56:33 | 63:37 | 0.529 | A | 39:61 | -0.4295 | 0.96 |
| 306*-304* | | 76:1_69:2 | 98:02 | 3.797 | A | 39:61 | -0.4295 | 4.23 |
| 51-52 | | 55:35 | 61:39 | 0.451 | A | 39:61 | -0.4295 | 0.88 |
| 307*-305* | | 92:1_74:2 | 98:02 | 4.1395 | A | 39:61 | -0.4295 | 4.57 |
| 53-54 | | 59:32 | 65:35 | 0.613 | A | 39:61 | -0.4295 | 1.04 |
| | Preference of H_D3H44 for L_TRAS over L_D3H44 and H_TRANS for L_TRANS over L_D3HH | 50:58_49:61_34:68_21:71_21:76 | 33:67 | -0.701 | N/A | N/A | N/A | N/A |
| 66-67 | | 92:20 | 82:18 | 1.549 | I | 33:67 | -0.701 | 2.25 |
| 57-58 | | 100:1_85:4 | 98:02 | 3.832 | I | 33:67 | -0.701 | 4.53 |
| 182-317* | | 83:03 | 97:03 | 3.41 | I | 33:67 | -0.701 | 4.11 |
| | Preference of H_D3H44 for FLAG_L_PERT over HA_L_D3H44 is consistent (inconsistency in observed ratios of H_D3H44 towards FLAG_L_D3H44 or HA_L_PERT likely due to HA-tag issue). Preference of H_PERT for L_PERT over L_D3H44. | 34:65_29:70_27;67_29:73_ 27:73_2:101_1:98 | 29:71 | -0.909 | N/A | N/A | N/A | N/A |
| 57-58 | | 90:3_85:4 | 96:04 | 3.1675 | K | 29:71 | -0.909 | 4.08 |
| 305*-307* | | 102:3_99:3_101:4_121:5_110:10_85:24 | 96:04 | 3.2045 | K | 29:71 | -0.909 | 4.11 |
| 93-26 | | 76:24_70:31 | 73:27 | 0.9895 | K | 29:71 | -0.909 | 1.9 |
| 48-47 | | 112:01 | 99:01 | 4.336 | F | 94:06 | 2.804 | 1.53 |
| 323*-324* | | 71:01 | 99:01 | 4.267 | F | 94:06 | 2.804 | 1.46 |
| | Inconsistency in observed ratios of H_D3H44 towards FLAG_L_D3H44 or HA_L_PERT likely due to HA-tag issue, as preference of H_D3H44 for FLAG_L_PERT over HA_L_D3H44 is consistent. Preference of H_PERT for L_PERT over L_D3H44. | 92:4_88:8_58:52_43:60_47:70 | 53:47 | 0.119 | N/A | N/A | N/A | N/A |
| 93-26 | | 89:1_88:6 | 97:03 | 3.5745 | G | 73:27 | 0.998 | 2.58 |

| Unique identifier set | H2-L2:H2-L1 | Normalized Median H2-L2:H2-L1 | H2-L2:H2-L1 Scalar (Median) | REF_WT for VAR2 | Normalized Median REF_WT for VAR2 H2-L2:H2-L1 | REF_WT for VAR2 H2-L2:H2-L1 Scalar (Median) | Δ (VAR2-REF_WT) H2-L2:H2-L1 Scalar |
|---|---|---|---|---|---|---|---|
| 58-57 | 110:1_94:1 | 99:01 | 4.6195 | E | 38:62 | -0.4975 | 5.12 |
| 3-19 | 81:45_60:41 | 62:38 | 0.472 | E | 38:62 | -0.4975 | 0.97 |
| 108-107 | 92:3_78:2 | 97:03 | 3.546 | E | 38:62 | -0.4975 | 4.04 |
| 308*-320* | 53:34_63:44 | 60:40 | 0.405 | E | 38:62 | -0.4975 | 0.9 |
| 319*-310* | 110:9_75:13 | 89:11 | 2.1055 | E | 38:62 | -0.4975 | 2.6 |
| 26-93 | 103:1_82:1 | 99:01 | 4.522 | E | 38:62 | -0.4975 | 5.02 |
| 65-72 | 101:1_79:8 | 97:03 | 3.477 | E | 62:38 | 0.4975 | 2.98 |
| 306*-304* | 97:1_101:3 | 98:02 | 3.981 | E | 62:38 | 0.4975 | 3.48 |
| 51-52 | 82:8_96:10 | 91:09 | 2.323 | E | 62:38 | 0.4975 | 1.83 |
| 307*-305* | 90:9_79:17 | 87:13 | 1.9365 | E | 62:38 | 0.4975 | 1.44 |
| 58-57 | 89:1_89:1 | 99:01 | 4.488 | A | 39:61 | -0.4295 | 4.92 |
| 3-19 | 59:35 | 63:37 | 0.527 | A | 39:61 | -0.4295 | 0.96 |
| 108-107 | 58:19 | 75:25 | 1.122 | A | 39:61 | -0.4295 | 1.55 |
| 309*-310* | 87:06 | 94:06 | 2.7 | A | 39:61 | -0.4295 | 3.13 |
| 26-93 | 103:1_73:1 | 99:01 | 4.4615 | A | 39:61 | -0.4295 | 4.89 |
| 65-72 | 66:13 | 84:16 | 1.644 | A | 61:39 | 0.4295 | 1.21 |
| 306*-304* | 103:1_92:1 | 99:01 | 4.548 | A | 61:39 | 0.4295 | 4.12 |
| 51-52 | 73:18 | 80:20 | 1.413 | A | 61:39 | 0.4295 | 0.98 |

TABLE 17-continued

| | | | | | | | | |
|---|---|---|---|---|---|---|---|---|
| 307*-305* | 73:17_73:20 | 80:20 | 1.402 | A | 61:39 | 0.4295 | 0.97 | |
| 53-54 | 63:15 | 81:19 | 1.459 | A | 61:39 | 0.4295 | 1.03 | |
| | 70:16_84:21_84:21_72:44_66:50 | 80:20 | 1.369 | N/A | N/A | N/A | N/A | |
| 66-67 | 115:1_104:1 | 99:01 | 4.6925 | B | 80:20 | 1.369 | 3.32 | |
| 57-58 | 105:1_94:1 | 99:01 | 4.5975 | B | 80:20 | 1.369 | 3.23 | |
| 182-317* | 72:12 | 86:14 | 1.791 | B | 80:20 | 1.369 | 0.42 | |
| | 106:1_104:1_123:2_105:6_126:9_102:7_113:15 | 94:06 | 2.804 | N/A | N/A | N/A | N/A | |
| 57-58 | 112:1_99:10 | 97:03 | 3.515 | F | 94:06 | 2.804 | 0.71 | |
| 305*-307* | 113:1_97:1_83:1_108:2_100:2_115:2 | 99:01 | 4.2825 | F | 94:06 | 2.804 | 1.48 | |
| 93-26 | 101:1_84:1 | 99:01 | 4.4435 | F | 94:06 | 2.804 | 1.64 | |
| 48-47 | 82:02 | 97:03 | 3.519 | K | 29:71 | −0.909 | 4.43 | |
| 323*-324* | 92:17 | 84:16 | 1.675 | K | 29:71 | −0.909 | 2.58 | |
| | 98:26_68:23_68:25_65:44_67:46 | 73:27 | 0.998 | N/A | N/A | N/A | N/A | |
| 93-26 | 96:1_69:32 | 94:06 | 2.673 | J | 53:47 | 0.119 | 2.55 | |

TABLE 18

| REF_WT | H1_Ab | H1_mutation | L1_Ab | L1_Mutation | L1_tag | L2_Ab | L2_mutation | L2_tag | Presence of H-L disulfide bond C233-C214) (y/n) | Observed trends |
|---|---|---|---|---|---|---|---|---|---|---|
| E | PERT | WT | PERT | WT | FLAG | PERT | WT | HA | n | Apparent tag dependence observed. Observed ratios are likely due to HA-tag cleavage rather than tag interference with pairing |
| A | TRAS | WT | TRAS | WT | FLAG | TRAS | WT | HA | n | Apparent tag dependence. Likely similar issue with HA-tag as above, but to a lesser extent |
| O | D3H44 | WT | D3H44 | WT | HA | D3H44 | WT | FLAG | n | No apparent tag dependence observed for these ratios |
| H | D3H44 | WT | D3H44 | WT | FLAG | TRAS | WT | HA | n | Preference of H_D3H44 for L_TRAS over L_D3H44 |
| I | D3H44 | WT | D3H44 | WT | HA | TRAS | WT | FLAG | n | |
| J | D3H44 | WT | D3H44 | WT | FLAG | PERT | WT | HA | n | Inconsistency in observed ratios of H_D3H44 towards FLAG_L_D3H44 or HA_L_PERT likely due to HA-tag issue, as preference of H_D3H44 for FLAG_L_PERT over HA_L_D3H44 is consistent |
| K | D3H44 | WT | D3H44 | WT | HA | PERT | WT | FLAG | n | |
| B | TRAS | WT | TRAS | WT | FLAG | D3H44 | WT | HA | n | Preference of H_TRAS for L_TRAS over L_D3H44 |
| C | TRAS | WT | TRAS | WT | HA | D3H44 | WT | FLAG | n | |
| M | TRAS | WT | TRAS | WT | FLAG | PERT | WT | HA | n | |
| N | TRAS | WT | TRAS | WT | HA | PERT | WT | FLAG | n | Likely no preference of H_TRAS for L_TRAS over L_PERT |
| F | PERT | WT | PERT | WT | FLAG | D3H44 | WT | HA | n | |
| G | PERT | WT | PERT | WT | HA | D3H44 | WT | FLAG | n | Preference of H_PERT for L_PERT over L_D3H44 |
| D | PERT | WT | PERT | WT | FLAG | TRAS | WT | HA | n | |
| L | PERT | WT | PERT | WT | HA | TRAS | WT | FLAG | n | Likely no preference of H_PERT for L_PERT over L TRAS |

| REF_WT | Normalized Median H1-L1:H1-L2 | Number of screening experiments | H1-L1 Tm (Range if n > 1) (° C.) | H1-L2 Tm (Range if n > 1) (° C.) | H1-L1 Antigen Affinity-TF (KD) (Range if n > 1) (nM) | H1-L1 Antigen Affinity-HER2 (KD) (Range if n > 1 (nM) |
|---|---|---|---|---|---|---|
| E | 81:20_79:20_70:29_78:34_78:47_57:35_56:36_65:53_65:53_53:50 | 62:38 | 10 | 73.25 | 73.26 | N/A | ND |
| A | 66:34_57:36_66:43_54:36_58:43_58:43 | 61:39 | 6 | 76.93 75.88 | 76.86 | N/A | 0.696 |
| O | 50:55_48:70 | 44:56 | 2 | (3.57) 75.77 | 75.77 | 0.0522 (0.08822) | N/A |
| H | 36:59_36:59_35:86_31:87_20:67 | 29:71 | 5 | (0.73) 75.88 | ND | 0.0622 (0.12039) | N/A |
| I | 50:58_49:61_34:68_21:71_21:76 | 33:67 | 5 | (3.57) 75.77 | ND | 0.0522 (0.08822) | N/A |
| J | 92:4_88:8_58:52_43:60_47:70 | 53:47 | 5 | (0.73) 75.88 | 79.47 | 0.0622 (0.12039) | N/A |

TABLE 18-continued

| | | | | | | | |
|---|---|---|---|---|---|---|---|
| K | 34:65_29:70_27:67_29:73_27:73_2:101_1:98 | 29:71 | 7 | (3.57) | 79.76 | 0.0522 (0.08822) | N/A |
| B | 70:16_84:21_84:21_72:44_66:50 | 80:20 | 5 | 76.93 | ND | N/A | 0.696 |
| C | 107:15_107:18_86:17_89:18_61:19 | 84:16 | 5 | 76.86 | ND | N/A | 0.413 |
| M | 45:43 | 51:49 | 1 | 76.93 | ND | N/A | 0.696 |
| N | 38:51 | 42:58 | 1 | 76.86 | ND | N/A | 0.413 |
| F | 106:1_104:1_123:2_105:6_126:9_102:7_113:15 | 94:06 | 7 | 73.25 | 66.43 | N/A | ND |
| G | 98:26_68:23_68:25_65:44_67:46 | 73:27 | 5 | 73.26 | 66.79 | N/A | ND |
| D | 68:43_66:42_55:56_56:58_48:60 | 49:51 | 5 | 73.25 | ND | N/A | ND |
| L | 42:58 | 42:58 | 1 | 73.26 | ND | N/A | ND |

TABLE 19

| Unique identifier | Fab Region | Design Type | H1_mutation | L1_mutation | L2_mutation |
|---|---|---|---|---|---|
| 57 | constant | electrostatic | L143K_D146G | Q124E_V133D | Q124R |
| 182 | variable | electrostatic | V37E_F100D | L89R_F98W | F98Y |
| 306* | constant | combination (steric + electrostatic) | A139G_K145T_D146G_Q179E_V190A | L135W | F116A_Q124E_L135A_T180E |
| 58 | constant | electrostatic | L143E_K145T | Q124R | Q124E_V133D |
| 107 | constant | steric | A139G_V190A | L135W | F116A_L135A |
| 304* | constant | combination (steric + electrostatic) | A139W_S186K | F116A_Q124E_L135A_T180E | L135W |
| 93 | variable | combination (steric + electrostatic) | Q39R | Q38E_F98W | Q38R_F98A |
| 165 | constant | combination (steric + electrostatic) | A139W | F116A_ L135A | S131R_ L135W |
| 65 | constant | electrostatic | K145T_Q179D_S188L | Q160K_T178R | Q124E_Q160E_T178D |
| 66 | constant | electrostatic | L143A_D146G_Q179R | Q124E_V133W_Q160E_T180E | V133A_Q160K_T178R |
| 313* | variable | steric | V37W | F98A | P44W |
| 314* | constant | combination (steric + electrostatic) | A139V_K145L_Q179E_S188G_V190S | F116A_S131K_V133G_S176F_T178A | F118W_V133S_S176A_T180E |
| 26 | variable | combination (steric + electrostatic) | V37W_Q39E | Q38R_F98A | Q38E_F98W |
| 324* | variable | steric | V37W_F100W | F98A | P44W_Q89W_F98A |
| 3 | constant | steric | F174V_P175S_S188G | S176L | V133S |
| 72 | constant | electrostatic | D146G_Q179R | Q124E_Q160E_T178D | Q160K_T178R |
| 307* | variable | combination (steric + electrostatic) | Q39R | Q38E | F98A |
| 305* | variable | combination (steric + electrostatic) | V37W | F98A | Q38E |
| 52 | variable | electrostatic | Q39E | Q38R | Q38E |
| 315* | constant | combination (steric + electrostatic) | A139W_S186K_S188A | F118W_V133S_S176A_T180E | F116A_S131K_V133G_S176F_T178A |
| 108 | constant | steric | A139W | F116A_L135A | L135W |
| 19 | constant | steric | S188L_V190Y | V133S | S176L |
| 51 | variable | electrostatic | Q39R | Q38E | Q38R |

| Unique identifier | Median Δ (VAR-REF_WT H1-L1:H1-L2 Scalar | H1-L1/L2 Systems | Number of Systems |
|---|---|---|---|
| 57 | 4.305 | TRAS-TRAS/TRAS; TRAS-TRAS/D3H44;PERT-PERT/PERT; PERT-PERT/D3H44; D3H44-D3H44/TRAS; D3H44-D3H44/PERT | 6 |
| 182 | 4.055 | D3H44-D3H44/TRAS; D3H44-D3H44/PERT | 2 |
| 306* | 3.99 | TRAS-TRAS/TRAS; TRAS-TRAS/D3H44; PERT-PERT/PERT; PERT-PERT/D3H44 | 4 |
| 58 | 3.23 | TRAS-TRAS/TRAS; TRAS-TRAS/D3H44; PERT-PERT/TRAS; PERT-PERT/PERT; PERT-PERT/D3H44 | 5 |
| 107 | 3.03 | TRAS-TRAS/TRAS; TRAS-TRAS/D3H44; PERT-PERT/PERT; PERT-PERT/D3H44 | 4 |
| 304* | 3.03 | TRAS-TRAS/TRAS; TRAS-TRAS/D3H44; PERT-PERT/TRAS; PERT-PERT/PERT; PERT-PERT/D3H44 | 5 |
| 93 | 2.9 | TRAS-TRAS/TRAS; TRAS-TRAS/D3H44; PERT-PERT/PERT; PERT-PERT/D3H44; D3H44-D3H44/PERT | 5 |
| 165 | 2.8 | TRAS-TRAS/D3H44; PERT-PERT/D3H44; D3H44-D3H44/PERT | 3 |
| 65 | 2.6 | TRAS-TRAS/TRAS; PERT-PERT/PERT; PERT-PERT/D3H44 | 3 |
| 66 | 2.565 | TRAS-TRAS/D3H44; PERT-PERT/D3H44; D3H44-D3H44/TRAS; D3H44-D3H44/PERT | 4 |

TABLE 19-continued

| | | | |
|---|---|---|---|
| 313* | 2.55 | TRAS-TRAS/D3H44; D3H44-D3H44/PERT | 2 |
| 314* | 2.495 | TRAS-TRAS/D3H44; PERT-PERT/D3H44 | 2 |
| 26 | 2.285 | TRAS-TRAS/TRAS; TRAS-TRAS/D3H44; PERT-PERT/TRAS; PERT-PERT/PERT; PERT-PERT/D3H44; D3H44-D3H44/PERT | 6 |
| 324* | 2.2 | D3H44-D3H44/TRAS; D3H44-D3H44/PERT | 2 |
| 3 | 2.13 | TRAS-TRAS/TRAS; TRAS-TRAS/D3H44; PERT-PERT/TRAS; PERT-PERT/PERT; PERT-PERT/D3H44 | 5 |
| 72 | 1.725 | TRAS-TRAS/TRAS; TRAS-TRAS/D3H44; PERT-PERT/TRAS; PERT-PERT/PERT; PERT-PERT/D3H44; D3H44-D3H44/TRAS | 6 |
| 307* | 1.71 | TRAS-TRAS/TRAS; TRAS-TRAS/D3H44; PERT-PERT/PERT; PERT-PERT/D3H44; D3H44-D3H44/PERT | 5 |
| 305* | 1.44 | TRAS-TRAS/TRAS; PERT-PERT/PERT; D3H44-D3H44/PERT | 3 |
| 52 | 1.405 | TRAS-TRAS/TRAS; PERT-PERT/TRAS; PERT-PERT/PERT; PERT-PERT/D3H44 | 4 |
| 315* | 1.19 | TRAS-TRAS/D3H44; PERT-PERT/D3H44 | 2 |
| 108 | 1.15 | TRAS-TRAS/TRAS; TRAS-TRAS/D3H44; PERT-PERT/TRAS; PERT-PERT/PERT; PERT-PERT/D3H44 | 5 |
| 19 | 0.945 | TRAS-TRAS/TRAS; TRAS-TRAS/D3H44; PERT-PERT/PERT; PERT-PERT/D3H44 | 4 |
| 51 | 0.935 | TRAS-TRAS/TRAS; TRAS-TRAS/D3H44; PERT-PERT/PERT; PERT-PERT/D3H44 | 4 |

TABLE 20

| Unique Identifier set | Fab Region | Design Type | H1_mutaton | L1_mutation | H2_mutation | L2_mutation |
|---|---|---|---|---|---|---|
| 306*-304* | constant | combination (steric electrostatic) | A139G_K145T_D146G_Q179E_V190A | L135W | A139W_S186K | F116A_Q124E_L135A_T180E |
| 307*-305* | variable | combination (steric electrostatic) | Q39R | Q38E | V37W | F98A |
| 3-19 | constant | steric | F174V_P175S_S188G | S176L | S188L_V190Y | V1335 |
| 93-26 | variable | combination (steric electrostatic) | Q39R | Q38E_F98W | V37W_Q39E | Q38R_F98A |
| 58-57 | constant | electrostatic | L143E_K1451 | Q124R | L143K_D146G | Q124E_V133D |
| 107-108 | constant | steric | A139G_V190A | L135W | A139W | F116A_L135A |
| 72-65 | constant | electrostatic | D146G_Q179R | Q124E_Q160E_T178D | K145T_Q179D_S188L | Q160K_T178R |
| 52-51 | variable | electrostatic | Q39E | Q38R | Q39R | Q38E |
| 319*-310* | variable | electrostatic | V37E_F100D | Q89R_F98W | WT | WT |

| Unique identifier set | Median Δ (VAR1-REF_WT) H1-L1:H1-L2 Scalar | H1-L1/H2-L2 Systems | Number of Systems | Median Δ (VAR2-REF_WT) H2-L2:H2-L1 Scalar |
|---|---|---|---|---|
| 306*-304* | 4.66 | PERT-PERT/PERT-PERT; TRAS-TRAS/TRAS-TRAS | 2 | 3.8 |
| 307*-305* | 4.57 | PERT-PERT/D3H44-D3H44; PERT-PERT/PERT-PERT; TRAS-TRAS/TRAS-TRAS | 3 | 1.44 |
| 3-19 | 3.84 | PERT-PERT/PERT-PERT; TRAS-TRAS/TRAS-TRAS | 2 | 0.965 |
| 93-26 | 3.735 | D3H44-D3H44/PERT-PERT; PERT-PERT/D3H44-D3H44; PERT-PERT/PERT-PERT;TRAS-TRAS/TRAS-TRAS | 4 | 3.27 |
| 58-57 | 3.545 | PERT-PERT/PERT-PERT; TRAS-TRAS/TRAS-TRAS; TRAS-TRAS/D3H44-D3H44; PERT-PERT/D3H44-D3H44 | 4 | 4.725 |
| 107-108 | 2.795 | PERT-PERT/PERT-PERT; TRAS-TRAS/TRAS-TRAS | 2 | 0.755 |
| 72-65 | 2.095 | PERT-PERT/PERT-PERT; TRAS-TRAS/TRAS-TRAS | 2 | 1.78 |
| 52-51 | 1.405 | PERT-PERT/PERT-PERT; TRAS-TRAS/TRAS-TRAS | 2 | 1.845 |
| 319*-310* | 2.33 | PERT-PERT/PERT-PERT; TRAS-TRAS/TRAS-TRAS | 2 | 2.865 |

TABLE 21

| Unique identifier | Fab Region | Design Type | H1_mutation | L1_mutation | L2_mutation | H1:L1:L2 DNA Ratio | H1-L1_H1-L2 |
|---|---|---|---|---|---|---|---|
| | | | WT | WT | W | 1:01:01 | 32.5_45.0_38.9_41.5 |
| 325* | variable | steric | V37W | F98A | F98W | 1:01:01 | 11.5_11.9_15.2_8.4 |
| 31 | variable | steric | WT | F98W | F98A | 1:01:01 | 29.7_38.9_40.9_44.4 |
| 52 | variable | electrostatic | Q39E | Q38R | Q38E | 1:01:01 | 19.1_28.5 |
| 51 | variable | electrostatic | Q39R | Q38E | Q38R | 1:01:01 | 25.4_23.7 |
| 108 | constant | steric | A139W | F116A_L135A | L135W | 1:01:01 | 12.1_28.4 |
| 305* | variable | combination (electrostatic + steric) | V37W | F98A | Q38E | 1:01:01 | 6.6_9.5_8.9 |

TABLE 21-continued

| | | | | | | | | |
|---|---|---|---|---|---|---|---|---|
| 307* | variable | combination (electrostatic + steric) | Q39R | | Q38E | | F98A | 1:01:01 | 10.1_9.6_9.9_8.6 |
| 19 | constant | steric | S188L_V190Y | | V133S | | S176L | 1:01:01 | 43.2_26.5 |
| 3 | constant | steric | F174V_P175S_S188G | | S176L | | V133S | 1:01:01 | 42.8_43.5 |
| 72 | constant | electrostatic | D146G_Q179R | | Q124E_Q160E_T178D | | Q160K_T178R | 1:01:01 | 7.1_6.3 |
| 65 | constant | electrostatic | K145T_Q179D_S188L | | Q160K_T178R | | Q124E_Q160E_T178D | 1:01:01 | 25.3_41.6 |

| Unique identifier | median H1-L1_H1-L2 | H1-L1_H1-L1 | median H1-L1_H1-L1 | H1-L2_H1-L2 | median H1-L2_H1-L2 |
|---|---|---|---|---|---|
|  | 40.2 | 3.7_11.5_4.6_24.1 | 8.05 | 63.8_43.5_55.7_34.4 | 49.6 |
| 325* | 11.7 | 84.1_84.9_82.1_90.3 | 84.5 | 4.4_2.9_2.6_1.2 | 2.75 |
| 31 | 39.9 | 66.7_52.9_51.5_42.4 | 52.2 | 3.6_8.1_7.6_13.0 | 7.85 |
| 52 | 23.8 | 80.9_52.5 | 66.7 | 0.0_18.8 | 9.4 |
| 51 | 24.55 | 71.1_71.3 | 71.2 | 3.6_4.9 | 4.25 |
| 108 | 20.25 | 87.9_71.4 | 79.65 | 0_0 | 0 |
| 305* | 8.9 | 92.6_86.2_88.7 | 88.7 | 0_3.8_2.3 | 2.3 |
| 307* | 9.75 | 89.9_90.3_89.8_91.0 | 90.1 | 0_0_0.3_0.3 | 0.15 |
| 19 | 34.85 | 36.7_72.4 | 54.55 | 20.1_0.7 | 10.4 |
| 3 | 43.15 | 47.1_47.2 | 47.15 | 10.1_8.9 | 9.5 |
| 72 | 6.7 | 92.9_93.7 | 93.3 | 0_0 | 0 |
| 65 | 33.45 | 71.8_29.0 | 50.4 | 3.0_29.3 | 16.15 |

TABLE 22

| Unique identifier set | Fab region | Design Type | H1-L1_Ab | H1_mutation | L1_mutation | H2-L2_Ab | H2_mutation |
|---|---|---|---|---|---|---|---|
| 305*-307* | variable | combination (electrostatic + steric) | D3H44 | V37W | F98A | PERT | Q39R |
| 154-152 | variable | combination (electrostatic + steric) | D3H44 | V37W_Q39E | Q38R_F98A | PERT | V37A_Q39R_W103V |
| 326*-23 | constant | electrostatic | D3H44 | S186R | Q124E_Q160E_T180E | PERT | K145L_Q179E |
| 327*-328* | combination of constant and variable | combination (electrostatic) | D3H44 | Q39E_S186R | Q38R_Q124E_Q160E_T180E | PERT | Q39R_K145L_Q179E |
| 329*-330* | constant | combination (electrostatic + steric) | *D3H44 | A139G_V190A | L135W | PERT | A139W_K145Y_Q179E |
| 331*-257 | constant | electrostatic | *D3H44 | D146G_Q179K | Q124E_Q160E_T180E | PERT | L143E_K145T |
| 329*-330* | constant | combination (electrostatic + steric) | *D3H44 | A139G_V190A | L135W | PERT | A139W_K145Y_Q179E |
| 332*-284 | constant | electrostatic | D3H44 | D146G_Q179K | Q124E_Q160E_T180E | PERT | L143E_K145T |
| 333*-334* | combination of constant and variable | combination (electrostatic) | D3H44 | Q39E_S186R | Q38R_Q160E_T180E | PERT | Q39R_K145T_Q179E |
| 335*-336* | combination of constant and variable | combination (electrostatic + steric) | D3H44 | V37W_L124E | F98A_V133A_S176K | PERT | L124R |
| 331*-257 | constant | electrostatic | *D3H44 | D146G_Q179K | Q124E_Q160E_T180E | PERT | L143E_K145T |
| 90-92 | variable | combination (electrostatic + steric) | D3H44 | V37W_Q39E | Q38R_F98A | PERT | V37I_Q39R |
| 34-39 | variable | combination (electrostatic + steric) | D3H44 | V37W_Q39E | Q38R_F98A | PERT | Q39R |
| 313*-337* | variable | steric | D3H44 | V37W | F98A | PERT | L45A |
| 336*-335* | combination of constant and variable | combination (electrostatic + steric) | D3H44 | L124R | F98W_V133G_S176D | PERT | V37W_L124E |
| 338*-299 | variable | steric | D3H44 | V37W_W103F | F98A | PERT | L45A |
| 313*-339* | variable | steric | D3H44 | V37W | F98A | PERT | W103V |
| 340*-337* | variable | steric | D3H44 | V37W_W103F | F98A | PERT | L45A |
| 340*-339* | variable | steric | D3H44 | V37W_W103F | F98A | PERT | W103V |
| 66-67 | constant | electrostatic | D3H44 | L143A_D146G_Q179R | Q124E_V133W_Q160E_T180E | PERT | K145T_Q179D_S188F |
| 57-58 | constant | electrostatic | *D3H44 | L143K_D146G | Q124E_V133D | PERT | L143E_K145T |
| 341*-342* | combination of constant and variable | combination (electrostatic + steric) | D3H44 | V37W_K145T_Q179E | F98A_S131K | PERT | S186R |

TABLE 22-continued

| | | | | | | | |
|---|---|---|---|---|---|---|---|
| 92-90 | variable | combination (electrostatic + steric) | *D3H44 | V37I_Q39R | Q38D_F98W | PERT | V37W_Q39E |
| 325*-31 | variable | steric | D3H44 | V37W | F98A | PERT | WT |
| 92-90 | variable | combination (electrostatic + steric) | *D3H44 | V37I_Q39R | Q38D_F98W | PERT | V37W_Q39E |
| 300-343* | variable | steric | D3H44 | V37W | F98A | PERT | W103V |
| 342*-341* | combination of constant and variable | combination (electrostatic + steric) | D3H44 | S186R | F98W_Q160E_T180E | PERT | V37W_K145T_Q179E |
| 344*-121 | variable | combination (electrostatic + steric) | D3H44 | F100W_W103F | F98L | PERT | Q39R |
| 345*-346* | combination of constant and variable | combination (steric) | D3H44 | V37W | F98A_L135W | PERT | A139W |
| 347*-348* | combination of constant and variable | combination (electrostatic + steric) | D3H44 | V37W_K145T_Q179E | F98A_S131K | PERT | WT |
| 57-58 | constant | electrostatic | *D3H44 | L143K_D146G | Q124E_V133D | PERT | L143E_K145T |
| 338*-349* | variable | steric | D3H44 | V37W_W103F | F98A | PERT | W103F |
| 300-349* | variable | steric | D3H44 | V37W | F98A | PERT | W103F |
| 106-97 | variable | combination (electrostatic + steric) | D3H44 | V37I_Q39D | Q38R_F98W | PERT | V37W_Q39R_W103F |
| 111-112 | combination of constant and variable | combination (electrostatic + steric) | D3H44 | Q39D_A139G_V190A | Q38R_L135W | PERT | Q39R_A139W |
| 350*-31 | variable | steric | D3H44 | V37W_W103F | F98A | PERT | WT |
| 338*-343* | variable | steric | D3H44 | V37W_W103F | F98A | PERT | W103V |
| 73-74 | variable | combination (electrostatic + steric) | D3H44 | V37I_Q39R | Q38E_F98W | PERT | V37W_Q39E_W103F |
| 300-299 | variable | steric | D3H44 | V37W | F98A | PERT | L45A |
| 152-154 | variable | combination (electrostatic + steric) | D3H44 | V37A_Q39R_W103V | Q38E_P44W | PERT | V37W_Q39E |
| 306*-304* | constant | combination (electrostatic + steric) | *D3H44 | A139G_K145T_D146G_Q179E_V190A | L135W | PERT | A139W_S186K |
| 107-108 | constant | steric | D3H44 | A139G_V190A | L135W | PERT | A139W |
| 307*-305* | variable | combination (electrostatic + steric) | D3H44 | Q39R | Q38E | PERT | V37W |
| 351*-312* | variable | steric | D3H44 | V37W | F98A | PERT | WT |
| 186-352* | variable | steric | D3H44 | WT | F98W | PERT | V37F |
| 353*-354* | constant | combination (electrostatic + steric) | D3H44 | S186R | L135W_Q160E_T180E | PERT | A139W_K145T_Q179E |
| 1-2 | constant | electrostatic | D3H44 | S186R | Q124E_Q160E_T178D | PERT | K145L_Q179E |
| 121-344* | variable | combination (electrostatic + steric) | D3H44 | Q39R | Q38E_F98W | PERT | F100W_W103F |
| 72-65 | constant | electrostatic | D3H44 | D146G_Q179R | Q124E_Q160E_T178D | PERT | K145T_Q179D_S188L |
| 312*-351* | variable | steric | D3H44 | WT | WT | PERT | V37W |
| 186-355* | variable | steric | D3H44 | WT | F98W | PERT | F100W_W103F |
| 356*-357* | variable | steric | D3H44 | V37F | F98L | PERT | W103F |
| 346*-345* | combination of constant and variable | combination (steric) | D3H44 | A139W | F98W_F116A | PERT | V37W |
| 343*-338* | variable | steric | D3H44 | W103V | P44F | PERT | V37W_W103F |
| 52-51 | variable | electrostatic | D3H44 | Q39E | Q38R | PERT | Q39R |
| 358*-359* | variable | steric | D3H44 | L45A | P44F | PERT | V37F |
| 348*-347* | combination of constant and variable | combination (electrostatic + steric) | D3H44 | WT | F98W | PERT | V37W_K145T_Q179E |
| 355*-186 | variable | steric | D3H44 | F100W_W103F | F98L | PERT | WT |
| 360*-359* | variable | steric | D3H44 | W103V | P44F | PERT | V37F |
| 313*-361* | variable | steric | D3H44 | V37W | F98A | PERT | W103F |
| 340*-361* | variable | steric | D3H44 | V37W_W103F | F98A | PERT | W103F |
| 357*-356* | variable | steric | D3H44 | W103F | P44W | PERT | V37F |
| 359*-362* | variable | steric | D3H44 | V37F | F98L | PERT | W103F |
| 186-363* | variable | steric | D3H44 | WT | F98W | PERT | V37F_W103F |
| 363*-186 | variable | steric | D3H44 | V37F_W103F | F98L | PERT | WT |
| 299-300 | variable | steric | D3H44 | L45A | P44F | PERT | V37W |

TABLE 22-continued

| | | | | | | | |
|---|---|---|---|---|---|---|---|
| 359*-358* | variable | steric | D3H44 | V37F | F98L | PERT | L45A |
| 356*-364* | variable | steric | D3H44 | V37F | F98L | PERT | L45A |
| | | | D3H44 | WT | WT | PERT | WT |
| 337*-340* | variable | steric | D3H44 | L45A | P44W | PERT | V37W_W103F |
| 339*-340* | variable | steric | D3H44 | W103V | P44W | PERT | V37W_W103F |
| 337*-313* | variable | steric | D3H44 | L45A | P44W | PERT | V37W |
| 364*-356* | variable | steric | D3H44 | L45A | P44W | PERT | V37F |
| 339*-313* | variable | steric | D3H44 | W103V | P44W | PERT | V37W |
| 314*-315* | constant | combination (electrostatic + steric) | D3H44 | A139V_K145L_ Q179E_S188G_ V190S | F116A_S131K_ V133G_S176F_ T178A | PERT | A139W_S186K_ S188A |
| 31-325* | variable | steric | D3H44 | WT | F98W | PERT | V37W |
| 349*-300 | variable | steric | D3H44 | W103F | P44F | PERT | V37W |
| 356*-365* | variable | steric | D3H44 | V37F | F98L | PERT | W103V |
| 31-350* | variable | steric | D3H44 | WT | F98W | PERT | V37W_W103F |
| 257-331* | constant | electrostatic | D3H44 | L143E_K145T | Q124R_Q160K_ T178R | PERT | D146G_Q179K |
| 19-3 | constant | steric | D3H44 | S188L_V190Y | V133S | PERT | F174V_P175S_ S188G |
| 352*-186 | variable | steric | D3H44 | V37F | F98L | PERT | WT |
| 366*-367* | constant | electrostatic | D3H44 | S186R | Q124E_Q160E_ T178D | PERT | L143E_K145T |
| 343*-300 | variable | steric | D3H44 | W103V | P44F | PERT | V37W |
| | | | D3H44 | WT | WT | PERT | WT |
| 328*-327* | combination of constant and variable | combination (electrostatic) | D3H44 | Q39R_K145L_ Q179E | Q38E_S131K | PERT | Q39E_S186R |
| 361*-313* | variable | steric | D3H44 | W103F | P44W | PERT | V37W |
| 361*-340* | variable | steric | D3H44 | W103F | P44W | PERT | V37W_W103F |
| 299-338* | variable | steric | D3H44 | L45A | P44F | PERT | V37W_ W103F |
| 368*-369* | constant | electrostatic | D3H44 | L143E_K145T_ S188L | Q124R | PERT | L143K |
| 370*-371* | combination of constant and variable | combination (electrostatic + steric) | D3H44 | Q39R_A139W | Q38E_F116A_L135V | PERT | Q39E_ A139G_ V190A |
| 359*-360* | variable | steric | D3H44 | V37F | F98L | PERT | W103V |
| 368*-372* | constant | electrostatic | D3H44 | L143E_K145T_ S188L | Q124R | PERT | L143R |
| 373*-374* | variable | steric | D3H44 | L45F | WT | PERT | L45A |
| 295-294 | constant | electrostatic | D3H44 | L124R | V133G_S176D | PERT | L124E |
| 375*-376* | constant | electrostatic | D3H44 | L143E_K145T_ S188L | Q124R | PERT | L143R |
| 377*-378* | variable | steric | D3H44 | L45A | P44F | PERT | L45F |
| 74-73 | variable | combination (electrostatic + steric) | D3H44 | V37W_Q39E_ W103F | Q38R_F98L | PERT | V37I_Q39R |
| 379*-380* | constant | electrostatic | D3H44 | L143E_K145T_ Q179E | Q124K_T178R | PERT | S186R |
| 381*-382* | combination of constant and variable | combination (electrostatic + steric) | D3H44 | Q39R_A139W | Q38E_F116A | PERT | Q39E |
| 383*-384* | constant | electrostatic | D3H44 | H172R | WT | PERT | H172T |
| 349*-338* | variable | steric | D3H44 | W103F | P44F | PERT | V37W_W103F |
| 334*-333* | combination of constant and variable | combination (electrostatic) | D3H44 | Q39R_K145T_ Q179E | Q38E_S131K | PERT | Q39E_S186R |
| 378*-377* | variable | steric | D3H44 | L45F | WT | PERT | L45A |
| 375*-385* | constant | electrostatic | D3H44 | L143E_K145T_ S188L | Q124R | PERT | L143K |
| | | | D3H44 | WT | WT | PERT | WT |
| 304*-306* | constant | combination (electrostatic + steric) | D3H44 | A139W_S186K | F116A_Q124E_ L135A_T180E | PERT | A139G_K145T_ D146G_Q179E_ V190A |
| 362*-359* | variable | steric | D3H44 | W103F | P44F | PERT | V37F |
| 386*-387* | combination of constant and variable | combination (electrostatic + steric) | D3H44 | Q39E_L124W | Q38R_V133A | PERT | Q39R_L124A |
| 388*-389* | constant | electrostatic | D3H44 | WT | WT | PERT | K145L_Q179E |
| 390*-391* | constant | electrostatic | D3H44 | L143E_K145T_ S188L | Q124R | PERT | S186R |
| 374*-392* | variable | steric | D3H44 | L45A | P44W | PERT | WT |
| 387*-386* | combination of constant and variable | combination (electrostatic + steric) | D3H44 | Q39R_L124A | Q38E_V133F | PERT | Q39E_L124W |
| 393*-394* | constant | electrostatic | D3H44 | K145T_S186E_ S188L | S131R | PERT | S186R |

TABLE 22-continued

| | | | | | | | |
|---|---|---|---|---|---|---|---|
| 395*-396* | constant | electrostatic | D3H44 | H172R | WT | PERT | H172T |
| 354*-353* | constant | combination (electrostatic + steric) | D3H44 | A139W_K145T_Q179E | F116A_S131K | PERT | S186R |
| 306*-304* | constant | combination (electrostatic + steric) | *D3H44 | A139G_K145T_D146G_Q179E_V190A | L135W | PERT | A139W_S186K |
| 397*-398* | constant | electrostatic | D3H44 | K145T_S186E_S188L | S131R | PERT | S186R |
| 399*-400* | constant | electrostatic | D3H44 | K145T_S186E_S188L | S131R | PERT | S186R |
| 401*-402* | constant | electrostatic | D3H44 | K145T_S186E_S188L | S131R | PERT | S186R |
| 403*-404* | constant | steric | D3H44 | A139W | F116A | PERT | WT |
| 382*-381* | combination of constant and variable | combination (electrostatic + steric) | D3H44 | Q39E | Q38R_L135W | PERT | Q39R_A139W |
| 405*-391* | constant | electrostatic | D3H44 | K145T_S186E_S188L | Q124R | PERT | S186R |
| 406*-407* | constant | electrostatic | D3H44 | K145T_S186E_S188L | S131R | PERT | S186R |
| 408*-377* | variable | steric | D3H44 | WT | WT | PERT | L45A |
| 409*-410* | constant | steric | D3H44 | L124W | V133A | PERT | L124A |
| 55-56 | variable | electrostatic vs hydrophobic | D3H44 | Q39M | Q38M | PERT | Q39R |
| 371*-370* | combination of constant and variable | combination (electrostatic + steric) | D3H44 | Q39E_A139G_V190A | Q38R_L135W | PERT | Q39R_A139W |
| 377*-408* | variable | steric | D3H44 | L45A | P44F | PERT | WT |
| 411*-384* | constant | electrostatic | D3H44 | H172R_T192K | WT | PERT | H172T |
| 412*-413* | constant | electrostatic | D3H44 | K145T_S186E_S188L | Q124R | PERT | S186R |
| 53-54 | variable | electrostatic | D3H44 | Q39R | Q38E | PERT | WT |
| 414*-413* | constant | electrostatic | D3H44 | L143E_K145T_S188L | Q124R | PERT | S186R |
| 415*-416* | constant | electrostatic | D3H44 | K145T_Q179E | S131K | PERT | S186R |
| 417*-418* | constant | steric | D3H44 | A139W_V190I | F116A_L135V | PERT | WT |
| | | | D3H44 | WT | WT | PERT | WT |
| 419*-420* | constant | electrostatic | D3H44 | L143E_K145T_S188L | Q124R | PERT | L143K |
| 421*-422* | constant | electrostatic | D3H44 | WT | WT | PERT | L143E_K145T |
| 374*-373* | variable | steric | D3H44 | L45A | P44W | PERT | L45F |
| 423*-418* | constant | steric | D3H44 | A139W | F116A_L135V | PERT | WT |
| 424*-260 | constant | electrostatic | D3H44 | L143E_K145T_Q179E | Q124K_T178R | PERT | S186R |
| 425*-404* | constant | steric | D3H44 | A139W_V190L | F116A | PERT | WT |
| 419*-426* | constant | electrostatic | D3H44 | L143E_K145T_S188L | Q124R | PERT | S186R |
| 427*-418* | constant | steric | D3H44 | A139W_V190L | F116A_L135V | PERT | WT |
| 428*-396* | constant | electrostatic | D3H44 | H172R_T192K | WT | PERT | H172T |
| 392*-374* | variable | steric | D3H44 | WT | WT | PERT | L45A |
| 429*-430* | constant | electrostatic | D3H44 | K145T_S186E_S188L | S131R | PERT | S186R |
| 54-53 | variable | electrostatic | D3H44 | WT | WT | PERT | Q39R |
| 431*-418* | constant | steric | D3H44 | A139W_G141L_V190S | F116A_L135V | PERT | WT |
| 432*-426* | constant | electrostatic | D3H44 | K145T_S186E_S188L | Q124R | PERT | S186R |
| 433*-434* | constant | steric | D3H44 | A139W_G141L_V190S | F116A_F118L_L135V | PERT | WT |
| 435*-283 | constant | electrostatic | D3H44 | L143E_K145T_S188L | Q124R | PERT | S186R |
| 56-55 | variable | electrostatic vs hydrophobic | D3H44 | Q39R | Q38E | PERT | Q39M |
| 435*-436* | constant | electrostatic | D3H44 | L143E_K145T_S188L | Q124R | PERT | L143K |
| 437*-326* | constant | electrostatic | D3H44 | K145T_Q179E | S131K | PERT | S186R |
| 438*-285 | constant | electrostatic | D3H44 | K145T_S186E_S188L | Q124R | PERT | S186R |
| 439*-283 | constant | electrostatic | D3H44 | K145T_S186E_S188L | Q124R | PERT | S186R |
| 440*-441* | constant | electrostatic | D3H44 | K145T_S186E_S188L | Q124R | PERT | S186R |
| | | | D3H44 | WT | WT | TRAS | WT |
| 331*-257 | constant | electrostatic | D3H44 | D146G_Q179K | Q124E_Q160E_T180E | TRAS | L143E_K145T |
| | | | D3H44 | WT | WT | PERT | WT |
| 332*-284 | constant | electrostatic | D3H44 | D146G_Q179K | Q124E_Q160E_T180E | TRAS | L143E_K145T |
| 90-92 | variable | combination (electrostatic + steric) | D3H44 | V37W_Q39E | Q38R_F98A | TRAS | V37I_Q39R |

TABLE 22-continued

| Unique identifier set | | | | H1 | H2 | L1 | | |
|---|---|---|---|---|---|---|---|---|
| 34-39 | variable | combination (electrostatic + steric) | D3H44 | V37W_Q39E | Q38R_F98A | TRAS | Q39R | |
| 39-34 | variable | combination (electrostatic + steric) | D3H44 | Q39R | Q38E | TRAS | V37W_Q39E | |
| 442*-23 | constant | electrostatic | D3H44 | S115K_S156K_S186R | Q124E_Q160E_T180E | TRAS | K145L_Q179E | |
| 92-90 | variable | combination (electrostatic + steric) | D3H44 | V37I_Q39R | Q38D_F98W | TRAS | V37W_Q39E | |
| 284-332* | constant | electrostatic | D3H44 | L143E_K145T | Q124R | TRAS | D146G_Q179K | |
| 257-331* | constant | electrostatic | D3H44 | L143E_K145T | Q124R_Q160K_T178R | TRAS | D146G_Q179K | |
| 443*-326* | constant | electrostatic | D3H44 | S115K_K145L_S156K_Q179E | S131K | TRAS | S186R | |
| | | | D3H44 | WT | WT | RAMU | WT | |
| 332*-284 | constant | electrostatic | D3H44 | D146G_Q179K | Q124E_Q160E_T180E | RAMU | L143E_K145T | |
| 34-39 | variable | combination (electrostatic + steric) | D3H44 | V37W_Q39E | Q38R_F98A | RAMU | Q39R | |
| 284-332* | constant | electrostatic | D3H44 | L143E_K145T | Q124R | RAMU | D146G_Q179K | |
| 90-92 | variable | combination (electrostatic + steric) | D3H44 | V37W_Q39E | Q38R_F98A | RAMU | V37I_Q39R | |
| 442*-23 | constant | electrostatic | D3H44 | S115K_S156K_S186R | Q124E_Q160E_T180E | RAMU | K145L_Q179E | |
| 257-331* | constant | electrostatic | D3H44 | L143E_K145T | Q124R_Q160K_T178R | RAMU | D146G_Q179K | |
| 331*-257 | constant | electrostatic | D3H44 | D146G_Q179K | Q124E_Q160E_T180E | RAMU | L143E_K145T | |
| 443*-326* | constant | electrostatic | D3H44 | S115K_K145L_S156K_Q179E | S131K | RAMU | S186R | |
| | | | D3H44 | WT | WT | PERT | WT | |
| 39-34 | variable | combination (electrostatic + steric) | D3H44 | Q39R | Q38E | RAMU | V37W_Q39E | |
| 92-90 | variable | combination (electrostatic + steric) | D3H44 | V37I_Q39R | Q38D_F98W | RAMU | V37W_Q39E | |
| | | | TRAS | WT | WT | RAMU | WT | |
| 257-331* | constant | electrostatic | TRAS | L143E_K145T | Q124R_Q160K_T178R | RAMU | D146G_Q179K | |
| 23-326* | constant | electrostatic | TRAS | K145L_Q179E | S131K | RAMU | S186R | |
| 284-332* | constant | electrostatic | TRAS | L143E_K145T | Q124R | RAMU | D146G_Q179K | |
| 34-39 | variable | combination (electrostatic + steric) | TRAS | V37W_Q39E | Q38R_F98A | RAMU | Q39R | |
| 326*-23 | constant | electrostatic | TRAS | S186R | Q124E_Q160E_T180E | RAMU | K145L_Q179E | |
| 92-90 | variable | combination (electrostatic + steric) | TRAS | V37I_Q39R | Q38D_F98W | RAMU | V37W_Q39E | |
| 90-92 | variable | combination (electrostatic + steric) | TRAS | V37W_Q39E | Q38R_F98A | RAMU | V37I_Q39R | |
| 332*-284 | constant | electrostatic | TRAS | D146G_Q179K | Q124E_Q160E_T180E | RAMU | L143E_K145T | |
| 39-34 | variable | combination (electrostatic + steric) | TRAS | Q39R | Q38E | RAMU | V37W_Q39E | |
| 331*-257 | constant | electrostatic | TRAS | D146G_Q179K | Q124E_Q160E_T180E | RAMU | L143E_K145T | |

| Unique identifier set | L2_mutation | H1:H2: L1:L2 DNA ratio | SEC step performed post pA? | Number of experiments | paired: mispaired species(all) | paired: mispaired species (mean) |
|---|---|---|---|---|---|---|
| | WT | 22:8:53:17 | Y | 2 | 3:97_2:98 | 2:98 |
| 305*-307* | Q38E | 24:6:56:14 | Y | 1 | 100:0 | 100:0 |
| 154-152 | Q38E_P44W | 15:15:35:35 | N | 1 | 100:0 | 100:0 |
| 326*-23 | S131K | 22:8:53:17 | N | 1 | 100:0 | 100:0 |
| 327*-328* | Q38E_S131K | 22:8:46:24 | N | 1 | 100:0 | 100:0 |
| 329*-330* | F116A_S131K_L135A | 15:15:35:35 | N | 1 | 100:0 | 100:0 |
| 331*-257 | Q124R_Q160K_T178R | 22:8:35:35 | N | 1 | 100:0 | 100:0 |
| 329*-330* | F116A_S131K_L135A | 15:15:35:35 | N | 1 | 100:0 | 100:0 |
| 332*-284 | Q124R | 22:8:53:17 | N | 1 | 98:2 | 98:2 |
| 333*-334* | Q38E_S131K | 22:8:46:24 | N | 1 | 98:2 | 98:2 |
| 335*-336* | F98W_V133G_S176D | 22:8:46:24 | N | 1 | 98:2 | 98:2 |
| 331*-257 | Q124R_Q160K_T178R | 22:8:46:24 | N | 1 | 97:3 | 97:3 |
| 90-92 | Q38D_F98W | 15:15:35:35 | N | 1 | 96:4 | 96:4 |
| 34-39 | Q38E | 15:15:35:35 | N | 1 | 96:4 | 96:4 |
| 313*-337* | P44W | 15:15:35:35 | N | 1 | 95:5 | 95:5 |

TABLE 22-continued

| | | | | | | |
|---|---|---|---|---|---|---|
| 336*-335* | F98A_V133A_S176K | 22:8:46:24 | N | 1 | 94:6 | 94:6 |
| 338*-299 | P44F | 22:8:46:24 | N | 1 | 94:6 | 94:6 |
| 313*-339* | P44W | 22:8:46:24 | N | 1 | 93:7 | 93:7 |
| 340*-337* | P44W | 15:15:35:35 | N | 1 | 92:8 | 92:8 |
| 340*-339* | P44W | 26:4:56:14 | N | 1 | 92:8 | 92:8 |
| 66-67 | V133A_Q160K_T178R | 22:8:53:17 | N | 1 | 92:8 | 92:8 |
| 57-58 | Q124R | 22:8:53:17 | N | 2 | 88:12_93:7 | 91:9 |
| 341*-342* | F98W_Q160E_T180E | 22:8:46:24 | N | 1 | 90:10 | 90:10 |
| 92-90 | Q38R_F98A | 20:10:40:30 | N | 1 | 89:11 | 89:11 |
| 325*-31 | F98W | 8:22:53:17 | Y | 1 | 88:12 | 88:12 |
| 92-90 | Q38R_F98A | 22:8:35:35 | N | 1 | 87:13 | 87:13 |
| 300-343* | P44F | 22:8:46:24 | N | 1 | 87:13 | 87:13 |
| 342*-341* | F98A_S131K | 22:8:46:24 | N | 1 | 87:13 | 87:13 |
| 344*-121 | Q38E_F98W | 22:8:46:24 | N | 1 | 86:14 | 86:14 |
| 345*-346* | F98W_F116A | 22:8:46:24 | N | 1 | 86:14 | 86:14 |
| 347*-348* | F98W | 22:8:46:24 | N | 1 | 85:15 | 85:15 |
| 57-58 | Q124R | 22:8:53:17 | N | 1 | 84:16 | 84:16 |
| 338*-349* | P44F | 22:8:46:24 | N | 1 | 83:17 | 83:17 |
| 300-349* | P44F | 22:8:46:24 | N | 1 | 82:18 | 82:18 |
| 106-97 | Q38E_F98L | 22:8:40:30 | N | 1 | 81:19 | 81:19 |
| 111-112 | Q38D_F116A_L135A | 22:8:53:17 | N | 1 | 80:20 | 80:20 |
| 350*-31 | F98W | 22:8:46:24 | N | 1 | 80:20 | 80:20 |
| 338*-343* | P44F | 22:8:46:24 | N | 1 | 80:20 | 80:20 |
| 73-74 | Q38E_F98L | 22:8:46:24 | N | 1 | 77:23 | 77:23 |
| 300-299 | P44F | 22:8:46:24 | N | 1 | 76:24 | 76:24 |
| 152-154 | Q38R_F98A | 22:8:53:17 | N | 1 | 72:28 | 72:28 |
| 306*-304* | F116A_Q124E_L135A_T180E | 22:8:53:17 | N | 1 | 71:29 | 71:29 |
| 107-108 | F116A_L135A | 15:15:17:53 | Y | 1 | 70:30 | 70:30 |
| 307*-305* | F98A | 22:8:46:24 | N | 1 | 70:30 | 70:30 |
| 351*-312* | WT | 22:8:46:24 | N | 1 | 69:31 | 69:31 |
| 186-352* | F98L | 22:8:46:24 | N | 1 | 66:34 | 66:34 |
| 353*-354* | F116A_S131K | 22:8:46:24 | N | 2 | 73:27_60:40 | 66:34 |
| 1-2 | S131K | 22:8:46:24 | Y | 1 | 65:35 | 65:35 |
| 121-344* | F98L | 22:8:46:24 | N | 1 | 65:35 | 65:35 |
| 72-65 | Q160K_T178R | 15:15:53:17 | Y | 1 | 63:37 | 63:37 |
| 312*-351* | F98A | 22:8:46:24 | N | 1 | 62:38 | 62:38 |
| 186-355* | F98L | 22:8:46:24 | N | 1 | 59:41 | 59:41 |
| 356*-357* | P44W | 22:8:46:24 | N | 1 | 58:42 | 58:42 |
| 346*-345* | F98A_L135W | 22:8:46:24 | N | 1 | 58:42 | 58:42 |
| 343*-338* | F98A | 22:8:46:24 | N | 1 | 58:42 | 58:42 |
| 52-51 | Q38E | 8:22:53:17 | Y | 1 | 58:42 | 58:42 |
| 358*-359* | F98L | 22:8:46:24 | N | 1 | 58:42 | 58:42 |
| 348*-347* | F98A_S131K | 22:8:46:24 | N | 1 | 56:44 | 56:44 |
| 355*-186 | F98W | 22:8:46:24 | N | 1 | 56:44 | 56:44 |
| 360*-359* | F98L | 22:8:46:24 | N | 1 | 56:44 | 56:44 |
| 313*-361* | P44W | 22:8:46:24 | N | 1 | 55:45 | 55:45 |
| 340*-361* | P44W | 22:8:46:24 | N | 1 | 51:49 | 51:49 |
| 357*-356* | F98L | 22:8:46:24 | N | 1 | 50:50 | 50:50 |
| 359*-362* | P44F | 22:8:46:24 | N | 1 | 50:50 | 50:50 |
| 186-363* | F98L | 22:8:46:24 | N | 1 | 49:51 | 49:51 |
| 363*-186 | F98W | 22:8:46:24 | N | 1 | 49:51 | 49:51 |
| 299-300 | F98A | 22:8:46:24 | N | 1 | 48:52 | 48:52 |
| 359*-358* | P44F | 22:8:46:24 | N | 1 | 48:52 | 48:52 |
| 356*-364* | P44W | 22:8:46:24 | N | 1 | 48:52 | 48:52 |
| | | 22:8:53:17 | Y | 2 | 3:97_2:98 | 2:98 |
| 337*-340* | F98A | 22:8:46:24 | N | 1 | 47:53 | 47:53 |
| 339*-340* | F98A | 22:8:46:24 | N | 1 | 47:53 | 47:53 |
| 337*-313* | F98A | 22:8:46:24 | N | 1 | 46:54 | 46:54 |
| 364*-356* | F98L | 22:8:46:24 | N | 1 | 46:54 | 46:54 |
| 339*-313* | F98A | 22:8:46:24 | N | 1 | 46:54 | 46:54 |
| 314*-315* | F118W_V133S_S176A_T180E | 22:8:53:17 | N | 1 | 44:56 | 44:56 |
| 31-325* | F98A | 22:8:46:24 | N | 1 | 42:58 | 42:58 |
| 349*-300 | F98A | 22:8:46:24 | N | 1 | 41:59 | 41:59 |
| 356*-365* | P44W | 22:8:46:24 | N | 1 | 41:59 | 41:59 |
| 31-350* | F98A | 22:8:46:24 | N | 1 | 40:60 | 40:60 |
| 257-331* | Q124E_Q160E_T180E | 22:8:56:14 | Y | 1 | 39:61 | 39:61 |
| 19-3 | S176L | 8:22:53:17 | Y | 1 | 38:62 | 38:62 |
| 352*-186 | F98W | 22:8:46:24 | N | 1 | 37:63 | 37:63 |
| 366*-367* | Q124R | 22:8:53:17 | Y | 1 | 36:64 | 36:64 |
| 343*-300 | F98A | 22:8:46:24 | N | 1 | 35:65 | 35:65 |
| 328*-327* | Q38R_Q124E_Q160E_T180E | 22:8:46:24 | N | 1 | 35:65 | 35:65 |
| 361*-313* | F98A | 22:8:46:24 | N | 1 | 33:67 | 33:67 |
| 361*-340* | F98A | 22:8:46:24 | N | 1 | 32:68 | 32:68 |
| 299-338* | F98A | 22:8:46:24 | N | 1 | 32:68 | 32:68 |
| 368*-369* | V133E | 22:8:46:24 | N | 1 | 31:69 | 31:69 |
| 370*-371* | Q38R_L135W | 22:8:46:24 | N | 1 | 31:69 | 31:69 |
| 359*-360* | P44F | 22:8:46:24 | N | 1 | 31:69 | 31:69 |

TABLE 22-continued

| | | | | | | |
|---|---|---|---|---|---|---|
| 368*-372* | V133E | 22:8:46:24 | N | 1 | 31:69 | 31:69 |
| 373*-374* | P44W | 22:8:46:24 | N | 1 | 30:70 | 30:70 |
| 295-294 | V133A_S176K | 22:8:46:24 | N | 1 | 30:70 | 30:70 |
| 375*-376* | Q124E_V133E | 22:8:46:24 | N | 1 | 29:71 | 29:71 |
| 377*-378* | WT | 22:8:46:24 | N | 1 | 29:71 | 29:71 |
| 74-73 | Q38E_F98W | 22:8:46:24 | N | 1 | 28:72 | 28:72 |
| 379*-380* | Q124E_T178E_T180E | 22:8:46:24 | N | 1 | 28:72 | 28:72 |
| 381*-382* | Q38R_L135W | 22:8:46:24 | N | 1 | 26:74 | 26:74 |
| 383*-384* | N137K_S174R | 22:8:46:24 | N | 1 | 25:75 | 25:75 |
| 349*-338* | F98A | 22:8:46:24 | N | 1 | 24:76 | 24:76 |
| 334*-333* | Q38R_Q160E_T180E | 22:8:46:24 | N | 1 | 23:77 | 23:77 |
| 378*-377* | P44F | 22:8:46:24 | N | 2 | 21:79_24:76 | 22:78 |
| 375*-385* | Q124E_V133E | 22:8:46:24 | N | 1 | 21:79 | 21:79 |
| | WT | 22:8:53:17 | Y | 2 | 3:97_2:98 | 2:98 |
| 304*-306* | L135W | 22:8:53:17 | N | 1 | 20:80 | 20:80 |
| 362*-359* | F98L | 22:8:46:24 | N | 1 | 20:80 | 20:80 |
| 386*-387* | Q38E_V133F | 22:8:46:24 | N | 1 | 19:81 | 19:81 |
| 388*-389* | S131K | 15:15:35:35 | N | 1 | 18:82 | 18:82 |
| 390*-391* | T178E_T180E | 22:8:46:24 | N | 1 | 18:82 | 18:82 |
| 374*-392* | WT | 22:8:46:24 | N | 1 | 18:82 | 18:82 |
| 387*-386* | Q38R_V133A | 22:8:46:24 | N | 1 | 18:82 | 18:82 |
| 393*-394* | Q160E_T178E | 22:8:46:24 | N | 1 | 18:82 | 18:82 |
| 395*-396* | S174R | 22:8:46:24 | N | 1 | 17:83 | 17:83 |
| | WT | 22:8:53:17 | Y | 2 | 3:97_2:98 | 2:98 |
| 354*-353* | L135W_Q160E_T180E | 22:8:46:24 | N | 1 | 16:84 | 16:84 |
| 306*-304* | F116A_Q124E_L135A_T180E | 22:8:53:17 | N | 1 | 16:84 | 16:84 |
| 397*-398* | T178E | 22:8:46:24 | N | 1 | 15:85 | 15:85 |
| 399*-400* | T178E_T180E | 22:8:46:24 | N | 1 | 15:85 | 15:85 |
| 401*-402* | Q124E_T178E | 22:8:46:24 | N | 1 | 14:86 | 14:86 |
| 403*-404* | L135W | 22:8:46:24 | N | 1 | 13:87 | 13:87 |
| 382*-381* | Q38E_F116A | 22:8:46:24 | N | 1 | 13:87 | 13:87 |
| 405*-391* | T178E_T180E | 22:8:46:24 | N | 1 | 13:87 | 13:87 |
| 406*-407* | Q124E_Q160E_T180E | 22:8:46:24 | N | 1 | 13:87 | 13:87 |
| 408*-377* | P44F | 22:8:46:24 | N | 1 | 12:88 | 12:88 |
| 409*-410* | V133F | 22:8:46:24 | N | 1 | 11:89 | 11:89 |
| 55-56 | Q38E | 22:8:46:24 | N | 1 | 11:89 | 11:89 |
| 371*-370* | Q38E_F116A_L135V | 22:8:46:24 | N | 1 | 11:89 | 11:89 |
| 377*-408* | WT | 22:8:46:24 | N | 1 | 11:89 | 11:89 |
| 411*-384* | N137K_S174R | 22:8:46:24 | N | 1 | 11:89 | 11:89 |
| 412*-413* | Q160E_T178E | 22:8:46:24 | N | 1 | 11:89 | 11:89 |
| 53-54 | WT | 22:8:46:24 | N | 1 | 11:89 | 11:89 |
| 414*-413* | Q160E_T178E | 22:8:46:24 | N | 1 | 10:90 | 10:90 |
| 415*-416* | Q160E_T180E | 22:8:46:24 | N | 1 | 10:90 | 10:90 |
| 417*-418* | L135W | 22:8:46:24 | N | 1 | 10:90 | 10:90 |
| | WT | 22:8:53:17 | Y | 2 | 3:97_2:98 | 2:98 |
| 419*-420* | Q124E_T178E | 22:8:46:24 | N | 1 | 10:90 | 10:90 |
| 421*-422* | Q124R | 15:15:35:35 | N | 1 | 10:90 | 10:90 |
| 374*-373* | WT | 22:8:46:24 | N | 1 | 9:91 | 9:91 |
| 423*-418* | L135W | 22:8:46:24 | N | 1 | 9:91 | 9:91 |
| 424*-260 | Q124E_Q160E_T180E | 22:8:46:24 | N | 1 | 9:91 | 9:91 |
| 425*-404* | L135W | 22:8:46:24 | N | 1 | 9:91 | 9:91 |
| 419*-426* | Q124E_T178E | 22:8:46:24 | N | 1 | 9:91 | 9:91 |
| 427*-418* | L135W | 22:8:46:24 | N | 1 | 9:91 | 9:91 |
| 428*-396* | S174R | 22:8:46:24 | N | 1 | 8:92 | 8:92 |
| 392*-374* | P44W | 22:8:46:24 | N | 1 | 8:92 | 8:92 |
| 429*-430* | Q160E_T180E | 22:8:46:24 | N | 1 | 8:92 | 8:92 |
| 54-53 | Q38E | 22:8:46:24 | N | 1 | 7:93 | 7:93 |
| 431*-418* | L135W | 22:8:46:24 | N | 1 | 7:93 | 6:94 |
| 432*-426* | Q124E_T178E | 22:8:46:24 | N | 1 | 6:94 | 6:94 |
| 433*-434* | L135W | 22:8:46:24 | N | 1 | 5:95 | 5:95 |
| 435*-283 | T178E | 22:8:46:24 | N | 1 | 5:95 | 5:95 |
| 56-55 | Q38M | 22:8:46:24 | N | 1 | 5:95 | 5:95 |
| 435*-436* | T178E | 22:8:46:24 | N | 1 | 3:97 | 3:97 |
| 437*-326* | Q124E_Q160E_T180E | 22:8:46:24 | N | 1 | 3:97 | 3:97 |
| 438*-285 | Q124E_Q160E_T180E | 22:8:46:24 | N | 1 | 2:98 | 2:98 |
| 439*-283 | T178E | 22:8:46:24 | N | 1 | 2:98 | 2:98 |
| 440*-441* | Q160E_T180E | 22:8:46:24 | N | 1 | 0:100 | 0:100 |
| | WT | 22:8:53:17 | N | 2 | 30:70_41:59 | 35:65 |
| 331*-257 | Q124R_Q160K_T178R | 20:10:53:17 | N | 1 | 97:3 | 97:3 |
| | WT | 22:8:53:17 | Y | 2 | 3:97_2:98 | 2:98 |
| 332*-284 | Q124R | 20:10:53:17 | N | 1 | 88:12 | 88:12 |
| 90-92 | Q38D_F98W | 20:10:53:17 | N | 1 | 86:14 | 86:14 |
| 34-39 | Q38E | 20:10:53:17 | N | 1 | 81:19 | 81:19 |
| 39-34 | Q38R_F98A | 20:10:53:17 | N | 1 | 78:22 | 78:22 |
| 442*-23 | S131K | 20:10:53:17 | N | 1 | 72:28 | 72:28 |
| 92-90 | Q38R_F98A | 20:10:53:17 | N | 1 | 68:32 | 68:32 |
| 284-332* | Q124E_Q160E_T180E | 20:10:53:17 | N | 1 | 58:42 | 57:43 |

TABLE 22-continued

| | | | | | | |
|---|---|---|---|---|---|---|
| 257-331* | Q124E_Q160E_T180E | 20:10:53:17 | N | 1 | 47:53 | 47:53 |
| 443*-326* | Q124E_Q160E_T180E | 20:10:53:17 | N | 1 | 42:58 | 42:58 |
| | WT | 22:8:53:17 | N | 2 | 25:75_42:58 | 33:67 |
| 332*-284 | Q124R | 20:10:53:17 | N | 1 | 82:18 | 82:18 |
| 34-39 | Q38E | 20:10:53:17 | N | 1 | 82:18 | 82:18 |
| 284-332* | Q124E_Q160E_T180E | 20:10:53:17 | N | 1 | 75:25 | 75:25 |
| 90-92 | Q38D_F98W | 20:10:53:17 | N | 1 | 74:26 | 74:26 |
| 442*-23 | S131K | 20:10:53:17 | N | 1 | 70:30 | 70:30 |
| 257-331* | Q124E_Q160E_T180E | 20:10:53:17 | N | 1 | 66:34 | 65:35 |
| 331*-257 | Q124R_Q160K_T178R | 20:10:53:17 | N | 1 | 58:42 | 58:42 |
| 443*-326* | Q124E_Q160E_T180E | 20:10:53:17 | N | 1 | 41:59 | 41:59 |
| | WT | 22:8:53:17 | Y | 2 | 3:97_2:98 | 2:98 |
| 39-34 | Q38R_F98A | 20:10:53:17 | N | 1 | 38:62 | 38:62 |
| 92-90 | Q38R_F98A | 20:10:53:17 | N | 1 | 23:77 | 22:78 |
| | WT | 8:22:35:35 | N | 2 | 46:54_52:48 | 49:51 |
| 257-331* | Q124E_Q160E_T180E | 8:22:35:35 | N | 1 | 93:7 | 93:7 |
| 23-326* | Q124E_Q160E_T180E | 8:22:35:35 | N | 1 | 89:11 | 89:11 |
| 284-332* | Q124E_Q160E_T180E | 8:22:35:35 | N | 1 | 79:21 | 79:21 |
| 34-39 | Q38E | 8:22:35:35 | N | 1 | 42:58 | 42:58 |
| 326*-23 | S131K | 8:22:35:35 | N | 1 | 35:65 | 35:65 |
| 92-90 | Q38R_F98A | 8:22:35:35 | N | 1 | 31:69 | 31:69 |
| 90-92 | Q38D_F98W | 8:22:35:35 | N | 1 | 26:74 | 26:74 |
| 332*-284 | Q124R | 8:22:35:35 | N | 1 | 22:78 | 22:78 |
| 39-34 | Q38R_F98A | 8:22:35:35 | N | 1 | 13:87 | 13:87 |
| 331*-257 | Q124R_Q160K_T178R | 8:22:35:35 | N | 1 | 5:95 | 5:95 |

| Unique identifier set | paired_over_ mispaired_Scalar | Δ (VAR-REF_WT) paired_over_ mispaired_Scalar | H1-L1_ H2-L2 (and H1-L2_ H2-L1) | H1-L1_ H2-L2 (and H1-L2_H2-L1) side peak | H1-L1_ H1-L1 | H1-L1_ H1-L2 | H1-L2_ H1-L2 | H2-L1_ H2-L1 |
|---|---|---|---|---|---|---|---|---|
| | −3.72 | 0 | 1.55 | not present | 0 | 0 | 0 | 0 |
| 305*-307* | 5 | 8.72 | 95 | 10 | 0 | 0 | 0 | 0 |
| 154-152 | 5 | 8.72 | 94.4 | 6.8 | 0 | 0 | 0 | 0 |
| 326*-23 | 5 | 8.72 | 80.8 | 4.2 | 1.9 | 0 | 0 | 0 |
| 327*-328* | 5 | 8.72 | 70.7 | 6.5 | 1.2 | 0 | 0 | 0 |
| 329*-330* | 5 | 8.72 | 61.9 | 3.1 | 0 | 0 | 0 | 0 |
| 331*-257 | 5 | 8.72 | 56.4 | 3.4 | 6.1 | 0 | 0 | 0 |
| 329*-330* | 5 | 8.72 | 42.2 | 3.2 | 0 | 0 | 0 | 0 |
| 332*-284 | 4.06 | 7.78 | 32.5 | 1.8 | 11.5 | 0 | 0 | 0 |
| 333*-334* | 4 | 7.72 | 85.9 | 7.2 | 0 | 0 | 0 | 0 |
| 335*-336* | 3.84 | 7.56 | 66.4 | 6.7 | 0 | 0 | 0 | 0 |
| 331*-257 | 3.51 | 7.23 | 50.5 | 3.4 | 2.8 | 0 | 0 | 0 |
| 90-92 | 3.2 | 6.92 | 90.6 | 4.3 | 0 | 0 | 0 | 0 |
| 34-39 | 3.18 | 6.9 | 89.6 | 3.9 | 0 | 0 | 0 | 0 |
| 313*-337* | 2.99 | 6.71 | 82.1 | 9.6 | 0 | 0 | 0 | 0 |
| 336*-335* | 2.68 | 6.4 | 64.9 | 10.4 | 0 | 0 | 1.5 | 0 |
| 338*-299 | 2.67 | 6.39 | 85.5 | 4.7 | 0 | 0 | 0 | 0 |
| 313*-339* | 2.6 | 6.32 | 82.1 | 7.9 | 0 | 0 | 0 | 0 |
| 340*-337* | 2.48 | 6.2 | 77.5 | 7.8 | 0 | 0 | 0 | 0 |
| 340*-339* | 2.47 | 6.19 | 12.2 | 1.6 | 3.2 | 0 | 0 | 0 |
| 66-67 | 2.42 | 6.14 | 26.6 | 2.2 | 3 | 0 | 0 | 0 |
| 57-58 | 2.31 | 6.03 | 56.4 | 3.05 | 1.8 | 0 | 0 | 0 |
| 341*-342* | 2.21 | 5.93 | 29.8 | 2.7 | 8.5 | 1.6 | 0 | 0 |
| 92-90 | 2.13 | 5.85 | 84.4 | 6.5 | 0 | 0 | 0 | 0 |
| 325*-31 | 1.96 | 5.68 | 81.8 | not annotated | 0 | 0 | 0 | 0 |
| 92-90 | 1.92 | 5.64 | 80 | 6 | 0 | 0 | 0 | 0 |
| 300-343* | 1.87 | 5.59 | 71.4 | 4.5 | 0 | 0 | 0 | 0 |
| 342*-341* | 1.87 | 5.59 | 52.1 | 3.8 | 2.4 | 0 | 0 | 0 |
| 344*-121 | 1.83 | 5.55 | 68.8 | 7.1 | 1.7 | 0 | 0 | 0 |
| 345*-346* | 1.79 | 5.51 | 66.9 | 7.7 | 0 | 0 | 0 | 0 |
| 347*-348* | 1.71 | 5.43 | 32.9 | 3.7 | 6.9 | 2.2 | 0 | 0 |
| 57-58 | 1.64 | 5.36 | 68.7 | 5 | 0 | 0 | 0 | 0 |
| 338*-349* | 1.61 | 5.33 | 57.5 | 5.1 | 0 | 0 | 0 | 0 |
| 300-349* | 1.53 | 5.25 | 75.4 | 6.6 | 0 | 0 | 0 | 0 |
| 106-97 | 1.45 | 5.17 | 44.2 | 12.8 | 2.1 | 0 | 0 | 0 |
| 111-112 | 1.37 | 5.09 | 73.6 | 1.6 | 0 | 0 | 0 | 0 |
| 350*-31 | 1.37 | 5.09 | 66.8 | 4.6 | 0 | 1.7 | 1 | 0 |
| 338*-343* | 1.36 | 5.08 | 53.6 | 3 | 1.5 | 0 | 0 | 0 |
| 73-74 | 1.18 | 4.9 | 26.6 | 1.6 | 1.3 | 0 | 0 | 0 |
| 300-299 | 1.17 | 4.89 | 29.8 | 2.3 | 8.3 | 4.2 | 0 | 0 |
| 152-154 | 0.92 | 4.64 | 57.9 | 3.5 | 0 | 0 | 0 | 0 |
| 306*-304* | 0.87 | 4.59 | 56.1 | 0.8 | 0 | 0 | 0 | 0 |
| 107-108 | 0.86 | 4.58 | 0 | not present | 0 | 0 | 0 | 0 |
| 307*-305* | 0.85 | 4.57 | 56.7 | 8 | 0 | 0 | 0 | 0 |
| 351*-312* | 0.79 | 4.51 | 62 | 4.9 | 0 | 0 | 0 | 0 |
| 186-352* | 0.68 | 4.4 | 63.3 | 5.4 | 0 | 0 | 0 | 0 |
| 353*-354* | 0.675 | 4.39 | 44.15 | 4.3 | 0.75 | 0.8 | 0 | 0 |
| 1-2 | 0.64 | 4.36 | 55.5 | not annotated | 1.2 | 0 | 1.3 | 0 |
| 121-344* | 0.62 | 4.34 | 54.8 | 4.5 | 0 | 0 | 0 | 0 |

TABLE 22-continued

| | | | | | | | | |
|---|---|---|---|---|---|---|---|---|
| 72-65 | 0.55 | 4.27 | 57.5 | not present | 0 | 0 | 0 | 0 |
| 312*-351* | 0.51 | 4.23 | 48.8 | 4.4 | 0 | 0 | 0 | 0 |
| 186-355* | 0.38 | 4.1 | 59.4 | 2 | 0 | 0 | 0 | 0 |
| 356*-357* | 0.32 | 4.04 | 51.4 | 7.3 | 0 | 0 | 0 | 0 |
| 346*-345* | 0.32 | 4.04 | 44.8 | 4.5 | 0 | 0 | 0 | 0 |
| 343*-338* | 0.32 | 4.04 | 42.3 | 3.8 | 0 | 0 | 0 | 0 |
| 52-51 | 0.32 | 4.04 | 38.6 | not present | 0 | 0 | 0 | 0 |
| 358*-359* | 0.3 | 4.02 | 46.4 | 3.5 | 0 | 0 | 0 | 0 |
| 348*-347* | 0.26 | 3.98 | 45 | 4.4 | 0 | 1.3 | 0 | 0 |
| 355*-186 | 0.24 | 3.96 | 10.3 | 0.8 | 3.5 | 3.1 | 1.5 | 0 |
| 360*-359* | 0.23 | 3.95 | 44.7 | 3.9 | 0 | 0 | 0 | 0 |
| 313*-361* | 0.21 | 3.93 | 47.3 | 5.6 | 0 | 0 | 0 | 1.6 |
| 340*-361* | 0.04 | 3.76 | 40.8 | 5.3 | 0 | 0 | 0 | 0 |
| 357*-356* | 0.02 | 3.74 | 46.3 | 3.1 | 0 | 0 | 0 | 0 |
| 359*-362* | 0.01 | 3.73 | 38.9 | 2.3 | 0 | 0 | 0 | 0 |
| 186-363* | −0.03 | 3.69 | 36.2 | 1.3 | 0 | 0 | 1 | 0 |
| 363*-186 | −0.03 | 3.69 | 33.2 | 3 | 0 | 0 | 0 | 0 |
| 299-300 | −0.07 | 3.65 | 39.2 | 4.5 | 0 | 0 | 0 | 0 |
| 359*-358* | −0.08 | 3.64 | 39.7 | 3.6 | 0 | 0 | 0 | 0 |
| 356*-364* | −0.1 | 3.62 | 42 | 5.5 | 0 | 0 | 0 | 0 |
| | −3.72 | 0 | 1.55 | not present | 0 | 0 | 0 | 0 |
| 337*-340* | −0.13 | 3.59 | 41.3 | 4.1 | 0 | 0 | 0 | 0 |
| 339*-340* | −0.13 | 3.59 | 40.3 | 2.8 | 0 | 0 | 0 | 0 |
| 337*-313* | −0.15 | 3.57 | 40.6 | 3.4 | 0 | 0 | 0 | 0 |
| 364*-356* | −0.15 | 3.57 | 37.1 | 3 | 0 | 0 | 0 | 0 |
| 339*-313* | −0.18 | 3.54 | 33.7 | 2.2 | 0 | 0 | 0 | 0 |
| 314*-315* | −0.23 | 3.49 | 9.5 | 0.2 | 1.7 | 0 | 0 | 0 |
| 31-325* | −0.34 | 3.38 | 33.6 | 2.6 | 0 | 0 | 0 | 0 |
| 349*-300 | −0.35 | 3.37 | 37.3 | 2.2 | 0 | 0 | 0 | 0 |
| 356*-365* | −0.36 | 3.36 | 25.7 | 3.4 | 0 | 0 | 1 | 0 |
| 31-350* | −0.42 | 3.3 | 30.7 | 3.2 | 0 | 0 | 0 | 0 |
| 257-331* | −0.44 | 3.28 | 30.2 | 6.3 | 0 | 0 | 2.1 | 0 |
| 19-3 | −0.48 | 3.24 | 16.8 | not present | 2.6 | 4.1 | 0 | 0 |
| 352*-186 | −0.52 | 3.2 | 27.5 | 3.2 | 0 | 0 | 4.1 | 0 |
| 366*-367* | −0.57 | 3.15 | 26.9 | not annotated | 1.8 | 0 | 0 | 0 |
| 343*-300 | −0.61 | 3.11 | 20 | 1.4 | 0 | 0 | 0 | 0 |
| | −3.72 | 0 | 1.55 | not present | 0 | 0 | 0 | 0 |
| 328*-327* | −0.63 | 3.09 | 5.3 | 1.1 | 2 | 6.5 | 6.9 | 0 |
| 361*-313* | −0.72 | 3 | 30.5 | 2 | 0 | 0 | 0 | 0 |
| 361*-340* | −0.74 | 2.98 | 29.2 | 1.6 | 0 | 0 | 0 | 0 |
| 299-338* | −0.77 | 2.95 | 27 | 1.4 | 0 | 0 | 0 | 0 |
| 368*-369* | −0.8 | 2.92 | 18.4 | 2.9 | 0 | 0 | 1.3 | 0 |
| 370*-371* | −0.8 | 2.92 | 17.9 | 1.4 | 0 | 1.1 | 2.4 | 0 |
| 359*-360* | −0.81 | 2.91 | 17.7 | 2.1 | 1.1 | 0 | 1.5 | 0 |
| 368*-372* | −0.81 | 2.91 | 14.3 | 1.7 | 0 | 1.2 | 3.6 | 0 |
| 373*-374* | −0.83 | 2.89 | 20 | 2.6 | 0 | 1.1 | 1.3 | 0 |
| 295-294 | −0.85 | 2.87 | 13.2 | 2.6 | 0 | 0 | 2.5 | 0 |
| 375*-376* | −0.89 | 2.83 | 15.7 | 2.9 | 0 | 0 | 1.9 | 0 |
| 377*-378* | −0.9 | 2.82 | 6.6 | 0.8 | 0 | 0 | 2.2 | 0 |
| 74-73 | −0.92 | 2.8 | 5.1 | 4.6 | 7.7 | 0 | 4.9 | 0 |
| 379*-380* | −0.96 | 2.76 | 7.6 | 1.4 | 0 | 2.8 | 5.4 | 0 |
| 381*-382* | −1.06 | 2.66 | 18.5 | 1.3 | 0 | 0 | 0 | 0 |
| 383*-384* | −1.09 | 2.63 | 13.7 | 1.8 | 1.2 | 0 | 0 | 0 |
| 349*-338* | −1.14 | 2.58 | 20.7 | 0.9 | 0 | 0 | 0 | 0 |
| 334*-333* | −1.19 | 2.53 | 1 | 0.3 | 0 | 3 | 5.4 | 0 |
| 378*-377* | −1.245 | 2.48 | 12.05 | 1.55 | 0.55 | 0 | 1.4 | 0 |
| 375*-385* | −1.3 | 2.42 | 11.1 | 2.4 | 0 | 0 | 0 | 0 |
| | −3.72 | 0 | 1.55 | not present | 0 | 0 | 0 | 0 |
| 304*-306* | −1.36 | 2.36 | 10.4 | 0.2 | 0 | 2.5 | 0 | 0 |
| 362*-359* | −1.37 | 2.35 | 9 | 0.4 | 0 | 0 | 3 | 0 |
| 386*-387* | −1.44 | 2.28 | 11.6 | 1.6 | 0 | 0 | 0 | 0 |
| 388*-389* | −1.52 | 2.2 | 11.6 | 1.9 | 0 | 0 | 0 | 0 |
| 390*-391* | −1.53 | 2.19 | 6.8 | 2.8 | 4.5 | 0 | 0 | 0 |
| 374*-392* | −1.54 | 2.18 | 11.2 | 1.5 | 0 | 0 | 0 | 0 |
| 387*-386* | −1.54 | 2.18 | 7.8 | 1.5 | 0 | 0 | 0 | 0 |
| 393*-394* | −1.54 | 2.18 | 7.1 | 1.1 | 5.3 | 0 | 1.2 | 0 |
| 395*-396* | −1.61 | 2.11 | 4.6 | 1.5 | 0 | 3 | 0 |
| | −3.72 | 0 | 1.55 | not present | 0 | 0 | 0 | 0 |
| 354*-353* | −1.66 | 2.06 | 7.8 | 1.3 | 0 | 1.8 | 6.9 | 0 |
| 306*-304* | −1.67 | 2.05 | 1.9 | 0.1 | 0 | 0 | 2.1 | 0 |
| 397*-398* | −1.72 | 2 | 7 | 1.3 | 4.8 | 0 | 1.3 | 0 |
| 399*-400* | −1.76 | 1.96 | 8.4 | 1.5 | 0 | 0 | 0 | 0 |
| 401*-402* | −1.84 | 1.88 | 5.5 | 1 | 4.8 | 0 | 0 | 0 |
| 403*-404* | −1.87 | 1.85 | 4.9 | 0.7 | 0 | 0 | 3.9 | 0 |
| 382*-381* | −1.88 | 1.84 | 8.3 | 1.3 | 0 | 0 | 0 | 0 |
| 405*-391* | −1.92 | 1.8 | 7.6 | 1.8 | 1.5 | 0 | 1.5 | 0 |
| 406*-407* | −1.93 | 1.79 | 4 | 0.6 | 5.6 | 0 | 0 | 0 |
| 408*-377* | −2.04 | 1.68 | 3.3 | 1.3 | 1 | 0 | 5.6 | 0 |
| 409*-410* | −2.06 | 1.66 | 3.5 | 0.6 | 0 | 0 | 0 | 0 |
| 55-56 | −2.1 | 1.62 | 4.9 | 1.9 | 0 | 0 | 0 | 0 |

TABLE 22-continued

| | | | | | | | | |
|---|---|---|---|---|---|---|---|---|
| 371*-370* | -2.11 | 1.61 | 6.7 | 0.7 | 0 | 0 | 0 | 0 |
| 377*-408* | -2.11 | 1.61 | 4.8 | 0.6 | 0 | 0 | 2.7 | 0 |
| 411*-384* | -2.12 | 1.6 | 5.4 | 0.7 | 0 | 6.5 | 0 | 0 |
| 412*-413* | -2.13 | 1.59 | 5.5 | 1.4 | 0 | 0 | 2.4 | 0 |
| 53-54 | -2.14 | 1.58 | 4.8 | 0.7 | 0 | 0 | 0 | 0 |
| 414*-413* | -2.18 | 1.54 | 4.7 | 1.8 | 2.1 | 0 | 0 | 0 |
| 415*-416* | -2.18 | 1.54 | 4.4 | 1 | 1.6 | 0 | 4.5 | 0 |
| 417*-418* | -2.19 | 1.53 | 5.3 | 0.4 | 0 | 0 | 3.2 | 0 |
| | -3.72 | 0 | 1.55 | not present | 0 | 0 | 0 | 0 |
| 419*-420* | -2.2 | 1.52 | 6.3 | 1.6 | 0 | 0 | 0 | 0 |
| 421*-422* | -2.25 | 1.47 | 3.4 | 0.3 | 0 | 0 | 0 | 0 |
| 374*-373* | -2.29 | 1.43 | 6.2 | 1.3 | 0 | 0 | 0 | 0 |
| 423*-418* | -2.3 | 1.42 | 4 | 0.4 | 0 | 0 | 3.2 | 0 |
| 424*-260 | -2.3 | 1.42 | 3.6 | 0.6 | 0 | 0 | 3.2 | 0 |
| 425*-404* | -2.31 | 1.41 | 3.8 | 0.6 | 0 | 0 | 2.4 | 0 |
| 419*-426* | -2.34 | 1.38 | 3.2 | 1 | 1.2 | 0 | 2.1 | 0 |
| 427*-418* | -2.35 | 1.37 | 3.6 | 0.4 | 0 | 0 | 4.6 | 0 |
| 428*-396* | -2.39 | 1.33 | 1.4 | 1.1 | 1.4 | 1.2 | 1.2 | 0 |
| 392*-374* | -2.44 | 1.28 | 3.3 | 1 | 0 | 0 | 0 | 0 |
| 429*-430* | -2.45 | 1.27 | 2.5 | 0.3 | 4.2 | 0 | 1.3 | 0 |
| 54-53 | -2.54 | 1.18 | 3 | 1 | 0 | 0 | 0 | 0 |
| 431*-418* | -2.67 | 1.05 | 4.2 | 0.5 | 0 | 0 | 3.8 | 0 |
| 432*-426* | -2.77 | 0.95 | 3.6 | 0.9 | 0 | 0 | 0 | 0 |
| 433*-434* | -2.88 | 0.84 | 3.5 | 0.5 | 0 | 0 | 1.6 | 0 |
| 435*-283 | -2.9 | 0.82 | 2.1 | 1 | 1.3 | 0 | 4.7 | 0 |
| 56-55 | -3.03 | 0.69 | 1.6 | 0.6 | 0 | 0 | 1.2 | 0 |
| 435*-436* | -3.41 | 0.31 | 1.4 | 0.5 | 0 | 0 | 2.1 | 0 |
| 437*-326* | -3.58 | 0.14 | 0 | 0.4 | 1.5 | 0 | 3.1 | 0 |
| 438*-285 | -3.75 | -0.03 | 1.2 | 0.5 | 0 | 0 | 2.1 | 0 |
| 439*-283 | -3.89 | -0.17 | 0 | 0.6 | 0 | 0 | 0 | 0 |
| 440*-441* | -5 | -1.28 | 0 | 0.4 | 0 | 0 | 1.1 | 0 |
| | -0.61 | 0 | 21.5 | 4.7 | 0 | 0 | 0 | 0 |
| 331*-257 | 3.62 | 4.23 | 63.3 | 1.7 | 2.5 | 0 | 0 | 0 |
| | -3.72 | 0 | 1.55 | not present | 0 | 0 | 0 | 0 |
| 332*-284 | 1.98 | 2.59 | 48.2 | 1.6 | 2.1 | 0 | 0 | 0 |
| 90-92 | 1.84 | 2.45 | 52.4 | 4.6 | 0 | 0 | 0 | 0 |
| 34-39 | 1.42 | 2.03 | 56.9 | 4.3 | 0 | 0 | 0 | 0 |
| 39-34 | 1.25 | 1.86 | 42 | 5.4 | 0 | 0 | 0 | 0 |
| 442*-23 | 0.92 | 1.53 | 37.7 | 4 | 0 | 0 | 0 | 0 |
| 92-90 | 0.75 | 1.36 | 56.4 | 9 | 0 | 0 | 0 | 0 |
| 284-332* | 0.3 | 0.91 | 17.2 | 1.8 | 0 | 0 | 0 | 0 |
| 257-331* | -0.11 | 0.5 | 8.9 | 0.8 | 0 | 0 | 0 | 0 |
| 443*-326* | -0.34 | 0.27 | 33.8 | 2.5 | 0 | 0 | 0 | 0 |
| | -0.685 | -0.01 | 24.85 | 3.9 | 0 | 0.95 | 0.95 | 0 |
| 332*-284 | 1.54 | 2.24 | 55.3 | 8 | 1.9 | 3.7 | 0 | 0 |
| 34-39 | 1.49 | 2.19 | 61 | 8 | 0 | 0 | 0 | 0 |
| 284-332* | 1.08 | 1.78 | 45.3 | 7.9 | 0 | 0 | 0 | 0 |
| 90-92 | 1.04 | 1.74 | 49 | 6.6 | 1.1 | 0 | 0 | 0 |
| 442*-23 | 0.87 | 1.57 | 41.2 | 9.2 | 0 | 0 | 0 | 0 |
| 257-331* | 0.64 | 1.34 | 22.1 | 3.9 | 0 | 0 | 0 | 0 |
| 331*-257 | 0.32 | 1.01 | 26.1 | 3.7 | 3.3 | 2.3 | 0 | 0 |
| 443*-326* | -0.37 | 0.32 | 29.2 | 3.9 | 0 | 0 | 0 | 0 |
| | -3.72 | 0 | 1.55 | not present | 0 | 0 | 0 | 0 |
| 39-34 | -0.48 | 0.21 | 19 | 3.8 | 5.1 | 3.9 | 0 | 0 |
| 92-90 | -1.24 | -0.55 | 8 | 1.6 | 4 | 1.7 | 0 | 0 |
| | -0.05 | 0 | 40.8 | 63 | 0 | 0 | 0 | 0 |
| 257-331* | 2.51 | 2.56 | 63.1 | 6.9 | 0 | 0 | 0 | 0 |
| 23-326* | 2.09 | 2.14 | 58.4 | 2.1 | 0 | 0 | 0 | 0 |
| 284-332* | 1.34 | 1.39 | 45.5 | 4.5 | 0 | 0 | 0 | 0 |
| 34-39 | -0.33 | -0.28 | 31.5 | 3.6 | 0 | 0 | 0 | 0 |
| 326*-23 | -0.64 | -0.59 | 23.3 | 1 | 0 | 0 | 0 | 0 |
| 92-90 | -0.79 | -0.74 | 20.3 | 1.5 | 0 | 0 | 0 | 0 |
| 90-92 | -1.04 | -0.99 | 14.4 | 1.4 | 0 | 0 | 0 | 0 |
| 332*-284 | -1.29 | -1.24 | 12.3 | 1.2 | 0 | 0 | 0 | 0 |
| 39-34 | -1.94 | -1.89 | 7.9 | 1.1 | 0 | 0 | 0 | 1.1 |
| 331*-257 | -2.9 | -2.85 | 2.7 | 0.4 | 0 | 0 | 0 | 1.1 |

| Unique identifier set | H2-L1_ H2-L2 | H2-L2_ H2-L2 | H1-L1_ H2-L1 | H1-L2_ H2-L2 | H1-L1 | H1-L2 | H2-L1 | H2-L2 |
|---|---|---|---|---|---|---|---|---|
| | 0 | 0 | 0 | 96.9 | 0 | 0.7 | 0 | 0.9 |
| 305*-307* | 0 | 2.8 | 0 | 0 | 2.2 | 0 | 0 | 0 |
| 154-152 | 0 | 0 | 0 | 0 | 3.1 | 0 | 0 | 2.5 |
| 326*-23 | 0 | 0 | 0 | 0 | 14 | 0 | 0 | 3.3 |
| 327*-328* | 0 | 0 | 0 | 0 | 26.6 | 0 | 0 | 1.5 |
| 329*-330* | 0 | 1.1 | 0 | 0 | 2.6 | 0 | 0 | 34.3 |
| 331*-257 | 0 | 0 | 0 | 0 | 33.9 | 0 | 0 | 3.6 |
| 329*-330* | 0 | 2.4 | 0 | 0 | 0 | 0 | 0 | 55.4 |
| 332*-284 | 0 | 0 | 1.7 | 0 | 54.3 | 0 | 0 | 0 |
| 333*-334* | 0 | 0 | 0 | 1.8 | 9.3 | 0 | 0 | 3 |

TABLE 22-continued

| | | | | | | | | |
|---|---|---|---|---|---|---|---|---|
| 335*-336* | 0 | 4.2 | 0 | 0 | 25.4 | 2.1 | 0 | 2 |
| 331*-257 | 2.9 | 0 | 0 | 0 | 42.6 | 0 | 0 | 1.3 |
| 90-92 | 0 | 0 | 0 | 3.9 | 2.3 | 0 | 0 | 3.2 |
| 34-39 | 0 | 0 | 0 | 4 | 2.8 | 0 | 0 | 3.7 |
| 313*-337* | 2.1 | 1.3 | 0 | 2.7 | 1.1 | 0 | 0 | 10.7 |
| 336*-335* | 1.1 | 9 | 3.8 | 0 | 18.6 | 0 | 0 | 1.1 |
| 338*-299 | 0 | 0 | 0 | 6.5 | 3.6 | 0 | 0 | 4.5 |
| 313*-339* | 0 | 1.5 | 5.1 | 1.8 | 5.1 | 0 | 0 | 4.4 |
| 340*-337* | 0 | 0 | 0 | 7.7 | 1.4 | 0 | 0 | 13.4 |
| 340*-339* | 0 | 1.9 | 2 | 0 | 74.9 | 5.8 | 0 | 0 |
| 66-67 | 0 | 0 | 2.2 | 0 | 62.2 | 6 | 0 | 0 |
| 57-58 | 3.15 | 1.15 | 0 | 5.15 | 27.35 | 1.1 | 0 | 3.9 |
| 341*-342* | 0 | 0 | 0 | 2.2 | 51.8 | 6.1 | 0 | 0 |
| 92-90 | 0 | 0 | 8.8 | 1.8 | 2.3 | 0 | 0 | 2.7 |
| 325*-31 | 0 | 1.9 | 6.3 | 5 | 0 | 0 | 1.1 | 4 |
| 92-90 | 2.9 | 1.2 | 3.1 | 6.8 | 4.1 | 0 | 0 | 1.9 |
| 300-343* | 0 | 0 | 1.8 | 9.2 | 9.2 | 2.4 | 0 | 6 |
| 342*-341* | 0 | 0 | 13.3 | 0 | 32.2 | 0 | 0 | 0 |
| 344*-121 | 0 | 0 | 2.7 | 7.1 | 13.9 | 4 | 0 | 1.8 |
| 345*-346* | 0 | 0 | 1.6 | 7.7 | 15.4 | 5 | 0 | 3.5 |
| 347*-348* | 0 | 2.5 | 0 | 3.6 | 38.4 | 9.5 | 0 | 4.1 |
| 57-58 | 0 | 0 | 0 | 14.1 | 12.1 | 2.1 | 0 | 3 |
| 338*-349* | 0 | 1.3 | 4.2 | 7.6 | 0 | 0 | 4.8 | 24.6 |
| 300-349* | 2.2 | 0 | 5 | 10.6 | 2.3 | 0 | 0 | 4.4 |
| 106-97 | 0 | 0 | 13 | 0 | 34.7 | 6 | 0 | 0 |
| 111-112 | 0 | 0 | 11.8 | 7.3 | 0 | 0 | 1.2 | 6.1 |
| 350*-31 | 0 | 0 | 11.2 | 4.4 | 12.9 | 1.9 | 0 | 0 |
| 338*-343* | 1.4 | 0 | 1.3 | 8.8 | 22.2 | 9 | 0 | 2.2 |
| 73-74 | 0 | 0 | 3.3 | 2.7 | 48.6 | 17.6 | 0 | 0 |
| 300-299 | 1.4 | 0 | 0 | 5.7 | 38.2 | 12.4 | 0 | 0 |
| 152-154 | 0 | 0 | 5.9 | 18.9 | 10.2 | 3.7 | 0 | 3.4 |
| 306*-304* | 0 | 1.1 | 7.8 | 19.1 | 13.3 | 2.5 | 0 | 0 |
| 107-108 | 0 | 3.9 | 0 | 29.8 | 0 | 0 | 0 | 66.3 |
| 307*-305* | 0 | 0 | 6.5 | 19.1 | 8.8 | 4.4 | 0 | 4.5 |
| 351*-312* | 0 | 1.1 | 2.1 | 27.3 | 2.3 | 1.8 | 0 | 3.4 |
| 186-352* | 0 | 0 | 14.1 | 9.8 | 1.8 | 3.8 | 6 | 1.3 |
| 353*-354* | 0 | 0.5 | 0 | 30.4 | 8.85 | 2.75 | 0 | 11.75 |
| 1-2 | 1.9 | 1.1 | 2.7 | 28.7 | 2 | 0 | 0 | 5.6 |
| 121-344* | 0 | 0 | 15 | 14.6 | 7 | 3.5 | 1.8 | 3.4 |
| 72-65 | 0 | 0 | 5.4 | 30 | 2.1 | 0 | 1.1 | 3.8 |
| 312*-351* | 0 | 1.3 | 10 | 20.2 | 4.6 | 3.5 | 3.8 | 7.7 |
| 186-355* | 0 | 0 | 10.9 | 29.7 | 0 | 0 | 0 | 0 |
| 356*-357* | 0 | 0 | 8.1 | 31.7 | 1.8 | 2.2 | 0 | 4.9 |
| 346*-345* | 1 | 0 | 9.2 | 25.5 | 10 | 6.2 | 0 | 3.1 |
| 343*-338* | 1.7 | 3.4 | 14 | 20.1 | 7.7 | 4.1 | 2.2 | 4.4 |
| 52-51 | 1.1 | 14 | 7.1 | 33.9 | 0 | 0 | 0 | 5.3 |
| 358*-359* | 1.4 | 2.1 | 20.3 | 13.5 | 4.7 | 3.5 | 3.8 | 4.3 |
| 348*-347* | 0 | 0 | 27.9 | 7.8 | 2.4 | 0 | 6.6 | 9 |
| 355*-186 | 0 | 0 | 1.3 | 7.4 | 42.2 | 30.7 | 0 | 0 |
| 360*-359* | 0 | 0 | 29 | 7.9 | 9 | 4.2 | 3.1 | 2.1 |
| 313*-361* | 2.1 | 0 | 36.3 | 1.8 | 5.2 | 0 | 3.1 | 2.7 |
| 340*-361* | 0 | 0 | 43.1 | 1.7 | 7.2 | 1.3 | 2.9 | 3.1 |
| 357*-356* | 0 | 0 | 1.7 | 37.6 | 1.3 | 7 | 3.2 | 2.9 |
| 359*-362* | 0 | 0 | 1.3 | 37.2 | 11.4 | 11.2 | 0 | 0 |
| 186-363* | 0 | 0 | 9.6 | 8.6 | 13 | 31.6 | 0 | 0 |
| 363*-186 | 0 | 0 | 2.1 | 32.5 | 16.1 | 16.1 | 0 | 0 |
| 299-300 | 0 | 0 | 14.9 | 29.8 | 3.2 | 3.6 | 3.3 | 5.9 |
| 359*-358* | 0 | 0 | 0 | 48.3 | 3.2 | 3.7 | 0 | 5.1 |
| 356*-364* | 0 | 0 | 0 | 49 | 2.3 | 3.5 | 0 | 3.2 |
| | 0 | 0 | 0 | 96.9 | 0 | 0.7 | 0 | 0.9 |
| 337*-340* | 0 | 0 | 11.7 | 36.3 | 5.4 | 5.3 | 0 | 0 |
| 339*-340* | 0 | 0 | 14.5 | 31.1 | 4.8 | 5.7 | 1.9 | 1.7 |
| 337*-313* | 0 | 0 | 11.5 | 36.4 | 1.5 | 3.1 | 2.8 | 4 |
| 364*-356* | 0 | 0 | 21.9 | 23.5 | 4.4 | 4.3 | 4.1 | 4.7 |
| 339*-313* | 0 | 1.4 | 5.8 | 35.7 | 8.2 | 11.6 | 1.4 | 2.2 |
| 314*-315* | 0 | 0 | 6.2 | 13.2 | 32 | 36.3 | 0 | 1.2 |
| 31-325* | 0 | 0 | 6.7 | 42.2 | 4.5 | 6.4 | 3.1 | 3.4 |
| 349*-300 | 0 | 0 | 2.6 | 45.5 | 3 | 10.5 | 0 | 1.1 |
| 356*-365* | 1.1 | 1.7 | 1.2 | 29.7 | 12.1 | 26 | 0 | 1.6 |
| 31-350* | 0 | 0 | 6.1 | 43.3 | 4.1 | 8.9 | 2.1 | 4.8 |
| 257-331* | 1.1 | 1.6 | 0 | 54.7 | 1.9 | 3.1 | 0 | 5.4 |
| 19-3 | 0 | 6.1 | 2.5 | 55.1 | 0 | 0 | 0 | 12.8 |
| 352*-186 | 0 | 0 | 1.1 | 41 | 9.8 | 16.6 | 0 | 0 |
| 366*-367* | 0 | 2 | 2.7 | 59 | 1.6 | 2.1 | 0 | 3.9 |
| 343*-300 | 0 | 0 | 1.1 | 35.1 | 15.3 | 28.5 | 0 | 0 |
| | 0 | 0 | 0 | 96.9 | 0 | 0.7 | 0 | 0.9 |
| 328*-327* | 0 | 0 | 0 | 6.8 | 27.5 | 45.1 | 0 | 0 |
| 361*-313* | 0 | 0 | 1 | 55.5 | 0 | 8.6 | 2 | 2.3 |
| 361*-340* | 0 | 0 | 0 | 59.1 | 0 | 7.2 | 1.4 | 3 |
| 299-338* | 0 | 0 | 2.6 | 54.6 | 4.6 | 11.2 | 0 | 0 |

TABLE 22-continued

| | | | | | | | | |
|---|---|---|---|---|---|---|---|---|
| 368*-369* | 0 | 0 | 0 | 43.6 | 11 | 24.1 | 0 | 1.5 |
| 370*-371* | 0 | 0 | 0 | 31.2 | 13.2 | 34.2 | 0 | 0 |
| 359*-360* | 0 | 1.7 | 0 | 54.8 | 6 | 12.8 | 0 | 4.3 |
| 368*-372* | 0 | 0 | 0 | 27.9 | 16.4 | 36.6 | 0 | 0 |
| 373*-374* | 0 | 0 | 0 | 55.9 | 7.1 | 11.3 | 0 | 3.3 |
| 295-294 | 0 | 2.6 | 1.5 | 56.6 | 6.9 | 9.5 | 0 | 7.2 |
| 375*-376* | 0 | 1.6 | 0 | 36.5 | 11.9 | 32.4 | 0 | 0 |
| 377*-378* | 0 | 1.2 | 0 | 28.9 | 13.3 | 39.9 | 0 | 7.9 |
| 74-73 | 0 | 1.4 | 0 | 58.4 | 0 | 7 | 1.2 | 14.2 |
| 379*-380* | 0 | 0 | 0 | 19.1 | 20.1 | 45.1 | 0 | 0 |
| 381*-382* | 0 | 1.3 | 0 | 74.2 | 0 | 0 | 0 | 6 |
| 383*-384* | 0 | 0 | 0 | 60.7 | 4.2 | 14.1 | 0 | 6.1 |
| 349*-338* | 0 | 0 | 0 | 49.2 | 3.5 | 26.6 | 0 | 0 |
| 334*-333* | 0 | 0 | 0 | 3.6 | 22.4 | 64.6 | 0 | 0 |
| 378*-377* | 0 | 0 | 0 | 70.2 | 2.05 | 6.1 | 0 | 7.75 |
| 375*-385* | 0 | 0 | 0 | 56 | 8.2 | 22.6 | 0 | 2.1 |
| | 0 | 0 | 0 | 96.9 | 0 | 0.7 | 0 | 0.9 |
| 304*-306* | 0 | 0 | 0 | 62.3 | 7.6 | 14.9 | 0 | 2.4 |
| 362*-359* | 0 | 8.6 | 0 | 27 | 1.5 | 49.7 | 0 | 1.2 |
| 386*-387* | 0 | 0 | 1.3 | 64.1 | 6.3 | 15.4 | 0 | 1.2 |
| 388*-389* | 0 | 0 | 0 | 77.8 | 1.3 | 4.3 | 0 | 5 |
| 390*-391* | 0 | 0 | 0 | 64.2 | 4 | 18 | 0 | 2.5 |
| 374*-392* | 0 | 0 | 2.6 | 61.4 | 6.4 | 18.4 | 0 | 0 |
| 387*-386* | 0 | 1.3 | 0 | 75.5 | 1.6 | 7 | 0 | 6.9 |
| 393*-394* | 0 | 0 | 0 | 61.9 | 3.5 | 19.3 | 0 | 1.7 |
| 395*-396* | 0 | 1.8 | 0 | 64.8 | 1.7 | 15.6 | 0 | 7 |
| | 0 | 0 | 0 | 96.9 | 0 | 0.7 | 0 | 0.9 |
| 354*-353* | 0 | 1 | 0 | 41.7 | 7.2 | 33.6 | 0 | 0 |
| 306*-304* | 0 | 0 | 3.2 | 29.7 | 13.9 | 49.2 | 0 | 0 |
| 397*-398* | 0 | 0 | 0 | 57.4 | 3.4 | 26.1 | 0 | 0 |
| 399*-400* | 0 | 1.3 | 0 | 71.1 | 3.2 | 14 | 0 | 1.8 |
| 401*-402* | 0 | 0 | 0 | 74.5 | 1.8 | 11.8 | 0 | 1.6 |
| 403*-404* | 0 | 1.5 | 1.5 | 51.1 | 5.8 | 30.1 | 0 | 1.2 |
| 382*-381* | 0 | 0 | 0 | 77.2 | 1.8 | 9.5 | 0 | 3.1 |
| 405*-391* | 0 | 0 | 0 | 59.5 | 3.7 | 26.2 | 0 | 0 |
| 406*-407* | 0 | 0 | 0 | 81.7 | 0 | 5.5 | 0 | 3.1 |
| 408*-377* | 0 | 2.1 | 0 | 71.9 | 0 | 11 | 0 | 5.1 |
| 409*-410* | 0 | 3.9 | 0 | 81.8 | 0 | 6.9 | 0 | 3.9 |
| 55-56 | 0 | 1.4 | 1.9 | 77.3 | 1.5 | 9.9 | 0 | 3.1 |
| 371*-370* | 0 | 0 | 0 | 71.4 | 2.6 | 17.7 | 0 | 1.5 |
| 377*-408* | 0 | 0 | 0 | 65.6 | 4.8 | 20.8 | 0 | 1.2 |
| 411*-384* | 0 | 0 | 0 | 61.6 | 3.9 | 21.1 | 0 | 1.4 |
| 412*-413* | 0 | 0 | 0 | 60.5 | 5.1 | 26.6 | 0 | 0 |
| 53-54 | 0 | 0 | 1.8 | 79.3 | 1.7 | 8.4 | 0 | 4 |
| 414*-413* | 0 | 0 | 0 | 80.6 | 1.3 | 9.2 | 0 | 2.1 |
| 415*-416* | 0 | 0 | 0 | 56.4 | 4.2 | 29 | 0 | 0 |
| 417*-418* | 0 | 1.1 | 0 | 60.5 | 3.7 | 26.2 | 0 | 0 |
| | 0 | 0 | 0 | 96.9 | 0 | 0.7 | 0 | 0.9 |
| 419*-420* | 0 | 0 | 0 | 78.2 | 2.5 | 11.8 | 0 | 1.2 |
| 421*-422* | 0 | 0 | 0 | 88.8 | 0 | 1.7 | 0 | 6.1 |
| 374*-373* | 0 | 0 | 0 | 85.9 | 0 | 4.9 | 0 | 3 |
| 423*-418* | 0 | 1.9 | 0 | 61.5 | 2.1 | 26.2 | 0 | 1.1 |
| 424*-260 | 0 | 0 | 0 | 44.4 | 5.5 | 43.3 | 0 | 0 |
| 425*-404* | 0 | 2.6 | 0 | 75.9 | 1.6 | 12.6 | 0 | 1 |
| 419*-426* | 0 | 0 | 0 | 58.6 | 3.3 | 30.5 | 0 | 1.1 |
| 427*-418* | 0 | 1.1 | 1.4 | 51.3 | 2.9 | 34 | 0 | 1.1 |
| 428*-396* | 0 | 0 | 0 | 74.7 | 0 | 14.5 | 0 | 5.6 |
| 392*-374* | 0 | 0 | 0 | 86 | 0 | 6 | 0 | 4.7 |
| 429*-430* | 0 | 0 | 0 | 65.1 | 1.2 | 25.6 | 0 | 0 |
| 54-53 | 0 | 0 | 0 | 72.6 | 4.3 | 20.1 | 0 | 0 |
| 431*-418* | 0 | 0 | 0 | 66.7 | 2.3 | 23 | 0 | 0 |
| 432*-426* | 0 | 0 | 0 | 75.2 | 2.3 | 18.9 | 0 | 0 |
| 433*-434* | 0 | 0 | 1.2 | 80.6 | 1.8 | 11.3 | 0 | 0 |
| 435*-283 | 0 | 0 | 0 | 65.4 | 1.8 | 24.7 | 0 | 0 |
| 56-55 | 0 | 0 | 0 | 59.8 | 1.8 | 34.5 | 0 | 1.2 |
| 435*-436* | 0 | 0 | 0 | 61.6 | 1.8 | 33.1 | 0 | 0 |
| 437*-326* | 0 | 0 | 0 | 60 | 0 | 34.2 | 0 | 1.2 |
| 438*-285 | 0 | 0 | 0 | 58.9 | 1.1 | 36.8 | 0 | 0 |
| 439*-283 | 0 | 0 | 0 | 90.9 | 0 | 7.1 | 0 | 2 |
| 440*-441* | 0 | 0 | 0 | 79.1 | 0 | 19.8 | 0 | 0 |
| | 0 | 1.3 | 8.55 | 39.65 | 4.1 | 12.25 | 4.15 | 8.55 |
| 331*-257 | 0 | 0 | 2.6 | 0 | 31.6 | 0 | 0 | 0 |
| | 0 | 0 | 0 | 96.9 | 0 | 0.7 | 0 | 0.9 |
| 332*-284 | 0 | 0 | 1.9 | 4.6 | 37.6 | 5.6 | 0 | 0 |
| 90-92 | 3.7 | 2.1 | 3.9 | 0 | 4.8 | 2.7 | 3.4 | 26.9 |
| 34-39 | 1.3 | 0 | 3 | 10.5 | 3.5 | 3.3 | 1.3 | 20.2 |
| 39-34 | 0 | 2.6 | 5.3 | 10.5 | 4 | 1.7 | 4.7 | 29.1 |
| 442*-23 | 0 | 1.2 | 13.7 | 0 | 4.3 | 0 | 14.8 | 28.3 |
| 92-90 | 1 | 0 | 11.2 | 15.4 | 7.3 | 3.1 | 1.5 | 4.2 |
| 284-332* | 1.1 | 8.3 | 0 | 34.1 | 2.4 | 5.8 | 1.4 | 29.6 |

TABLE 22-continued

|  |  |  |  |  |  |  |  |  |
|---|---|---|---|---|---|---|---|---|
| 257-331* | 0 | 5 | 0 | 45.3 | 0 | 7.4 | 0 | 33.4 |
| 443*-326* | 0 | 0 | 1.6 | 46.1 | 7.8 | 10.7 | 0 | 0 |
|  | 0 | 0 | 0 | 27.25 | 1.6 | 30.5 | 6.55 | 7.35 |
| 332*-284 | 0 | 0 | 12.4 | 0 | 19.9 | 1.6 | 0 | 5.2 |
| 34-39 | 0 | 0 | 5 | 9.1 | 8 | 2.5 | 1.8 | 12.5 |
| 284-332* | 0 | 0 | 4 | 14.7 | 3.8 | 1.7 | 5 | 25.5 |
| 90-92 | 0 | 0 | 17.6 | 1.2 | 9.4 | 0 | 7.4 | 14.3 |
| 442*-23 | 0 | 0 | 14.7 | 0 | 2 | 0 | 14.8 | 27.2 |
| 257-331* | 0 | 0 | 1 | 30.4 | 2.2 | 1.7 | 1.4 | 41.2 |
| 331*-257 | 0 | 0 | 36.3 | 0 | 25 | 0 | 3.4 | 3.6 |
| 443*-326* | 0 | 0 | 13.1 | 33.8 | 8.7 | 11 | 1.3 | 2.9 |
|  | 0 | 0 | 0 | 96.9 | 0 | 0.7 | 0 | 0.9 |
| 39-34 | 0 | 0 | 35.5 | 0 | 5.5 | 1.6 | 20.7 | 8.7 |
| 92-90 | 0 | 0 | 58.2 | 0 | 7.2 | 0 | 17.6 | 3.3 |
|  | 0 | 0 | 15.8 | 13.9 | 1.55 | 3.15 | 18.4 | 6.45 |
| 257-331* | 0 | 0 | 4.2 | 1.2 | 2.1 | 0 | 2.1 | 27.4 |
| 23-326* | 0 | 1.6 | 5.2 | 2.2 | 0 | 0 | 3.6 | 29 |
| 284-332* | 0 | 0 | 11 | 0 | 1.3 | 0 | 9.8 | 32.3 |
| 34-39 | 0 | 0 | 46.2 | 0 | 2.1 | 0 | 12 | 8.3 |
| 326*-23 | 0 | 0 | 45.7 | 0 | 1.2 | 0 | 19.8 | 10.1 |
| 92-90 | 0 | 0 | 45.2 | 0 | 1.6 | 0 | 23.6 | 9.2 |
| 90-92 | 0 | 0 | 57.5 | 1.1 | 5.2 | 0 | 15.3 | 6.4 |
| 332*-284 | 0 | 0 | 53.1 | 0 | 2.2 | 0 | 25.3 | 7.1 |
| 39-34 | 0 | 0 | 62.1 | 0 | 1.5 | 0 | 24.1 | 3.2 |
| 331*-257 | 0 | 0 | 51.6 | 0 | 0 | 0 | 42.2 | 2.5 |

TABLE 23

| Unique identifier set | Fab region | Design Type | H1-L1_Ab | H1_mutation | L1_mutation | H2-L2_Ab | H2_mutation | L2_mutation | H1:H2:L1:L2 DNA ratio | SEC step performed post pA? |
|---|---|---|---|---|---|---|---|---|---|---|
| 340*-339* | variable | steric | D3H44 | V37W_W103F | F98A | PERT | W103V | P44W | 18:12:35:35 | N |
| 340*-339* | variable | steric | D3H44 | V37W_W103F | F98A | PERT | W103V | P44W | 18:12:46:24 | N |
| 340*-339* | variable | steric | D3H44 | V37W_W103F | F98A | PERT | W103V | P44W | 18:12:56:14 | N |
| 340*-339* | variable | steric | D3H44 | V37W_W103F | F98A | PERT | W103V | P44W | 22:8:35:35 | N |
| 340*-339* | variable | steric | D3H44 | V37W_W103F | F98A | PERT | W103V | P44W | 22:8:46:24 | N |
| 340*-339* | variable | steric | D3H44 | V37W_W103F | F98A | PERT | W103V | P44W | 22:8:56:14 | N |
| 340*-339* | variable | steric | D3H44 | V37W_W103F | F98A | PERT | W103V | P44W | 26:4:35:35 | N |
| 340*-339* | variable | steric | D3H44 | V37W_W103F | F98A | PERT | W103V | P44W | 26:4:46:24 | N |
| 340*-339* | variable | steric | D3H44 | V37W_W103F | F98A | PERT | W103V | P44W | 26:4:56:14 | N |

| Unique identifier set | Number of experiments | paired:mispaired species (all) | paired:mispaired species (mean) | paired_over_mispaired_Scalar | H1-L1_H2-L2 (and H1-L2_H2-L1) | H1-L1_H2-L2 (and H1-L2_H2-L1) side peak | H1-L1_H1-L1 |
|---|---|---|---|---|---|---|---|
| 340*-339* | 1 | 84:16 | 84:16 | 1.66 | 77.2 | 5.7 | 0 |
| 340*-339* | 1 | 87:13 | 87:13 | 1.87 | 80.5 | 6.4 | 0 |
| 340*-339* | 1 | 86:14 | 86:14 | 1.84 | 36.8 | 3.4 | 2.1 |
| 340*-339* | 1 | 78:22 | 78:22 | 1.25 | 33 | 2.8 | 2 |
| 340*-339* | 2 | 80:20_81:19 | 81:19 | 1.425 | 31.35 | 3.7 | 0.9 |
| 340*-339* | 1 | 89:11 | 89:11 | 2.07 | 34.5 | 3.2 | 0 |
| 340*-339* | 1 | 75:25 | 75:25 | 1.1 | 4.7 | 0.8 | 7.5 |
| 340*-339* | 1 | 81:19 | 81:19 | 1.47 | 7.9 | 1 | 6.9 |
| 340*-339* | 1 | 92:8 | 92:8 | 2.47 | 12.2 | 1.6 | 3.2 |

| Unique identifier set | H1-L1_H1-L2 | H1-L2_H1-L2 | H2-L1_H2-L1 | H2-L1_H2-L2 | H2-L2_H2-L2 | H1-L1_H2-L1 | H1-L2_H2-L2 | H1-L1 | H1-L2 | H2-L1 | H2-L2 |
|---|---|---|---|---|---|---|---|---|---|---|---|
| 340*-339* | 0 | 0 | 0 | 1.7 | 2 | 2.6 | 11.7 | 1.1 | 0 | 0 | 3.6 |
| 340*-339* | 0 | 0 | 0 | 1.9 | 3.4 | 7.1 | 4.4 | 0 | 0 | 0 | 2.8 |
| 340*-339* | 0 | 0 | 0 | 1.4 | 1.8 | 6 | 1.1 | 45.5 | 5.2 | 0 | 0 |
| 340*-339* | 0 | 0 | 0 | 0 | 1.3 | 1.1 | 6.6 | 41.5 | 14.6 | 0 | 0 |
| 340*-339* | 0 | 0 | 0 | 1.9 | 2.95 | 5 | 2.9 | 44.65 | 8.8 | 0.75 | 0.8 |
| 340*-339* | 0 | 0 | 0 | 1.5 | 2.8 | 4.7 | 0 | 51.3 | 5 | 0 | 0 |
| 340*-339* | 2.9 | 0 | 0 | 0 | 0 | 0 | 1.1 | 62.7 | 21 | 0 | 0 |
| 340*-339* | 1.8 | 0 | 0 | 0 | 0 | 0 | 1.3 | 66.5 | 15.6 | 0 | 0 |
| 340*-339* | 0 | 0 | 0 | 0 | 1.9 | 2 | 0 | 74.9 | 5.8 | 0 | 0 |

TABLE 24

| Unique identifier set | Fab region | Design Type | H1-L1_Ab | H1_mutation | L1_mutation | H2-L2_Ab | H2_mutation | L2_mutation | H1:H2:L1:L2 DNA ratio |
|---|---|---|---|---|---|---|---|---|---|
| 335*-336* | combination of constant and variable | combination (electrostatic + steric) | D3H44 | V37W_L124E | F98A_V133A_S176K | PERT | L124R | F98W_V133G_S176D | 22:8:35:35 |
| 333*-334* | combination of constant and variable | combination (electrostatic) | D3H44 | Q39E_S186R | Q38R_Q160E_T180E | PERT | Q39R_K145T_Q179E | Q38E_S131K | 22:8:46:24 |
| 326*-23 | constant | electrostatic | D3H44 | S186R | Q124E_Q160E_T180E | PERT | K145L_Q179E | S131K | 22:8:56:14 |
| 331*-257 | constant | electrostatic | D3H44 | D146G_Q179K | Q124E_Q160E_T180E | PERT | L143E_K145T | Q124R_Q160K_T178R | 22:8:46:24 |
| 154-152 | variable | combination (electrostatic + steric) | D3H44 | V37W_Q39E | Q38R_F98A | PERT | V37A_Q39R_W103V | Q38E_P44W | 15:15:35:35 |
| 313*-337* | variable | steric | D3H44 | V37W | F98A | PERT | L45A | P44W | 22:8:46:24 |
| 340*-337* | variable | steric | D3H44 | V37W_W103F | F98A | PERT | L45A | P44W | 15:15:35:35 |
| 336*-335* | combination of constant and variable | combination (electrostatic + steric) | D3H44 | L124R | F98W_V133G_S176D | PERT | V37W_L124E | F98A_V133A_S176K | 22:8:46:24 |
| 92-90 | variable | combination (electrostatic + steric) | D3H44 | V37L_Q39R | Q38D_F98W | PERT | V37W_Q39E | Q38R_F98A | 22:8:35:35 |
| 66-67 | constant | electrostatic | D3H44 | L143A_D146G_Q179R | Q124E_V133W_Q160E_T180E | PERT | K145T_Q179D_S188F | V133A_Q160K_T178R | 18:12:35:35 |
| 340*-339* | variable | steric | D3H44 | V37W_W103F | F98A | PERT | W103V | P44W | 18:12:46:24 |
| 329*-330* | constant | combination (electrostatic + steric) | *D3H44 | A139G_V190A | L135W | PERT | A139W_K145Y_Q179E | F116A_S131K_L135A | 20:10:46:24 |
| 329*-330* | constant | combination (electrostatic + steric) | *D3H44 | A139G_V190A | L135W | PERT | A139W_K145Y_Q179E | F116A_S131K_L135A | 22:8:46:24 |
| 300-349* | variable | steric | D3H44 | V37W | F98A | PERT | W103F | P44F | 22:8:46:24 |
| 152-154 | variable | combination (electrostatic + steric) | D3H44 | V37A_Q39R_W103V | Q38E_P44W | PERT | V37W_Q39E | Q38R_F98A | 264:56:14 |
| 92-90 | variable | combination (electrostatic + steric) | *D3H44 | V37L_Q39R | Q38D_F98W | PERT | V37W_Q39E | Q38R_F98A | 20:10:40:30 |
| 34-39 | variable | combination (electrostatic + steric) | D3H44 | V37W_Q39E | Q38R_F98A | PERT | Q39R | Q38E | 22:8:46:24 |
| 332*-284 | constant | electrostatic | D3H44 | D146G_Q179K | Q124E_Q160E_T180E | TRAS | L143E_K145T | Q124R | 20:10:53:17 |
| 331*-257 | constant | electrostatic | D3H44 | D146G_Q179K | Q124E_Q160E_T180E | TRAS | L143E_K145T | Q124R_Q160K_T178R | 20:10:53:17 |

TABLE 24-continued

| | | | | | | | | | |
|---|---|---|---|---|---|---|---|---|---|
| 90-92 | variable | combination (electrostatic + steric) | D3H44 | V37W_Q39E | | Q38R_F98A | TRAS | V37L_Q39R | Q38D_F98W | 20:10:53:17 |
| 92-90 | variable | combination (electrostatic + steric) | D3H44 | V37L_Q39R | | Q38D_F98W | TRAS | V37W_Q39E | Q38R_F98A | 20:10:53:17 |
| 34-39 | variable | combination (electrostatic + steric) | D3H44 | V37W_Q39E | | Q38R_F98A | TRAS | Q39R | Q38E | 20:10:53:17 |
| 39-34 | variable | combination (electrostatic + steric) | D3H44 | Q39R | | Q38E | TRAS | V37W_Q39E | Q38R_F98A | 20:10:53:17 |
| 442*-23 | constant | electrostatic | D3H44 | S115K_S156K_S186R | | Q124E_Q160E_T180E | TRAS | K145L_Q179E | S131K | 20:10:53:17 |
| 257-331* | constant | electrostatic | D3H44 | L143E_K145T | | Q124R_Q160K_T178R | TRAS | D146G_Q179K | Q124E_Q160E_T180E | 20:10:53:17 |
| 284-332* | constant | electrostatic | D3H44 | L143E_K145T | | Q124R | TRAS | D146G_Q179K | Q124E_Q160E_T180E | 20:10:53:17 |
| 443*-326* | constant | electrostatic | D3H44 | S115K_K145L_S156K_Q179E | | S131K | TRAS | S186R | Q124E_Q160E_T180E | 20:10:53:17 |
| 34-39 | variable | combination (electrostatic + steric) | D3H44 | V37W_Q39E | | Q38R_F98A | RAMU | Q39R | Q38E | 20:10:53:17 |
| 332*-284 | constant | electrostatic | D3H44 | D146G_Q179K | | Q124E_Q160E_T180E | RAMU | L143E_K145T | Q124R | 20:10:53:17 |
| 331*-257 | constant | electrostatic | D3H44 | L143E_K145T | | Q124R_Q160K_T178R | RAMU | D146G_Q179K | Q124E_Q160E_T180E | 20:10:53:17 |
| 284-332* | constant | electrostatic | D3H44 | L143E_K145T | | Q124R | RAMU | D146G_Q179K | Q124E_Q160E_T180E | 20:10:53:17 |
| 90-92 | variable | combination (electrostatic + steric) | D3H44 | V37W_Q39E | | Q38R_F98A | RAMU | V37L_Q39R | Q38D_F98W | 20:10:53:17 |
| 442*-23 | constant | electrostatic | D3H44 | S115K_S156K_S186R | | Q124E_Q160E_T180E | RAMU | K145L_Q179E | S131K | 20:10:53:17 |
| 331*-257 | constant | electrostatic | D3H44 | D146G_Q179K | | Q124R_Q160K_T178R | RAMU | L143E_K145T | Q124R_Q160K_T178R | 20:10:53:17 |
| 443*-326* | constant | electrostatic | D3H44 | S115K_K145L_S156K_Q179E | | S131K | RAMU | S186R | Q124E_Q160E_T180E | 20:10:53:17 |
| 92-90 | variable | combination (electrostatic + steric) | D3H44 | V37L_Q39R | | Q38D_F98W | RAMU | V37W_Q39E | Q38R_F98A | 20:10:53:17 |
| 39-34 | variable | combination (electrostatic + steric) | D3H44 | Q39R | | Q38E | RAMU | V37W_Q39E | Q38R_F98A | 20:10:53:17 |
| 257-331* | constant | electrostatic | TRAS | L143E_K145T | | Q124R_Q160K_T178R | RAMU | D146G_Q179K | Q124E_Q160E_T180E | 8:22:35:35 |
| 23-326* | constant | electrostatic | TRAS | K145L_Q179E | | S131K | RAMU | S186R | Q124E_Q160E_T180E | 8:22:35:35 |
| 284-332* | constant | electrostatic | TRAS | L143E_K145T | | Q124R | RAMU | D146G_Q179K | Q124E_Q160E_T180E | 8:22:35:35 |
| 92-90 | variable | combination (electrostatic + steric) | TRAS | V37L_Q39R | | Q38D_F98W | RAMU | V37W_Q39E | Q38R_F98A | 8:22:35:35 |

TABLE 24-continued

| | | | | | | | | | |
|---|---|---|---|---|---|---|---|---|---|
| 34-39 | variable | combination (electrostatic + steric) | TRAS | V37W_Q39E | Q38R_F98A | RAMU | Q39R | Q38E | 8:22:35:35 |
| 90-92 | variable | combination (electrostatic + steric) | TRAS | V37W_Q39E | Q38R_F98A | RAMU | V37L_Q39R | Q38D_F98W | 8:22:35:35 |
| 332*-284 | constant | electrostatic | TRAS | D146G_Q179K | Q124E_Q160E_T180E | RAMU | L143E_K145T | Q124R | 8:22:35:35 |
| 326*-23 | constant | electrostatic | TRAS | S186R | Q124E_Q160E_T180E | RAMU | K145L_Q179E | S131K | 8:22:35:35 |
| 39-34 | variable | combination (electrostatic + steric) | TRAS | Q39R | Q38E | RAMU | V37W_Q39E | Q38R_F98A | 8:22:35:35 |
| 331*-257 | constant | electrostatic | TRAS | D146G_Q179K | Q124E_Q160E_T180E | RAMU | L143E_K145T | Q124R_Q160K_T178R | 8:22:35:35 |

| Unique identifier set | SEC step performed post pA? | Number of experiments | paired:mispaired species | paired_over_mispaired_Scalar | H1-L1_H2-L2 | H1-L1_H2-L2 (and H1-L2_H2-L1) side peak | H1-L1_H1-L1 | H1-L1_H1-L2 | H1-L2_H1-L2 |
|---|---|---|---|---|---|---|---|---|---|
| 335*-336* | N | | 100:0 | 5 | 88.6 | 12 | 0 | 0 | 0 |
| 333*-334* | N | | 100:0 | 5 | 73.2 | 5 | 0 | 0 | 0 |
| 326*-23 | N | 1 | 99:1 | 4.41 | 12 | 0.6 | 5.9 | 0 | 0 |
| 331*-257 | N | 1 | 99:1 | 4.41 | 2.7 | 0.3 | 10.3 | 0 | 0 |
| 154-152 | N | 1 | 98:2 | 3.89 | 67.3 | 2.6 | 0 | 0 | 0 |
| 313* | N | 1 | 97:3 | 3.62 | 57.5 | 3.6 | 1 | 0 | 0 |
| 337* | N | 1 | 96:4 | 3.08 | 68.3 | 5.6 | 0 | 0 | 0 |
| 340* | N | 1 | 93:7 | 2.57 | 71.1 | 7.2 | 0 | 0 | 0 |
| 337* | N | 1 | 92:8 | 2.42 | 42.5 | 3 | 1.4 | 0 | 0 |
| 336* | N | 1 | 91:9 | 2.27 | 22.8 | 1 | 3.3 | 0 | 0 |
| 335* | N | 1 | 85:15 | 1.72 | 55.5 | 4.5 | 0 | 0 | 0 |
| 92-90 | N | 1 | 83:17 | 1.56 | 26.3 | 1.3 | 0 | 0 | 0 |
| 66-67 | N | 1 | 83:17 | 1.56 | 19.5 | 1.1 | 1.1 | 0 | 0 |
| 340* | N | 1 | 77:23 | 1.2 | 34.8 | 1.9 | 0 | 0 | 0 |
| 339* | N | 1 | 71:29 | 0.91 | 47.2 | 2.5 | 0 | 0 | 0 |
| 329* | N | 1 | 68:32 | 0.75 | 41.3 | 1 | 0 | 0 | 0 |
| 330* | N | 1 | 19:81 | −1.46 | 2.2 | 0.9 | 0 | 0 | 0 |
| 329* | N | 1 | 96:4 | 3.23 | 47.4 | 1.4 | 2 | 0 | 0 |
| 300-349* | N | 1 | 88:12 | 1.96 | 61.7 | 2.2 | 0 | 0 | 0 |
| 152-154 | N | 1 | 87:13 | 1.87 | 66.8 | 4.7 | 0 | 0 | 0 |
| 92-90 | N | 1 | 81:19 | 1.45 | 32.1 | 4.7 | 0 | 0 | 0 |
| 34-39 | N | 1 | 79:21 | 1.31 | 59.7 | 5.5 | 0 | 0 | 0 |
| 332*-284 | N | 1 | 74:26 | 1.06 | 56.6 | 8.1 | 0 | 0 | 0 |
| 331*-257 | N | 1 | 68:32 | 0.75 | 41.4 | 3.8 | 1.2 | 1.7 | 0 |
| 442*-23 | N | | | | | | | | |

TABLE 24-continued

| Unique identifier set | SEC step performed post pA? | Number of experiments | paired:mispaired species | H2-L1_H2-L1 | H2-L2_H2-L2 | H1-L1_H2-L2 | H1-L1_H2-L1 | H1-L2_H2-L2 | H1-L1 | H1-L2 | H2-L1 | H2-L2 |
|---|---|---|---|---|---|---|---|---|---|---|---|---|
| 257-331* | N | 1 | | 0 | 64:36 | 1.1 | 0.58 | 31.4 | 2.8 | 0 | 0 | 0 |
| 284-332* | N | 1 | | 0 | 49:51 | | -0.04 | 28.4 | 3.5 | 0 | 0 | 0 |
| 443* | N | 1 | | 0 | 44:56 | | -0.24 | 31.3 | 2.3 | 0 | 0 | 0 |
| 326* | | | | | | | | | | | | |
| 34-39 | N | 1 | | 0 | 81:19 | | 1.42 | 61.2 | 7.6 | 0 | 0 | 0 |
| 332*-284 | N | 1 | | 0 | 80:20 | | 1.41 | 58.9 | 7.6 | 2.1 | 4.9 | 0 |
| 257-331* | N | 1 | | 0 | 80:20 | | 1.39 | 12.7 | 2 | 0 | 0 | 0 |
| 284-332* | N | 1 | | 0 | 77:23 | | 1.23 | 19.5 | 3.5 | 0 | 0 | 0 |
| 90-92 | N | 1 | | 0 | 74:26 | | 1.03 | 40.5 | 5.1 | 0 | 0 | 0 |
| 442*-23 | N | 1 | | 0 | 69:31 | | 0.78 | 28.2 | 6 | 0 | 0 | 0 |
| 331*-257 | N | 1 | | 0 | 58:42 | | 0.32 | 29.5 | 4 | 3.4 | 2.5 | 0 |
| 443*- | N | 1 | | 0 | 41:59 | | -0.37 | 22.3 | 3 | 0 | 0 | 0 |
| 326* | | | | | | | | | | | | |
| 92-90 | N | 1 | | 0 | 39:61 | | -0.45 | 22.2 | 4.1 | 4.7 | 2.7 | 0 |
| 39-34 | N | 1 | | 0 | 34:66 | | -0.68 | 10.2 | 1.7 | 2.7 | 1.7 | 0 |
| 257-331* | N | 1 | | 0 | 96:4 | | 3.03 | 54.6 | 5.2 | 0 | 0 | 0 |
| 23-326* | N | 1 | | 0 | 91:9 | | 2.29 | 28.4 | 1.3 | 0 | 0 | 0 |
| 284-332* | N | 1 | | 0 | 79:21 | | 1.33 | 57.9 | 5.5 | 0 | 0 | 0 |
| 92-90 | N | 1 | | 0 | 38:62 | | -0.51 | 14.6 | 1.3 | 0 | 0 | 0 |
| 34-39 | N | 1 | | 0 | 37:63 | | -0.55 | 17.8 | 1.8 | 0 | 0 | 0 |
| 90-92 | N | 1 | | 0 | 20:80 | | -1.4 | 7.2 | 0.8 | 0 | 0 | 0 |
| 332*-284 | N | 1 | | 0 | 13:87 | | -1.89 | 5.6 | 0.7 | 0 | 0 | 0 |
| 326*-23 | N | 1 | | 0 | 11:89 | | -2.12 | 5.1 | 0.3 | 0 | 0 | 0 |
| 39-34 | N | 1 | | 0 | 7:93 | | -2.6 | 2.7 | 0.6 | 0 | 0 | 0 |
| 331*-257 | N | 1 | | 0 | 2:98 | | -3.75 | 1.1 | 0.2 | 0 | 0 | 0 |

| Unique identifier set | H2-L1_H2-L1 | paired:mispaired species | paired_over_mispaired_Scalar | H1-L1_H2-L2 (and H1-L2_H2-L1) | H1-L1_H2-L2 (and H1-L2_H2-L1) side peak | H1-L2 | H2-L1 | H2-L2 |
|---|---|---|---|---|---|---|---|---|
| 335*- | 0 | 0 | 1.2 | 1.9 | 46.2 | 1.2 | 0 | 3.3 |
| 336* | | | | | | | | |
| 333*- | 0 | 0 | 1 | 0 | 64.5 | 0 | 0 | 2.4 |
| 334* | | | | | | | | |
| 326*-23 | 0 | 0 | | 0 | 80.8 | 1.2 | 0 | 0 |
| 331*-257 | 0 | 0 | | 0 | 85.9 | 1.2 | 0 | 0 |
| 154-152 | 0 | 0 | | 0 | 25.9 | 2 | 0 | 4.8 |
| 313*- | 0 | 0 | | 0 | 37.7 | 2.6 | 0 | 1.1 |
| 337* | | | | | | | | |
| 340*- | 0 | 0 | | 4.4 | 1.2 | 0 | 0 | 26.1 |
| 337* | | | | | | | | |
| 336*- | 0 | 0 | 1.2 | 4.2 | 4.1 | 0 | 1.1 | 13.2 |
| 335* | | | | | | | | |

| Unique identifier set | SEC step performed post pA? | Number of experiments | paired:mispaired species | paired_over_mispaired_Scalar | H1-L1_H2-L2 (and H1-L2_H2-L1) | H1-L1_H2-L2 (and H1-L2_H2-L1) side peak | H1-L1_H1-L1 | H1-L1_H1-L2 | H1-L2_H1-L2 |
|---|---|---|---|---|---|---|---|---|---|
| 92-90 | | | | 1.2 | 1.9 | 46.2 | 3.6 | 0 | 1.9 |
| 66-67 | | | | 1 | 0 | 64.5 | 8.4 | 0 | 0 |
| 340*-339* | | | | 7.3 | 2.3 | 1.9 | 0 | 5.6 | 26.2 |

TABLE 24-continued

| Unique identifier set | H2-L1_H2-L1 | H2-L1_H2-L2 | H2-L2_H2-L2 | H1-L1_H2-L1 | H1-L1_H2-L2 | H1-L2_H2-L2 | H1-L1 | H1-L2 | H2-L1 | H2-L2 |
|---|---|---|---|---|---|---|---|---|---|---|
| 329*-330* | 0 | 0 | 0 | 1.6 | 1.5 | 11.9 | 1.9 | 0 | 3.9 | 52.8 |
| 329*-330* | 0 | 0 | 0 | 0 | 0 | 6.2 | 60.3 | 11.2 | 0 | 1.8 |
| 300-349* | 0 | 0 | 1.2 | 0 | 0 | 23.1 | 0 | 0 | 0 | 40.9 |
| 152-154 | 0 | 0 | 0 | 0 | 12.3 | 10.2 | 24.1 | 6.1 | 0 | 0 |
| 92-90 | 0 | 0 | 0 | 0 | 0 | 20.2 | 23.3 | 12 | 0 | 3.3 |
| 34-39 | 0 | 0 | 0 | 0 | 77.2 | 0 | 16.6 | 0 | 4 | 0 |
| 332*-284 | 0 | 0 | 0 | 0 | 0 | 1.4 | 46.7 | 2.4 | 0 | 0 |
| 331*-257 | 0 | 0 | 0 | 0 | 12.4 | 1.2 | 25.9 | 2.5 | 0 | 12.5 |
| 90-92 | 4.8 | 0 | 4.5 | 0 | 3.3 | 12.4 | 7.4 | 0 | 4 | 44.3 |
| 92-90 | 0 | 0 | 0 | 0 | 2.6 | 13.1 | 0 | 3.7 | 0 | 14.7 |
| 34-39 | 2.7 | 0 | 0 | 0 | 1.7 | 11 | 4.3 | 0 | 3.1 | 13.1 |
| 39-34 | 0 | 0 | 0 | 0 | 9.9 | 0 | 4.5 | 1.8 | 14.3 | 22.1 |
| 442*-23 | 0 | 0 | 4.5 | 0 | 16 | 26.8 | 3.2 | 6.4 | 0 | 26.3 |
| 257-331* | 2.8 | 0 | 9.3 | 0 | 0 | 43.3 | 1.8 | 5.1 | 0 | 5.4 |
| 284-332* | 2.5 | 0 | 0 | 0 | 0 | 40.1 | 6 | 14.4 | 0 | 0 |
| 443*-326* | 0 | 0 | 0 | 0 | 1.3 | 12.8 | — | — | — | — |
| 34-39 | 0 | 0 | 0 | 0 | 5 | 9.2 | 5.6 | 2.3 | 2.9 | 13.8 |
| 332*-284 | 0 | 0 | 0 | 0 | 13.1 | 0 | 13.9 | 1.6 | 0 | 5.5 |
| 257-331* | 0 | 0 | 1.6 | 0 | 0 | 18.7 | 1.2 | 0 | 1.3 | 64.5 |
| 284-332* | 0 | 0 | 2.8 | 0 | 1.9 | 8.8 | 0 | 0 | 11.9 | 55 |
| 90-92 | 0 | 0 | 0 | 0 | 10.4 | 1.7 | 2.5 | 0 | 14.2 | 30.8 |
| 442*-23 | 0 | 0 | 0 | 0 | 10.6 | 0 | 1.3 | 0 | 20.7 | 39.1 |
| 331*-257 | 0 | 0 | 0 | 0 | 35.3 | 0 | 20.7 | 0 | 4.3 | 4.2 |
| 443*-326* | 0 | 0 | 0 | 0 | 6.9 | 23.8 | 18.7 | 28.4 | 0 | 0 |
| 92-90 | 0 | 0 | 0 | 0 | 42.9 | 0 | 5.7 | 1.9 | 13.6 | 6.4 |
| 39-34 | 1.1 | 0 | 0 | 0 | 21 | 0 | 3.3 | 1.8 | 40.8 | 17.5 |
| 257-331* | 0 | 0 | 0 | 0 | 2.4 | 0 | 1.7 | 0 | 2.2 | 39.2 |
| 23-326* | 0 | 0 | 3.3 | 0 | 2.1 | 0 | 0 | 0 | 7.1 | 59.1 |
| 284-332* | 0 | 0 | 0 | 0 | 15.6 | 0 | 2.4 | 0 | 5.4 | 18.8 |
| 92-90 | 0 | 0 | 0 | 0 | 22.9 | 1.2 | 0 | 0 | 38.3 | 23 |
| 34-39 | 0 | 0 | 0 | 0 | 31.8 | 0 | 1.2 | 0 | 31.7 | 17.5 |
| 90-92 | 1.1 | 0 | 0 | 0 | 45 | 0 | 1.8 | 0 | 35.2 | 10.8 |
| 332*-284 | 1.6 | 0 | 0 | 0 | 34.4 | 0 | 0 | 0 | 51.4 | 7.5 |
| 326*-23 | 0 | 0 | 0 | 0 | 37.1 | 0 | 0 | 0 | 50.5 | 5.6 |
| 39-34 | 0 | 0 | 0 | 0 | 81.4 | 0 | 2.9 | 0 | 11.7 | 1.3 |
| 331*-257 | 1.1 | 0 | 0 | 0 | 55.2 | 0 | 0 | 0 | 41.4 | 1.2 |

| Unique identifier set | H2-L1_H2-L1 | H2-L1_H2-L2 | H2-L2_H2-L2 | H1-L1_H2-L1 | H1-L1_H2-L2 | H1-L2_H2-L2 | H1-L1 | H1-L2 | H2-L1 | H2-L2 |
|---|---|---|---|---|---|---|---|---|---|---|
| 335*-336* | 0 | 0 | 0 | 0 | 0 | 0 | 7.1 | 0 | 0 | 3.3 |
| 333*-334* | 0 | 0 | 0 | 0 | 0 | 0 | 24.3 | 0 | 0 | 2.4 |
| 326*-23 | 0 | 0 | 0 | 0 | 0 | 0 | 80.8 | 1.2 | 0 | 0 |
| 331*-257 | 0 | 0 | 0 | 0 | 0 | 0 | 85.9 | 1.2 | 0 | 0 |
| 154-152 | 0 | 0 | 0 | 0 | 0 | 0 | 25.9 | 2 | 4 | 4.8 |
| 313*-337* | 0 | 0 | 0 | 0 | 0 | 0 | 37.7 | 2.6 | 0 | 1.1 |
| 340*-337* | 0 | 0 | 4.4 | 0 | 0 | 4.4 | 1.2 | 0 | 0 | 26.1 |
| 336*-335* | 1.8 | 0 | 0 | 0 | 0 | 4.2 | 4.1 | 0 | 1.1 | 13.2 |
| 39-34 | 1.2 | 1.5 | 0 | 0 | 0 | 1.9 | 46.2 | 3.6 | 0 | 1.9 |
| 92-90 | — | — | — | — | — | — | — | — | — | — |

TABLE 24-continued

| | | | | | | |
|---|---|---|---|---|---|---|
| 66-67 | 0 | 0 | 1 | 0 | 64.5 | 0 |
| 340*-339* | 0 | 1.2 | 7.3 | 2.3 | 1.9 | 8.4 |
| 329*-330* | 0 | 1.6 | 1.5 | 11.9 | 1.9 | 0 |
| 329*-330* | 0 | 0 | 0 | 6.2 | 60.3 | 11.2 |
| 300-349* | 0 | 1.2 | 0 | 23.1 | 0 | 0 |
| 152-154 | 0 | 0 | 12.3 | 10.2 | 24.1 | 6.1 |
| 92-90 | 0 | 0 | 0 | 20.2 | 23.3 | 12 |
| 34-39 | 0 | 0 | 77.2 | 0 | 16.6 | 0 |
| 332*-284 | 0 | 0 | 0 | 1.4 | 46.7 | 2.4 |
| 331*-257 | 0 | 0 | 12.4 | 0 | 25.9 | 0 |
| 90-92 | 4.8 | 4.5 | 3.3 | 1.2 | 7.4 | 2.5 |
| 92-90 | 0 | 0 | 2.6 | 12.4 | 0 | 0 |
| 34-39 | 2.7 | 0 | 1.7 | 13.1 | 4.3 | 3.7 |
| 39-34 | 0 | 0 | 9.9 | 11 | 4.5 | 1.8 |
| 442*-23 | 0 | 0 | 16 | 0 | 3.2 | 0 |
| 257-331* | 2.8 | 4.5 | 0 | 26.8 | 1.8 | 6.4 |
| 284-332* | 2.5 | 9.3 | 0 | 43.3 | 6 | 5.1 |
| 443*-326* | 0 | 0 | 1.3 | 40.1 | 12.8 | 14.4 |
| 34-39 | 0 | 0 | 5 | 9.2 | 5.6 | 2.3 |
| 332*-284 | 0 | 0 | 13.1 | 0 | 13.9 | 1.6 |
| 257-331* | 1.6 | 0 | 0 | 18.7 | 1.2 | 0 |
| 284-332* | 2.8 | 0 | 1.9 | 8.8 | 0 | 0 |
| 90-92 | 0 | 0 | 10.4 | 1.7 | 2.5 | 0 |
| 442*-23 | 0 | 0 | 10.6 | 0 | 1.3 | 0 |
| 331*-257 | 0 | 0 | 35.3 | 0 | 20.7 | 0 |
| 443*-326* | 0 | 3.3 | 6.9 | 23.8 | 18.7 | 28.4 |
| 92-90 | 0 | 0 | 42.9 | 0 | 5.7 | 1.9 |
| 39-34 | 1.1 | 0 | 21 | 0 | 3.3 | 1.8 |
| 257-331* | 0 | 0 | 2.4 | 0 | 1.7 | 0 |
| 23-326* | 0 | 0 | 2.1 | 0 | 0 | 0 |
| 284-332* | 0 | 0 | 15.6 | 0 | 2.4 | 0 |
| 92-90 | 0 | 0 | 22.9 | 1.2 | 0 | 0 |
| 34-39 | 0 | 0 | 31.8 | 0 | 1.2 | 0 |
| 90-92 | 0 | 0 | 45 | 0 | 1.8 | 0 |
| 332*-284 | 1.1 | 0 | 34.4 | 0 | 0 | 0 |
| 326*-23 | 1.6 | 0 | 37.1 | 0 | 0 | 0 |
| 39-34 | 0 | 0 | 81.4 | 0 | 2.9 | 0 |
| 331*-257 | 1.1 | 0 | 55.2 | 0 | 0 | 0 |

| | | |
|---|---|---|
| 0 | 0 | |
| 5.6 | 26.2 | |
| 3.9 | 52.8 | |
| 0 | 1.8 | |
| 0 | 40.9 | |
| 0 | 0 | |
| 4 | 3.3 | |
| 0 | 0 | |
| 0 | 0 | |
| 1.5 | 12.5 | |
| 4 | 44.3 | |
| 0 | 14.7 | |
| 3.1 | 13.1 | |
| 14.3 | 22.1 | |
| 0 | 26.3 | |
| 0 | 5.4 | |
| 0 | 0 | |
| 2.9 | 13.8 | |
| 0 | 5.5 | |
| 1.3 | 64.5 | |
| 11.9 | 55 | |
| 14.2 | 30.8 | |
| 20.7 | 39.1 | |
| 4.3 | 4.2 | |
| 0 | 0 | |
| 13.6 | 6.4 | |
| 40.8 | 17.5 | |
| 2.2 | 39.2 | |
| 7.1 | 59.1 | |
| 5.4 | 18.8 | |
| 38.3 | 23 | |
| 31.7 | 17.5 | |
| 35.2 | 10.8 | |
| 51.4 | 7.5 | |
| 50.5 | 5.6 | |
| 11.7 | 1.3 | |
| 41.4 | 1.2 | |

TABLE 25

| Unique identifier set | H1-L1_H2-L2 Tm (° C.) | pH | SEC purification performed post pA? | Antigen affinity –TF, KD (nM) | Antigen affinity –HER2, KD(nM) |
|---|---|---|---|---|---|
| 300-349* | 69.66, 79.94 | 7 | y | ND | ND |
| 340*-337* | 69, 75.54 | 7 | y | 1.31 | 2.8 |
| 340*-339* | 69, 75.94 | 7 | y | 1.34 | 12.9 |
| 326*-23 | 77.16 | 7 | y | 0.03 | 4.14 |
| 92-90 | 70.42, 73 | 7 | y | 0.01 | 7.09 |
| 313*-337* | 70.65, 78.26 | 7 | y | 0.9 | 3.29 |
| 333*-334* | 72.07 | 7 | y | 0.02 | 1.02 |
| 335*-336* | 69.5, 76.5 | 7 | y | 1.04 | 4.71 |
| 336*-335* | 65.2, 75.35 | 7 | y | 0.01 | 16.7 |
| 329*-330* | 72.57 | 7 | n | 0.04 | 3.69 |
| # 329*-330* | 71.99 | 7 | n | 0.04 | 5.16 |
| # 92-90 | 70.53 | 7 | n | 0.03 | 10.4 |
| 154-152 | 75.5 | 7 | n | 0.6 | NB |
| 300-349* | 70.62, 80.1 | 7 | n | 0.4 | 6.49 |
| 333*-334* | 72.89 | 4 | n | ND | ND |
| 327*-328* | 74.69 | 4 | n | ND | ND |
| 313*-339* | 77.53 | 4 | n | ND | ND |
| 338*-299 | 75.98 | 4 | n | ND | ND |
| 313*-337* | 77.39 | 4 | n | ND | ND |
| 331*-257 | 77.83 | 4 | n | ND | ND |
| 332*-284 | 77.22 | 4 | n | ND | ND |
| 326*-23 | 78.53 | 4 | n | ND | ND |
| 92-90 | 69.6, 72 | 4 | n | ND | ND |
| 34-39 | 73.35 | 4 | n | ND | ND |
| 325*-31 | 78.17 | 4 | n | ND | ND |
| 305*-307* | 78.35 | 4 | n | ND | ND |
| 90-92 | 70.43 | 4 | n | ND | ND |

TABLE 26

| H1-L1_Ab | H1_mutation | L1_mutation | L1_tag | H2-L2_Ab | H2_mutation | L2_mutation | L2_tag | H1:H2:L1:L2 DNA ratio | SEC step performed post pA? | Number of experiments |
|---|---|---|---|---|---|---|---|---|---|---|
| D3H44 | WT | WT | HA | PERT | WT | WT | FLAG | 22:8:53:17 | Y | 2 |
| D3H44 | WT | WT | none | PERT | WT | WT | FLAG | 22:8:53:17 | Y | 1 |
| D3H44 | WT | WT | FLAG | PERT | WT | WT | HA | 22:8:53:17 | Y | 1 |

| H1-L1_Ab | paired:mispaired species (all) | Pair'ed:mispaired species (mean) | paired_over_mispaired_Scalar | H1-L1_H2-L2 (and H1-L2_H2-L1) | H1-L1_H2-L2 (and H1-L2_H2-L1) side peak | H1-L1_H1-L1 | H1-L1_H1-L2 |
|---|---|---|---|---|---|---|---|
| D3H44 | 3:97_2:98 | 2:98 | −3.72 | 1.55 | | 0 | 0 |
| D3H44 | 18:82 | 18:82 | −1.5 | 18.2 | | 0 | 0 |
| D3H44 | 1:99 | 1:99 | −4.59 | 0 | | 0 | 1.3 |

| H1-L1_Ab | H1-L2_H1-L2 | H2-L1_H2-L1 | H2-L1_H2-L2 | H2-L2_H2-L2 | H1-L1_H2-L1 | H1-L2_H2-L2 | H1-L1 | H1-L2 | H2-L1 | H2-L2 |
|---|---|---|---|---|---|---|---|---|---|---|
| D3H44 | 0 | 0 | 0 | 0 | 0 | 96.9 | 0 | 0.7 | 0 | 0.9 |
| D3H44 | 0 | 0 | 0 | 0 | 5.4 | 76.4 | 0 | 0 | 0 | 0 |
| D3H44 | 0 | 0 | 10 | 1 | 2 | 85.6 | 0 | 0 | 0 | 0 |

TABLE 27

| Unique identifier set | H1_mutation | L1_mutation | H2_mutation | L2_mutation |
|---|---|---|---|---|
| 92-90 | V37I_Q39R | Q38D_F98W | V37W_Q39E | Q38R_F98A |
| 111-112 | Q39D_A139G_V190A | Q38R_L135W | Q39R_A139W | Q38D_F116A_L135A |
| 57-58 | L143K_D146G | Q124E_V133D | L143E_K145T | Q124R |
| 66-67 | L143G_D146G_Q179R | Q124E_V133W_Q160E_T180E | K145T_Q179D_S188F | V133A_Q160K_T178R |
| 106-97 | V37I_Q39D | Q38D_F98W | V37W_Q39R_W103F | Q38E_F98L |
| 1-2 | S186R | Q124E_Q160E_T178D | K145L_Q179E | S131K |

TABLE 27-continued

| Unique identifier set | H1_mutation | L1_mutation | H2_mutation | L2_mutation |
|---|---|---|---|---|
| 152-154 | V37A_Q39R_W103V | Q38E_P44W | V37W_Q39E | Q38R_F98A |
| 72-65 | D146G_Q179R | Q124E_Q160E_T178D | K145T_Q179D_S188L | Q160K_T178R |
| 107-108 | A139G_V190A | L135W | A139W | F116A_L135A |

TABLE 30

| Unique identifier set | H1_mutation | L1_mutation | H2_mutation | L2_mutation |
|---|---|---|---|---|
| 164-165 | A139G_K145L_Q179E_V190A | S131R_L135W | A139W | F116A_L135A |
| 236-237 | A139G_K145L_Q179E_V190A | S131R_L135W | A139W | F116S_L135A |
| 306*-304*, 304*-306* | A139G_K145T_D146G_Q179E_V190A | L135W | A139W_S186K | F116A_Q124E_L135A_T180E |
| 208-209 | A139G_S188G_V190A | L135W_S176L_T178S | A139W_S188H_V190S | F116S_L135A_S176A |
| 215-216 | A139G_S188G_V190A | V133G_L135W_S176F_T178A | A139W_S188A | F116S_L135A_S176A |
| 194-195 | A139G_V190A | F98W_L135W | V37W_W103H_A139W | F98L_F116A_L135A |
| 107-108, 108-107 | A139G_V190A | L135W | A139W | F116A_L135A |
| | A139G_V190A | L135W | A139W | F116A_L135V |
| 329*-330* | A139G_V190A | L135W | A139W_K145Y_Q179E | F116A_S131K_L135A |
| 103-104 | A139G_V190A | L135W_N137A | A139W | F116A_L135A |
| 211-212 | A139I | F118W_V133S | A139S | L135R |
| 224-225 | A139I | F118W_V133S | A139V_V190S | WT |
| 139-140 | A139I_K145T_D146G_Q179E_S188G_V190S | F116A_V133G_S176F_T178A | S186K_S188H_V190G | F118W_Q124E_V133S_S176A_T178S_T180E |
| 231-232 | A139I_K145T_D146G_S188G_V190S | F116A_V133G_S176F_T178A | S186K_S188H_V190G | F118W_V133S_S176A_T178S_T180E |
| | A139I_V190S | F116A | A139V | F118W_V133S |
| 246-225 | A139I_V190S | WT | A139I | F118W_V133S |
| | A139V | F118W_V133S | A139W_V190S | F116A |
| | A139V | F118W_V133S | V190G | F116A |
| 314*-315* | A139V_K145L_Q179E_S188G_V190S | F116A_S131K_V133G_S176F_T178A | A139W_S186K_S188A | F118W_V133S_S176A_T180E |
| | A139V_V190S | F116A | A139V | F118W_V133S |
| 403*-404* | A139W | F116A | WT | L135W |
| 423*-418* | A139W | F116A_L135V | WT | L135W |
| | A139W | F118W_V133S | V190G | F116S |
| 346*-345*, 345*-346* | A139W | F98W_F116A | V37W | F98A_L135W |
| 196-197 | A139W | F98W_F116A_L135A | V37W_W103H_A139G_V190A | F98L_L135W |
| 433*-434* | A139W_G141L_V190S | F116A_F118L_L135V | WT | L135W |
| 431*-418* | A139W_G141L_V190S | F116A_L135V | WT | L135W |
| 354*-353*, | A139W_K145T_Q179E | F116A_S131K | S186R | L135W_Q160E_T180E |
| 353*-354* | A139W_V190A | F116A | A139W | WT |
| | A139W_V190A | F116A | WT | WT |
| 417*-418* | A139W_V190I | F116A_L135V | WT | L135W |
| 425*-404* | A139W_V190L | F116A | WT | L135W |
| 427*-418* | A139W_V190L | F116A_L135V | WT | L135W |
| | A139W_V190S | F116A | A139W | WT |
| | A139W_V190S | F116A | WT | WT |
| | A139W_V190S | F116S | A139W | F118W_V133S |
| 64-78 | D146G_Q179K | Q124E_Q160E_T178D | K145E_D146G_Q179D_S188L | Q160K_T178R |
| 69-78 | D146G_Q179K | Q124E_Q160E_T178D | K145T_Q179D_S188F | Q160K_T178R |
| 65-78 | D146G_Q179K | Q124E_Q160E_T178D | K145T_Q179D_S188L | Q160K_T178R |
| 61-71 | D146G_Q179K | Q124E_Q160E_T178D | L143E_K145T | Q124R_Q160K_T178R |
| 113-78 | D146G_Q179K | Q124E_Q160E_T178D | L143E_K145T | Q160K_T178R |
| 5-6 | D146G_Q179K | Q124E_Q160E_T180E | K145E_D146G_Q179D_S188L | Q160K_T178R |
| 23-24 | D146G_Q179K | Q124E_Q160E_T180E | K145L_Q179E | S131K |
| 9-5 | D146G_Q179K | Q124E_Q160E_T180E | K145T_Q179D_S188L | Q160K_T178R |
| 332*-284, 284-332* | D146G_Q179K | Q124E_Q160E_T180E | L143E_K145T | Q124R |

TABLE 30-continued

| Unique identifier set | H1_mutation | L1_mutation | H2_mutation | L2_mutation |
|---|---|---|---|---|
| 331*-257, 257-331* | D146G_Q179K | Q124E_Q160E_T180E | L145E_K145T | Q124R_Q160K_T178R |
| 5-59 | D146G_Q179K | Q124E_Q160E_T180E | L145E_K145T | Q160K_T178R |
| 201-83 | D146G_Q179K | Q124E_V133W_Q160E_T180E | K145E_D146G_Q179D_S188F | Q160K_T178R |
| 80-83 | D146G_Q179K | Q124E_V133W_Q160E_T180E | K145T_Q179D_S188L | Q160K_T178R |
| 85-83 | D146G_Q179K | Q124E_V133W_Q160E_T180E | K145T_Q179D_S188L | Q160K_T178R |
| 72-64 | D146G_Q179R | Q124E_Q160E_T178D | K145E_D146G_Q179D_S188L | Q160K_T178R |
| 234-238 | D146G_Q179R | Q124E_Q160E_T178D | K145T_Q179D_S188L | T178R |
| 72-69 | D146G_Q179R | Q124E_Q160E_T178D | K145T_Q179D_S188L | Q160K_T178R |
| 72-65, 65-72 | D146G_Q179R | Q124E_Q160E_T178D | L145E_K145T | Q160K_T178R |
| 60-61 | D146G_Q179R | Q124E_Q160E_T178D | L145E_K145T | Q124R_Q160K_T178R |
| 72-113 | D146G_Q179R | Q124E_Q160E_T180E | K145E_D146G_Q179D_S188L | Q160K_T178R |
| 7-6 | D146G_Q179R | Q124E_Q160E_T180E | K145T_Q179D_S188L | V133A_Q160K_T178R |
| 7-9 | D146G_Q179R | Q124E_Q160E_T180E | K145T_Q179D_S188L | Q160K_T178R |
| 7-59 | D146G_Q179R | Q124E_Q160E_T180E | L145E_K145T | Q160K_T178R |
| 81-201 | D146G_Q179R | Q124E_V133W_Q160E_T180E | K145E_D146G_Q179D_S188F | Q160K_T178R |
| 79-114 | D146G_Q179R | Q124E_V133W_Q160E_T180E | K145E_D146G_Q179D_S188F | V133A_Q160K_T178R |
| 80-81 | D146G_Q179R | Q124E_V133W_Q160E_T180E | K145T_Q179D_S188F | Q160K_T178R |
| 67-79 | D146G_Q179R | Q124E_V133W_Q160E_T180E | K145T_Q179D_S188L | V133A_Q160K_T178R |
| 85-81 | D146G_Q179R | Q124E_V133W_Q160E_T180E | K145T_Q179D_S188L | Q160K_T178R |
| 68-79 | D146G_Q179R | Q124E_V133W_Q160E_T180E | K145T_Q179D_S188L | V133A_Q160K_T178R |
| 63-64 | D146G_S186R | Q124E_Q160E_T178D | K145E_D146G_Q179D_S188L | Q160K_T178R |
| 234-235 | D146G_S186R | Q124E_Q160E_T178D | K145E_D146G_Q179D_S188L | T178R |
| 63-69 | D146G_S186R | Q124E_Q160E_T178D | K145T_Q179D_S188F | Q124R_Q160K_T178R |
| 63-65 | D146G_S186R | Q124E_Q160E_T178D | K145T_Q179D_S188L | Q160K_T178R |
| 62-61 | D146G_S186R | Q124E_Q160E_T178D | K145T_Q179D_S188L | Q124R_Q160K_T178R |
| 63-113 | D146G_S186R | Q124E_Q160E_T180E | K145T_Q179D_S188L | Q160K_T178R |
| 8-6 | D146G_S186R | Q124E_Q160E_T180E | L145E_K145T | Q160K_T178R |
| 8-9 | D146G_S186R | Q124E_Q160E_T180E | L145E_K145T | Q160K_T178R |
| 8-59 | D146G_S186R | Q124E_Q160E_T180E | L145E_K145T | Q160K_T178R |
| 207-203 | F100M_W103H | P44W_L89W | V37W_F100W_W103L | F98A |
| 207-205 | F100M_W103H | P44W_L89W | V37W_F100W_W103L | F98A |
| 202-203 | F100M_W103V | P44W_L89W | V37W_F100W_W103L | F98A |
| 202-205 | F100M_W103V | P44W_L89W | V37W_F100W_W103L | F98A |
| | F100W | F98L | V37I | WT |
| | F100W | F98L | WT | WT |
| 296-297 | F100W | F98M | W103F | Y36W |
| 344*-121, 121-344* | F100W_W103F | F98L | Q39R | Q38E_F98W |
| 355*-186, 186-355* | F100W_W103F | F98L | WT | F98W |
| 298-297 | F100W_W103F | F98M | W103F | Y36W |
| 254-255 | F174A_S188G | S176W | F174G_S188A | WT |
| 10-11 | F174V_P175S_S188G | S176L | F174V_S188L | S176G |
| 3-70 | F174V_P175S_S188G | S176L | F174V_S188L | V133S |
| 12-13 | F174V_P175S_S188G | S176L | F174V_S188L | WT |
| 18-11 | F174V_P175S_S188G | S176L | F174V_S188L | S176G |
| 3-133 | F174V_P175S_S188G | S176L | F174W_S188L | V133S |
| 12-15 | F174V_P175S_S188G | S176L | F174W_S188L | WT |
| 20-11 | F174V_P175S_S188G | S176L | S188L | S176G |

TABLE 30-continued

| Unique identifier set | H1_mutation | L1_mutation | H2_mutation | L2_mutation |
|---|---|---|---|---|
| 3-4 | F174V_P175S_S188G | S176L | S188L | V133S |
| 12-14 | F174V_P175S_S188G | S176L | S188L | WT |
| 3-19, 19-3, 19-3 | F174V_P175S_S188G | S176L | S188L_V190Y | V133S |
| 383*-384* | H172R | WT | H172T | N137K_S174R |
| 395*-396* | H172R | WT | H172T | S174R |
| 411*-384* | H172R_T192K | WT | H172T | N137K_S174R |
| 428*-396* | H172R_T192K | WT | H172T | S174R |
| 82-201 | K145E_D146G_Q179D_S188F | Q160K_T178R | L143A_D146G_Q179R | Q124E_V133W_Q160E_T180E |
| 66-114 | K145E_D146G_Q179D_S188F | V133A_Q160K_T178R | L143A_D146G_Q179R | Q124E_V133W_Q160E_T180E |
| 1-2, 1-2 | K145L_Q179E | S131K | S186R | Q124E_V133W_Q160E_T180E |
| 23-326*, 326*-23, 442*-23, 443*-326* | K145L_Q179E | S131K | S186R | Q124E_Q160E_T180E |
| 388*-389* | K145T_Q179D_S188F | S131K | WT | WT |
| 80-82 | K145T_Q179D_S188F | Q160K_T178R | L143A_D146G_Q179R | Q124E_V133W_Q160E_T180E |
| 66-67 | K145T_Q179D_S188F | V133A_Q160K_T178R | L143A_D146G_Q179R | Q124E_V133W_Q160E_T180E |
| 85-82 | K145T_Q179D_S188L | Q160K_T178R | L143A_D146G_Q179R | Q124E_V133W_Q160E_T180E |
| 66-68 | K145T_Q179D_S188L | V133A_Q160K_T178R | L143A_D146G_Q179R | Q124E_V133W_Q160E_T180E |
| 437*-326* | K145T_Q179E | S131K | S186R | Q124E_Q160E_T180E |
| 415*-416* | K145T_Q179E | S131R | S186R | Q160E_T180E |
| 438*-285 | K145T_S186E_S188L | Q124R | S186R | Q124E_Q160E_T180E |
| 432*-426* | K145T_S186E_S188L | Q124R | S186R | Q124E_T178E |
| 412*-413* | K145T_S186E_S188L | Q124R | S186R | Q160E_T178E |
| 440*-441* | K145T_S186E_S188L | Q124R | S186R | Q160E_T180E |
| 439*-283 | K145T_S186E_S188L | Q124R | S186R | T178E |
| 405*-391* | K145T_S186E_S188L | S131R | S186R | T178E_T180E |
| 406*-407* | K145T_S186E_S188L | S131R | S186R | Q124E_Q160E_T180E |
| 401*-402* | K145T_S186E_S188L | S131R | S186R | Q160E_T178E |
| 393*-394* | K145T_S186E_S188L | S131R | S186R | Q160E_T180E |
| 429*-430* | K145T_S186E_S188L | S131R | S186R | Q160E_T180E |
| 397*-398* | K145T_S186E_S188L | S131R | S186R | T178E |
| 399*-400* | K145T_S186E_S188L | S131R | S186R | T178E_T180E |
| 409*-410* | L124A | V133F | L124W | V133A |
| 294-295, 295-294 | L124E | V133A_S176K | L124R | V133G_S176D |
| 288-289 | L124E | V133G_S176R | L124R | V133A_S176D |
| 263-264 | L124E | V133G_S176R | L124R | V133G_S176D |
| 271-272 | L124E_H172R | V133A_S176K | L124E_H172A | V133A_S174W_S176D |
| 267-268 | L124E_H172R | V133G_S176R | L124E_H172A | V133A_S174W_S176D |
| 261-262 | L124E_H172R | V133G_S176R | L124E_H172A | V133G_S174W_S176D |
| 275-276 | L124E_H172W | V133A_S176K | L124E_H172T | V133A_S174R_S176D |
| 286-287 | L124E_H172W | V133G_S176R | L124E_H172T | V133A_S174R_S176D |
| 269-270 | L124E_H172W | V133G_S176R | L124R_H172T | V133G_S174R_S176D |
| 336*-335*, 335*-336* | L124R | F98W_V133G_S176D | V37W_L124E | F98A_V133A_S176K |
| 308*-320* | L124S | WT | L124W | F118A |
| 265-266 | L143E_K145T | Q124K_T178R | S186R | Q124E |
| 259-260 | L143E_K145T | Q124K_T178R | S186R | Q124E_Q160E_T180E |
| 277-281 | L143E_K145T | Q124R | L143K | Q124E |
| 58-57, 57-58 | L143E_K145T | Q124R | L143K_D146G | Q124E_V133D |
| 277-278 | L143E_K145T | Q124R | L143R | Q124E |

TABLE 30-continued

| Unique identifier set | H1_mutation | L1_mutation | H2_mutation | L2_mutation |
|---|---|---|---|---|
| 277-280 | L143E_K145T | Q124R | S186R | Q124E |
| 366*-367* | L143E_K145T | Q124R | S186R | Q124E_Q160E_T178D |
| 284-285 | L143E_K145T | Q124R | S186R | Q124E_Q160E_T180E |
| 282-283 | L143E_K145T | Q124R | S186R | T178E |
| 277-279 | L143E_K145T | Q124R | WT | Q124E |
| 421*-422* | L143E_K145T | Q124R | WT | WT |
| 257-258 | L143E_K145T | Q124R_Q160K_T178R | S186R | Q124E_Q160E_T180E |
| 424*-260 | L143E_K145T_Q179E | Q124K_T178R | S186R | Q124E_Q160E_T180E |
| 379*-380* | L143E_K145T_Q179E | Q124K_T178R | S186R | Q124E_T178E_T180E |
| 290-291 | L143E_K145T_S188L | Q124K | L143K | Q124E |
| 290-293 | L143E_K145T_S188L | Q124K | L143R | Q124E |
| 290-292 | L143E_K145T_S188L | Q124R | S186R | Q124E |
| 303-281 | L143E_K145T_S188L | Q124R | L143K | Q124E |
| 419*-420* | L143E_K145T_S188L | Q124R | L143K | Q124E_T178E |
| 375*-385* | L143E_K145T_S188L | Q124R | L143K | Q124E_V133E |
| 435*-436* | L143E_K145T_S188L | Q124R | L143K | T178E |
| 368*-369* | L143E_K145T_S188L | Q124R | L143K | V133E |
| 303-278 | L143E_K145T_S188L | Q124R | L143R | Q124E |
| 375*-376* | L143E_K145T_S188L | Q124R | L143R | Q124E_V133E |
| 368*-372* | L143E_K145T_S188L | Q124R | L143R | V133E |
| 303-280 | L143E_K145T_S188L | Q124R | S186R | Q124E |
| 419*-426* | L143E_K145T_S188L | Q124R | S186R | Q124E_T178E |
| 414*-413* | L143E_K145T_S188L | Q124R | S186R | Q160E_T178E |
| 435*-283 | L143E_K145T_S188L | Q124R | S186R | T178E |
| 390*-391* | L143E_K145T_S188L | Q124R | S186R | T178E_T180E |
| 303-279 | L143E_K145T_S188L | Q124R | S186R | Q124E |
| 377*-378*, 378*-377* | L45A | P44F | WT | WT |
| 358*-359*, 359*-358* | L45A | P44F | L45F | F98L |
| 299-300, 300-299 | L45A | P44F | V37F | F98A |
| 299-338*, 338*-299 | L45A | P44F | V37W_W103F | F98A |
| 377*-408*, 408*-377* | L45A | P44F | WT | WT |
| 374*-373*, 373*-374* | L45A | P44W | L45F | F98L |
| 364*-356*, 356*-364* | L45A | P44W | V37F | F98A |
| 337*-313*, 313*-337* | L45A | P44W | V37W | F98L |
| 337*-340*, 340*-337* | L45A | P44W | V37W_W103F | F98A |
| 374*-392*, 392*-374* | L45A | P44W | WT | WT |
| 249-250 | L45W | Y87G | V37A_W103H | P44W |
| 86-184 | Q39D | Q38N_T85K | Q39K | Q38N_T85E |
| 21-22 | Q39D | Q38R | Q39R | Q38D |
| 75-76 | Q39D | Q38R | Q39R | Q38D_F98W |
| 16-84 | Q39D | Q38R | Q39R | Q38E_F98W |

TABLE 30-continued

| Unique identifier set | H1_mutation | L1_mutation | H2_mutation | L2_mutation |
|---|---|---|---|---|
| 161-142 | Q39D | Q38R | V37A_Q39R_W103V | Q38D_P44W |
| 162-163 | Q39D | Q38R | V37A_Q39R_W103V | Q38E_P44W |
| 75-77 | Q39D | Q38R | V37L_Q39R | Q38D_F98W |
| 16-17 | Q39D | Q38R | V37L_Q39R | Q38E_F98W |
| 135-136 | Q39D | Q38R | V37W_Q39R | Q38D_F98A |
| 35-36 | Q39D | Q38R | V37W_Q39R | Q38E_F98A |
| 137-138 | Q39D | Q38R_F98W | V37W_Q39R | Q38D_F98A |
| 41-42 | Q39D | Q38R_F98W | V37W_Q39R | Q38E_F98A |
| 145-147 | Q39D | Q38R_F98W | V37W_Q39R_W103F | Q38D_F98L |
| 96-97 | Q39D | Q38R_F98W | V37W_Q39R_W103F | Q38E_F98L |
| 145-146 | Q39D | Q38R_F98W | V37W_Q39R_W103H | Q38D_F98L |
| 96-132 | Q39D | Q38R_F98W | V37W_Q39R_W103H | Q38E_F98L |
| 111-112 | Q39D_A139G_V190A | Q38R_L135W | Q39R_A139W | Q38D_F116A_L135A |
| 192-193 | Q39D_A139W | Q38R_F116A_L135A | Q39R_A139G_V190A | Q38D_L135W |
| 86-87 | Q39E | Q38N_T85K | Q39K | Q38N_T85E |
| 127-128 | Q39E | Q38N_T85K | V37W_Q39R | Q38N_T85E_F98A |
| 233-131 | Q39E | Q38N_T85K_F98W | V37W_Q39R | Q38N_T85E_F98A |
| 239-243 | Q39E | Q38N_T85K_F98W | V37W_Q39R_W103F | Q38N_T85E_F98L |
| 239-240 | Q39E | Q38N_T85K_F98W | V37W_Q39R_W103H | Q38N_T85E_F98L |
| 301-302 | Q39E | Q38N_T85R | Q39R | Q38E_T85E |
| 22-44 | Q39E | Q38R | Q39R | Q38D |
| 99-76 | Q39E | Q38R | Q39R | Q38D_F98W |
| 52-51, 51-52 | Q39E | Q38R | Q39R | Q38E |
| 43-84 | Q39E | Q38R | Q39R | Q38E_F98W |
| 141-142 | Q39E | Q38R | V37W_Q39R | Q38E_P44W |
| 168-163 | Q39E | Q38R | V37A_Q39R_W103V | Q38D_F98A |
| 99-77 | Q39E | Q38R | V37L_Q39R | Q38E_P44W |
| 43-17 | Q39E | Q38R | V37L_Q39R | Q38E_F98W |
| 190-191 | Q39E | Q38R | V37W | F98A |
| 206-136 | Q39E | Q38R | V37W_Q39R | Q38D_F98A |
| 37-36 | Q39E | Q38R | V37W_Q39R | Q38E_F98A |
| 273-274 | Q39E | Q38R_F98W | Q39R_F100W_W103F | Q38E_F98M |
| 210-138 | Q39E | Q38R_F98W | V37W_Q39R | Q38D_F98A |
| 105-42 | Q39E | Q38R_F98W | V37W_Q39R | Q38E_F98A |
| 200-147 | Q39E | Q38R_F98W | V37W_Q39R_W103F | Q38D_F98L |
| 126-97 | Q39E | Q38R_F98W | V37W_Q39R_W103F | Q38E_F98L |
| 200-146 | Q39E | Q38R_F98W | V37W_Q39R_W103H | Q38D_F98L |
| 126-132 | Q39E | Q38R_F98W | V37W_Q39R_W103H | Q38E_F98L |
| 382*-381*, 381*-382* | Q39E | Q38R_L135W | Q39R_A139W | Q38E_F116A |
| 371*-370*, 370*-371* | Q39E_A139G_V190A | Q38R_L135W | Q39R_A139W | Q38E_F116A_L135V |
| 386*-387*, 387*-386* | Q39E_L124W | Q38R_V133A | Q39R_L124A | Q38E_V133F |
| 327*-328*, 328*-327* | Q39E_S186R | Q38R_Q124E_Q160E_T180E | Q39R_K145L_Q179E | Q38E_S131K |
| 333*-334*, 334*-333* | Q39E_S186R | Q38R_Q160E_T180E | Q39R_K145T_Q179E | Q38E_S131K |
| 170-171 | Q39K | Q38N_T85E | V37A_Q39E_W103H | Q38N_P44W_T85K |
| 170-172 | Q39K | Q38N_T85E | V37A_Q39E_W103V | Q38N_P44W_T85K |

TABLE 30-continued

| Unique identifier set | H1_mutation | L1_mutation | H2_mutation | L2_mutation |
|---|---|---|---|---|
| 86-88 | Q39K | Q38N_T85E | V37L_Q39E | Q38N_T85K |
| 119-120 | Q39K | Q38N_T85E_F98W | V37L_Q39E | Q38N_T85K_F98A |
| 226-228 | Q39K | Q38N_T85E_F98W | V37W_Q39E_W103F | Q38N_T85K_F98L |
| 226-227 | Q39K | Q38N_T85E_F98W | V37W_Q39E_W103F | Q38N_T85K_F98L |
| 55-56, 56-55 | Q39M | Q38M | Q39R | Q38E |
| 22-151 | Q39R | Q38D | V37L_Q39R | Q38R |
| 45-28 | Q39R | Q38D | V37W_Q39D | Q38R_F98A |
| 27-28 | Q39R | Q38D | V37W_Q39E | Q38R_F98A |
| 89-98 | Q39R | Q38D_F98W | V37W_Q39D | Q38R_F98L |
| 115-122 | Q39R | Q38D_F98W | V37W_Q39D_W103F | Q38R_F98L |
| 115-217 | Q39R | Q38D_F98W | V37W_Q39D_W103H | Q38R_F98L |
| 89-90 | Q39R | Q38D_F98W | V37W_Q39E | Q38R_F98L |
| 115-116 | Q39R | Q38D_F98W | V37W_Q39E_W103F | Q38R_F98L |
| 115-218 | Q39R | Q38D_F98W | V37W_Q39E_W103H | Q38R_F98L |
| 123-124 | Q39R | Q38D_F98W | V37W_W103F | F98L |
| 123-219 | Q39R | Q38D_F98W | V37W_W103H | F98L |
| 307*-305*, 305*-307* | Q39R | Q38E | V37W | F98A |
| 39-40 | Q39R | Q38E | V37W_Q39D | Q38R_F98A |
| 39-34, 34-39 | Q39R | Q38E | V37W_Q39E | Q38R_F98A |
| 53-54, 54-53 | Q39R | Q38E | WT | WT |
| 93-38 | Q39R | Q38E_F98W | V37W_Q39D | Q38R_F98L |
| 118-91 | Q39R | Q38E_F98W | V37W_Q39D_W103F | Q38R_F98L |
| 118-143 | Q39R | Q38E_F98W | V37W_Q39D_W103H | Q38R_F98L |
| 93-26, 26-93 | Q39R | Q38E_F98W | V37W_Q39E | Q38R_F98L |
| 118-74 | Q39R | Q38E_F98W | V37W_Q39E_W103F | Q38R_F98L |
| 118-144 | Q39R | Q38E_F98W | V37W_Q39E_W103H | Q38R_F98L |
| 121-95 | Q39R | Q38E_F98W | V37W_W103F | F98L |
| 121-175 | Q39R | Q38E_F98W | V37W_W103H | F98L |
| 342*-341*, 341*-342* | S186R | F98W_Q160E_T180E | V37W_K145T_Q179E | F98A_S131K |
| | S188I | WT | WT | S176V_T178L |
| 198-199 | V37A_Q39E_W103H | Q38N_P44W_T85K | V37W_Q39K | Q38N_T85E_F98A |
| 220-199 | V37A_Q39E_W103V | Q38N_P44W_T85K | V37W_Q39K | Q38N_T85E_F98A |
| 213-214 | V37A_Q39K_W103H | Q38N_P44W_T85E | V37W_Q39E | Q38N_T85K_F98A |
| 173-174 | V37A_Q39R_W103H | Q38D_P44W | V37W | F98A |
| 148-149 | V37A_Q39R_W103V | Q38D_P44W | V37W_Q39D | Q38R_F98A |
| 148-150 | V37A_Q39R_W103V | Q38D_P44W | V37W_Q39E | Q38R_F98A |
| 158-159 | V37A_Q39R_W103V | Q38E_P44W | V37W | F98A |
| 152-153 | V37A_Q39R_W103V | Q38E_P44W | V37W_Q39D | Q38R_F98A |
| 152-154, 154-152 | V37A_Q39R_W103V | Q38E_P44W | V37W_Q39E | Q38R_F98A |
| | V37A_W103H | P44W | V37A_W103V | F98L |
| | V37A_W103H | P44W | V37A_W103V | F98W |
| | V37A_W103H | P44W | V37L_F100W | F98L |
| 242-244 | V37A_W103H | P44W | V37T_A93Q_W103T | F98A |
| 250-256 | V37A_W103H | P44W | V37T_A93Q_W103T | Y87G |
| 241-242 | V37A_W103H | P44W | V37W | F98A |
| 177-157 | V37A_W103H | P44W_F98W | V37W_W103H | F98L |
| | | | V37W | F98A |

TABLE 30-continued

| Unique identifier set | H1_mutation | L1_mutation | H2_mutation | L2_mutation |
|---|---|---|---|---|
| 221-222 | V37A_W103H_A139G_V190A | P44W_L135W | V37W_A139W | F98A_F116A_L135A |
| 189-157 | V37A_W103V | P44W | V37W | F98A |
| 101-102 | V37A_W103V | P44W_F98W | V37W | F98A |
| 229-230 | V37E | L89R_F98T | WT | W TABLE 30-continued

| Unique identifier set | H1_mutation | L1_mutation | H2_mutation | L2_mutation |
|---|---|---|---|---|
| 125-124 | V37I_Q39R | Q38D_F98W | V37W_W103F | F98L |
| 125-219 | V37I_Q39R | Q38D_F98W | V37W_W103H | F98L |
| 33-40 | V37I_Q39R | Q38E | V37W_Q39D | Q38R_F98A |
| 33-34 | V37I_Q39R | Q38E | V37W_Q39E | Q38R_F98A |
| 25-38 | V37I_Q39R | Q38E_F98W | V37W_Q39D | Q38R_F98A |
| 73-91 | V37I_Q39R | Q38E_F98W | V37W_Q39D_W103F | Q38R_F98L |
| 73-143 | V37I_Q39R | Q38E_F98W | V37W_Q39D_W103H | Q38R_F98L |
| 25-26 | V37I_Q39R | Q38E_F98W | V37W_Q39E | Q38R_F98A |
| 73-74, 74-73 | V37I_Q39R | Q38E_F98W | V37W_Q39E_W103F | Q38R_F98L |
| 73-144 | V37I_Q39R | Q38E_F98W | V37W_Q39E_W103H | Q38R_F98L |
| 94-95 | V37I_Q39R | Q38E_F98W | V37W_W103F | F98L |
| 94-175 | V37I_Q39R | Q38E_F98W | V37W_W103H | F98L |
| 166-157 | V37I_W103H | P44W_F98W | V37W | F98A |
| 156-157 | V37T_A93Q_W103L | P44W_F98W | V37W | F98A |
| 169-157 | V37T_A93Q_W103T | P44W_F98W | V37W | F98A |
| 223-179 | V37T_A93Q_W103T | P44W_L89W_F98A | V37W_F100W | F98A |
| 167-157 | V37T_A93Q_W103V | P44W_F98W | V37W | F98A |
| 204-179 | V37T_A93Q_W103V | P44W_L89W_F98A | V37W_F100W | F98A |
| 300-349*, 349*-300 | V37W | F98A | W103F | P44F |
| 313*-361*, 361*-313* | V37W | F98A | W103F | P44W |
| 157-176 | V37W | F98A | W103H | P44W_F98W |
| 300-343*, 343*-300 | V37W | F98A | W103V | P44F |
| 313*-339*, 339*-313* | V37W | F98A | W103V | P44W |
| 157-178 | V37W | F98A | W103V | P44W_F98W |
| 325*-31, 31-325* | V37W | F98A | WT | F98W |
| 46-30 | V37W | F98A | WT | L89F_F98W |
| 351*-312*, 312*-351* | V37W | F98A | WT | WT |
| 31-32 | V37W_A93V | F98A | WT | F98W |
| 29-30 | V37W_A93V | F98A | WT | L89F_F98W |
| 179-245 | V37W_F100W | F98A | W103H | P44W_L89W_F98A |
| 179-180, 323*-324* | V37W_F100W | F98A | W103V | P44W_L89W_F98A |
| 247-248 | V37W_F100W_W103L | L89W_F98A | V37W_F100W | F98A |
| 347*-348*, 348*-347* | V37W_K145T_Q179E | F98A_S131K | WT | F98W |
| 338*-349*, 349*-338* | V37W_W103F | F98A | W103F | P44F |
| 340*-361*, 361*-340* | V37W_W103F | F98A | W103F | P44W |
| 338*-343*, 343*-338* | V37W_W103F | F98A | W103V | P44F |

TABLE 30-continued

| Unique identifier set | H1_mutation | L1_mutation | H2_mutation | L2_mutation |
|---|---|---|---|---|
| 340*-339*, 339*-340* | V37W_W103F | F98A | W103V | P44W |
| 350*-31, 31-350* | V37W_W103F | F98A | WT | F98W |
| | V37W_W103F | F98L | WT | F98W |
| 186-187 | V37W_W

TABLE 31

| H1_mutaton | L1_mutation | H2_mutation | L2_mutation |
|---|---|---|---|
| A139W | F116A | WT | L135W |
| H172T | S174R | H172R | WT |
| K145T_Q179E and/or K145T_S186E | L143E_K145T and/or S131K and/or T178R and/or Q124R | S186R and/or Q179K and/or L143K | T178E and/or Q124E and/or T180E or Q160E and/or V133E |
| F174V_P175S_S188G | S176L | S188L | V133S |
| S188G | S176L | S188L | S176A |
| L124A | V133F | L124W | V133A |
| L124E | V133G_S176R | L124R | V133A_S176D |
| V37W | F98A | WT | WT |
| F100W | F98L | WT | WT |
| Q39E | Q38R | Q39R | Q38E |
| Q39E | Q38N_T85K | Q39K | Q38N_T85E |
| Q39M | Q38M | Q39R | Q38E |
| F100W | F98M | W103F | Y36W |
| V37E | L89R_F98T | WT | WT |
| L45A | P44F | WT | WT |
| W103V | P44W | V37W | F98A |

Key for Tables 14-27 and 30-31

Table 14. LCCA data for D3H44 system, in Fab pair format
Table 15. Additional LCCA data for D3H44 system, in Fab pair format
Table 16. LCCA data for selected pure and mixed systems
Table 17. LCCA data for selected pure and mixed systems, in Fab pair format
Table 18. WT LCCA_data for selected pure and mixed systems
Table 19. Table 17 data summary
Table 20. Table 18 data summary
Table 21. Mab assay data for D3H44 system
Table 22. SMCA data for selected systems, pH 4
Table 23. DNA titration example for SMCA experiments -continued Key for Tables 14-27 and 30-31

Table 24. SMCA data for selected systems, pH 7
Table 25. Thermal Stability and Antigen binding data for selected SMCA designs
Table 26. SMCA data for selected WT (vis-a-vis light chain tags)
Table 27. Successful designs in both LCCA (D3H44) and at least one tested SMCA system
Table 30. Design library
Table 31. Core designs

We claim:

1. An isolated antigen binding polypeptide construct comprising at least a first heterodimer and a second heterodimer, the first heterodimer comprising a first immunoglobulin G (IgG) heavy chain polypeptide sequence (H1) and a first immunoglobulin light chain polypeptide sequence (L1), and binding to a first epitope; and the second heterodimer comprising a second immunoglobulin G (IgG) heavy chain polypeptide sequence (H2) and a second immunoglobulin light chain polypeptide sequence (L2), and binding to a second epitope, wherein at least one of the H1 or L1 sequences of the first heterodimer is distinct from the corresponding H2 or L2 sequence of the second heterodimer, H1 and H2 each comprise a heavy chain variable domain ($V_H$ domain) and a heavy chain constant domain ($C_{H1}$ domain), and L1 and L2 each comprise a light chain variable domain ($V_L$ domain) and a light chain constant domain ($C_L$ domain);

wherein H1 preferentially pairs with L1 as compared to L2 and H2 preferentially pairs with L2 as compared to L1;

wherein:
a) H1 comprises amino acid substitutions 145L and 179E, L1 comprises amino acid substitution 131K, H2 comprises amino acid substitutions 146G and 179K, and L2 comprises amino acid substitutions 124E, 160E and 180E;
b) H1 comprises amino acid substitutions 145T and 179E, L1 comprises amino acid substitution 131K, H2 comprises amino acid substitution 186R, and L2 comprises amino acid substitution 180E;
c) H1 comprises amino acid substitutions 139W, 145T, and 179E, L1 comprises amino acid substitutions 986A and 131K, H2 comprises amino acid substitution 186R, and L2 comprises amino acid substitutions 135W, 160E and 180E;
d) H1 comprises amino acid substitutions 37W, 145T and 179E, L1 comprises amino acid substitutions 98A and 131K, H2 comprises amino acid substitution 186R, and L2 comprises amino acid substitutions 98W, 160E and 180E;
e) H1 comprises amino acid substitutions 37W, 145T and 179E, L1 comprises amino acid substitutions 98A and 131K, and L2 comprises amino acid substitution 98W;
f) H1 comprises amino acid substitutions 145L and 179E, L1 comprises amino acid substitution 131K, H2 comprises amino acid substitution 186R, and L2 comprises amino acid substitutions 124E, 160E and 178D; or
g) H1 comprises amino acid substitutions 145L and 179E, and L1 comprises amino acid substitution 131K;
wherein when both L1 and L2 are co-expressed with at least one of H1 and H2, the pairing of H1-L1 to H1-L2 and the pairing of H2-L2 to H2-L1 is greater than the pairing of H1-L1 to H1-L2 and the pairing of H2-L2 to H2-L1 in the absence of the amino acid substitutions,
and wherein the numbering of amino acid residues is according to Kabat.

2. The construct of claim 1, wherein H1, H2, L1 and L2 are co-expressed in a cell or a mammalian cell, or H1, H2, L1 and L2 are co-expressed in a cell-free expression system, or H1, H2, L1 and L2 are co-produced, or H1, H2, L1 and L2 are co-produced via a redox production system.

3. The construct of claim 2, wherein the first immunoglobulin light chain polypeptide sequence and/or the second immunoglobulin light chain polypeptide sequence is a kappa light chain polypeptide.

4. The construct of claim 2, wherein the construct further comprises an Fc comprising two heavy chain constant domain polypeptides, each comprising a $C_{H3}$ sequence, wherein the heavy chain polypeptides are coupled, with or without one or more linkers, to the first heterodimer and the second heterodimer.

5. The construct of claim 4, wherein the Fc is a human Fc, a human IgG1 Fc, a human IgA Fc, a human IgG Fc, a human IgD Fc, a human IgE Fc, a human IgM Fc, a human IgG2 Fc, a human IgG3 Fc, or a human IgG4 Fc.

6. The construct of claim 5, wherein the Fc is a heterodimeric Fc.

7. The construct of claim 6, wherein the Fc comprises one or more modifications in at least one of the $C_{H3}$ sequences that promote the formation of a heterodimeric Fc with stability comparable to a wild-type homodimeric Fc.

8. The construct of claim 7, wherein:
a) one of the $C_{H3}$ sequences comprises the amino acid substitutions L351Y, F405A, Y407V and the other comprises the amino acid substitutions T366L, K392M, T394W;
b) one of the $C_{H3}$ sequences comprises the amino acid substitutions L351Y, F405A, Y407V and the other comprises the amino acid substitutions T366L, K392L, T394W;
c) one of the $C_{H3}$ sequences comprises the amino acid substitutions T350V, L351Y, F405A, Y407V and the other comprises the amino acid substitutions T350V, T366L, K392M, T394W;
d) one of the $C_{H3}$ sequences comprises the amino acid substitutions T350V, L351Y, F405A, Y407V and the other comprises the amino acid substitutions T350V, T366L, K392L, T394W; or
e) one of the $C_{H3}$ sequences comprises the amino acid substitutions T350V, L351Y, S400E, F405A, Y407V and the other comprises the amino acid substitutions T350V, T366L, N390R, K392M, T394W,
wherein the numbering of amino acid residues of the $C_{H3}$ sequences is according to the EU numbering system.

9. The construct of claim 8, wherein the Fc further comprises at least one $C_{H2}$ sequence.

10. The construct of claim 9, wherein the Fc comprises one or more modifications to promote selective binding of Fc-gamma receptors.

11. The construct of claim 4, wherein the one or more linkers are one or more polypeptide linkers, comprising one or more antibody hinge regions or one or more IgG1 hinge regions.

12. The construct according to claim 1, wherein the sequences of each of H1, H2, L1, and L2 are derived from human or humanized sequences.

13. The construct according to claim 1, wherein the construct is multispecific or bispecific.

14. The construct according to claim 8, wherein the construct is conjugated to a therapeutic agent or drug.

15. A pharmaceutical composition comprising the construct of claim 1 and a pharmaceutically acceptable carrier.

16. The pharmaceutical composition according to claim 15, further comprising one or more substances selected from the group consisting of a buffer, an antioxidant, a low molecular weight molecule, a drug, a protein, an amino acid, a carbohydrate, a lipid, a chelating agent, a stabilizer, and an excipient.

17. An isolated polynucleotide or set of isolated polynucleotides comprising at least one sequence that encodes the construct according to claim 1.

18. The isolated polynucleotide of claim 17, wherein the polynucleotide or set of polynucleotides is cDNA.

19. A vector or set of vectors comprising the isolated polynucleotide or set of isolated polynucleotides according to claim 17.

20. The vector or set of vectors according to claim 19, which is selected from the group consisting of a plasmid, a multi-cistronic vector, a viral vector, a non-episomal mammalian vector, an expression vector, and a recombinant expression vector.

21. An isolated cell comprising the vector or set of vectors according to claim 19.

22. The isolated cell according to claim 21, wherein the cell is a hybridoma, a Chinese Hamster Ovary (CHO) cell, or a HEK293 cell.

23. A method of obtaining the construct according to claim 1 from a host cell culture, the method comprising the steps of:
(a) obtaining a host cell culture comprising at least one host cell comprising one or more nucleic acid sequences encoding the construct; and
(b) recovering the construct from the host cell culture.

24. The method of claim 23, wherein the construct comprises an Fc comprising at least two $C_{H3}$ sequences, wherein the Fc is coupled, with or without one or more linkers, to the first heterodimer and the second heterodimer.

25. The method of claim 24, wherein the Fc is a heterodimer, optionally comprising one or more amino acid modifications.

* * * * *

UNITED STATES PATENT AND TRADEMARK OFFICE
CERTIFICATE OF CORRECTION

| | | |
|---|---|---|
| PATENT NO. | : 11,286,293 B2 | |
| APPLICATION NO. | : 16/122417 | |
| DATED | : March 29, 2022 | |
| INVENTOR(S) | : Adam Louis Corper et al. | |

It is certified that error appears in the above-identified patent and that said Letters Patent is hereby corrected as shown below:

On the Title Page

At the (73) Assignee, please delete "ZYMEWORKS INC," and insert --ZYMEWORKS BC INC.--

Signed and Sealed this
Thirtieth Day of May, 2023

Katherine Kelly Vidal
*Director of the United States Patent and Trademark Office*